(12) United States Patent
Herr et al.

(10) Patent No.: US 8,512,415 B2
(45) Date of Patent: Aug. 20, 2013

(54) POWERED ANKLE-FOOT PROTHESIS

(75) Inventors: Hugh M. Herr, Somerville, MA (US);
Jeff A. Weber, San Francisco, CA (US);
Samuel K. Au, Sunnyvale, CA (US);
Bruce Wayne Deffenbaugh, Honolulu, HI (US); Lee Harris Magnusson, Bremen, ME (US); Andreas G. Hofmann, Boston, MA (US); Benjamin B. Aisen, New York, NY (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/157,727

(22) Filed: Jun. 12, 2008

(65) Prior Publication Data

US 2011/0257764 A1   Oct. 20, 2011

Related U.S. Application Data

(63) Continuation-in-part of application No. 11/395,448, filed on Mar. 31, 2006, now abandoned, and a continuation-in-part of application No. 11/495,140, filed on Jul. 29, 2006, now abandoned, said application No. 11/395,448 is a continuation-in-part of application No. 11/642,993, filed on Dec. 19, 2006, now abandoned, which is a continuation-in-part of application No. 11/395,448, and a continuation-in-part of application No. 11/495,140, and a continuation-in-part of application No. 11/499,853, filed on Aug. 4, 2006, now Pat. No. 7,313,463, and a continuation-in-part of application No. 11/600,291, filed on Nov. 15, 2006, now abandoned.

(60) Provisional application No. 60/934,223, filed on Jun. 12, 2007, provisional application No. 60/666,876, filed on Mar. 31, 2005, provisional application No. 60/704,517, filed on Aug. 1, 2005, provisional application No. 60/751,680, filed on Dec. 19, 2005.

(51) Int. Cl.
*A61F 2/64* (2006.01)
*A61F 2/48* (2006.01)
*A61F 2/68* (2006.01)

(52) U.S. Cl.
USPC .................................. 623/24; 623/47; 623/53

(58) Field of Classification Search
USPC .............................. 623/24, 27, 44, 46, 47, 53
See application file for complete search history.

(56) References Cited

U.S. PATENT DOCUMENTS 2,489,291 A   11/1949   Henschke et al.
2,529,968 A   11/1950   Sartin
(Continued)

FOREIGN PATENT DOCUMENTS

EP   1393866   3/2004
EP   1408892   4/2004
(Continued)

OTHER PUBLICATIONS

Willaimson, Matthew M., Series Elastic Actuators, MIT Artificial Intelligence Laboratory, Jan. 1995.*

(Continued)

*Primary Examiner* — Bruce E Snow
*Assistant Examiner* — Brian Dukert
(74) *Attorney, Agent, or Firm* — Hamilton, Brook, Smith & Reynolds, P.C.

(57) ABSTRACT

A powered ankle-foot prosthesis, capable of providing human-like power at terminal stance that increase amputees metabolic walking economy compared to a conventional passive-elastic prosthesis. The powered prosthesis comprises a unidirectional spring, configured in parallel with a force-controllable actuator with series elasticity. The prosthesis is controlled to deliver the high mechanical power and net positive work observed in normal human walking.

23 Claims, 75 Drawing Sheets

(56) References Cited

U.S. PATENT DOCUMENTS

| | | | |
|---|---|---|---|
| 3,098,645 | A | 7/1963 | Owens |
| 3,207,497 | A | 9/1965 | Schoonover |
| 3,844,279 | A | 10/1974 | Konvalin |
| 4,442,390 | A | 4/1984 | Davis |
| 4,463,291 | A | 7/1984 | Usry |
| 4,518,307 | A | 5/1985 | Bloch |
| 4,532,462 | A | 7/1985 | Washbourn et al. |
| 4,546,295 | A | 10/1985 | Wickham et al. |
| 4,546,296 | A | 10/1985 | Washbourn et al. |
| 4,546,297 | A | 10/1985 | Washbourn et al. |
| 4,546,298 | A | 10/1985 | Wickham et al. |
| 4,569,352 | A | 2/1986 | Petrofsky et al. |
| 4,600,357 | A | 7/1986 | Coules |
| 4,657,470 | A | 4/1987 | Clarke et al. |
| 4,843,921 | A | 7/1989 | Kremer |
| 4,865,376 | A | 9/1989 | Leaver et al. |
| 4,872,803 | A | 10/1989 | Asakawa |
| 4,909,535 | A * | 3/1990 | Clark et al. ............. 280/5.515 |
| 4,921,293 | A | 5/1990 | Ruoff et al. |
| 4,921,393 | A | 5/1990 | Andeen et al. |
| 4,923,474 | A | 5/1990 | Klasson et al. |
| 4,923,475 | A | 5/1990 | Gosthnian et al. |
| 4,936,295 | A | 6/1990 | Crane |
| 4,964,402 | A | 10/1990 | Grim et al. |
| 4,989,161 | A | 1/1991 | Oaki |
| 5,012,591 | A | 5/1991 | Asakawa |
| 5,049,797 | A | 9/1991 | Phillips |
| 5,062,673 | A | 11/1991 | Mimura |
| 5,088,478 | A | 2/1992 | Grim |
| 5,092,902 | A | 3/1992 | Adams et al. |
| 5,112,296 | A | 5/1992 | Beard et al. |
| 5,174,168 | A | 12/1992 | Takagi et al. |
| 5,181,933 | A | 1/1993 | Phillips |
| 5,252,102 | A | 10/1993 | Singer et al. |
| 5,294,873 | A | 3/1994 | Seraji |
| RE34,661 | E | 7/1994 | Grim |
| 5,327,790 | A | 7/1994 | Levin et al. |
| 5,367,790 | A | 11/1994 | Gamow et al. |
| 5,383,939 | A | 1/1995 | James |
| 5,405,409 | A | 4/1995 | Knoth |
| 5,442,270 | A | 8/1995 | Tetsuaki |
| 5,443,521 | A | 8/1995 | Knoth et al. |
| 5,456,341 | A | 10/1995 | Garnjost et al. |
| 5,458,143 | A | 10/1995 | Herr |
| 5,476,441 | A | 12/1995 | Durfee et al. |
| 5,502,363 | A | 3/1996 | Tasch et al. |
| 5,514,185 | A | 5/1996 | Phillips |
| 5,556,422 | A | 9/1996 | Powell, III et al. |
| 5,571,205 | A | 11/1996 | James |
| 5,643,332 | A | 7/1997 | Stein |
| 5,650,704 | A | 7/1997 | Pratt et al. |
| 5,662,693 | A | 9/1997 | Johnson et al. |
| 5,701,686 | A | 12/1997 | Herr et al. |
| 5,718,925 | A | 2/1998 | Kristinsson et al. |
| 5,748,845 | A | 5/1998 | Labun et al. |
| 5,776,205 | A | 7/1998 | Phillips |
| 5,885,809 | A | 3/1999 | Effenberger et al. |
| 5,888,212 | A | 3/1999 | Petrofsky et al. |
| 5,888,213 | A | 3/1999 | Sears et al. |
| 5,898,948 | A | 5/1999 | Kelly et al. |
| 5,910,720 | A | 6/1999 | Williamson et al. |
| 5,932,230 | A | 8/1999 | DeGrate |
| 5,944,760 | A * | 8/1999 | Christensen ............. 623/55 |
| 5,971,729 | A | 10/1999 | Kristinsson et al. |
| 5,972,036 | A | 10/1999 | Kristinsson et al. |
| 5,980,435 | A | 11/1999 | Joutras et al. |
| 6,029,374 | A | 2/2000 | Herr et al. |
| 6,056,712 | A | 5/2000 | Grim |
| 6,067,892 | A | 5/2000 | Erickson |
| 6,071,313 | A | 6/2000 | Phillips |
| 6,136,039 | A | 10/2000 | Kristinsson et al. |
| 6,144,385 | A | 11/2000 | Girard |
| 6,202,806 | B1 | 3/2001 | Sandrin et al. |
| 6,223,648 | B1 | 5/2001 | Erickson |
| 6,240,797 | B1 | 6/2001 | Morishima et al. |
| 6,267,742 | B1 | 7/2001 | Krivosha et al. |
| 6,416,703 | B1 | 7/2002 | Kristinsson et al. |
| 6,443,993 | B1 | 9/2002 | Koniuk |
| 6,456,884 | B1 | 9/2002 | Kenney |
| 6,478,826 | B1 | 11/2002 | Phillips et al. |
| 6,485,776 | B2 | 11/2002 | Janusson et al. |
| 6,507,757 | B1 | 1/2003 | Swain et al. |
| 6,511,512 | B2 | 1/2003 | Phillips et al. |
| 6,517,503 | B1 | 2/2003 | Naft et al. |
| 6,585,774 | B2 | 7/2003 | Dean, Jr. et al. |
| 6,589,289 | B2 | 7/2003 | Ingimarsson |
| 6,592,539 | B1 | 7/2003 | Einarsson et al. |
| 6,610,101 | B2 | 8/2003 | Herr et al. |
| 6,626,952 | B2 | 9/2003 | Janusson et al. |
| 6,660,042 | B1 | 12/2003 | Curcie et al. |
| 6,666,796 | B1 | 12/2003 | MacCready |
| 6,706,364 | B2 | 3/2004 | Janusson et al. |
| 6,752,774 | B2 | 6/2004 | Townsend et al. |
| 6,764,520 | B2 | 7/2004 | Deffenbaugh et al. |
| 6,811,571 | B1 | 11/2004 | Phillips |
| D503,480 | S | 3/2005 | Ingimundarson et al. |
| D503,802 | S | 4/2005 | Bjarnason |
| 6,887,279 | B2 | 5/2005 | Phillips et al. |
| 6,923,834 | B2 | 8/2005 | Karason |
| 6,936,073 | B2 | 8/2005 | Karason |
| 6,942,629 | B2 | 9/2005 | Hepburn et al. |
| 6,945,947 | B2 | 9/2005 | Ingimundarson et al. |
| 6,966,882 | B2 | 11/2005 | Horst |
| 6,969,408 | B2 | 11/2005 | Lecomte et al. |
| 7,001,563 | B2 | 2/2006 | Janusson et al. |
| 7,025,793 | B2 | 4/2006 | Egilsson |
| 7,029,500 | B2 | 4/2006 | Martin |
| 7,037,283 | B2 | 5/2006 | Karason et al. |
| D523,149 | S | 6/2006 | Bjarnason |
| 7,063,727 | B2 | 6/2006 | Phillips et al. |
| 7,077,818 | B2 | 7/2006 | Ingimundarson et al. |
| 7,094,058 | B2 | 8/2006 | Einarsson |
| 7,094,212 | B2 | 8/2006 | Karason et al. |
| D527,825 | S | 9/2006 | Ingimundarson et al. |
| D529,180 | S | 9/2006 | Ingimundarson et al. |
| 7,101,487 | B2 | 9/2006 | Hsu et al. |
| 7,105,122 | B2 | 9/2006 | Karason |
| 7,107,180 | B2 | 9/2006 | Karason |
| 7,118,601 | B2 | 10/2006 | Yasui et al. |
| 7,118,602 | B2 | 10/2006 | Bjarnason |
| 7,136,722 | B2 | 11/2006 | Nakamura et al. |
| D533,280 | S | 12/2006 | Wyatt et al. |
| 7,144,429 | B2 | 12/2006 | Carstens |
| 7,145,305 | B2 | 12/2006 | Takenaka et al. |
| 7,154,017 | B2 | 12/2006 | Sigurjonsson et al. |
| 7,161,056 | B2 | 1/2007 | Gudnason et al. |
| 7,169,188 | B2 | 1/2007 | Carstens |
| 7,169,189 | B2 | 1/2007 | Bjarnason et al. |
| 7,169,190 | B2 | 1/2007 | Phillips et al. |
| 7,198,071 | B2 | 4/2007 | Bisbee, III et al. |
| 7,198,610 | B2 | 4/2007 | Ingimundarson et al. |
| 7,217,060 | B2 | 5/2007 | Ingimarsson |
| 7,220,889 | B2 | 5/2007 | Sigurjonsson et al. |
| 7,223,899 | B2 | 5/2007 | Sigurjonsson |
| 7,227,050 | B2 | 6/2007 | Sigurjonsson et al. |
| 7,230,154 | B2 | 6/2007 | Sigurjonsson |
| 7,235,108 | B2 | 6/2007 | Carstens |
| 7,240,876 | B2 | 7/2007 | Doubleday et al. |
| 7,266,910 | B2 | 9/2007 | Ingimundarson |
| 7,270,644 | B2 | 9/2007 | Ingimundarson |
| 7,279,009 | B2 | 10/2007 | Herr et al. |
| 7,288,076 | B2 | 10/2007 | Grim et al. |
| 7,295,892 | B2 | 11/2007 | Herr et al. |
| RE39,961 | E | 12/2007 | Petrofsky et al. |
| 7,303,538 | B2 | 12/2007 | Grim et al. |
| 7,304,202 | B2 | 12/2007 | Sigurjonsson et al. |
| 7,311,686 | B1 | 12/2007 | Iglesias et al. |
| 7,313,463 | B2 | 12/2007 | Herr et al. |
| D558,884 | S | 1/2008 | Ingimundarson et al. |
| 7,335,233 | B2 | 2/2008 | Hsu et al. |
| 7,347,877 | B2 | 3/2008 | Clausen et al. |
| D567,072 | S | 4/2008 | Ingimundarson et al. |
| 7,371,262 | B2 | 5/2008 | Lecomte et al. |
| 7,377,944 | B2 | 5/2008 | Janusson et al. |

| | | | | | |
|---|---|---|---|---|---|
| RE40,363 E | 6/2008 | Grim et al. | 7,846,213 B2 | 12/2010 | Lecomte et al. |
| 7,381,860 B2 | 6/2008 | Gudnason et al. | 7,862,620 B2 | 1/2011 | Clausen et al. |
| 7,393,364 B2 | 7/2008 | Martin | 7,863,797 B2 | 1/2011 | Calley |
| 7,396,975 B2 | 7/2008 | Sigurjonsson et al. | 7,867,182 B2 | 1/2011 | Iglesias et al. |
| 7,402,721 B2 | 7/2008 | Sigurjonsson et al. | 7,867,284 B2 | 1/2011 | Bedard |
| 7,411,109 B2 | 8/2008 | Sigurjonsson et al. | 7,867,285 B2 | 1/2011 | Clausen et al. |
| D576,781 S | 9/2008 | Chang et al. | 7,867,286 B2 | 1/2011 | Einarsson |
| D577,828 S | 9/2008 | Ingimundarson et al. | 7,868,511 B2 | 1/2011 | Calley |
| 7,423,193 B2 | 9/2008 | Sigurjonsson et al. | 7,879,110 B2 | 2/2011 | Phillips |
| 7,427,297 B2 | 9/2008 | Patterson et al. | 7,891,258 B2 | 2/2011 | Clausen et al. |
| 7,429,253 B2 | 9/2008 | Shimada et al. | 7,892,195 B2 | 2/2011 | Grim et al. |
| 7,431,708 B2 | 10/2008 | Sreeramagiri | D634,438 S | 3/2011 | Hu |
| 7,431,737 B2 | 10/2008 | Ragnarsdottir et al. | D634,852 S | 3/2011 | Hu |
| 7,438,843 B2 | 10/2008 | Asgeirsson | 7,896,826 B2 | 3/2011 | Hu et al. |
| 7,449,005 B2 | 11/2008 | Pickering et al. | 7,896,827 B2 | 3/2011 | Ingimundarson et al. |
| 7,455,696 B2 | 11/2008 | Bisbee, III et al. | 7,896,927 B2 | 3/2011 | Clausen et al. |
| D583,956 S | 12/2008 | Chang et al. | 7,909,884 B2 | 3/2011 | Egilsson et al. |
| 7,459,598 B2 | 12/2008 | Sigurjonsson et al. | 7,910,793 B2 | 3/2011 | Sigurjonsson et al. |
| 7,465,281 B2 | 12/2008 | Grim et al. | 7,914,475 B2 | 3/2011 | Wyatt et al. |
| 7,465,283 B2 | 12/2008 | Grim et al. | 7,918,765 B2 | 4/2011 | Kruijsen et al. |
| 7,468,471 B2 | 12/2008 | Sigurjonsson et al. | D637,942 S | 5/2011 | Lee et al. |
| 7,470,830 B2 | 12/2008 | Sigurjonsson et al. | 7,935,068 B2 | 5/2011 | Einarsson |
| 7,488,349 B2 | 2/2009 | Einarsson | D640,380 S | 6/2011 | Tweardy et al. |
| 7,488,864 B2 | 2/2009 | Sigurjonsson et al. | D640,381 S | 6/2011 | Tweardy et al. |
| D588,753 S | 3/2009 | Ingimundarson et al. | 7,959,589 B2 | 6/2011 | Sreeramagiri et al. |
| 7,503,937 B2 | 3/2009 | Asgeirsson et al. | D641,482 S | 7/2011 | Robertson et al. |
| 7,513,880 B2 | 4/2009 | Ingimundarson et al. | D641,483 S | 7/2011 | Robertson et al. |
| 7,513,881 B1 | 4/2009 | Grim et al. | 7,981,068 B2 | 7/2011 | Thorgilsdottir et al. |
| D592,755 S | 5/2009 | Chang et al. | 7,985,193 B2 | 7/2011 | Thorsteinsson et al. |
| D592,756 S | 5/2009 | Chang et al. | D643,537 S | 8/2011 | Lee |
| 7,527,253 B2 | 5/2009 | Sugar et al. | 7,992,849 B2 | 8/2011 | Sugar et al. |
| 7,531,006 B2 | 5/2009 | Clausen et al. | 7,998,221 B2 | 8/2011 | Lecomte et al. |
| 7,531,711 B2 | 5/2009 | Sigurjonsson et al. | 8,002,724 B2 | 8/2011 | Hu et al. |
| 7,534,220 B2 | 5/2009 | Cormier et al. | 8,007,544 B2 | 8/2011 | Jonsson et al. |
| 7,544,214 B2 | 6/2009 | Gramnas | 8,016,781 B2 | 9/2011 | Ingimundarson et al. |
| 7,549,970 B2 | 6/2009 | Tweardy | 8,021,317 B2 | 9/2011 | Arnold et al. |
| D596,301 S | 7/2009 | Campos et al. | 8,025,632 B2 | 9/2011 | Einarsson |
| 7,578,799 B2 | 8/2009 | Thorsteinsson et al. | 8,025,699 B2 | 9/2011 | Lecomte et al. |
| 7,581,454 B2 | 9/2009 | Clausen et al. | 8,026,406 B2 | 9/2011 | Janusson et al. |
| 7,597,672 B2 | 10/2009 | Kruijsen et al. | D646,394 S | 10/2011 | Tweardy et al. |
| 7,597,674 B2 | 10/2009 | Hu et al. | D647,622 S | 10/2011 | Lee et al. |
| 7,597,675 B2 | 10/2009 | Ingimundarson et al. | D647,623 S | 10/2011 | Thorgilsdottir et al. |
| 7,618,463 B2 | 11/2009 | Oddsson et al. | D647,624 S | 10/2011 | Thorgilsdottir et al. |
| 7,632,315 B2 | 12/2009 | Egilsson | 8,034,120 B2 | 10/2011 | Egilsson et al. |
| 7,637,957 B2 | 12/2009 | Ragnarsdottir et al. | 8,038,636 B2 | 10/2011 | Thorgilsdottir et al. |
| 7,637,959 B2 | 12/2009 | Clausen et al. | 8,043,244 B2 | 10/2011 | Einarsson et al. |
| 7,641,700 B2 | 1/2010 | Yasui | 8,043,245 B2 | 10/2011 | Campos et al. |
| 7,650,204 B2 | 1/2010 | Dariush | 8,048,007 B2 | 11/2011 | Roy |
| 7,662,191 B2 | 2/2010 | Asgeirsson | 8,048,013 B2 | 11/2011 | Ingimundarson et al. |
| D611,322 S | 3/2010 | Robertson | 8,048,172 B2 | 11/2011 | Jonsson et al. |
| 7,674,212 B2 | 3/2010 | Kruijsen et al. | 8,052,760 B2 | 11/2011 | Egilsson et al. |
| 7,691,154 B2 | 4/2010 | Asgeirsson et al. | 8,057,550 B2 | 11/2011 | Clausen et al. |
| 7,696,400 B2 | 4/2010 | Sigurjonsson et al. | 2001/0029400 A1 | 10/2001 | Deffenbaugh et al. |
| 7,704,218 B2 | 4/2010 | Einarsson et al. | 2002/0052663 A1 | 5/2002 | Herr et al. |
| D616,555 S | 5/2010 | Thorgilsdottir et al. | 2002/0092724 A1 | 7/2002 | Koleda |
| D616,556 S | 5/2010 | Hu | 2002/0138153 A1 | 9/2002 | Koniuk |
| 7,713,225 B2 | 5/2010 | Ingimundarson et al. | 2003/0093021 A1 | 5/2003 | Goffer |
| D616,996 S | 6/2010 | Thorgilsdottir et al. | 2003/0125814 A1 | 7/2003 | Paasivaara et al. |
| D616,997 S | 6/2010 | Thorgilsdottir et al. | 2003/0139783 A1 | 7/2003 | Kilgore et al. |
| D618,359 S | 6/2010 | Einarsson | 2003/0163206 A1 | 8/2003 | Yasui et al. |
| 7,727,174 B2 | 6/2010 | Chang et al. | 2003/0195439 A1 | 10/2003 | Caselnova |
| 7,736,394 B2 | 6/2010 | Bedard et al. | 2004/0039454 A1 | 2/2004 | Herr et al. |
| 7,745,682 B2 | 6/2010 | Sigurjonsson et al. | 2004/0049290 A1 | 3/2004 | Bedard |
| D620,124 S | 7/2010 | Einarsson | 2004/0054423 A1 | 3/2004 | Martin |
| 7,749,183 B2 | 7/2010 | Ingimundarson et al. | 2004/0064195 A1 | 4/2004 | Herr |
| 7,749,281 B2 | 7/2010 | Egilsson | 2004/0088025 A1 | 5/2004 | Gesotti |
| 7,762,973 B2 | 7/2010 | Einarsson et al. | 2004/0181118 A1 | 9/2004 | Kochamba |
| 7,770,842 B2 | 8/2010 | Benson | 2004/0181289 A1 | 9/2004 | Bedard et al. |
| 7,771,488 B2 | 8/2010 | Asgeirsson et al. | 2005/0007834 A1 | 1/2005 | Hidaka |
| 7,780,741 B2 | 8/2010 | Janusson et al. | 2005/0043614 A1 | 2/2005 | Huizenga et al. |
| 7,794,418 B2 | 9/2010 | Ingimundarson et al. | 2005/0049652 A1 | 3/2005 | Tong |
| 7,794,505 B2 | 9/2010 | Clausen et al. | 2005/0059908 A1 | 3/2005 | Bogert |
| 7,811,333 B2 | 10/2010 | Jonsson et al. | 2005/0085948 A1 | 4/2005 | Herr et al. |
| 7,811,334 B2 | 10/2010 | Ragnarsdottir et al. | 2005/0155444 A1 | 7/2005 | Otaki et al. |
| D627,079 S | 11/2010 | Robertson | 2005/0209707 A1 | 9/2005 | Phillips et al. |
| 7,833,181 B2 | 11/2010 | Cormier et al. | 2005/0228515 A1 | 10/2005 | Musallam et al. |
| 7,842,848 B2 | 11/2010 | Janusson et al. | 2006/0004307 A1 | 1/2006 | Horst |
| D628,696 S | 12/2010 | Robertson | 2006/0064047 A1 | 3/2006 | Shimada et al. |
| D629,115 S | 12/2010 | Robertson | 2006/0069448 A1 | 3/2006 | Yasui |

| | | | |
|---|---|---|---|
| 2006/0094989 A1 | 5/2006 | Scott et al. | |
| 2006/0213305 A1 | 9/2006 | Sugar et al. | |
| 2006/0224246 A1 | 10/2006 | Clausen et al. | |
| 2006/0249315 A1 | 11/2006 | Herr et al. | |
| 2006/0258967 A1 | 11/2006 | Fujil et al. | |
| 2006/0264790 A1 | 11/2006 | Kruijsen et al. | |
| 2006/0276728 A1 | 12/2006 | Ashihara et al. | |
| 2007/0016329 A1 | 1/2007 | Herr et al. | |
| 2007/0043449 A1 | 2/2007 | Herr et al. | |
| 2007/0050044 A1 | 3/2007 | Haynes et al. | |
| 2007/0123997 A1 | 5/2007 | Herr et al. | |
| 2007/0129653 A1 | 6/2007 | Sugar et al. | |
| 2007/0162152 A1 | 7/2007 | Herr et al. | |
| 2007/0267791 A1 | 11/2007 | Hollander et al. | |
| 2008/0114272 A1 | 5/2008 | Herr et al. | |
| 2008/0155444 A1 | 6/2008 | Pannese et al. | |
| 2009/0030530 A1 | 1/2009 | Martin | |
| 2009/0222105 A1 | 9/2009 | Clausen | |
| 2011/0224804 A1 | 9/2011 | Clausen et al. | |
| 2011/0245931 A1 | 10/2011 | Clausen et al. | |
| 2011/0260380 A1 | 10/2011 | Hollander et al. | |
| 2011/0278857 A1 | 11/2011 | Sugar et al. | |
| 2012/0271433 A1 | 10/2012 | Galea et al. | |

FOREIGN PATENT DOCUMENTS

| | | |
|---|---|---|
| EP | 1534117 | 6/2005 |
| WO | WO 03/068453 | 8/2003 |
| WO | WO 2004/017872 A1 | 3/2004 |
| WO | WO 2004/019832 A1 | 3/2004 |
| WO | WO 2010/027968 A2 | 3/2010 |

OTHER PUBLICATIONS

Hugh Herr, New Horizons for Orthotic and Prosthetic Technology: Artificial Muscle for Ambulation, 2004, The MIT Media Laboratory, pp. 1-9.*
Herr, Hugh et al. "New Horizons for Orthotic and Prosthetic Technology: Artificial Muscle for Ambulation," The MIT Media Laboratory, pp. 1-9, 2004.
Williamson, Matthew M., "Series Elastic Actuators," MIT Artificial Intelligence Laboratory, Jan. 1995.
Au, S.K. et al., "Powered Ankle-Foot Prosthesis for the Improvement of Amputee Ambulation," paper presented at the Proceedings of the 29$^{th}$ Annual International Conference of the IEEE Eng. Med. Bio. Soc., Cité Internationale, Lyon, France, (Aug. 2007).
International Search Report and Written Opinion for corresponding International Application No. PCT/US2010/022783, Dated: May 4, 2010.
Blaya, J.A., "Force-Controllable Ankle Foot Orthosis (AFO) to Assist Drop Foot Gait," submitted to the Department of Mechanical Engineering, Massachusetts Institute of Technology, Cambridge, Massachusetts (Feb. 2003), 88 pages.
Blaya, J.A. et al., "Adaptive Control of a Variable-Impedance Ankle-Foot Orthosis to Assist Drop Foot Gait," Artificial Intelligence Lab and Harvard-MIT Division Health Sciences and Technology, Boston, MA, 30 pages.
Blaya, J.A. et al., "Active Ankle Foot Orthoses (AAFO)," Retrieved from: http://www.ai.mit.edu. Artificial Intelligence Laboratory, Massachusetts Institute of Technology, Cambridge, Massachusetts, 3 pages.
Dollar, et al., "Lower Extremity Exoskeletions and Active Orthoses: Challenges and State-of-the-Art," IEEE Transcations on Robotics, vol. 24, No. 1, Feb. 2008, 15 pages.
Drake, C., "Foot & Ankle Splints or Orthoses," HemiHclp Information Sheet, London, United Kingdom, 3 pages, http://www.hemihelp.org.uk/leaflets/hbleaflets90.htm Retrieved on: Jun. 20, 2003.
Hogan, N., "Impedance Control: An Approach to Manipulation," Dept. of Mechanical Engineering and Labortory of Manufacturing and Productivity, Massachusetts Institute of Technology, Cambridge MA, pp. 304-313 (Jun. 1984).
Hogan, N., "Impedance Control: An Approach to Manipulation: Part II—Implementation," Journal of Dynamic Systems, Measurement and Control, 107: 8-16 (1985).
Hogan, N., "Impedance Control: An Approach to Manipulation: Part III—Application," Journal of Dynamics Systems, Measurement and Control. 107: 17-24 (1985).

Kim, J.-H. et al., "Realization of Dynamic Walking for the Humaniod Robot Platform KHR-1," Advanced Robotics, 18(7): 749-768, (2004).
Klute, G.K. et al., "Powering Lower Limb Prosthestics with Muscle-Like Actuators," Abstract in: Proceeding of the 1st Annual Meeting of the VA Rehabilitation Research and Development Service, "Enabling Veterans: Meeting the Challenge of Rehabilitation in the Next Millennium," Washington, D.C., p. 52 (Oct. 1998).
Klute, G.K. et al., "Artificial Muscles: Actuators for Biorobotic Systems," The International Journal of Robotics Research, 21(4): 295-309 (2002).
Klute, G.K. et al., "Artificial Muscles: Actuators for Lower Limb Prostheses," Abstract in: Proceedings of the 2nd Annual Meeting of the VA rehabilitation Research and Development Service, Feb. 20-22, 2000, p. 107.
Klute, G.K. et al., "Artificial Tendons: Biomechanical Design Properties for Prosthetic Lower Limbs," Chicago 2000 World Congress on Medical Physics and Biomedical Engineering, Chicago on Jul. 24-28, 2000, 4 pages.
Klute, G.K. et al., "Intelligent Transtibial Prostheses with Muscle-Like Actuators," 2002 American Physiological Society Intersociety Meeting: The Power of Comparative Physiology: Evolution, Integration, and Applied, 1 page.
Klute, G.K. et al., "Lower Limb Prostheses Powered by Muscle-Like Pneumatic Actuator," Submitted to Oleodinamica e Pneumatica, Publishe Tecniche Nuove, Milamo, Italy, Mar. 15, 2000, 6 pages.
Klute, G.K. et al., "McKibben Artificial Muscles: Pneumatic Actuators with Biomechanical Intelligence," IEEE/ASME 1999 International Conference on Advanced Intelligent Mechatronics, Atlanta, GA, pp. 221-226 (Sep. 1999).
Klute, G.K. et al., "Muscle-Like Pneumatic Actuators for Below-Knee Prostheses," Actuator 2000: 7th International Conference on New Actuators, Bremen, Germany on Jun. 9-21, 2000, pp. 289-292.
Klute, G.K. et al., "Variable Stiffness Prosthesis for Transtibial Amputees," Dept of Veteran Affairs, Seattle, WA USA, 2 pages.
International Search Report and Written Opinion for International Application No. PCT/US2009/055600, Mailed: Apr. 29, 2010 (23 pages).
International Search Report and Written Opinion for International Application No. PCT/US2010/047279, Mailed: Jan. 19, 2011 (11 pages).
International Search Report and Written Opinion for International Application No. PCT/US2011/031105, Mailed: Oct. 11, 2011 (16 pages).
J. Hitt et al., "The Sparky (Spring Ankle with Regenerative Kinetics) Projects: Design and Analysis of a Robotic Transtibial prosthesis with Regenerative Kinetics," in Proc. IEEE Int. Conf. Robot. Autom., Orlando, Fla., pp. 2939-2945, May 2006.
Sup, F. et al., "Design and Control of a Powered Transfemoral Prosthesis," The International Journal of Robotics Research, vol. 27, No. 2, pp. 263-273 (2008).
Geyer, H. et al., "A Muscle-Reflex Model That Encodes Principles of Legged Mechanics Predicts Human Walking Dynamics and Muscle Activities," IEEE Transactions on Neural Systems and Rehabilitation Engineering, vol. 18, No. 3, pp. 263-273 (Jun. 2010).
Geyer, H. et al., "Positive Force Feedback in Bouncing Gaits?," Proc. R Society. Lond. B, 270, pp. 2173-2183 (2003).
Abbas, J.J. et al., "Neural Network Control of Functional Neuromuscular Stimulation Systems: Computer Simulation Studies," IEEE Transactions on Biomedical Engineering, vol. 42, No. 11, Nov. 1995, pp. 1117-1127.
Abul-Haj, C.J. et al., "Functional Assessment of Control Systems for Cybernetic Elbow Prostheses—Part II: Application of the Technique," IEEE Transactions on Biomedical Engineering, vol. 17, No. 11, Nov. 1990, pp. 1037-1047.
Akazawa, K. et al., "Biomimetic EMG-Prosthesis-Hand, 18$^{th}$ Annual International Conference of the IEEE Engineering in Medicine and Biology Society," Amsterdam 1996, pp. 535 and 536.
Aminian, K. el al., "Estimation of Speed and Incline of Walking Using Neural Network," IEEE Transactions of Instrumentation and Measurement, 44(3): 743-746 (1995).
Anderson, F.C. et al., "Dynamic Optimization of Human Walking," Journal of Biomechanical Engineering, 123: 381-390 (2001).

Andrews, B.J. et al., "Hybrid FES Orthosis Incorporating Closed Loop Control and Sensory Feedback," *J. Biomed. Eng.*, 10: 189-195(1988).

Au, S.K. et al., "An Ankle-Foot Emulation System for the Study of Human Walking Biomechanics," Proceedings of the 2006 IEEE International Conference on Robotics and Automation, Orlando, FLA, May 2006, pp. 2939-2945.

Au, S.K. et al., "Biomechanical Design of a Powered Ankle-Foot Prosthesis," Proceedings of the 2007 IEEE 10$^{th}$ International Conference on Rehabilitation Robotics, Noordwijk, The Netherlands, Jun. 12-15, pp. 298-303.

Au, S.K. et al., "An EMG-Position Controlled System for an Active Ankle-Foot Prosthesis: An Initial Experimental Study," Proceedings of the 2005 IEEE 9$^{th}$ International Conference on Rehabilitation Robotics, Chicago, IL., pp. 375-379.

Au, S.K. et al., "Initial Experimental Study on Dynamic Interaction Between an Amputee and a Powered Ankle-Foot Prostheses," Harvard-MIT Division of Health Sciences and Technology, MIT, Cambridge, MA.

Arakawa, T. et al., "Natural Motion Generation of Biped Locomotion Robot Using Hierarchical Trajectory Generation Method Consisting of GA, EP Layers," Proceedings of the 1997 IEEE International Conference on Robotics and Automation, Albuquerque, NM., pp. 375-379.

Au, S.K. et al., "Powered Ankle—Foot Prosthesis Improves Walking Metabolic Economy," *IEEE Transactions on Robotics*, 25(1): 51-66 (2009).

Au, S.K. et al., "Powered Ankle—Foot Prosthesis for the Improvement of Amputee Ambulation," paper presented at the Proceedings of the 29$^{th}$ Annual International Conference of the IEEE EMBS Cité Internationale, Lyon, France, (Aug. 2007).

Au, S. et al., "Powered Ankle-Foot Prosthesis to Assist Level-Ground and Stair-Descent Gaits," *Neural Networks*, 21: 654-666 (2008).

Barth, D.G. et al., "Gait Analysis and Energy Cost of Below-Knee Amputees Wearing Six Different Prosthetic Feet," *JPO*, 4(2): 63 (1992).

Bateni, H. et al., "Kinematic and Kinetic Variations of Below-Knee Amputee Gait," *JPO*, 14(1):1-12 (2002).

Baten, Chris T.M. et al., "Inertial Sensing in Ambulatory Back Load Estimation," paper presented at the 18$^{th}$ Annual International Conference of the IEEE Engineering in Medicine and Biology Society, Amsterdam, 1996, pp. 497-498.

Blaya, J. et al., "Active Ankle Foot Orthoses (AAFO)," Artificial Intelligence Laboratory, Massachusetts Institute of Technology, Cambridge, MA, pp. 275-277.

Blaya, J.A. et al., "Adaptive Control of a Variable-Impedance Ankle-Foot Orthosis to Assist Drop-Foot Gait," IEEE Transactions on Neural Systems and Rehabilitation Engineering, 12(1): 24-31 (2004).

Blaya, J.A. et al., "Force-Controllable Ankle-Foot Orthosis (AFO) to Assist Drop Foot Gait," Massachusetts Institute of Technology, Feb. 2003, pp. 1-96.

Blickhan, R., "The Spring-Mass Model for Running and Hopping," *J. Biomechanics*, 22(11 /12): 1217-1227 (1989).

Bortz, J.E. "A New Mathematical Formulation for Strapdown Inertial Navigation," *IEEE Transactions on Aerospace and Electronic Systems*, AES-7(1): 61-66 (1971).

Bouten, C.V. et al., "Assessment of Energy Expenditure for Physical Activity Using a Triaxial Accelerometer," *Medicine and Science in Sports and Exercise*, pp. 1516-1523.

Brockway, J.M., "Derivation of Formulae Used to Calculate Energy Expenditure in Man," *Human Nutrition: Clinical Nutrition* (1987), 41C, pp. 463-471.

Brown, T. Graham, "On the Nature of the Fundamental Activity of the Nervous Centres; Together with an Analysis of the Conditioning of Rhythmic Activity in Progression, and a Theory of the Evolution of Function in the Nervous System," pp. 24-46.

AJG The American Journal of Gastroenterology, "Symptoms Diagnosis," 105(4): 1-875 (2010).

Chu, A. et al., "On the Biomimetic Design of the Berkeley Lower Extremity Exoskeleton," paper presented at the Proceedings of the 2005 IEEE International Conference on Robotics and Automation, Barcelona, Spain, (Apr. 2005) pp. 4556-4363.

American Journal of Physical Medicine & Rehabilitation, 71(5): 1-278 (1992).

Colgate, James Edward, "The Control of Dynamically Interacting Systems," Massachusetts Institute of Technology, Aug. 1988, pp. 1-15.

Collins, S.H. et al., "Controlled Energy Storage and Return Prosthesis Reduces Metabolic Cost of Walking," ISB XXth Congress-ASB 29$^{th}$ Annual Meeting, Jul. 31-Aug. 5, Cleveland, Ohio, pp. 804.

Collins, S.H. et al., "Efficient Bipedal Robots Based on Passive-Dynamic Walkers," Feb. 11, 2005, pp. 1-8.

Crago, P.E. et al., "New Control Strategies for Neuroprosthetic Systems," *Journal of Rehabilitation Research and Development*, vol. 33, No. 2, Apr. 1996, pp. 158-172.

Daley, M.A. et al., "Running Stability is Enhanced by a Proximo-Distal Gradient in Joint Neuromechanical Control," *The Journal of Experimental Biology*, vol. 210, pp. 383-394 (Feb. 2007).

Dapena, J. et al., "A Three-Dimensional Analysis of Angular Momentum in the Hammer Throw," Biomechanics Laboratory, Indiana University, IN, *Medicine and Science in Sports and Exercise*, vol. 21, No. 2, pp. 206-220 (1988).

Dietz, V. "Proprioception and Locomotor Disorders," *Nature Reviews*, vol. 3, pp. 781-790 (Oct. 2002).

Dietz, V. "Spinal Cord Pattern Generators for Locomotion," *Clinical Neurophysiology*, vol. 114, Issue 8, pp. 1-12 (Aug. 2003).

Doerschuk, P.C. et al., "Upper Extremity Limb Function Discrimination Using EMG Signal Analysis," *IEEE Transactions on Biomedical Engineering*, vol. BME-30, No. 1, Jan. 1983, pp. 18-28.

Doke, J. et al., "Mechanics and Energetics of Swinging the Human Leg," *The Journal of Experimental Biology*, vol. 208, pp. 439-445 (2005).

Dollar, A.M. et al., "Lower Extremity Exoskeletons and Active Orthoses: Challenges and State-of-the-Art," *IEEE Transactions on Robotics*, vol. 24, No. 1, Feb. 2008, pp. 1-15.

Donelan, J.M. et al., "Force Regulation of Ankle Extensor Muscle Activity in Freely Walking Cats," *Journal of Neurophysiology*, vol. 101, pp. 360-371 (2009).

Donelan, J.M. et al., "Mechanical work for Step-to-Step Transitions is a Major Determinant of the Metabolic Cost of Human Walking," *The Journal of Experimental Biology*, vol. 205, pp. 3717-3727 (2002).

Donelan, J.M. et al., "Simultaneous Positive and Negative External Mechanical Work in Human Walking," *Journal of Biomechanics*, vol. 35, 2002, pp. 117-124 (2002).

HemiHelp, "Ankle & Foot Splints or Orthoses," (AFOs).

HemiHelp, "Foot & Ankle Splints or Orthoses," pp. 1-5.

Drake, C., "Foot & Ankle Splints or Orthoses," pp. 1-3.

Eilenberg, M.F. "A Neuromuscular-Model Based Control Strategy for Powered Ankle-Foot Prostheses," Massachusetts Institute of Technology, pp. 1-90.

Ekeberg, Ö et al., "Computer Simulation of Stepping in the Hind Legs of the Cat: An Examination of Mechanisms Regulating the Stance-to-Swing Transition," *J. Neurophysical*, vol. 94, pp. 4256-4268 (2005).

Ekeberg, Ö et al., "Simulations of Neuromuscular Control in Lamprey Swimming," The Royal Society, *Phil. Trans. R. Soc. Land*, vol. 354, pp. 895-902 (1999).

Endo, K. et al.,"A Quasi-Passive Model of Human Leg Function in Level-Ground Walking," Proceedings of the 2006 IEEE/RSJ International Conference on Intelligent Robots and Systems, Oct. 9-15, 2006, Beijing, China, pp. 4935-4939.

Eppinger, S.D. et al., "Three Dynamic Problems in Robot Force Control," *IEEE Transactions on Robotics and Automation*, vol. 8, No. 6, pp. 772-778 (Dec. 1992).

Esquenazi, A. et al., "Rehabilitation After Amputation," vol. 91, No. 1, pp. 1-22 (Jan. 2001).

Farley, C.T. et al., "Energetics of Walking and Running: Insights From Simulated Reduced-Gravity Experiments," Harvard University, pp. 2709-2712.

Farry, K.A. et al., "Myoelectric Teleoperation of a Complex Robotic Hand," *IEEE Transactions on Robotics and Automation*, vol. 12, No. 5, pp. 775-778 (Oct. 1996).

Featherstone, R., "Robot Dynamics Algorithms," Edinburgh University, pp. 1-173.

Fite, K. et al., "Design and Control of an Electrically Powered Knee Prosthesis," Proceedings of the 2007 IEEE 10$^{th}$ International Conference on Rehabilitation Robotics, Jun. 12-15, The Netherlands, pp. 902-905.

Flowers, W.C., "A Man-Interactive Simulator System for Above-Knee Prosthetics Studies," MIT, pp. 1-94.

Fod, A. et al., "Automated Derivation of Primitives for Movement Classification," *Autonomous Robots*, vol. 12, No. 1, pp. 39-54 (Jan. 2002).

Frigon, A. et al., "Experiments and Models of Sensorimotor Interactions During Locomotion," *Biological Cybernetics*, vol. 95, pp. 606-627 (2006).

Fujita et al., "Joint Angle Control with Command Filter for Human Ankle Movement Using Functional Electrical Stimulation," IEEE Ninth Annual Conference of the Engineering in Medicine and Biology Society.

Fukuda, O. et al., "A Human-Assisting Manipulator Teleoperated by EMG Signals and Arm Motions," *IEEE Transactions on Robotics and Automation*, vol. 19, No. 2, pp. 210-222 (Apr. 2003).

Gates, D.H. Thesis: "Characterizing Ankle Function During Stair Ascent, Descent, and Level Walking for Ankle Prosthesis and Orthosis Design," Boston University, pp. 1-84.

Gerritsen, K.G.M. et al., "Direct Dynamics Simulation of the Impact Phase in Heel-Toe Running," *J. Biomechanics*, vol. 28, No. 6, pp. 661-668 (1995).

Geyer, H. et al., "A Muscle-Reflex Model that Encodes Principles of Legged Mechanics Produces Human Walking Dynamics and Muscle Activities," IEEE Transactions on Neural Systems and Rehabilitation Engineering, vol. X, No. X, pp. 1-10 (Date not provided).

Geyer, H. et al., "Compliant Leg Behavior Explains Basic Dynamics of Walking and Running," *Proc. R. Soc. B*, vol. 273, pp. 2861-2867 (2006).

Geyer, H. et al., "Positive Force Feedback in Bouncing Gaits?," *Proc. R. Soc. Lond, B*, vol. 270, pp. 2173-2183 (2003).

Ghigliazza, R.M. et al., "A Simply Stabilized Running Model," University of Pennsylvania, *SIAM Journal on Applied Dynamical Systems*, vol. 2, Issue 2, pp. 187-218 (May 8, 2004).

Giszter, S., et al., "Convergent Force Fields Organized in the Frog's Spinal Cord," *Journal of Neuroscience*, 13(2): 467-491 (1993).

Godha, S. et al., "Integrated GPS/INS System for Pedestrian Navigation in a Signal Degraded Environment," University of Calgary, Canada, pp. 1-14.

Goswami, A., "Postural Stability of Biped Robots and the Foot-Rotation Indicator (FRI) Point," *The International Journal of Robotics Research*, vol. 18, No. 6, pp. 523-533 (Jun. 1999).

Goswami, A. et al., "Rate of Change of Angular Momentum and Balance Maintenance of Biped Robots," Proceedings of the 2004 IEEE International Conference on Robotics and Automation, New Orleans, LA, Apr. 2004, pp. 3785-3790.

Graupe, D. et al., "A Microprocessor System for Multifunctional Control of Upper-Limb Prostheses via Myoelectric Signal Identification," *IEEE Transactions on Automatic Control*, vol. 23, No. 4, pp. 538-544 (Aug. 1978).

Gregoire, L. et al., "Role of Mono- and Biarticular Muscles in Explosive Movements," *International Journal of Sports Medicine*, vol. 5, No. 6, pp. 299-352 (Dec. 1984).

Grillner, S. and Zangger, P., "On the Central Generation of Locomotion in the Low Spinal Cat," *Experimental Brain Research*, 34: 241-261 (1979).

Grimes, D.L., "An Active Multi-Mode Above-Knee Prosthesis Controller," unpublished doctoral dissertation, Massachusetts Institute of Technology (1979).

Gunther, M. et al., "Human Leg Design: Optimal Axial Alignment Under Constraints," *J. Math. Biol.*, 48: 623-646 (2004).

Günther, M., and Ruder, H., "Synthesis of Two-Dimensional Human Walking: a test of the λ-model," *Biol. Cybern.*, 89: 89-106 (2003).

Gu, W.J., "The Regulation of Angular Momentum During Human Walking," unpublished doctoral dissertation, Massachusetts Institute of Technology (2003).

Brady, M. et al., "Robot Motion: Planning and Control," The MIT Press, Cambridge (1982).

Hansen, A.H., et al., "The Human Ankle During Walking: Implications for Design of Biomimetic Ankle Prostheses," *Journal of Biomechanics*, 37: 1467-1474 (2004).

Hayes, W.C., et al., "Leg Motion Analysis During Gait by Multiaxial Accelerometry: Theoretical Foundations and Preliminary Validations," *Journal of Biomechanical Engineering*, 105: 283-289 (1983).

Heglund, N. et al., "A Simple Design for a Force-Plate to Measure Ground Reaction Forces," *J. Exp. Biol.*, 93: 333-338 (1981).

Herr, H.M. et al., "A Model of Scale Effects in mammalian Quadrupedal Running," *The Journal of Experimental Biology*, 205: 959-967 (2002).

Herr, H.M., and Popovic, M., "Angular Momentum in Human Walking," *The Journal of Experimental Biology*, 211: 467-481 (2008).

Herr, H.M., and McMahon, T.A., "A Trotting Horse Model," *The International Journal of Robotics Research*, 19: 566-581 (2000).

Herr, H.M., and Wilkenfeld, A., "User-adaptive Control of a Magnetorheological Prosthetic Knee," *Industrial Robot: An International Journal*, 30(1): 42-55 (2003).

Heyn, A., et al., "The Kinematics of the Swing Phase Obtained From Accelerometer and Gyroscope Measurements," paper presented at the 18$^{th}$ Annual International Conference of the IEEE Engineering in Medicine and Biology Society, Amsterdam (1996).

Hill, A.V., "The Heat of Shortening and the Dynamic Constants of Muscle," *Proc. R. Soc. Lond.*, 126: 136-195 (1938).

Hirai, K., et al., "The Development of Honda Humanoid Robot," paper presented at the 1998 IEEE International Conference on Robotics & Automation (1998).

Hitt, J.K., et al., "The Sparky (Spring Ankle with Regenerative Kinetics) Project: Design and Analysis of a Robotic Transtibial Prosthesis with Regenerative Kinetics," Proceedings of the ASME International Design Engineering Technical Conferences and Computers and Information in Engineering Conference, Las Vegas, Nevada (2007).

Hofbaur, M.W., et al., "Hybrid Diagnosis with Unknown Behavioral Modes," Proceedings of the 13$^{th}$ International Workshop on Principles of Diagnosis (DX02) (2002).

Hofbaur, M.W., and Williams, B.C., "Mode Estimation of Probabilistic Hybrid Systems," MIT Space Systems and Artificial Intelligence Laboratories and Graz University of Technology, Department of Automatic Control.

Hof, A.L., et al., "Calf Muscle Moment, Work and Efficiency in Level Walking: Role of Series Elasticity," *J. Biochem.*, 16: 523-537 (1983).

Hofmann, A., et al., "A Sliding Controller for Bipedal Balancing Using Integrated Movement of Contact and Non-Contact Limbs," Proceedings of the 2004 IEEE/RSJ International Conference on Intelligence Robots and Systems, Japan (2004).

Hofmann, A.G., "Robust Execution of Bipedal Walking Tasks From Biomechanical Principles," unpublished doctoral dissertation for Massachusetts Institute of Technology (2006).

Hogan, N., "A Review of the Methods of Processing EMG for Use as a Proportional Control Signal," *Biomedical Engineering*, 11(3): 81-86 (1976).

Hogan, N., "Impedance Control—An Approach to Manipulation," unpublished doctoral dissertation for Department of Mechanical Engineering and Laboratory of Manufacturing and Productivity, Massachusetts Institute of Technology, pp. 304-313.

Hogan, N., and Buerger, S.P., "Impedance and Interaction Control, Robots and Automation Handbook."

Hogan, N., "Impedance Control: An Approach to Manipulation, Part III—Applications," *Journal of Dynamic Systems, Measurement, and Control*, 107: 17-24 (1985).

Hogan, N., "Impedance Control: An Approach to Manipulation: Part II—Implementation," *Journal of Dynamic Systems, Measurement, and Control*,107: 8-16 (1985).

Hogan, N., "Impedance Control: An Approach to Manipulation: Part I—Theory," *Journal of Dynamic Systems, Measurement, and Control*, 107: 1-7 (1985).

Hollander, K.W. et al., "Adjustable Robotic Tendon using a 'Jack Spring'™," Proceedings of the 2005 IEEE, 9$^{th}$ International Conference on Rehabilitation Robotics, Jun. 28-Jul. 1, 2005, Chicago, IL, USA, pp. 113-118.

Howard, R.D., Thesis: "Joint and Actuator Design for Enhanced Stability in Robotic Force Control," Submitted to the Dept. of Aeronautics and Astronautics on Aug. 8, 1990 in partial fulfillment of the requirements for the degree of Doctor of Philosophy.

Huang, H.-P. et al., "Development of a Myoelectric Discrimination System for a Multi-Degree Prosthetic Hand," Proceedings of the 1999 IEEE, International Conference on Robotics & Automation, Detroit, Michigan, (1999).

Huang, Q. et al., "Planning Walking Patterns for a Biped Robot," *IEEE Transactions on Robotics and Automation*,17(3): 280-289 (Jun. 2001).

Hultborn, H., "Spinal reflexes, mechanisms and concepts: From Eccles to Lundberg and beyond," *Progress in Neurobiology*,78: 215-232 (2006).

Ijspeert, A.J., "Central pattern generators for locomotion control in animals and robots: a review," *Preprint of Neural Networks*, vol. 21, No. 4, pp. 642-653 (2008).

Ijspeert, A.J. et al., "From swimming to walking with a salamander robot driven by a spinal cord model," pp. 1-5.

Ivashko, D.G. et al., "Modeling the spinal cord neural circuitry controlling cat hindlimb movement during locomotion," *Neurocomputing*, 52-54, pp. 621-629 (2003).

International Search Report and Written Opinion for International Application No. PCT/US2009/055600, Mailed: Apr. 29, 2010.

International Preliminary Report on Patentability for International Application No. PCT/US2010/047279; Mailed: Mar. 15, 2012.

International Search Report and Written Opinion for International Application No. PCT/US2010/047279; Mailed: Jan. 19, 2011.

International Search Report and Written Opinion for International Application No. PCT/US2011/031105, Mailed: Oct. 11, 2011.

Johansson, J.L. et al., "A Clinical Comparison of Variable-Damping and Mechanically Passive Prosthetic Knee Devices," Variable-Damping vs. Mechanically Passive Prosthetic Knees, Aug. 2005.

Johnson, C.T. et al., "Experimental Identification of Friction and Its Compensation in Precise, Position Controlled Mechanisms," *IEEE Transactions on Industry Applications*, vol. 28, No. 6, pp, 1392-1398 (Nov./Dec. 1992).

Jonic, S. et al., "Three Machine Learning Techniques for Automatic Determination of Rules to Control Locomotion," *IEEE Transactions on Biomedical Engineering*, vol. 46, No. 3, pp. 300-310 (Mar. 1999).

Kadaba, M.P. et al., "Measurement of Lower Extremity Kinematics During Level Walking," *Journal of Orthapedic Research*, pp. 383-392, 1990.

Kadaba, M.P. et al., "Repeatability of Kinematic, Kinetic, and Electromyographic Data in Normal Adult Gait," *Journal of Orthapedic Research*, pp. 849-860, 1989.

Kajita, S. et al., "A Hop towards Running Humanoid Biped," Proceedings of the 2004 IEEE International Conference on Robotics & Automation, pp. 629-635, 2004.

Kajita, S. et al., "Biped Walking on a Low Friction Floor," Proceedings of the 2004 IEEE/RSJ International Conference on Intelligent Robots & Systems, pp. 3546-3552, Sep. 28-Oct. 2, 2004, Sendai, Japan.

Kajita, S. et al., "Resolved Momentum Control: Humanoid Motion Planning based on the Linear and Angular Momentum," Proceedings of the 2003 IEEE/RSJ International Conference on Intelligent Robots & Systems, pp. 1644-1650 (2003).

Kaneko, K. et al., "Humanoid Robot HRP-2," Proceedings of the 2004 IEEE International Conference on Robotics & Automation, pp. 1083-1090 (Apr. 2004).

Kapti, A.O. et al., "Design and control of an active artificial knee joint," *Mechanism and Machine Theory*, vol. 41, pp. 1477-1485 (2006).

Katie, D. et al., "Survey of Intelligent Control Techniques for Humanoid Robots," *Journal of Intelligent and Robotic Systems*, vol. 37, pp. 117-141 (2003).

Kerrigan, D.C. et al., "A refined view of the determinants of gait: Significance of heel," *Archives of Physical Medicine and Rehabilitation*, vol. 81, Issue 8, pp. 1077-1080 (Aug. 2000).

Kerrigan, D.C. el al., "Quantification of pelvic rotation as a determinant of gait," Archives of Physical Medicine and Rehabilitation, vol. 82, Issue 2, pp. 217-220 (Feb. 2001).

Khatib, O. et al., "Coordination and Decentralized Cooperation of Multiple Mobile Manipulators," *Journal of Robotic Systems*, 13(11): 755-764 (1996).

Khatib, O. et al., "Whole-Body Dynamic Behavior and Control of Human-Like Robots," *International Journal of Humanoid Robotics*, vol. 1, No. 1, pp. 29-43 (2004).

Kidder, S.M. et al., "A System for the Analysis of Foot and Ankle Kinematics During Gait," *IEEE Transactions on Rehabilitation Engineering*, vol. 4, No. 1, pp. 25-32 (Mar. 1996).

Kim, J.-H. et al., "Realization of dynamic walking for the humanoid robot platform KHR-1," *Advanced Robotics*, vol. 18, No. 7, pp. 749-768 (2004).

Kirkwood, C.A. et al., "Automatic detection of gait events: a case study using inductive learning techniques," *J. Biomed. Eng.*, vol. 11, pp, 511-516 (Nov. 1989).

Kitayama, I. et al., "A Microcomputer Controlled Intelligent A/K Prosthesis—Fundamental Development," Proceedings, Seventh World Congress of ISPO, Jun. 28-Jul. 3, 1992, Chicago, Illinois, USA, 25 pages.

Klute, G.K. et al., "Artificial Muscles: Actuators for Lower Limb Prostheses," Abstract in: Proceedings of the $2^{nd}$ Annual Meeting of the VA Rehabilitation Research and Development Service, Washington, D.C., Feb. 20-22, 2000, p. 107.

Klute, G.K. et al., "Artificial Muscles: Actuators for Biorobotic Systems," *The International Journal of Robotics Research*, vol. 21, pp. 295-309 (2002).

Klute, G.K. et al., "Artificial Muscles: Biomechanical Design Properties for Prosthetic Lower Limbs," Chicago 2000 World Congress on Medical Physics and Biomedical Engineering, Chicago on Jul. 24-28, 2000, 4 pages.

Klute, G.K. et al, "Intelligent transtibial prostheses with muscle-like actuators," 2002 American Physiological Society Intersociety Meeting: The Power of Comparative Physiology: Evolution, Integration, and Applied, 1 page abstract.

Klute, G.K. et al., "Lower Limb Prostheses Powered by Muscle-like Pneumatic Actuators," Submitted to Oleodinamica e Pneumatica, Publisher Tecniche Nuove, Milano, Italy, Mar. 15, 2000, pp. 1-6.

Klute, G.K. et al., "McKibben Artificial Muscles: Pneumatic Actuators with Biomechanical Intelligence," IEEE/ASME 1999 International Conference on Advanced Intelligent Mechatronics (AIM '99), Atlanta, GA, Sep. 19-22, 1999, pp. 221-226.

Klute, G.K. et al., "Mechanical properties of prosthetic limbs: Adapting to the patient," *Journal of Rehabilitation Research and Development*, vol. 38, No. 3, pp. 299-307 (May/Jun. 2001).

Klute, G.K. et al., "Muscle-like Pneumatic Actuators for Below-knee Prostheses," "Actuator 2000: $7^{th}$ International Conference on New Actuators," Bremen, Germany on Jun. 19-21, 2000, pp. 289-292.

Klute, G.K. et al., "Powering Lower Limb Prosthetics with Muscle-like Actuators," Abstract in: Proceedings of the $1^{st}$ Annual Meeting of the VA Rehabilitation Research and Development Service, "Enabling Veterans: Meeting the Challenge of Rehabilitation in the Next Millenium," Washington, D.C., Oct. 1-3, 1998, p. 52.

Klute, G.K. et al., "Variable Stiffness Prosthesis for Transtibial Amputees," 2 pages.

Koganezawa, K. et al., *Biomedical Engineering 1987*, 2.3: Control Aspects of Artificial Leg, pp. 71-85.

Kondak, K. et al., "Control and Online Computation of Stable Movement for Biped Robots," Proceedings of the 2003 IEEE/RSJ, Int'l Conference on Intelligent Robots and Systems, Las Vegas, Nevada, Oct. 2003, pp. 874-879.

Kostov, A. et al., "Machine Learning in Control of Functional Electrical Stimulation Systems for Locomotion," *IEEE Transactions on Biomedical Engineering*, vol. 42, No. 6, pp. 541-551 (Jun. 1995).

Kuo, A.D., "A Simple Model of Bipedal Walking Predicts the Preferred Speed—Step Length Relationship," *Transactions of the ASME*, vol. 123, pp. 264-269 (Jun. 2001).

Kuo, A.D., "Energetics of Actively Powered Locomotion Using the Simplest Walking Model," *Journal of Biomechanical Engineering*, vol. 124, pp. 113-120 (Feb. 2002).

Lafortune, M.A., "Three-Dimensional Acceleration of the Tibia During Walking and Running," *J. Biomechanics*, vol. 24, No. 10, pp. 877-886 (1991).

LeBlanc, M.K. et al., "Generation and Transfer of Angular Momentum in the Javelin Throw," American Society of Biomechanics, Presented at the $20^{th}$ Annual Meeting of the American Society of Biomechanics, Atlanta, Georgia, Oct. 17-19, 1996, 4 pages.

Light, L.H. et al., "Skeletal Transients on Heel Strike in Normal Walking with Different Footwear," J. Biomechanics, vol. 13, pp. 477-480 (1980).

Li, C. et al., "Research and Development of the Intelligently-Controlled Prosthetic Ankle Joint," Proceedings of the 2006 IEEE International Conference on Mechatronics and Automation, Jun. 25-28, 2006, Luoyana, China, pp. 1114-1119.

Liu, X. et al., "Development of a Lower Extremity Exoskeleton for Human Performance Enhancement," Proceedings of 2004 IEEE/RSJ International Conference on Intelligent Robots and Systems, Sep. 28-Oct. 2, 2004, Sendai, Japan, 3889-3894.

Lloyd, R. et al., "Kinetic changes associated with load carriage using two rucksack designs," Ergonomics, vol. 43, No. 9, pp. 1331-1341 (2000).

Luinge, H.J., Inertial Sensing of Human Movement, Twente University Press, Enschede, the Netherlands, 80 pages (Feb. 15, 1973).

Lundberg, A., "Reflex control of stepping," The Norwegian Academy of Science and Letters, The Nansen Memorial Lecture, Oct. 10, 1968, 40 pages.

Macfarlane, P.A. et al., "Gait Comparisons for Below-Knee Amputees Using a Flex-Foot(TM) Versus a Conventional Prosthetic Foot," JPO 1991, vol. 3, No. 4, pp. 150, htt://www.oandp.org/jpo/library/printArticle.asp?printArticleId=1991_04_150, Retrieved on: Feb. 9, 2012, 10 pages.

Maganaris, C.N., "Force-length characteristics of in vivo human skeletal muscle," Acta Physiol Scand, 172: 279-285 (2001).

Maganaris, C.N., "Force-Length Characteristics of the in Vivo Human Gastroenemius Muscle," Clinical Anatomy, 16: 215-223 (2003).

Martens, W.L. J., "Exploring the Information Content and Some Applications of Body Mounted Piezo-Resistive Accelerometers," 3 pages.

Maufroy, C. et al., "Towards a general neural controller for quadrupedal locomotion," Neural Networks, 21: 667-681 (2008).

Mayagoitia, R.E. et al., "Accelerometer and rate gyroscope measurement of kinematics: an inexpensive alternative to optical motion analysis systems," Journal of Biomechanics, 35: 537-542 (2002).

McFadyen, B.J. et al., "An Integrated Biomechanical Analysis of Normal Stair Ascent and Descent," J. Biomechanics, vol. 21, No. 9, pp. 733-744 (1988).

McGeer, T., "Passive Dynamic Walking," The International Journal of Robotics Research, 9, pp. 62-88 (1990).

McGreer, T., Chapter 4: "Principles of Walking and Running," Advances in Comparative and Environmental Physiology, vol. 11, pp. 113-139 (1992).

McIntosh, A.S. et al., "Gait dynamics on an inclined walkway," Journal of Biomechanics, vol. 39, Issue 13, pp. 2491-2502 (2006).

McMahon, T.A. et al., "Groucho Running," pp. 2326-2337 (1987).

McMahon, T.A. et al., "The Mechanics of Running: How Does Stiffness Couple with Speed?" J. Biomechanics, vol. 23, Suppl. 1, pp. 65-78 (1990).

Minassian, K. et al., "Human lumbar cord circuitries can be activated by extrinsic tonic input to generate locomotor-like activity," Human Movement Science, 26: 275-295 (2007).

Mochon, S. et al., "Ballistic Walking," J. Biomechanics, vol. 13, pp. 49-57 (1980).

Molen, N.H., "Energy/Speed Relation of Below-Knee Amputees Walking on a Motor-Driven Treadmill," Physiol, 31: 173-185 (1973).

Morris, J.R.W., "Accelerometry—A Technique for the Measurement of Human Body Movements," J. Biomechanics, vol. 6, pp. 729-736 (1973).

Muraoka, T. et al., "Muscle fiber and tendon length changes in the human vastus lateralis during show pedaling," J. Appl. Physiol., 91: 2035-2040 (2001).

Nakagawa, A., "Intelligent Knee Mechanism and the Possibility to Apply the Principle to the Other Joints," paper presented at the Proceedings of the 20th Annual International Conference of the IEEE Engineering in Medicine and Biology Society, 20(5): 2282-2287 (1998).

Neal, R. M. et al., "A View of the EM Algorithm That Justifies Incremental, Sparse, and Other Variants," pp. 1-14.

Ng, S.K. et al., "Fuzzy Model Identification for Classification of Gait Events in Paraplegics," IEEE Transactions on Fuzzy Systems, 5(4) (1997).

Nielsen, D.H. et al., "Comparison of Energy Cost and Gait Efficiency during Ambulation in Below-Knee Ampuees Using Different Prosthetic Feet," JPO, 1:24-31, http://www.oandp.org/jpo/library/1989_01_024.asd, Retrieved on: Feb. 7, 2012.

Oda, T. et al. "In Vivo Length-Force Relationships on Muscle Fiber and Muscle Tendon Complex in the Tibialis Anterior Muscle," International Journal of Sport and Health Sciences, 3:245-252 (2005).

Ogihara, N., and Yamazaki, N., "Generation of Human Bipedal Locomotion by a Bio-Mimetic Neuro-Musculo-Skeletal Model," Biol. Cybern., 84: 1-11 (2001).

Palmer, M.L., "Sagittal Plane Characterization of Normal Human Ankle Function Across a Range of Walking Gait Speeds," Unpublished master's thesis, Massachusetts Institute of Technology, Massachusetts (2002).

Paluska, D., and Herr, H., "Series Elasticity and Actuator Power Output," paper presented at the Proceedings of the 2006 IEEE International Conference on Robotics and Automation (2006).

Paluska, D., and Herr H., "The Effect of Series Elasticity on Actuator Power and Work Output: Implications for Robotic and Prosthetic Joint Design," Robotics and Autonomous Systems, 54:667-673 (2006).

Pang, M.Y.C. and Yang, J.F., "The Initiation of the Swing Phase in Human Infact Stepping: Importance of Hip Position and Leg Loading," Journal of Physiology, 528(2):389-404 (2000).

Dubowsky, S., "Transactions of the ASME," Journal of Mechanisms, Transmissions, and Automation in Design, 106(1): 102-107 (1984).

Paul, C., et al., "Development of a Human Neuro-Musculo-Skeletal Model for Investigation of Spinal Cord Injury," Biol. Cybern., 93:153-170 (2005).

Pearson, K., et al., "Assessing Sensory Function in Locomotor Systems Using neurp-mechanical Simulations," Trends in Neurosciences, 29(11): 626-631 (2006).

Pearson, K.G., "Generating the Walking Gait: Role of Sensory Feedback," Progress in Brain Research, 143:123-129 (2004).

Perry, J., et al., "Efficiency of Dynamic Elastic Response Prosthetic Feet," Journal of Rehabilitation Research, 30(1):137-143 (1993).

Davids, J.R., "Book Reviews" Journal of Pediatric Orthopedics, pp. 815, No date given.

Petrofsky, J.S.., et al., "Feedback Control System for Walking in Man," Comput. Biol. Med. 14(2):135-149 (1984).

Pfeffer, L.E., et al., "Experiments with a Dual-Armed, Cooperative, Flexible-Drivetrain Robot System," paper presented at the IEEE, Aerospace Robotics Laboratory, Department of Aeronautics and Astronautics, Stanford University (1993).

Popovic, M., et al., "Angular Momentum Primitives for Human Walking: Biomechanics and Control," paper presented at the Proceedings IEEE/RSJ International Conference on Intelligent Robots and Systems, 1685-1691 (2004).

Popovic, M., et al., "Angular Momentum Regulation During Human Walking: Biomechanics and Control," paper presented at the Proceedings IEEE International Conference on Robotics and Automation, 2405-2411 (2004).

Popovic, M., et al., "Conservation of Angular Momentum During Human Locomotion," MIT Artificial Intelligence Laboratory, pp. 231-232 (2002).

Popovic, D., et al., "Control Aspects of Active Above-Knee Prosthesis," Int. J. Man-Machine Studies, 35:751-767 (1991).

Popovic, D. and Sinkjaer, T., "Control of Movement for the Physically Disabled: Control for Rehabilitation Technology," (Springer Publisher) pp. 270-302, No date given.

Popovic, M.R., et al., "Gait Identification and Recognition Sensor," paper presented at the Proceedings of 6th Vienna International Workshop on Functional Electrostiumlation (Sep. 1998).

Popovic, M.B. and Herr, H., "Global Motion Control and Support Base Planning," pp. 1-8.

Popovic, M.B. and Herr, H., "Ground Reference Points in Legged Locomotion: Definitions, Biological Trajectories and Control Implications," Mobile Robots Towards New Applications, ISBN 3-86611-314-5, pp. 79-104 (2006).

Popovic, M.B., et al., "Zero Spin Angular Momentum Control: Definition and Applicability," pp. 1-16.

Pratt, G.A., "Legged Robots at MIT: What's New Since Raibert." Paper presented at the meeting of the IEEE, Robotics and Automation Magazine (Sep. 2000).

Pratt, G.A., "Low Impedance Walking Robots," *Integ. and Comp. Biol.*, 42: 174-181 (2002).

Pratt, J.E., et al., "The RoboKnee: An Exoskeleton for Enhancing Strength and Endurance During Walking." Paper presented at the Proceedings of the 2004 IEEE International Conference on Robotics & Automation, New Orleans, LA (Apr. 2004).

Pratt, G.A. and Williamson, M.M., "Series Elastic Actuators." Paper presented at the meeting of the IEEE, pp. 399-406 (1995).

Prochazka, A. and Yakovenko, S., "The Neuromechanical Tuning Hypothesis," *Progress in Brain Research*, 165: 257-267 (2007).

Prochazka, A., et al., "Sensory Control of Locomotion: Reflexes Versus Higher-Level Control," *Sensorimotor Control of Movement and Posture*, pp. 357-367 (2002).

Prochazka, A., et al., "Positive Force Feedback Control of Muscles," *The American Physiological Society*, pp. 3226-3236 (1997).

Raibert, M.H., "Legged Robots that Balance," MIT Press, Cambridge, MA, p. 89 (1985).

Rassier, D.E., et al., "Length Dependence of Active Force Production in Skeletal Muscle," *The American Physiological Society*, pp. 1445-1457 (1999).

Riener, R., et al., "Stair Ascent and Descent at Different Inclinations," *Gait and Posture*, 15: 32-44 (2002).

Rietman, J.S., et al., "Gait Analysis in Prosthetics: Opinions, Ideas and Conclusions," *Prosthetics and Orthotics International*, 26: 50-57 (2002).

Robinson, D.W., "Design and Analysis of Series Elasticity in Closed-Loop Actuator Force Control." Unpublished doctoral dissertation, Massachusetts Institute of Technology (2000).

Robinson, D.W., et al., "Series Elastic Actuator Development for a Biomimetic Walking Robot." Paper presented at the IEEE/ASME International Conf. on Adv. Intelligent Mechatronics (Sep. 19-22, 1999).

Rosen, J., et al., "A Myosignal-Based Powered Exoskeleton System," *IEEE Transaction on Systems, Man, and Cybernetics—Part A: Systems and Humans*, 31(3): 210-222 (2001).

Ruina, A., et al., "A Collisional Model of the Energetic Cost of Support Work Qualitatively Explains Leg Sequencing in Walking and Galloping, Pseudo-Elastic Leg Behavior in Running and the Walk-To-Run Transition," *J. of Theoretical Biology*, 237: 170-192 (2005).

Rybak, I.A., et al., "Modelling Spinal Circuitry Involved in Locomotor Pattern Generation: Insights from Deletions During Fictive Locomotion," *J. Physiol.*, 577(2): 617-639 (2006).

Rybak, I.A., et al., "Modelling Spinal Circuitry Involved in Locomotor Pattern Generation: Insights from the Effects of Afferent Stimulation," *J. Physiol.*, 577(2): 641-658 (2006).

Sanderson, D.J. and Martin. P.E., "Lower Extremity Kinematic and Kinetic Adaptations in Unilateral Below-Knee Amputees During Walking," *Gait & Posture*, 6(2): 126-136 (1997).

Sanger, T.D., "Human Arm Movements Described by a Low-Dimensional Superposition of Principal Components," *The J. of Neuroscience*, 20(3): 1066-1072 (2000).

Saranli, U., et al., "RHex: A Simple and Highly Mobile Hexapod Robot," *The International Journal of Robotics Research*, pp. 616-631 (2001).

Sarrigeorgidis, K. and Kyriakopoulos, K.J., "Motion Control of the N.T.U.A. Robotic Snake on a Planar Surface." Paper presented at the Proceedings of the 1998 IEEE International Conference on Robotics & Automation, Leuven, Belgium (May 1998).

Schaal, S. and Atkeson, C.G., "Constructive Incremental Learning from Only Local Information," *Neural Computation*, 10(8): 2047-2084 (1998).

Schaal, S., "Is Imitation Learning the Route to Humanoid Robots?", *Trends in Cognitive Sciences*, 3: 233-242 (1999).

Scott, S.H. and Winter, D.A., "Biomechanical Model of the Human Foot: Kinematics and Kinetics During the Stance Phase of Walking," *J. Biomechanics*, 26(9): 1091-1104 (1993).

Sentis, L. and Khatib, O., "Task-Oriented Control of Humanoid Robots Through Prioritization." Paper presented at the IEEE-RAS/RSJ International Conference on Humanoid Robots, pp. 1-16.

Seyfarth, A., et al., "A Movement Criterion for Running," *J. of Biomechanics*, 35: 649-655 (2002).

Seyfarth, A., et al., "Stable Operation of an Elastic Three-Segment Leg," *Biol. Cybern.*, 84: 365-382 (2001).

Seyfarth, A., et al., "Swing-Leg Retraction: A Simple Control Model for Stable Running," *The J. of Experimental Biology*, 206: 2547-2555 (2003).

Giszter et al., "Convergent Force Fields Organized in the Frog's Spinal Cord," The Journal of Neuroscience, Feb. 1993, pp. 467-491.

Sinkjacr, T., et al., "Major role for sensory feedback in soleus EMG activity in the stance phase of walking in man," *Journal of Physiology*, 523.3: 817-827 (2000).

Skinner, H.B., and Effeney, D.J., "Gait Analysis in Amputees," *American Journal of Physical Medicine*, 64(2): 82-89 (1985).

Smidt, G.L., et al., "An Automated Accelerometry System for Gait Analysis," *J. Biomechanics*, 10: 367-375 (1977).

Srinivasan, M., "Energetics of Legged Locomotion: Why is Total Metabolic Cost Proportional to the Cost of Stance Work." ISB XXth Congress—ASB $29^{th}$ Annual Meeting, Cleveland, OH (Jul. 31-Aug. 5.

Stepien, J., et al., "Activity Levels Among Lower-Limb Amputees: Self-Report Versus Step Activity Monitor," *Arch. Phys. Med. Rehabil.*, 88: 896-900 (2007).

Sugano, S., et al., "Force Control of the Robot Finger Joint equipped with Mechanical Compliance Adjuster," Proceedings of the 1992 IEEE/RSJ International Conference on Intelligent Robots and Systems, Raleigh, NC (Jul. 1992).

Sugihara, T., et al., "Realtime Humanoid Motion Generation through ZMP Manipulation based on Inverted Pendulum Control," Proceedings of the 2002 IEEE International Conference on Robotics & Automation, Washington, DC (May 2002).

Sup, F., et al., "Design and Control of a Powered Transfemoral Prosthesis," *The International Journal of Robotics Research*, 27(2): 263-273 (2008).

Taga, G., "A model of the neuro-musculo-skeletal system for human locomotion," *Biol. Cybern.*, 73: 97-111 (1995).

Takayuki, F., et al., "Biped Locomotion using Multiple Link Virtual Inverted Pendulum Model," *T.IEE Japan*, 120-C (2): 208-214 (2000).

Thoroughman, K., and Shadmehr, R., "Learning of action through adaptive combination of motor primitives," *Nature*, 407: 742-747(2000).

Tomović, R., and McHee, R.B., "A Finite State Approach to the Synthesis of Bioengineering Control Systems," *IEEE Transactions on Human Factors in Electronics*, 7(2): 65-69 (1966).

Tong, K., and Granat, M., "A practical gait analysis system using gyroscopes," *Medical Engineering & Physics*, 21: 87-94 (1999).

Türker, K., "Electromyography: Some Methodological Problems and Issues," *Phys. Ther.*, 73: 698-710 (1993).

Van den Bogert, A.J., et al., "A Method for Inverse Dynamic Analysis Using Accelerometry," *J. Biochemechanics*, 29(7): 949-954 (1996).

Van den Bogert, A. J., "Exotendons for Assistance of Human Locomotion," Biomedical Engineering OnLine, BioMed Central, 2(17):1-8 (2003).

Veltink, P.H., et al.. "The Feasibility of Posture and Movement Detection by Accelerometry," paper presented at the IEEE meeting (1993).

Vukobratovic, M., Juricic, D., "Contribution to the Synthesis of Biped Gait," paper presented at the IEEE Transactions on Bio-Medical Engineering, BME-16(1) (Jan. 1969).

Vukobratovic, M., and Stepanenko, J., :Mathematical Models of General Anthropomorphic Systems, Mathematical Biosciences, 17: 191-242 (1973).

Walsh, C.J., et al., "Biomimetic Design of an Under-Actuated Leg Exoskeleton for Load-Carrying Augmentation," Unpublished Master's thesis, Massachusetts Institute of Technology, Cambridge, MA (2006).

Waters, R.L., et al., "Energy Cost of Walking of Amputees: The Influence of Level of Amputation," *The Journal of Bone and Joint Surgery*, 58A(1): 42-46 (1976).

Wilkenfeld, A., and Herr, H., "An Auto-Adaptive External Knee Prosthesis," MIT Lab., No date given.

Wilkenfeld, A., "Biologically Inspired Autoadaptive Control of a Knee Prosthesis," unpublished doctoral dissertation, Massachusetts Institute of Technology, Cambridge, MA (2000).

Willemsen, A.Th.M., et al., "Automatic Stance-Swing Phase Detection from Accelerometer Data for Peroneal Nerve Stimulation," presented at the meeting of IEEE Transactions on Biomedical Engineering, 37(12):1201-1208 (1990).

Willemsen, A.Th.M., et al., "Real-Time Gait Assessment Utilizing a New Way of Accelerometry," *J. Biomechanics*, 23(8):859-863 (1990).

Williams, B.C., et al., "Mode Estimation of Model-Based Programs: Monitoring Systems with Complex Behavior," paper submitted to Massachusetts Institute of Technology, Cambridge, MA, No date given.

Williamson, M.M., "Series Elastic Actuators," A.I. Technical Report submitted to Massachusetts Institute of Technology, Cambridge, Massachusetts (Jan. 1995).

FF, D.A., and Sienko, S.E., "Biomechanics of Below-Knee Amputee Gait," *J. Biomechanics*, 21(5):361-367 (1988).

Winter, D.A., "Energy Generation and Absorption at the Ankle and Knee during Fast, Natural, and Slow Cadences," *Clinical Orthopedics and Related Research*, 175: 147-154 (1983).

Winter, D.A., and Robertson, D.G.E., "Joint Torque and Energy Patterns in Normal Gait," Biol. Cybernetics, 29:137-142 (1978).

Wisse, M., "Essentials of Dynamic Walking: Analysis and Design of Two-legged Robots," No date given.

Woodward, M.I. and Cunningham, J.L., "Skeletal Accelerations Measured During Different Exercises," *Proc. Instn. Mech. Engrs.*, 207: 79-85 (1993).

Wu, G. and Ladin, Z., "The Study of Kinematic Transients in Locomotion Using the Integrated Kinematic Sensor," *IEEE Transactions on Rehabilitation Engineering*, 4(3): 193-200 (1996).

Yakovenko, S., et al., "Contribution of Stretch Reflexes to Locomotor Control: A Modeling Study," *Biol. Cybern.*, 90: 146-155 (2004).

Yun, X., "Dynamic State Feedback Control of Constrained Robot Manipulators." Paper presented at the Proceedings of the 27th Conference on Decision and Control, Austin, TX (Dec. 1988).

Zlatnik, D., et al., "Finite-State Control of a Trans-Femoral (TF) Prosthesis," *IEEE Transactions on Control Systems Technology*, 10(3): 408-420 (2002).

\* cited by examiner

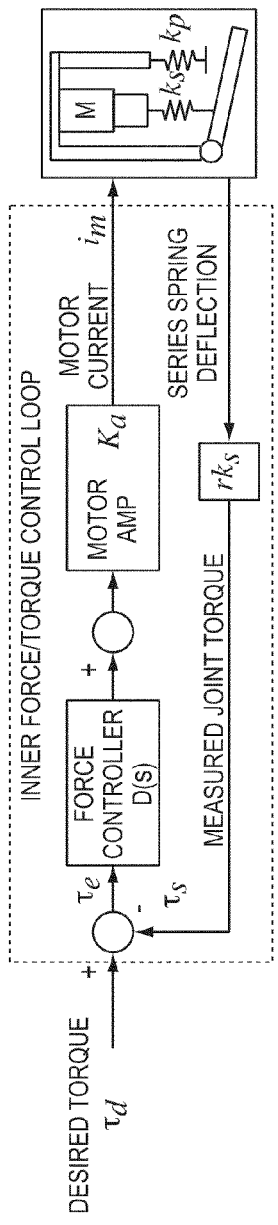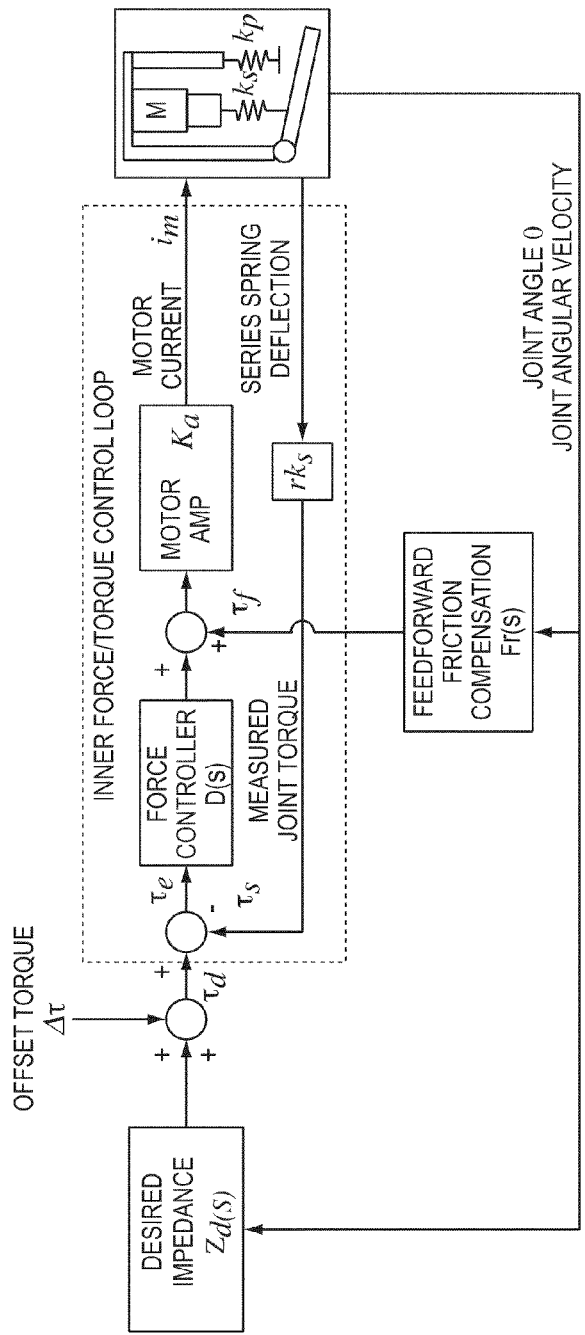
FIG. 26A
FIG. 26B

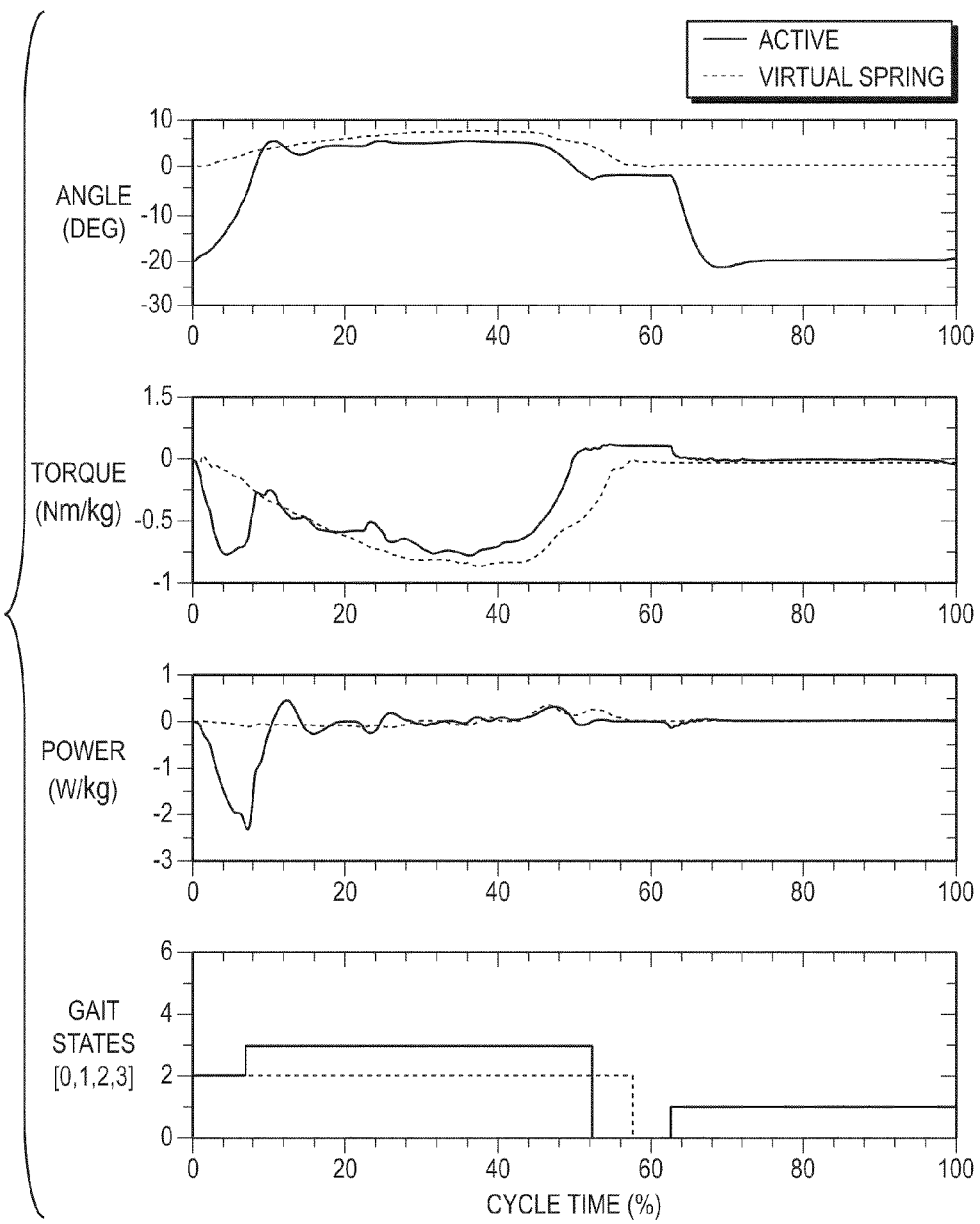

POWERED ANKLE-FOOT PROTHESIS

CROSS REFERENCE TO RELATED APPLICATIONS

This application claims the benefit of the filing date of Provisional U.S. Patent Application Ser. No. 60/934,223 filed on Jun. 12, 2007.

This application is a continuation in part of, and claims the benefit of the filing date of, U.S. patent application Ser. No. 11/395,448 filed on Mar. 31, 2006 now abandoned which claimed the benefit of the filing date of U.S. Provisional Patent Application Ser. No. 60/666,876 filed on Mar. 31, 2005 and further claimed the benefit of the filing date of U.S. Provisional Patent Application Ser. No. 60/704,517 filed on Aug. 1, 2005.

This application is also a continuation in part of, and claims the benefit of the filing date of, U.S. patent application Ser. No. 11/495,140 filed on Jul. 29, 2006 now abandoned which claimed the benefit of the filing dates of the above noted above-noted U.S. Provisional Patent Application Ser. No. 60/666,876 and Ser. No. 60/704,517 and was a continuation in part of the above-noted U.S. patent application Ser. No. 11/395,448.

This application is also a continuation in part of U.S. patent application Ser. No. 11/642,993 filed on Dec. 19, 2006 now abandoned which was a continuation in part of the above noted U.S. patent application Ser. No. 11/395,448 and the above noted application Ser. No. 11/495,140, and was also a continuation in part of U.S. patent application Ser. No. 11/499,853 filed on Aug. 4, 2006 now U.S. Pat. No. 7,313,463, and U.S. patent application Ser. No. 11/600,291 filed on Nov. 15, 2006 now abandoned. Application Ser. No. 11/642,993 further claimed the benefit of the filing date of U.S. Provisional Patent Application Ser. No. 60/751,680 filed on Dec. 19, 2005.

The present application claims the benefit of the filing date of each of the foregoing patent applications and incorporates the disclosure of each of the foregoing applications herein by reference.

FIELD OF THE INVENTION

This invention relates generally to prosthetic devices and artificial limb and joint systems, including robotic, orthotic, exoskeletal limbs, and more particularly, although in its broader aspects not exclusively, to artificial feet and ankle joints.

BRIEF DESCRIPTION OF THE DRAWINGS

In the detailed description which follows, frequent reference will be made to the attached drawings, in which:

FIGS. 26A, 26B and 26C contains block diagrams for the low-level servo controllers.

FIG. 60 illustrates prosthetic ankle stair-descent performance.

DETAILED DESCRIPTION

Figure 1:
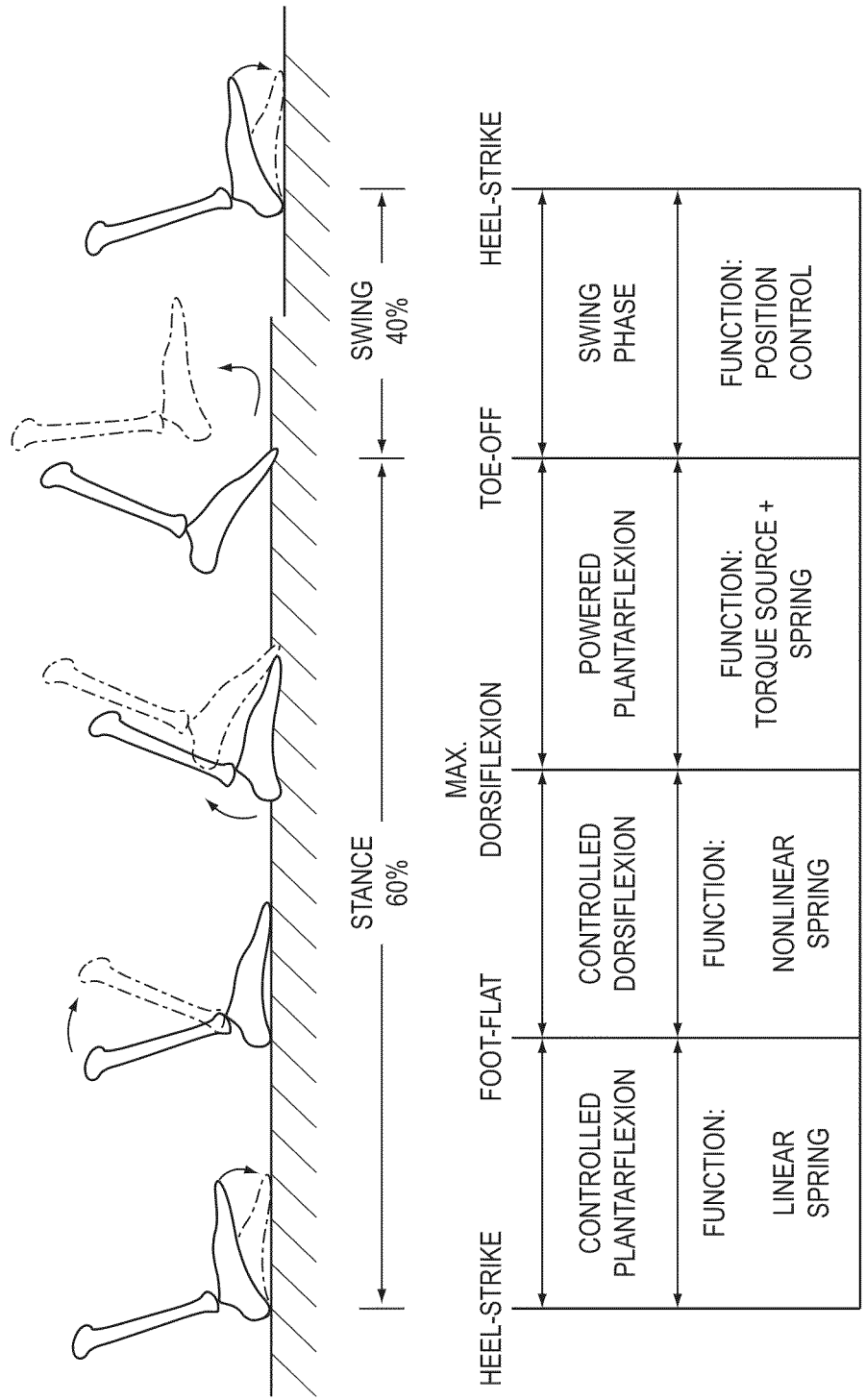
FIG. 1 depicts normal human ankle biomechanics for level-ground walking.

In the course of the following description, reference will be made to the papers, patents and publications presented in a list of references at the conclusion of this specification. When cited, each listed reference will be identified by a numeral within curly-braces indicating its position within this list.

Today's commercially available below-knee prostheses are completely passive during stance, and consequently, their mechanical properties remain fixed with walking speed and terrain. These prostheses typically comprise elastic bumper springs or carbon composite leaf springs that store and release energy during the stance period, e.g. the Flex-Foot or the Seattle-Lite {A-1} {A-2}.

Lower extremity amputees using these conventional passive prostheses experience many problems during locomotion. For example, transitional amputees expend 2030% more metabolic power to walk at the same speed than able-bodied individuals, and therefore, they prefer a slower walking speed to travel the same distance. Thus, their self-selected walking speed is normally 30-40% lower than the mean speed of intact individuals {A-3} {A-4}. Also, many clinical studies report that amputees exhibit an asymmetrical gait pattern {A-6} {A-7} {A-8}. For example, unilateral below-knee amputees generally have higher than normal hip extension, knee flexion, and ankle dorsiflexion on the unaffected side. On the affected side, such individuals have less than normal hip and knee flexion during stance. Additionally, there is a significant ankle power difference between the affected and unaffected sides during ankle powered plantar flexion in walking.

There are many differences between the mechanical behavior of conventional ankle-foot prostheses during the walking cycle and that of the human ankle-foot complex. Most notably, the human ankle performs more positive mechanical work than negative, especially at moderate to fast walking speeds {A-10}-{A-15}. Researchers hypothesize that the primary source of energy loss in walking is to "pay" for the redirection of the center of mass velocity during step-to-step transitions {A-17} {A-18} {A-19}. Researchers have shown that supplying energy through the ankle joint to redirect the center of mass is more economical than to exert power through the hip joint alone {A-17} {A-19}. These biomechanical results may explain why transtibial amputees require more metabolic energy to walk than intact individuals. Using a conventional passive prosthesis, a leg amputee can only supply energy through the hip joint to power center of mass dynamics, producing a pathological gait pattern {A-6} {A-7} {A-8}.

It is hypothesized that the inability of conventional passive prostheses to provide net positive work over the stance period is the main cause for the aforementioned clinical problems. The goal is to evaluate the hypothesis through development of a physical prototype of a ankle-foot prosthesis1 to demonstrate its benefits to a transtibial amputee ambulation. The term "powered ankle-foot prosthesis" as used herein refers to an ankle-foot prosthesis that can provide sufficient net positive work during the stance period of walking to propel an amputee.

Although the idea of a powered ankle-foot prosthesis has been discussed since the late 1990s, only one attempt has been made to develop such a prosthesis to improve the locomotion of amputees. Klute {A-20} attempted to use an artificial pneumatic muscle, called McKibben actuator to develop a powered ankle-foot prosthesis. Although the mechanism was built, no further publications have demonstrated its capacity to improve amputee gait compared to conventional passive-elastic prostheses.

More recent work has focused on the development of quasi-passive ankle-foot prostheses {A-21} {A-22} {A-23}. Collins and Kuo {A-21} advanced a foot system that stores elastic energy during early stance, and then delays the release of that energy until late stance, in an attempt to reduce impact losses of the adjacent leg. Since the device did not include an actuator to actively plantar flex the ankle, no net work was performed throughout stance. Other researchers {A-22} {A-23} have built prostheses that use active damping or clutch mechanisms to allow ankle angle adjustment under the force of gravity or the amputee's own weight.

In the commercial sector, the most advanced ankle-foot prosthesis, the Ossur Proprio Foot™ {A-1}, has an electric motor to adjust foot position during the swing phase to achieve foot clearance during level-ground walking. Although active during the swing phase, the Proprio ankle joint is locked during stance, and therefore becomes equivalent to a passive spring foot. Consequently, the mechanism cannot provide net positive power to the amputee.

According to {A-6} {A-9} {A-26}, two main engineering challenges hinder the development of a powered ankle-foot prosthesis.

Mechanical design: With current actuator technology, it is challenging to build an ankle-foot prosthesis that matches the size and weight of the human ankle, but still provides a sufficiently large instantaneous power and torque output to propel an amputee. For example, a 75 kg person has an ankle-foot weight of approximately 2.5 kg, and the peak power and torque output at the ankle during walking at 1.7 m/s can be up to 350 W and 150 Nm, respectively {A-10} {A-12} {A-9}. Current ankle-foot mechanisms for humanoid robots are not appropriate for this application, as they are either too heavy or not powerful enough to meet the human-like specifications required for a prosthesis {A-27} {A-28}.

Control system design: A powered prosthesis must be position and impedance controllable. Often robotic ankle controllers follow pre-planned kinematic trajectories during walking {A-27} {A-28}, whereas the human ankle is believed to operate in impedance control mode during stance and position control mode during swing {A-11} {A-12}. Furthermore, for the ease of use, only local sensing for the prosthesis is preferable, which adds extra constraints on the control system design. Finally, there is no clear control target or "gold standard" for the prosthesis to be controlled, against which to gauge the effectiveness. It is unclear what kind of prosthetic control strategy is effective for the improvement of amputee ambulation.

Understanding normal walking biomechanics provides the basis for the design and control of the powered prosthesis. The biomechanics of normal human ankle-foot for level-ground walking are reviewed below, followed by an overview of conventional ankle-foot prostheses. Finally, the typical locomotion problems experienced by the transtibial amputees using conventional prostheses are described.

Walking is a highly coordinated behavior accomplished by intricate interaction of the musculo-skeletal system. Researchers have spent many efforts to understand the corresponding principle for human walking {A-29} {A-24} {A-10} {A-25} {A-31} {-30}. Preliminary introduction to human walking can be obtained through Inman {A-24} and Perry {A-25}. Winter {A-10} {A-32} {A-33} also provides a detailed analysis of kinematic, kinetic and muscle activation patterns of human gait.

The discussion below focuses on providing the basic concepts of human walking, in particular, the function of human ankle in the sagittal plane during level-ground walking. Along the lines of the research in {A-11}-{A-14} {A-25}, the function of the human ankle is characterized in terms of simple mechanical elements, rather than using a complex biomechanical model. Such simple functional models motivate and simplify the design and control of the powered prosthesis. They also provide a means by which the performance of any artificial ankle could be measured against that of a biological ankle {A-11}.

Figure 2:
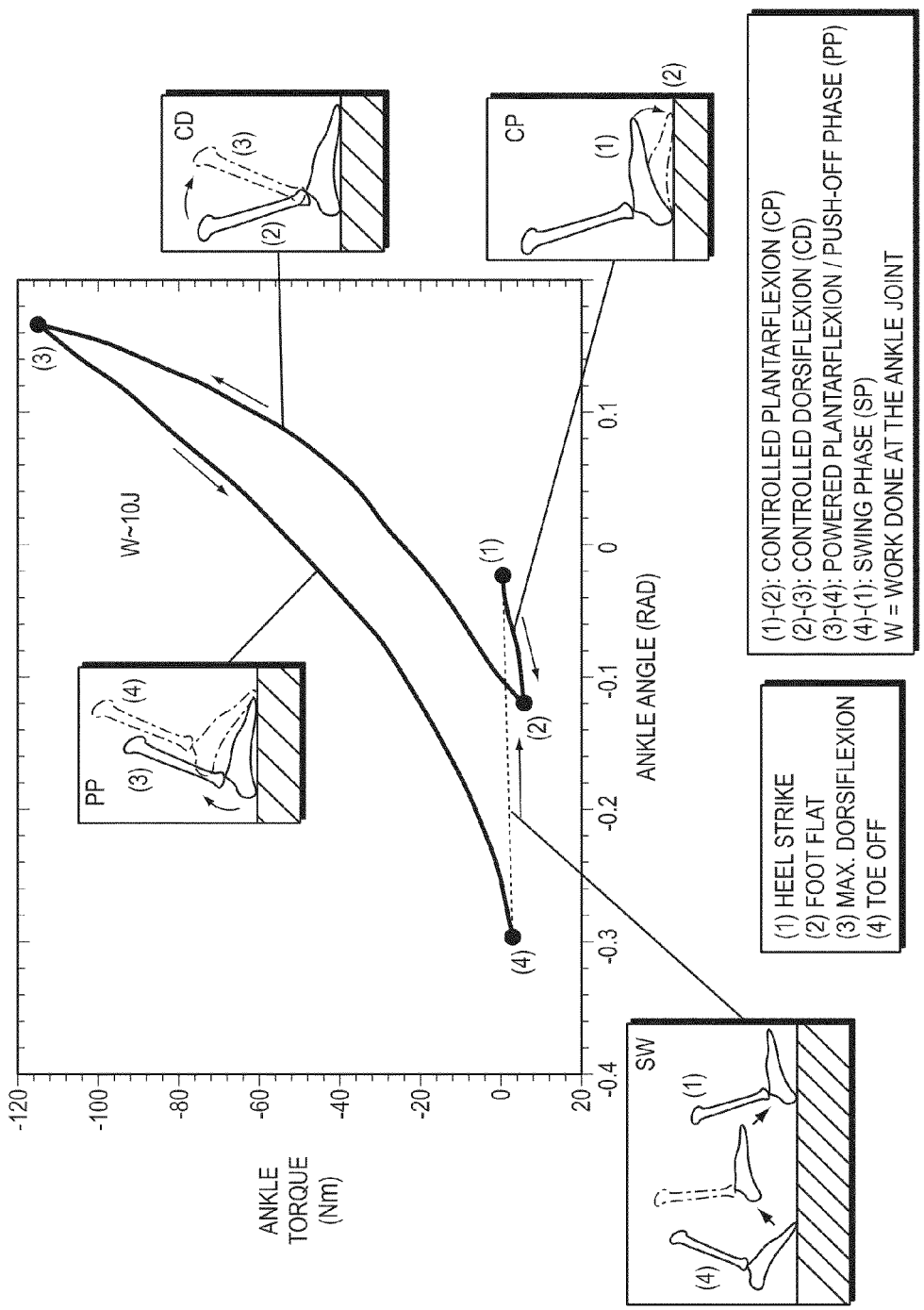
FIG. 2 shows a typical ankle torque-angle behavior.

A level-ground walking gait cycle is typically defined as beginning with the heel strike of one foot and ending at the next heel strike of the same foot {A-24} {A-25}. The main subdivisions of the gait cycle are the stance phase (about 60% of a gait cycle) and the swing phase (about 40% of a cycle) (FIG. 1). The swing phase (SW) represents the portion of the gait cycle when the foot is off the ground. The stance phase begins at heel-strike when the heel touches the floor and ends at toe-off when the same foot rises from the ground surface. From {A-11} {A-12}, the stance phase of walking can be divided into three sub-phases: Controlled Plantar Flexion (CP), Controlled Dorsiflexion (CD), and Powered Plantar Flexion (PP). These phases of gait are described in FIG. 1. In addition, FIG. 2 shows the typical ankle torque-angle characteristics for a 75 kg person walking at a self-selected speed (1.25 m/sec). The detailed descriptions for each sub-phase are provided below.

Controlled Plantar Flexion (CP): CP begins at heel-strike and ends at foot-flat. Simply speaking, CP describes the process by which the heel and forefoot initially make contact with the ground. In {A-11} {A-12} {A-25}, researchers showed that ankle joint behavior during CP is consistent with a linear spring response with joint torque proportional to joint position. As can be seen in FIG. 2, segment (1)-(2) illustrates the linear spring behavior of the ankle.

Controlled Dorsiflexion (CD): CD begins at foot-flat and continues until the ankle reaches a state of maximum dorsiflexion Ankle torque versus position during the CD period can often be described as a nonlinear spring where stiffness increases with increasing ankle position. The main function of the human ankle during CD is to store the elastic energy necessary to propel the body upwards and forwards during the PP phase {A-11}-{A-15}. Segment (2)-(3) in FIG. 2 reveals the nonlinear spring behavior of the human ankle joint during CD.

Powered Plantar Flexion (PP): PP begins after CD and ends at the instant of toe-off. Because the work generated during PP is more than the negative work absorbed during the CP and CD phases for moderate to fast walking speeds {A-10}-{A-15}, additional energy is supplied along with the spring energy stored during the CD phase to achieve the high plantar 11 flexion power during late stance. Therefore, during PP, the ankle can be modeled as a torque source in parallel with the CD spring. The area W enclosed by the points (2), (3), and (4) shows the amount net work done at the ankle.

Swing Phase (SW): SW begins at toe-off and ends at heel-strike. It represents the portion of the gait cycle when the foot is off the ground. During SW, the ankle can be modeled as a position source to reset the foot to a desired equilibrium position before the next heel strike.

In summary, for level ground walking, human ankle provides three main functions:
 1. it behaves as a spring with variable stiffness from CP to CD;
 2. it provides additional energy for push-off during PP; and
 3. it behaves as a position source to control the foot orientation during SW.

Figure 4:
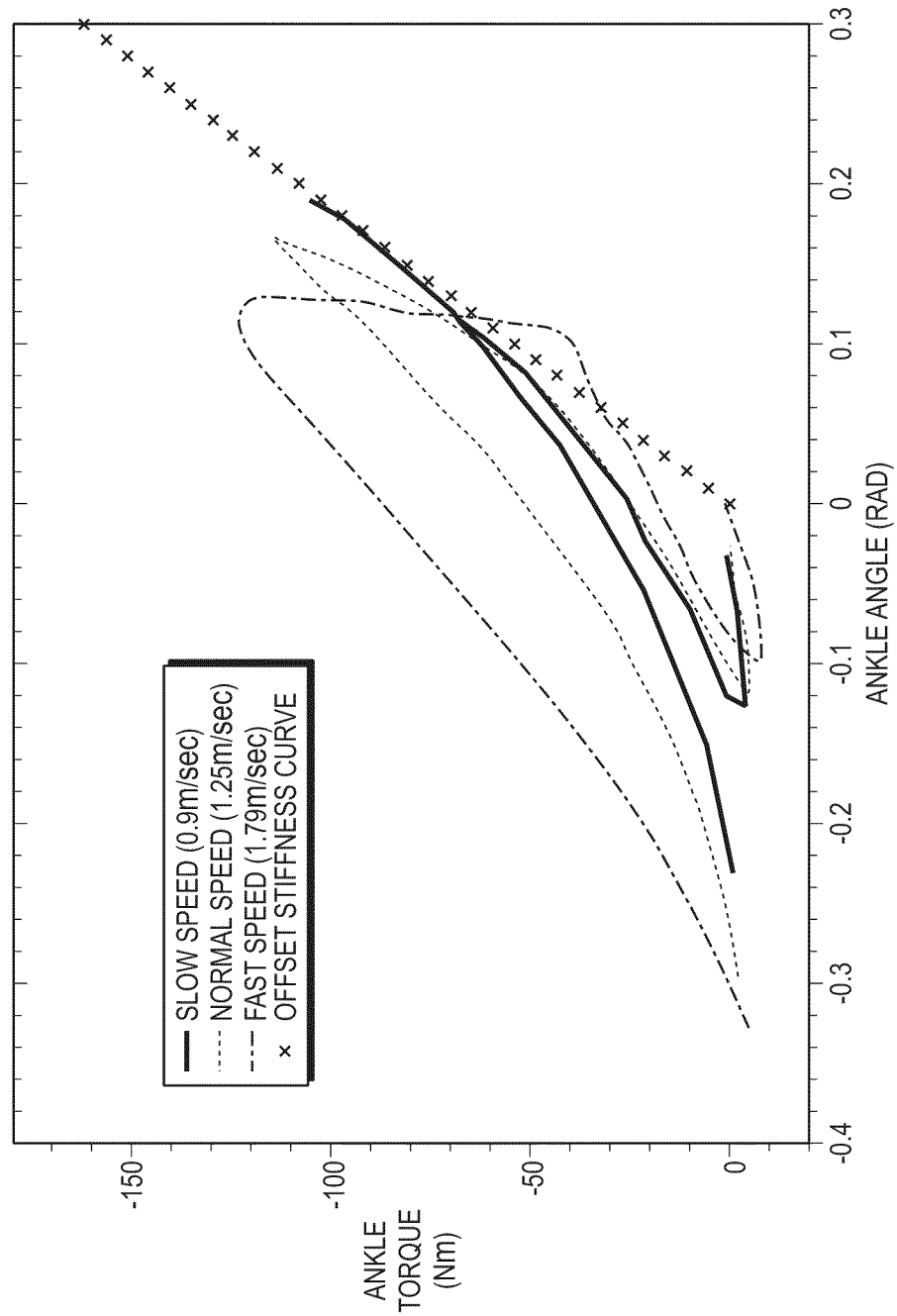
FIG. 4 depicts ankle torque-angle/velocity behavior for different walking speeds.

As revealed in FIG. 4, the net work done at the ankle joint is approximately zero for slow walking speed. This suggests that the normal human ankle can be modeled as a spring at slow walking speed (0.9 m/s). Approaching the fast walking speed (1.8 m/s), there is a dramatic increase in the quasi-static stiffness1 of human ankle from CD to early PP, consequently, more net positive work has done at the ankle joint. This phenomenon motivates us to model the ankle behavior as a combination of a spring component and a constant offset torque source during PP. Details of the model description will be discussed below.

Besides, it is shown that there is a lower bound (or offset value) in the quasi-static stiffness from CD to PP for all walking speeds (FIG. 4). Quasi-static stiffness is the slope of the measured ankle torque-angle curve of the human ankle during walking. This also motivates the design of using a physical spring, configured in parallel to the joint of the powered Conventional Ankle-Foot Prostheses Conventional ankle-foot prostheses used by lower limb amputees can be divided into two main categories: non energy-storing feet and energy-storing feet (or dynamic elastic response feet). A typical example of the non energy-storing feet is the Solid Ankle, Cushioned Heel (SACH) foot {A-2}. The SACH foot is composed of a rigid longitudinal keel with a solid ankle. A wedge of polyurethane foam provides cushioning in the heel section, with hyperextension of the rubber toe section possible during late stance. It was designed with the goal of restoring basic walking and simple occupational tasks and was once considered as the optimum compromise between durability and functional effectiveness, as well as being of reasonable cost in the early 80's {A-2}.

Energy-storing feet were introduced in the late 80's due to the incorporation of modern lightweight, elastic materials into the design of ankle-foot prostheses. These prostheses were designed to deform during heel contact and mid-stance and rebound during late stance to simulate the "push-off" characteristics of a normal ankle. They were designed for very active unilateral or bilateral transtibial amputees to foster springy walking, running and jumping but may be used by all lower-limb amputees {A-2}.

The most advanced ankle-foot prosthesis, the Ossur's Proprio Foot™ {A-1}, has an electric motor to adjust the orientation of a low profile Flex-foot during the swing phase. As its ankle joint is locked during stance, the prosthesis behaves equivalent to a typical energy-storing feet during the stance period of walking.

Whatever, conventional ankle-foot prostheses can only partially restore the functions of a biological ankle-foot described in Section 2.1. A brief summary of functional comparison between a biological ankle-foot and conventional prostheses is shown below based on the results from {A-2} {A-10} {A-11} {A-12}.

Normal human ankle has a larger range of movement than conventional passive-elastics prostheses.

Normal human ankle stiffness varies within each gait cycle and also with walking speed. Although most conventional prostheses are designed to have stiffness variations within a gait cycle, these stiffness variations are limited and are only designed for a particular walking speed.

Normal human ankle provides a significant amount of net positive work during the stance period of level-ground walking, stair ascent, and slope climbing. The conventional prostheses, including the Proprio Foot™, cannot provide any net positive work during stance.

Normal human ankle behaves as a rotary damper during the early stance of stair descent to absorb a significant amount of impact energies/power {A-12}. Due to the passive-elastic nature, most of conventional prostheses cannot absorb/dissipate such a large amount of energy during stair descent. Consequently, during stair descent, amputees need to place their prostheses on each step gently to minimize the impact and also use either their knee or hip joints to dissipate the extra energy {A-69} {A-68}.

Transtibial Amputee Gait

The gait of transtibial (or below-knee (B/K)) amputee subjects has been extensively studied by means of kinematics and kinetics analysis, as well as energy cost techniques {A-6} {A-7} {A-8}. Results from these studies indicates that the transtibial amputee gait demonstrates a distinct different from the gait of an able-individual. This section focuses on the gait of unilateral transtibial amputees using the conventional passive-elastic ankle-foot prostheses. The following shows the common observations in amputee gait, compared to normal gait:

The average B/K amputee's self-selected speed (0.97 m/s) is slower than mean normal (1.3 m/s) {A-6}.

Average stride length of an B/K amputee is slightly shorter, as compared to the mean normal {A-6}.

There is a distinct asymmetry in B/K amputees' gait.

The range of ankle movement on the affected side (or prosthetic side) is smaller or limited, compared to that of the unaffected side {A-7} {A-8}.

Hip extension moment on the affected side from early to mid-stance is greater than normal, that results in above-normal energy generation by the hip joint on the affected side. It is believed that this extra amount of energy is used to partially compensate the lack of active push-off in the prostheses {A-6} {A-8}.

Due to the above-normal hip extension, the knee flexion moment on the affected side during early stance is below the mean normal value. Consequently, the power generated by the knee joint during the early stance are near zero {A-6} {A-8}.

There is a significant ankle power difference between the affected and unaffected sides during ankle powered plantar flexion in walking {A-6} {A-7} {A-8}.

Transtibial amputees are known to spend greater amounts of energy while walking than non-amputees do {A-3} {A-4} {A-5}. The magnitude of disparity appears to be dependent on the cause of amputation {A-37} {A-40}. Young adult traumatic amputee, while expending energy at a 25 percent greater rate than normal walking, accomplished only 87 percent of the normal velocity. Due to lack the necessary physiological vigor and strength, dysvascular amputees expended energy at a 38 percent greater rate than normal walking, while only accomplished 45 percent of the normal velocity.

All the differences in the gait can be attributed to an attempt by the amputee to compensate for the missing prosthetic ankle-power generation by producing more power at the hip. Researchers also conducted experiments to study the effect of different ankle-foot prostheses, including the nonenergy-storing and energy-storing feet on amputee gait {A-7} {A-34} {A-36} {A-35}. Although most amputee subjects comment that energy-storing feet are better than the non-energy-storing one, results from these studies indicate that there is no significant difference in amputee gait associated with these two kinds of prosthetic feet (e.g. SACH foot vs. Flex-foot). Although {A-39} has shown that traumatic amputee's walking metabolic cost can be slightly improved when using energy-storing feet, in general, there is also no significant differences in amputee walking metabolic cost associated with these feet {A-38} {A-37}, Desired Ankle Behavior Regarding the control issues of the powered ankle-foot prosthesis, there is no clear control target or "gold standard" for the prosthesis to be controlled, against which to gauge the effectiveness. The following section proposes a stance phase control scheme that mimics the quasi-static stiffness behavior and power generation characteristics of the human ankle during steady state walking, called target stance phase behavior. It us hypothesized that an ankle-foot prosthesis using this control scheme increases a transtibial amputee walking economy.

Target Stance Phase Behavior

The key question for the control is to define a target walking behavior for the prosthesis. For the swing phase, the desired ankle behavior is just to re-position the foot to a predefined equilibrium position. For the stance phase control, instead of simply tracking ankle kinematics, researchers {A-11} {A-12} {A-14} suggest that one simple way is to let the prosthesis mimic the "quasi-static stiffness", that is the slope of the measured ankle torque-angle curve during stance. This quasi-static stiffness curve describes the energy (net work) flow characteristics between the human ankle and the environment during steady state walking.

A leading goal of the stance phase control for the powered prosthesis is to mimic the quasi-static stiffness curve, so as to deliver net positive work to an amputee. Using the biomechanical descriptions in {A-11} {A-12}, the quasi-static stiffness curve (FIG. 5) can be decomposed into two main components:

(i) a spring whose stiffness varies in a similar manner as the normal human ankle does in CP and CD;

(ii) a torque source that provides positive net work during late stance phase. The torque source is assumed to be active between points (4) and (3). Such a functional decomposition allows us to study the effect of performing net positive work during stance on amputee ambulation independent of the stiffness variation.

For the ease of experimentation and clinical evaluation, these two components are simplified and parametized and then used to provide the target stance phase behavior for the prosthesis as depicted in FIG. 5. Detailed descriptions for each component are summarized as follows:

1. A torsional spring with a stiffness $K_{ankle}$ that varies with the sign of the ankle angle $\theta$ as follows.

$$K_{ankle} = \begin{cases} K_{CP} & \theta \leq 0 \\ K_{CD} & \theta > 0 \end{cases} \quad (3.1)$$

When the ankle angle is positive, the stiffness value will be set to $K_{CD}$. When the ankle angle is negative, the stiffness value will be set to $K_{CP}$.

2. A constant offset torque $\Delta\tau$ that models the torque source during PP. This offset torque will be applied in addition to the torsional spring $K_{CD}$ during PP. The torque threshold $\tau_{pp}$ determines the moment at which the offset torque is applied, indicated by the point (4) in FIG. 5. The total work done $\Delta W$ at the ankle joint by the torque source is $$\Delta W = \Delta\tau \left( \frac{\tau_{pp}}{K_{CD}} + \frac{\Delta\tau}{K_{CP}} \right) \quad (3.2)$$

The $$\frac{\tau_{pp}}{K_{cp}}$$

indicates the starting ankle angle at which the torque source is applied while $$\frac{\Delta\tau}{K_{CP}}$$

represents the stopping ankle angle at which the control system stop applying the torque source to the ankle joint.

Using the stance phase control scheme (FIG. 5), one can conduct experiment to study the clinical effect of a particular parameter value (e.g. KCP) to amputee ambulation. In particular, the control scheme facilitates the study of the clinical effect of performing the net positive work to amputee ambulation because the amount of net positive work performed at the ankle joint can be controlled based on Eqn. (3.2). It is noted that the conventional passive prostheses only provide the spring behavior but fail to supply the function of the torque source to thrust the body upwards and forwards during PP. Our designed prosthesis eventually will provide both functions during stance. An ankle-foot prosthesis that can provide the target stance phase behavior may improve a transtibial amputee walking economy.

Mechanical Design and Analysis

The discussion below presents a novel, motorized ankle-foot prosthesis, called the "MIT Powered Ankle-Foot Prosthesis." This prosthesis exploits both series and parallel elasticity with an actuator to fulfill the demanding human-ankle specifications. The discussion begins by describing the design specifications of a powered ankle-foot prosthesis and then presents the overall design architecture of the proposed prosthesis. Several design analyses which guide the selection of system components are presented, followed by a description of the physical embodiment of the prosthesis and present the experimental results for the system characterization.

Design Specifications

Using the biomechanical descriptions presented above and the results from {A-11} {A-12} {A-24}, the design goals for the prosthesis are summarized as follows:

the prosthesis should be at a weight and height similar to the intact limb.

the system must deliver a large instantaneous output power and torque during push-off.

the system must be capable of changing its stiffness as dictated by the quasi-static stiffness of an intact ankle.

the system must be capable of controlling joint position during the swing phase.

the prosthesis must provide sufficient shock tolerance to prevent damage to the mechanism during the heel-strike.

It is important to note that the prosthesis and controller designs are not independent. Rather, they are integrated to ensure that the inherent prosthesis dynamics do not inhibit controller's ability to specify desired dynamics. In the remainder of this section, the target parameters for the design goals are outlined.

Size and Weight: The height of normal human ankle-foot-shank complex (measured from the ground to the knee joint) is about 50 cm for a 75 kg person with a total height of 175 cm {A-25}. In average, the level of amputations for a transtibial amputee is about two third of the length of normal human ankle-foot-shank complex, which is about 32 cm {A-2}. A rough estimation of the weight of the missing limb for that given height is around 2.5 kg. In fact, it is favorable to minimize the height of prosthesis because the shorter the length of a prosthesis is, the more amputees can fit to it.

Range of Joint Rotation: The proposed range of joint rotation for the prosthesis is based on normal human ankle range of motion during walking {A-24}. The maximum plantarflexion (20-25 degrees) occurs just as the foot is lifted off the ground, while the maximum dorsiflexion (10-15 degrees) happens during CD.

Figure 3:
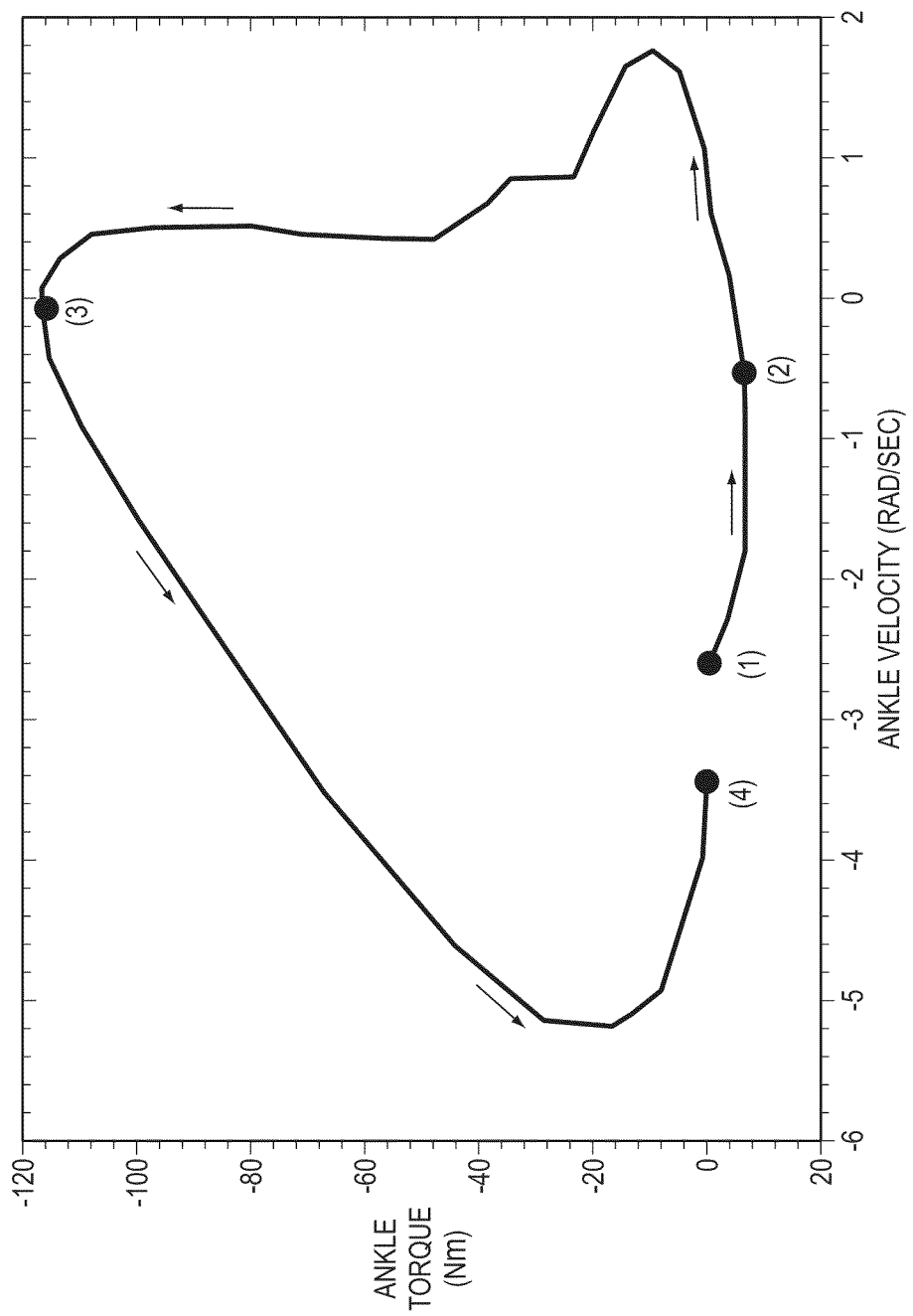
FIG. 3 illustrates a typical ankle torque-velocity behavior.

Torque and Speed: According to {A-11} {A-12}, the measured peak velocity, torque, and power of the human ankle during the stance period of walking can be as high as 5.2 rad/s, 140 Nm, and 350 W, respectively (FIG. 3). Rather than just satisfying the peak conditions, the maximum torque-speed characteristic of the prosthesis is designed to bracket that of the human ankle during walking.

Torque Bandwidth: The torque bandwidth is computed based on the power spectrum of the nominal ankle torque data for one gait cycle. The torque bandwidth is defined at the frequency range over which covers 70% of the total power of the signal. Analyzing the normal human ankle data in {A-12}, the torque bandwidth was found to be about 3.5 Hz in which the ankle torque varies between 50 to 140 Nm. The goal is to design a torque/force controller whose bandwidth is larger than the specified torque bandwidth (3.5 Hz). More specifically, this controller should be able to output any torque level between 50-140 Nm at 3.5 Hz. It implicitly suggests that the large force bandwidth of the open-loop system need to be much larger than 3.5 Hz, otherwise, the inherent prosthesis dynamics may inhibit controller's ability to specify desired dynamics.

Net Positive Work: In the literature, the average values of the net positive work done at the ankle joint for medium and fast walking speeds of a 75 kg person are about 10 J and 20 J, respectively {A-11} {A-12}.

Offset Stiffness: The offset stiffness during CD is obtained by computing the average slope of the measured human ankle torque-angle curve of the human ankle during CD {A-11} {A-12}. The mean value of the offset stiffness is about 550 Nm/rad and is applicable to a large range of walking speed from 1 m/s to 1.8 m/s.

A summary of the parameters values of the above design goals are provided in the following table:

TABLE 4.1

Design Specifications

| | |
|---|---|
| Weight (kg) | 2.5 |
| Max. Allowable Dorsiflexion (deg) | 15 |
| Max. Allowable Plantarflexion (deg) | 25 |
| Peak Torque (Nm) | 140 |
| Peak Velocity (rad/s) | 5.2 |
| Peak Power (W) | 350 |
| Torque Bandwidth (Hz) | 3.5 |
| Net Work Done (J) | 10 J at 1.3 m/s |
| Offset Stiffness During CD (Nm/rad) | 550 |

Overall Mechanical Design

It is challenging to build an ankle-foot prosthesis that matches the size and weight of an intact ankle, but still provides a sufficiently large instantaneous power output and torque for the powered plantarflexion {A-6} {A-9}. Typical design approaches {A-27} {A-28} that use a small-sized actuator along with a high gear-ratio transmission to actuate ankle-foot mechanism may not be sufficient to overcome these design challenges for the two reasons. First, due to the high transmission ratio, this approach may have difficulty in generating a large instantaneous output power because the effective motor inertia has significantly increased by N2, where N is the gearing reduction ratio. Second, the large reduction ratio also reduces the system's tolerance to the impact load. During walking, there is a substantial amount of impact load applying on the prosthesis during the heel-strike. This may cause damage to the transmission.

The design approach uses a parallel spring with a force-controllable actuator with series elasticity to actuate an ankle-foot mechanism. The parallel spring and the force-controllable actuator serve as the spring component and the torque source in FIG. 5, respectively. The prosthetic ankle-foot system requires a high mechanical power output as well as a large peak torque. The parallel spring shares the payload with the force-controllable actuator, thus the required peak force from the actuator system is significantly reduced. Consequently, a smaller transmission ratio can be used, and a larger force bandwidth is obtained. The series elasticity is also an important design feature for the ankle-foot prosthesis as it can prevent damage to the transmission due to shock loads, especially at heel-strike.

Figure 6:
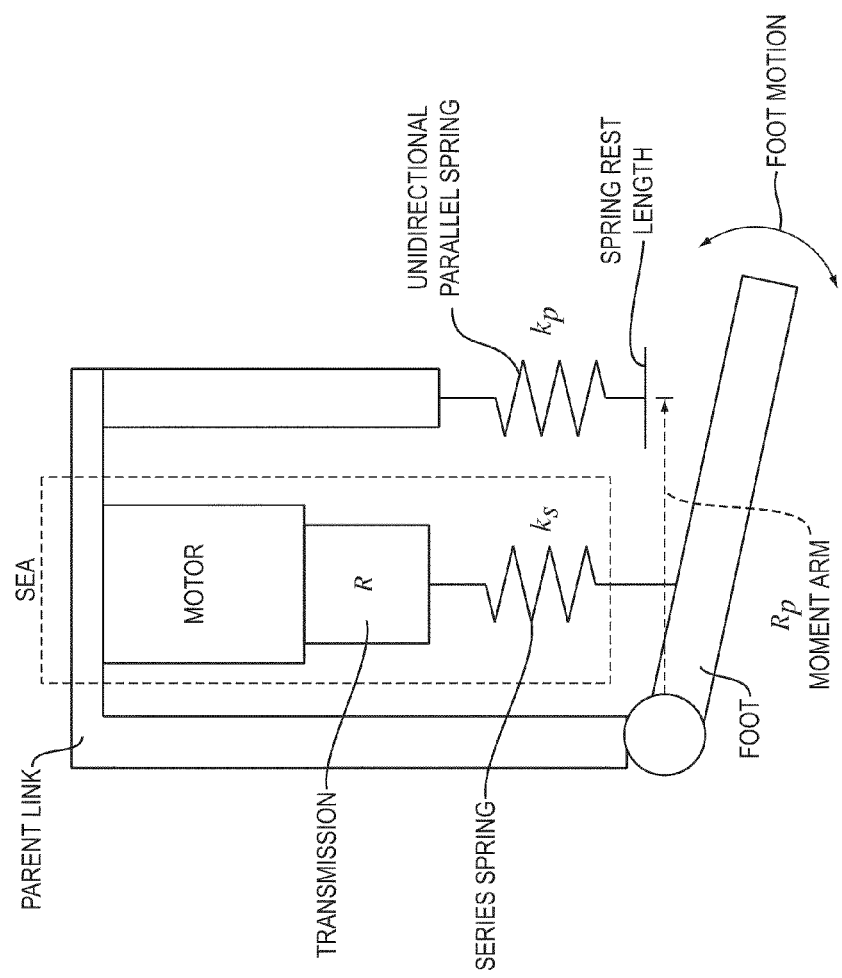
FIG. 6 shows a model of the actuator with series and parallel elasticity.

The basic architecture of the mechanical design is shown in FIG. 6. As can be seen, there are five main mechanical elements in the system: a high power output dace. motor, a transmission, a series spring, a unidirectional parallel spring, and a carbon composite leaf spring prosthetic foot. The first three components are combined to form a force-controllable actuator, called Series-Elastic Actuator (SEA). A SEA, previously developed for legged robots {A-41} {A-42}, consists of a dc motor in series with a spring (or spring structure) via a mechanical transmission. The SEA provides force control by controlling the extent to which the series spring is compressed. Using a linear potentiometer, we can obtain the force applied to the load by measuring the deflection of the series spring.

Figure 7:
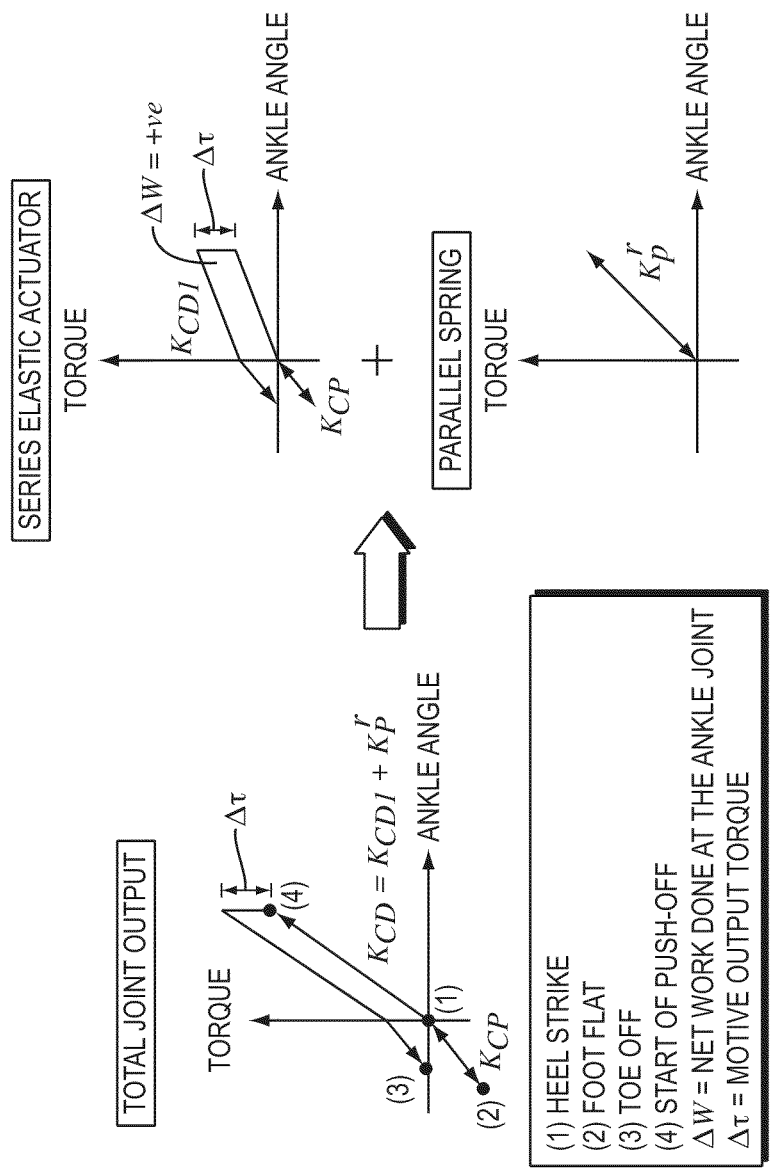
FIG. 7 exploiting the parallel and series elasticity with an actuator.

In this application, the SEA is used to modulate the joint stiffness as well as provide the constant offset torque fit. As can be seen in FIG. 7, the SEA provides a stiffness value KCP during CP and a stiffness value $K_{CD1}$ from CD to PP. From points (4) to (3), it supplies both the stiffness value KCD1 and a constant, offset torque fit.

Due to the demanding output torque and power requirements, a physical spring, configured in parallel to the SEA, is used so that the load borne by the SEA is greatly reduced. Because of the reduced load, the SEA will have a substantially large force bandwidth to provide the active push-off during PP. To avoid hindering the foot motion during swing phase, the parallel spring is implemented as an unidirectional spring that provides an offset rotational stiffness value Kpr only when the ankle angle is larger than zero degree (FIG. 7).

Figure 8:
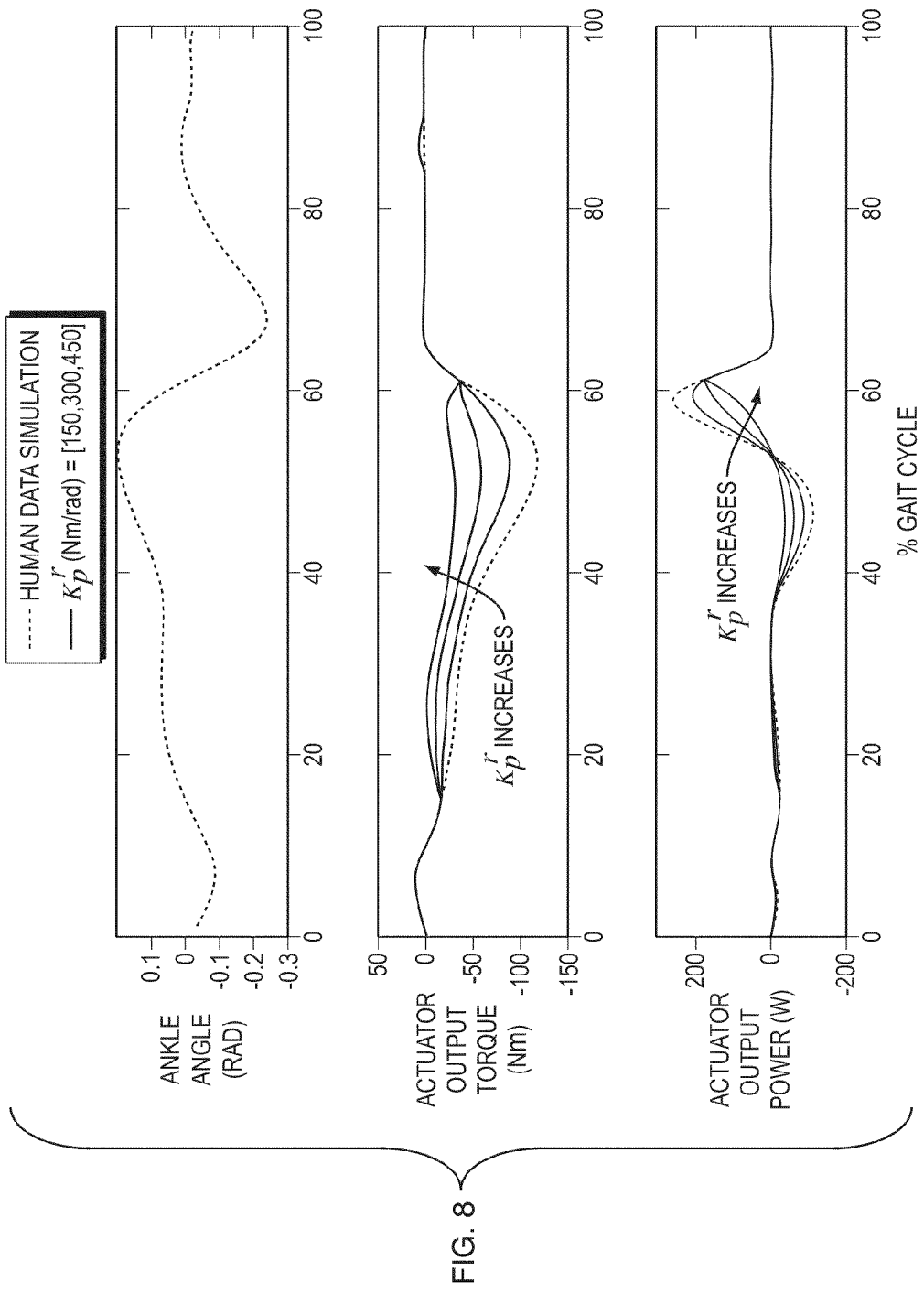
FIG. 8 depicts simulation of the required actuator output torque and power for different parallel springs.

To further understand the benefits of the parallel spring, a simulation was conducted to illustrate the effect of the parallel spring to the reduction of the actuator output torque and power. In the simulation, kinematics of the normal human ankle (FIG. 8) was applied to the prosthesis depicted in FIG. 6, while the prosthesis were required to output a similar torque and power profiles as the normal human ankle does for a gait cycle. Assuming that the force-controllable actuator (SEA) in the prosthesis is a perfect torque source and is able to output any given torque trajectory. If there is no parallel spring, the actuator output torque and power behavior have to be the same as that of a normal human ankle. When the stiffness of the parallel spring was increased, the actuator output torque and power were significantly reduced. (FIG. 8). For example, in the simulation, the required peak actuator output power (174 W) with $K^r_p$=300 rads was about 35% less than the case (265 W) without the parallel spring. Furthermore, with that parallel spring, the peak output torque was reduced from 118Nm to 60Nm. In addition, the positive work done by the actuator was reduced from 18.3 J to 11.8 J. Although increasing the parallel spring stiffness can substantially reduce the actuator peak output torque and power, the stiffness of the parallel spring should not be set above the nominal offset stiffness. If the parallel spring is too stiff for the amputee user, the force controllable actuator may need to provide negative stiffness to compensate the excess stiffness of the parallel spring.

The elastic leaf spring foot is used to emulate the function of a human foot that provides shock absorption during foot strike, energy storage during the early stance period, and energy return in the late stance period. A standard prosthetic foot, Flex Foot LP Vari-Flex {A-1} is used in the prototype.

System Model

Figure 9B:
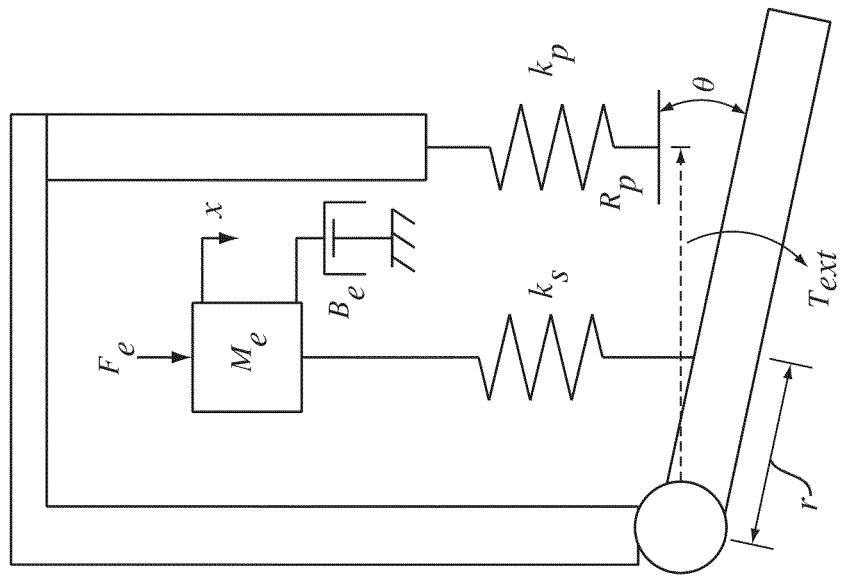
FIGS. 9A and 9B: linear models for the prosthesis. (a) rotary domain (b) translational domain.
Figure 9A:
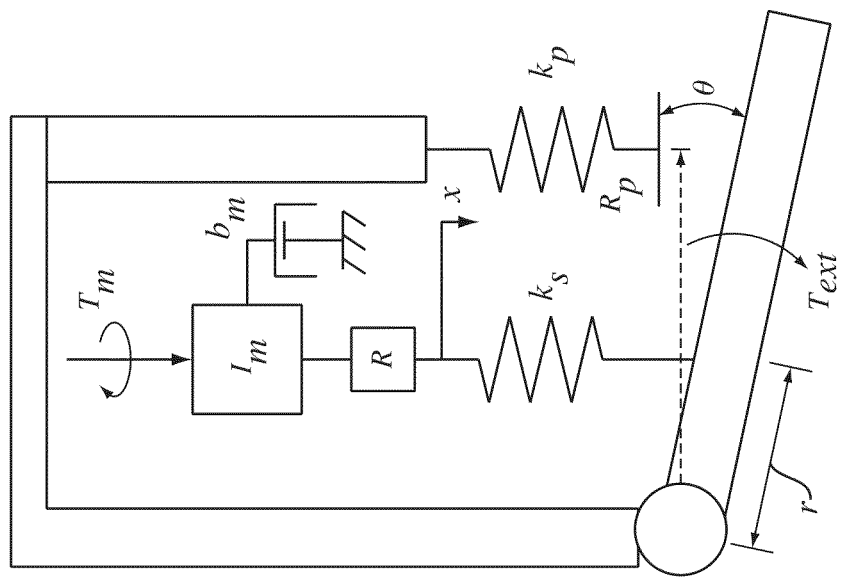

A linear model is proposed in FIGS. 9A and 9B that is sufficient to describe the essential linear behavior of the prosthesis. The model is adopted from the standard SEA model {A-42}, except that this model is applied to a rotational joint system and also include a unidirectional parallel spring into the model. Referring to the FIG. 9A, the motor is modeled as a torque source Tm with a rotary internal inertia Im, applying a force to the series spring ks through a transmission R. The damping term bm represents the brush and bearing friction acting on the motor. x and θ are the linear displacement of the series spring and the angular displacement of the ankle joint, respectively.

In this model, we assume the foot is a rigid body with negligible inertia because it is relatively very small compared to the effective motor inertia, i.e., Text=rFs where Text and r are the moment arm of the spring about the ankle joint and the torque exerted by the environment to the prosthesis. This model ignores the amplifier dynamics, nonlinear friction, internal resonances, and other complexities.

Figure 44:
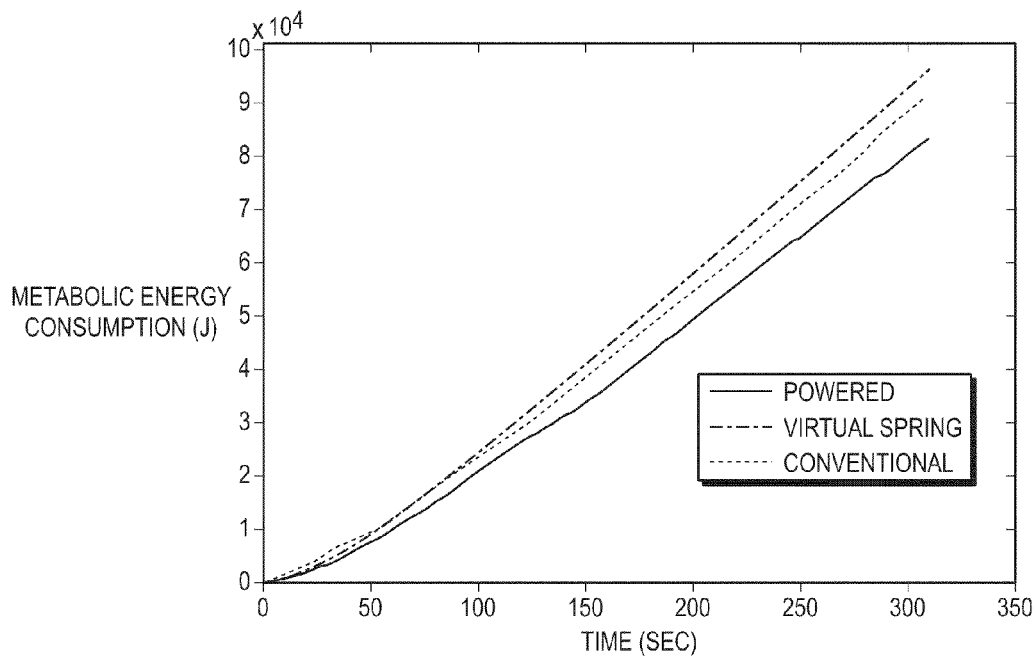
FIG. 44 illustrates a study of metabolic energy consumption of an amputee participant.
Figure 45:
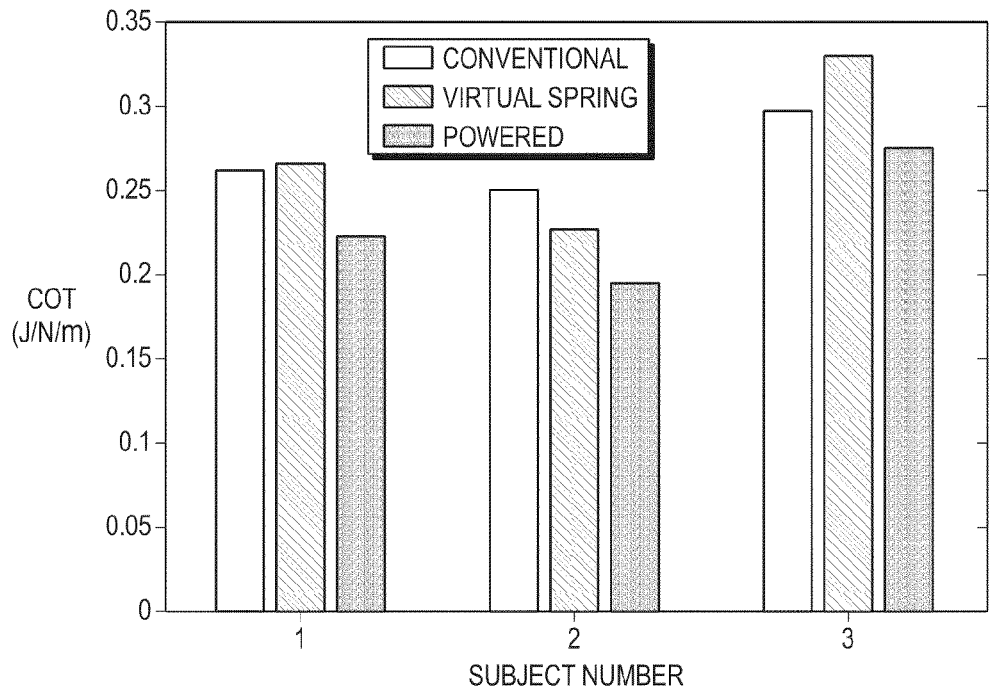
FIG. 45 depicts the metabolic cost of transport for three participants.
Figure 46A:
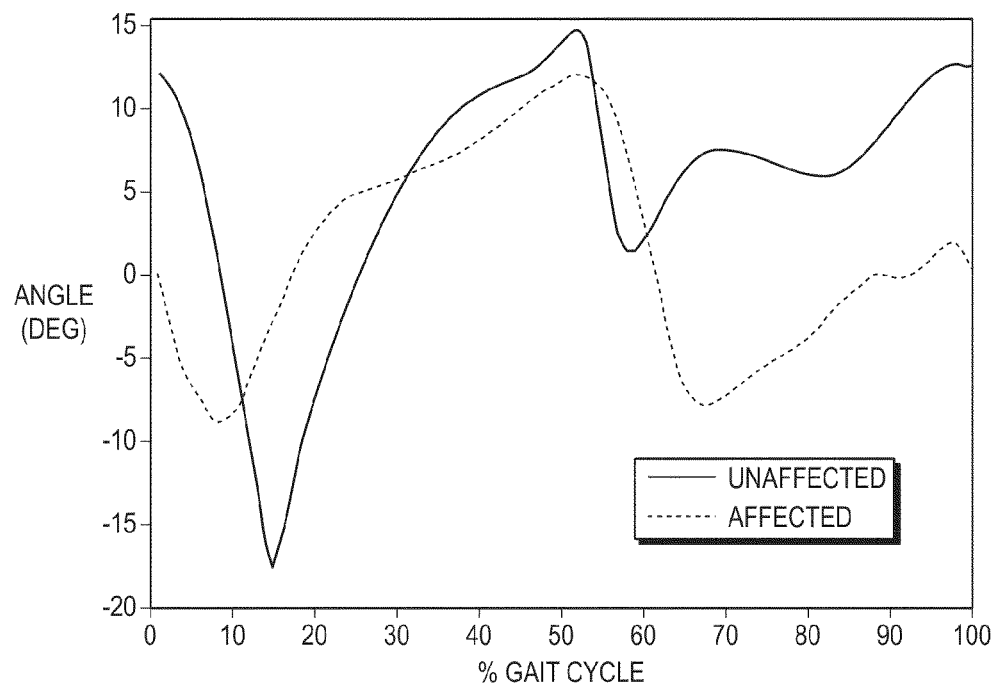
FIGS. 46A and 46B depict the kinematics of ankle joints associated with the two experimental conditions.
Figure 46B:
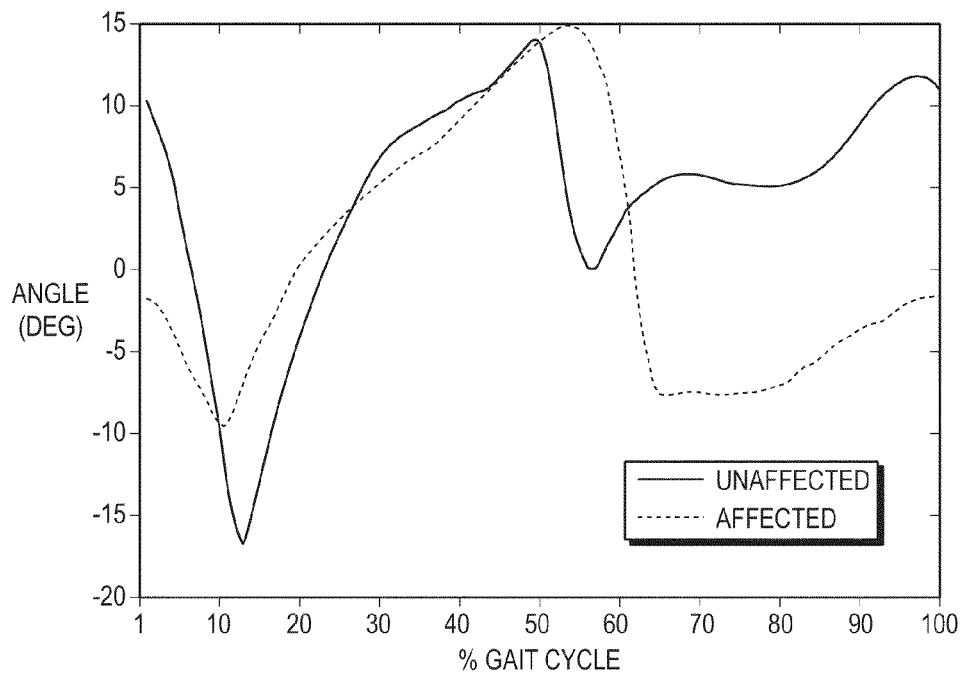
Figure 47:
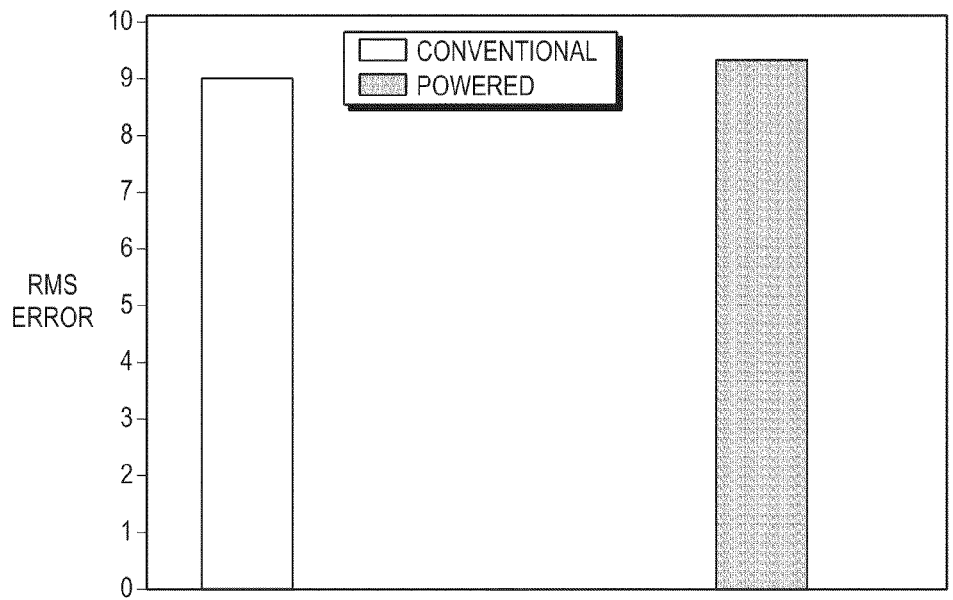
FIG. 47 depicts the kinematics differences of the ankle joint between the affected and unaffected sides for the two experimental conditions.
Figure 48:
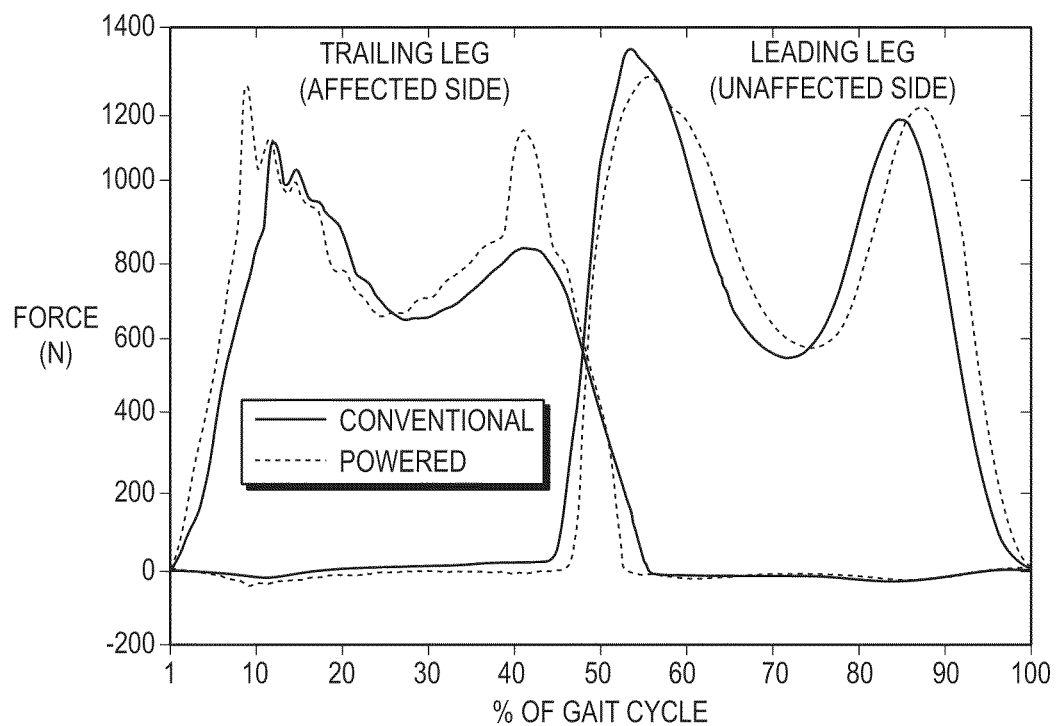
FIG. 48 depicts the average vertical ground reaction forces for both leading and trailing legs over one gait cycle.
Figure 49A:
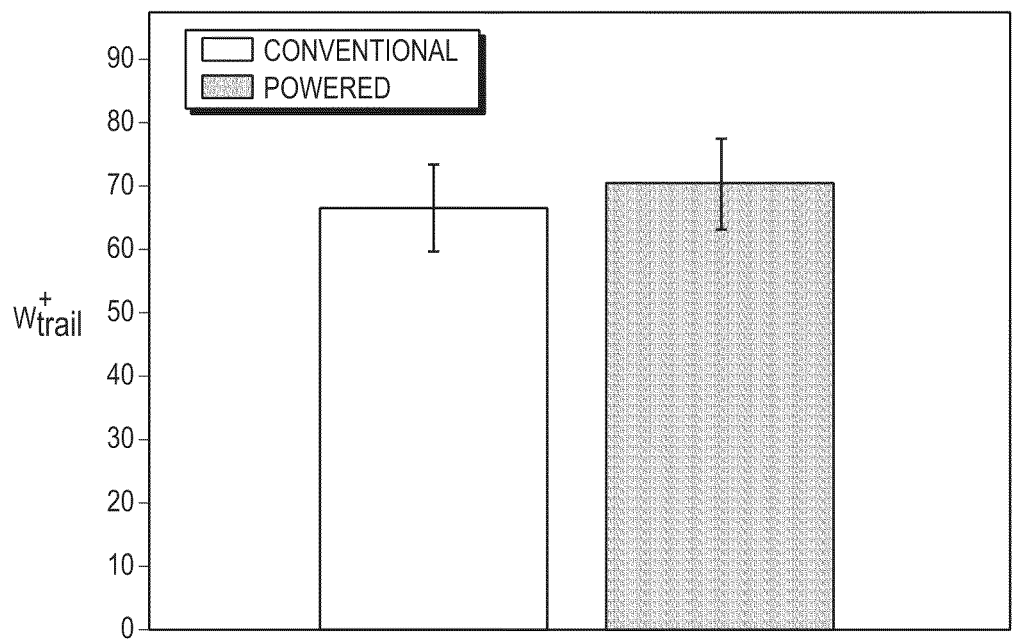
FIGS. 49A and 49B show comparisons of the external work done on the com by each limb for two experimental conditions.
Figure 49B:
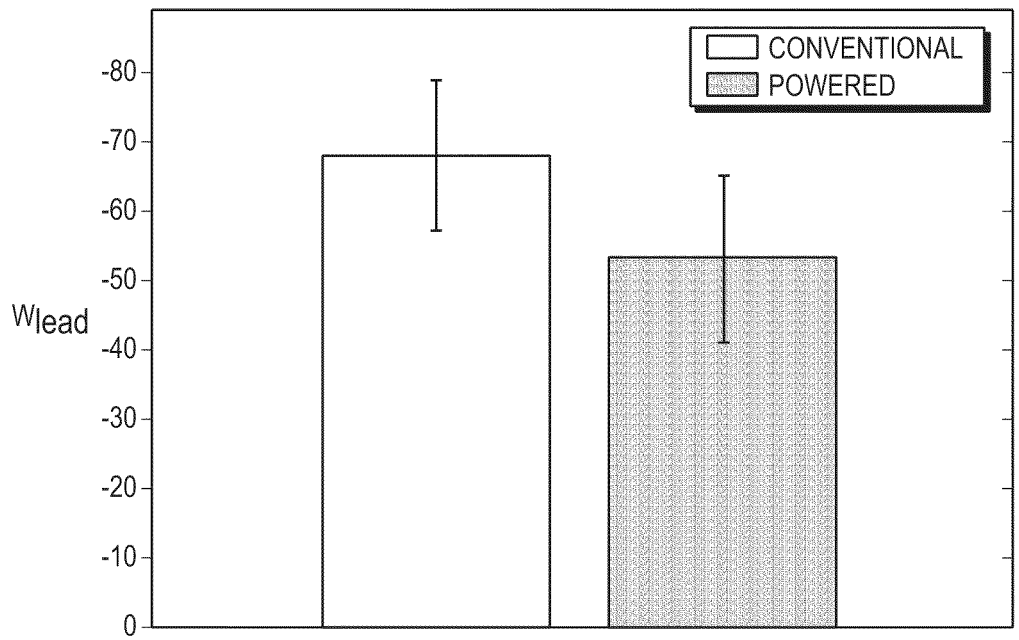
Figure 50:
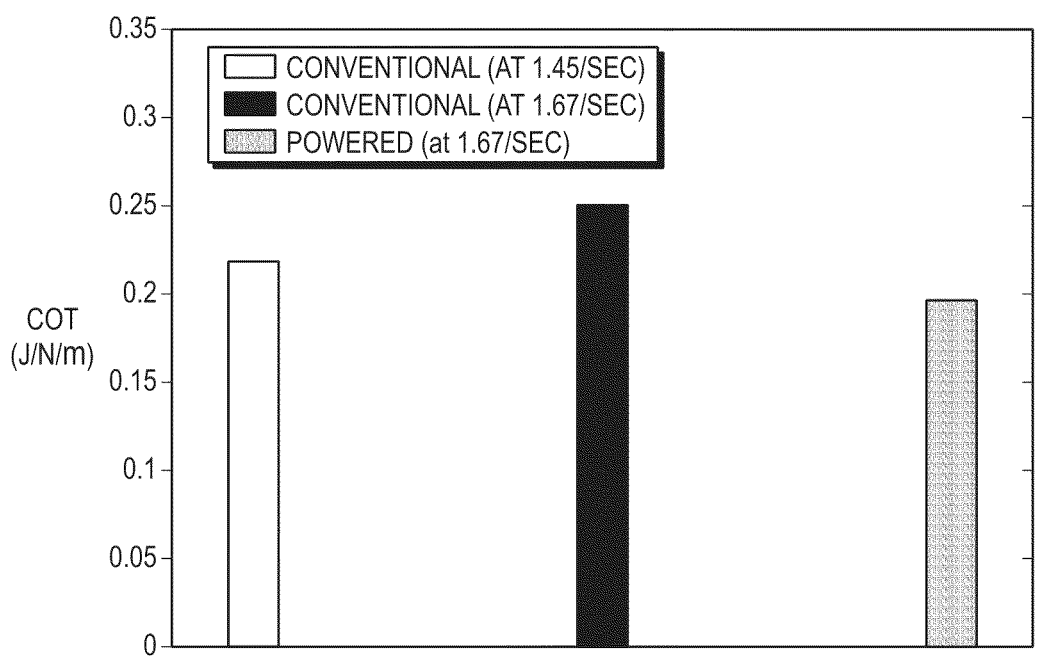
FIG. 50 shows comparisons of the metabolic cost of transport for a participant for different walking speeds.
Figure 51A:
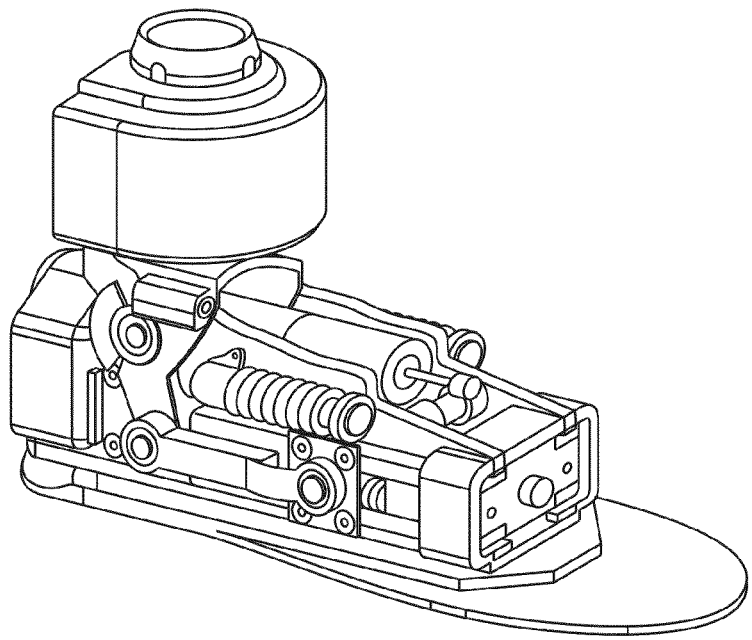
FIGS. 51A and 51B show a prototype ankle-foot prosthesis.
Figure 51B:
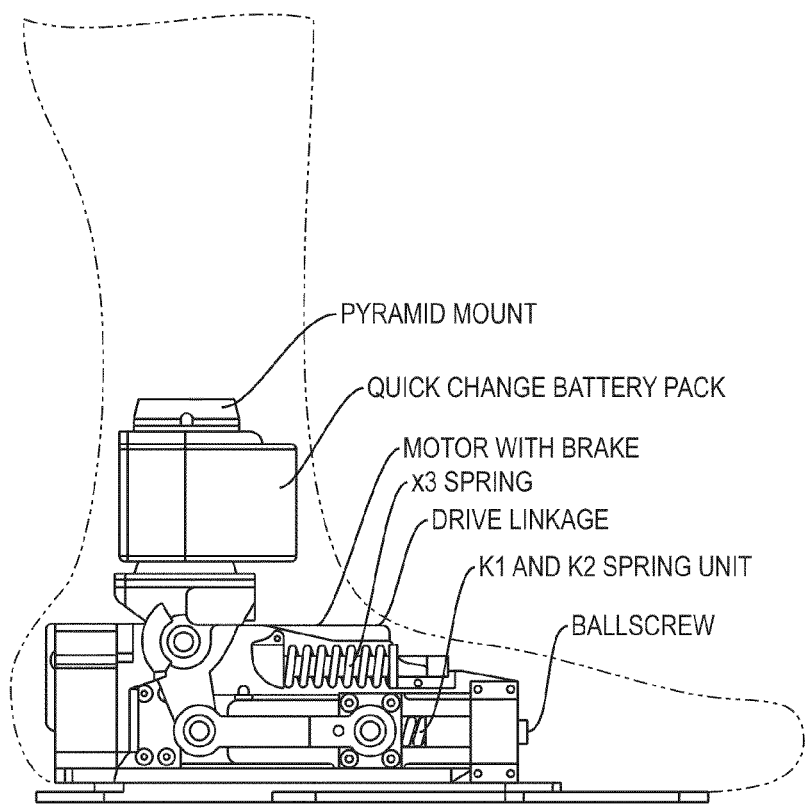

For simplicity, we then convert the model into translational domain (see FIG. 44(b)). Me, Be, and Fe represent the effective mass, damping, and linear force acting on effective mass, respectively. These components are defined as follows: Me=$I_m$R, Fe=$T_m$R, Be =$B_m$R. The equation of motion becomes:

$$M_e \ddot{x} + B_e \dot{x} = F_e + F_s \quad (4.1)$$

$$F_s = k_s(r\theta - x) \quad (4.2)$$

while the total external torque or total joint torque $$T_{ext} = \begin{cases} rF_s & \theta < 0 \\ rF_s + R_p k_p \theta & \theta \geq 0 \end{cases} \quad (4.3)$$

Eqns. (4.1) and (4.2) are the standard dynamic equations for a SEA {A-42}. Eqn. (4.3) reveals that with the parallel spring, less spring force Fs is required for a given total joint torque. This model is used to guide the design and control analysis presented below.

Design Analysis

In this section, both steady-state and dynamic design analyses are proposed to guide the design of the powered prosthesis. These analyses focus on designing the prosthesis to satisfy the torque-speed characteristic and torque bandwidth requirement specified in Section 4.1. The steady-state analysis assists in designing the maximum torque-speed characteristic of the prosthesis to bracket that of the human ankle during walking. The dynamic analyses guides us to select the system components (e.g. series spring) to maximize the prosthesis output acceleration and meet the torque bandwidth requirement. The details of the analyses are described as follows.

Steady-State Analysis for Design

The purpose of the steady-state analysis provides a calculation on the maximum torque/power-speed characteristic of the prosthesis. This help us select the actuator and transmission for the prosthesis such that its maximum torque/power-speed characteristics can match with that of an intact ankle (FIG. 3). This analysis focuses on the effect of the actuator saturation and transmission ratio to the maximum torque-speed characteristic, thus the effect of the parallel spring, series spring, and the frictional loss in the brush motor are not taken into account in this analysis. The actuator and transmission selection will then be verified using the dynamic analysis discussed in Section 4.4.2. With this assumption, the ankle joint torque becomes Text=rRTm. Because motors have limits to the instantaneous torque and velocity output capabilities, a motor's performance is generally bounded by $$T_m(\omega) \leq T_m^{max} - \omega \left( \frac{T_m^{max}}{\omega^{max}} \right) \quad (4.4)$$

where $T_m$, w, $T_m^{max}$, $w^{max}$ are the motor torque, motor velocity, motor stall torque, and maximum motor velocity, respectively. Let $R_{total}$=rR be the total transmission ratio of the system. Then the torque-speed characteristics of the prosthesis is bounded by $$T_{ext}(\dot{\theta}) \leq R_{total} T_m^{max} - R_{total} \dot{\theta} \left( \frac{T_m^{max}}{\omega^{max}} \right) \quad (4.5)$$

If we define a torque trajectory $T_h(\dot{\theta})$ that represents the normal human ankle torque-speed characteristic as shown in FIG. 3, the design goal is to have $T_{ext}(\dot{\theta})$ always greater than $T_h(\dot{\theta})$ for any given velocity or $$T_h(\dot{\theta}) < T_{ext}(\dot{\theta}) \quad \forall \dot{\theta} \quad (4.6)$$

$$\leq R_{total} T_m^{max} - R_{total} \dot{\theta} \left( \frac{T_m^{max}}{\omega^{max}} \right) \quad \forall \dot{\theta} \quad (4.7)$$

Figure 10A:
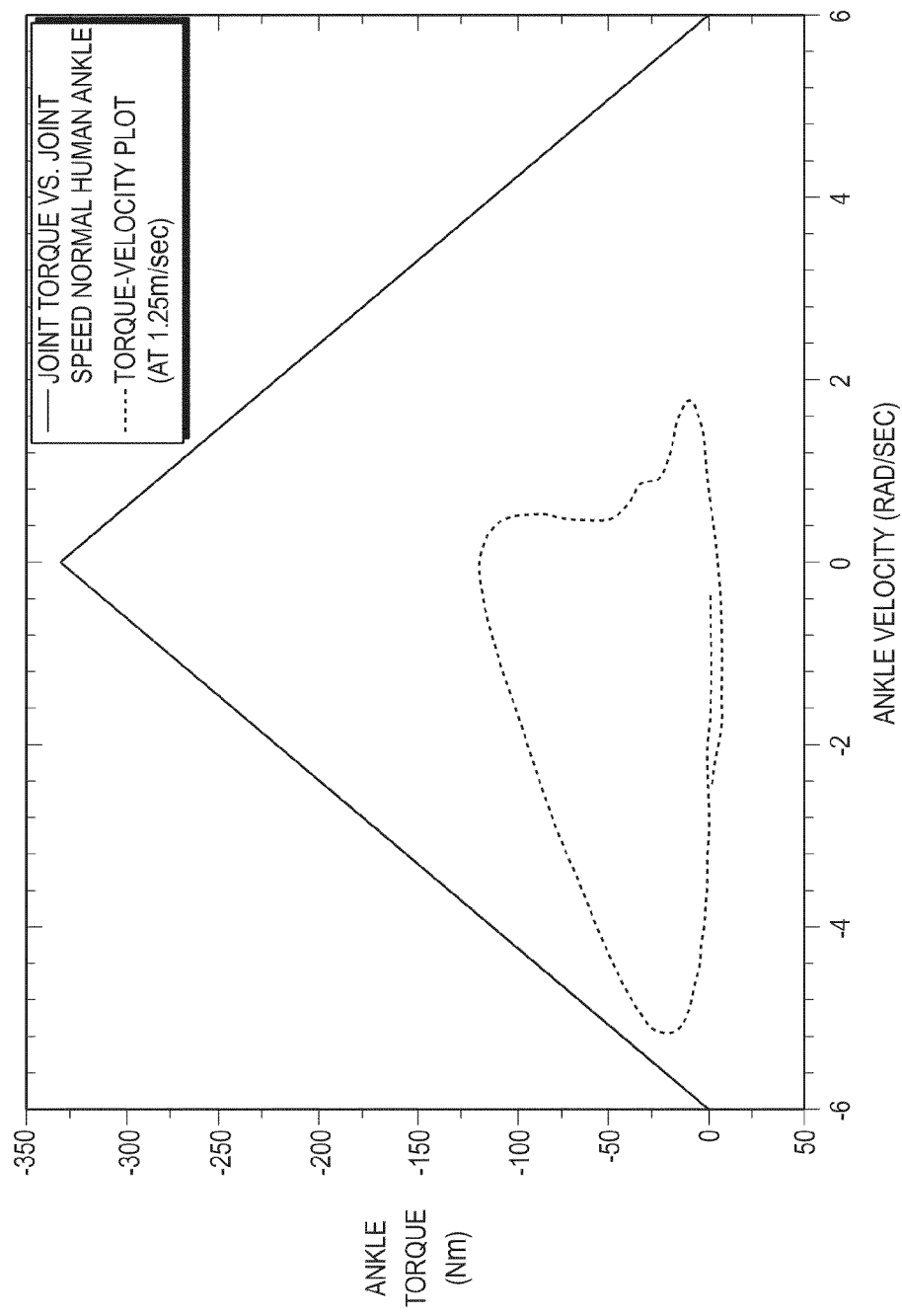
FIGS. 10A and 10B: comparisons of the maximum joint torque/power-speed characteristic of the prosthesis to that of the normal human ankle during walking.
Figure 10B:
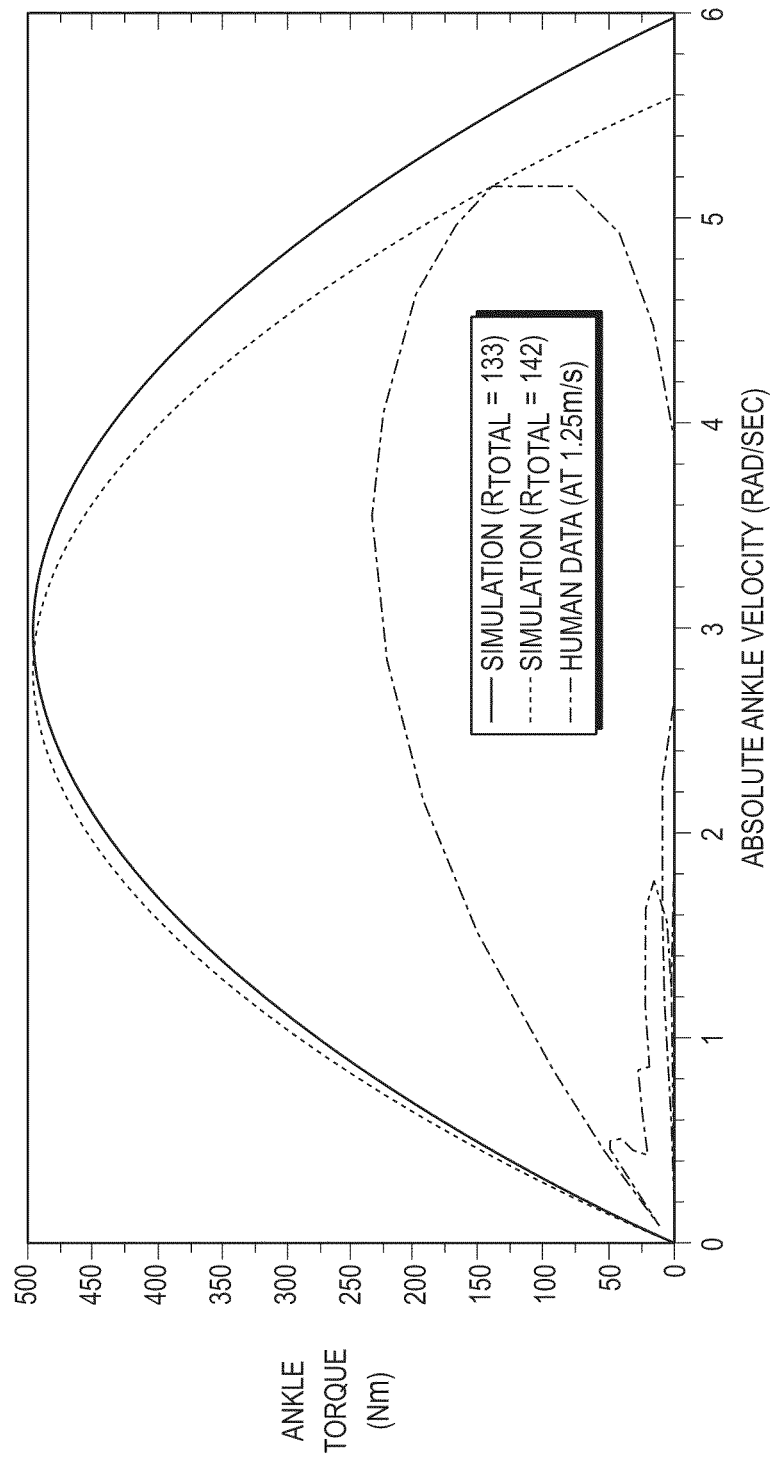

Eqn. (4.7) demonstrates the primary design goal of the prosthesis, i.e., the selection of the motor and transmission values for the prosthesis should always satisfy Eqn. (4.7). Practically, there are many other engineering factors that may reduce the maximum torque output of the actual prototype such as frictional loss, stiction, current saturation of motor amplifier, and geometry of the transmission, it is favorable to have the maximum output torque at least two times larger than the required one. FIGS. 10A and 10B shows a simulation of the maximum torque/power-speed characteristics of the prosthesis with different total transmission ratios. In the simulation, a d.c. brush motor from Maxon, Inc with a part number RE-40 was used. Its stall torque and the maximum angular velocity of the motor are up to 2.5 Nm and 7580 rpm, respectively. To Eqn. (4.7), we used a transmission ratio R~3560 and moment arm r=0.0375 m, i.e. Rtotal=133. As indicated in FIG. (a), the contour of the maximum torque profile of the designed prosthesis was always larger than that of the normal human ankle. Furthermore, the power output characteristics of the prosthesis was designed to match with that of the intact ankle during walking, where they both output peak power around 3 rad/s. It was also found that the maximum allowable transmission ratio is about 142. Eqn. (4.7) will not be satisfied for any $R_{total}$ larger than 142 for the given motor.

Dynamic Analysis for Design

Satisfying the torque/power-speed constraint in the steady-state analysis is the basic design requirement for the prosthesis. However, it does not guarantee that the prosthesis is actually capable of mimicking the normal ankle behaviors in the dynamic condition. This section explores the system output acceleration and its relationship to the choice of the transmission ratio and parallel spring and the output force bandwidth of the prosthesis in the consideration of motor saturation.

System Output Acceleration

The primary performance measure for a powered ankle-foot prosthesis is determined by how fast the prosthesis can output a constant offset torque Δt to an amputee user during PP. The key to maximizing the step response performance is to maximize the system output acceleration. According to {A-49} {A-51}, there are two basic principles of maximizing the system output acceleration for a given load: (a) If the source inertia is adjustable, the source inertia should be minimized; (b) For a given source inertia, select a transmission ratio such that the input and output impedance of the system can be matched. However, in practice, motors always have a finite inertia which is not adjustable. Thus, in general, the second approach is normally used to maximize the system output acceleration in machine design.

Figure 11:
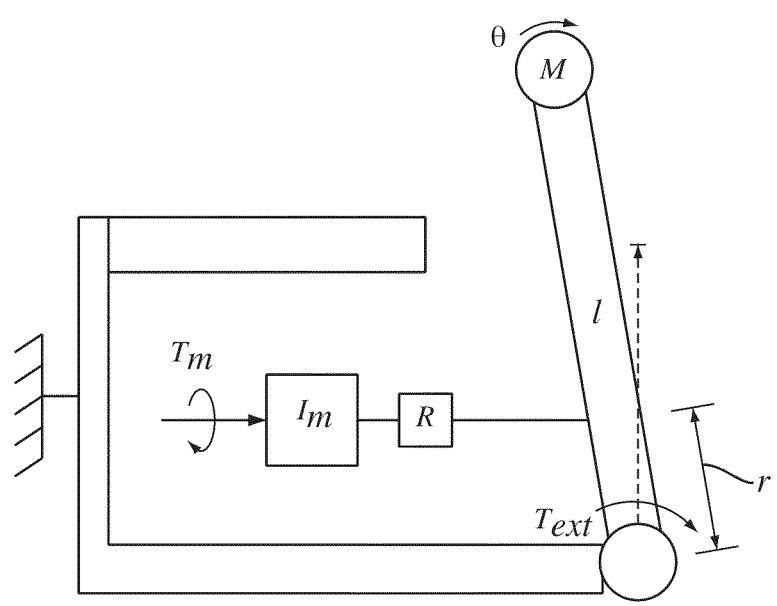
FIG. 11 depicts model to study the system output acceleration.

The model shown in FIG. 11 represents the prosthesis driving a fixed load mass M and provides insights into the effect of the load mass and the transmission ratio to the output acceleration for a given actuator torque and internal inertia. The effect of the parallel, series elasticity, the frictional loss in the system will be considered later in this section.

The dynamic equation of this model can be written as $$\ddot{\theta} = \frac{T_m R_{total}}{Ml^2 + I_m R_{total}^2} \quad (4.8)$$

where $R_{total}=rR$. Differentiating Eqn. (4.8) with respect to $R_{total}$ gives the optimal transmission ratio $$R_{opt} = \sqrt{\frac{Ml^2}{I_m}} \quad (4.9)$$

The maximum output joint acceleration $\ddot{\theta}_{max}$ for a given actuator effort is $$\ddot{\theta}_{max} = \frac{T_m}{2\sqrt{I_m M}} \quad (4.10)$$

Figure 12:
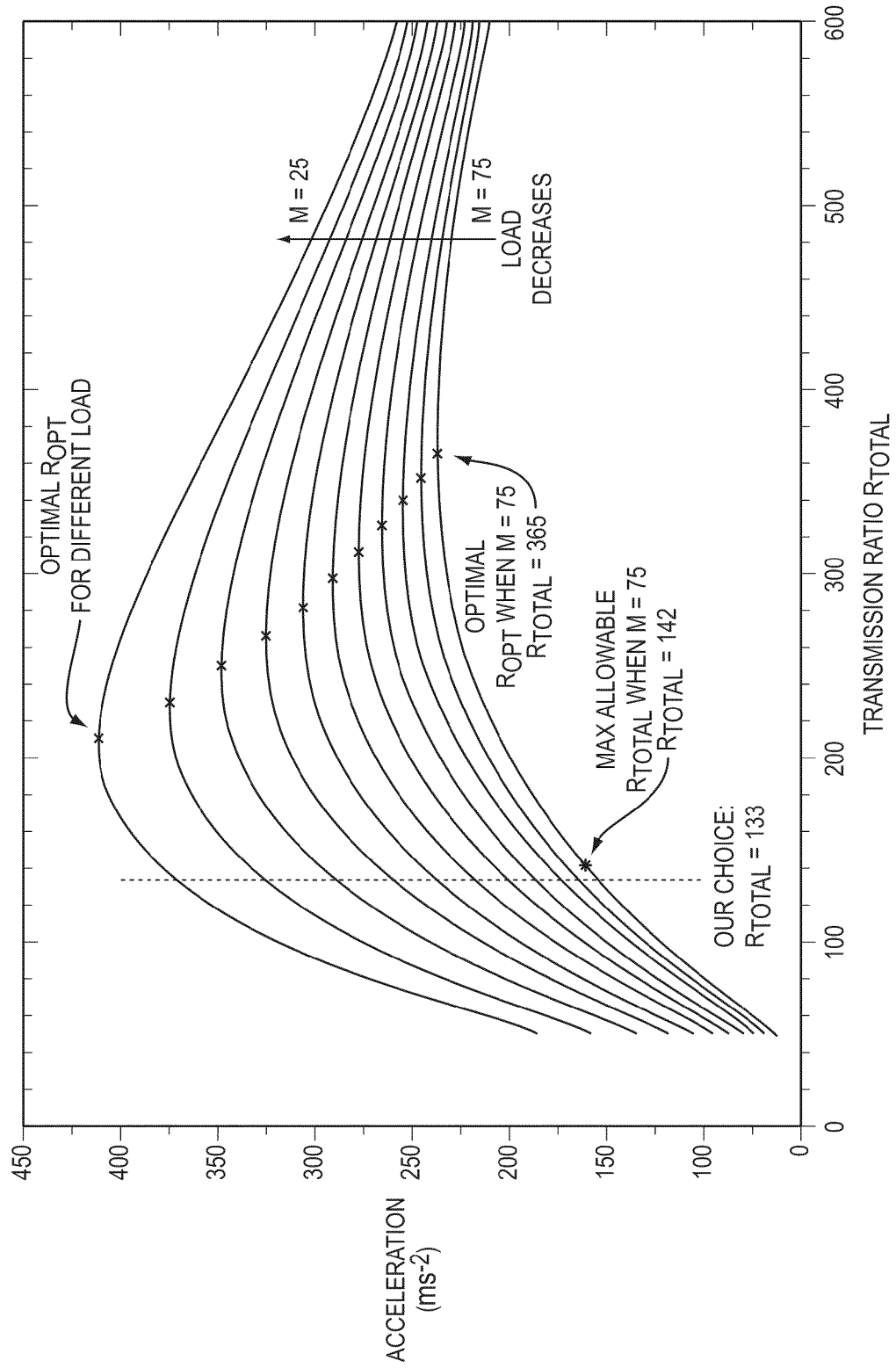
FIG. 12 depicts the system output acceleration of various transmission ratio and load mass.

FIG. 12 shows the system output acceleration of various transmission ratios and load masses. In this simulation, the motor inertia Im=134 g-cm2 and load mass from 25-75 kg. Using the optimal transmission ratio does not guarantee that the system can fulfill the torque-speed constraints specified in Eqn. (4.7). It is noted that for a given motor inertia, the optimal transmission ratio is always larger than the allowable transmission ratio (Rtotal=142) obtained in Section 4.4.1.

According to {A-51}, adding the frictional loss or damping term into the model will only lower the peak acceleration, but not significantly change the overall relationship between the transmission ratio and the output acceleration for a given actuator effort as shown in FIG. 12.

Figure 13:
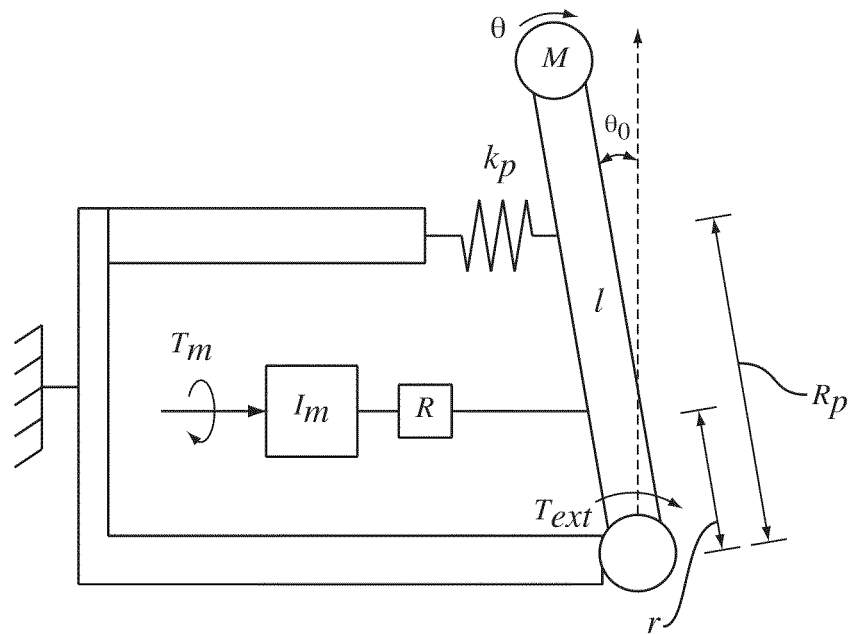
FIG. 13 depicts a model to study the system output acceleration with the unidirectional spring.

The effect of the model with parallel elasticity can be described using the model in FIG. 13. Consider the case when the motor drives the load mass forward while the unidirectional spring has been preloaded by an angle θo. The instantaneous system acceleration can then be written as $$\ddot{\theta} = \frac{T_m R_{total} + K_p R_p \theta_o}{Ml^2 + I_m R_{total}^2} \quad (4.11)$$

Besides the term KpRpθo due to the parallel spring, Eqn. (4.11) is exactly the same as Eqn. (4.8). This term allows the system to output the acceleration with less actuator effort. In other words, the system can generate higher peak acceleration for a given actuator effort. In addition, differentiating Eqn. (4.11) w.r.t $R_{total}$ will give us the same optimal transmission ratio as described in Eqn. (4.9).

The series spring affect the dynamic behavior of the system. Generally speaking, adding a series spring degrades performance properties of the prosthesis such as the system output acceleration and system bandwidth {A-42}. In the next section, some basic principles that guide the selection of the series spring to satisfy the desired dynamic requirements are discussed.

Large Force Bandwidth of the System

Before designing any controllers for a SEA, we need to guarantee that the system will not run into any saturation or system limitation within the operating range of the torque level and bandwidth. One suggested index to measure the limitation of the system's dynamic performance is the "large force bandwidth" {A-42}. Large force bandwidth is defined as the frequency range over which the actuator can oscillate at a force amplitude Fsmax due to the maximum input motor force, Fsat {A-42}. The series elasticity substantially reduces the system bandwidth at large force due to motor saturation. The stiffer the spring is, the higher SEA bandwidth is at large force. The design goal is to select a proper series spring ks such that the large force bandwidth of the SEA is much greater than the required force bandwidth in Table 4.1.

Figure 14:
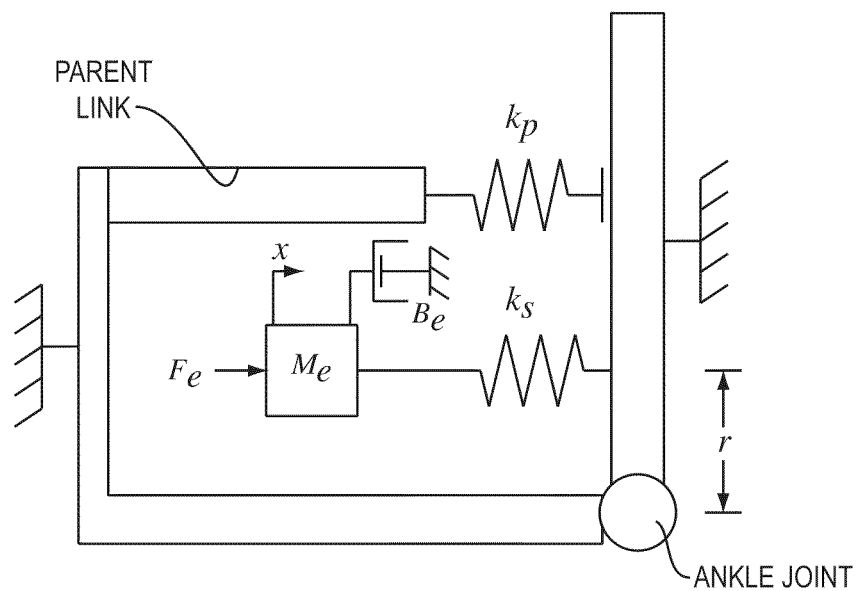
FIG. 14 illustrates a system bandwidth analysis.

To study the large force bandwidth, both ends of the prosthesis are fixed (see FIG. 14), consequently, the parallel spring does not affect the dynamic of the system.

The spring force Fs is considered as the system output. This system is a standard SEA with fixed end condition {A-42}. The transfer function Gfixed(s) between the input Fe and output force Fs of the system is defined as:

$$G_{fixed}(s) = \frac{F_s}{F_e} = \frac{k_s}{M_e s^2 + B_e s + k_s} \quad (4.12)$$

The motor saturation can be thought of as a input motor force $F_{sat}$ in parallel with parallel with a damper of a appropriate damping ratio $$B_{sat} = \frac{F_{sat}}{V_{sat}},$$

where $F_{sat}$, $V_{sat}$ are the maximum motor force and velocity due to the motor saturation, respectively. They are defined as $$F_{sat} = RT_{motor}^{max} \text{ and } V_{sat} = \frac{w^{max}}{R}.$$

Incorporating the damping term $B_{sat}$ into the Eqn. (4.12), the transfer function that describes the large force bandwidth is:

$$\frac{F_s^{max}}{F_{sat}} = \frac{k_s}{M_e s^2 + \left(B_e + \frac{F_{sat}}{V_{sat}}\right)s + k_s} \qquad (4.13)$$

where $F_s^{max}$ is the maximum output force. As can be seen in Eqn. (4.13), the large force bandwidth is independent of the control system, but depends on the intrinsic system dynamics that are determined by the choices of the motor, transmission ratio, and the spring constant.

Figure 15:
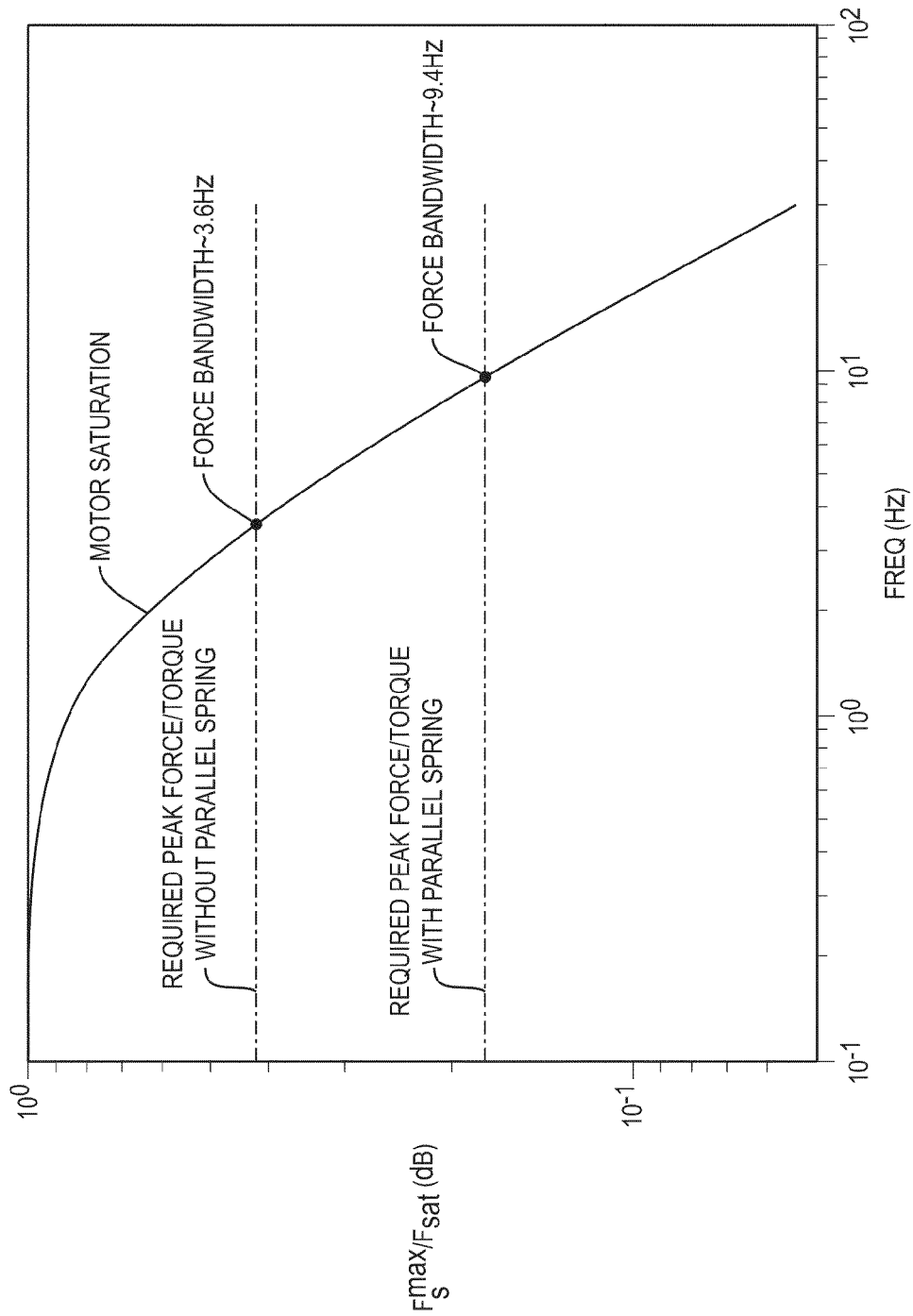
FIG. 15 depicts simulation result for the large force bandwidth due to motor saturation.

FIG. 15 graphically shows the large force bandwidth of the system. In the simulation, ks was set to be 1200 kN/m, while the same motor parameters and transmission ratio were used as in Section 4.4.1. The corresponding model parameters for Eqn. (4.13) were computed and are shown in Table 5.1. The value of the frictional loss Be was based on a measurement from the actual prototype (see Section 4.5.2).

TABLE 4.2

Model Parameters

| Parameters | $F_{sat}$ | $V_{sat}$ | $M_e$ | $B_e$ |
|---|---|---|---|---|
| Values | 7654N | 0.23 m/s | 170 kg | 8250 Ns/m |

As shown in FIG. 15, the estimated large force bandwidth of the system without the parallel spring is 3.6 Hz at 120 Nm, which is slightly larger than the required force bandwidth of the system (3.5 Hz). Note that the lower the required force, the larger the force bandwidth.

Although this simulation only described the output force bandwidth for a fixed-end condition, it can also provide some insights into the effect of the parallel spring on the system bandwidth. According to Eqn. (4.3), the parallel spring shared some of the payloads of the SEA, and the required peak force for the system was significantly reduced. For example, given Rp=0.0375 m, kp=380 rad/s, θ=10 rad, Text=120 Nm, the required peak torque for the SEA is only 50 Nm, and the estimated force bandwidth (9.4 Hz) becomes almost three times larger than the designed one. In practice, it is favorable to design a system whose large force bandwidth is several times larger than the required bandwidth as there are many factors that can substantially reduce the large force bandwidth, such as unmodeled friction.

Figure 16:
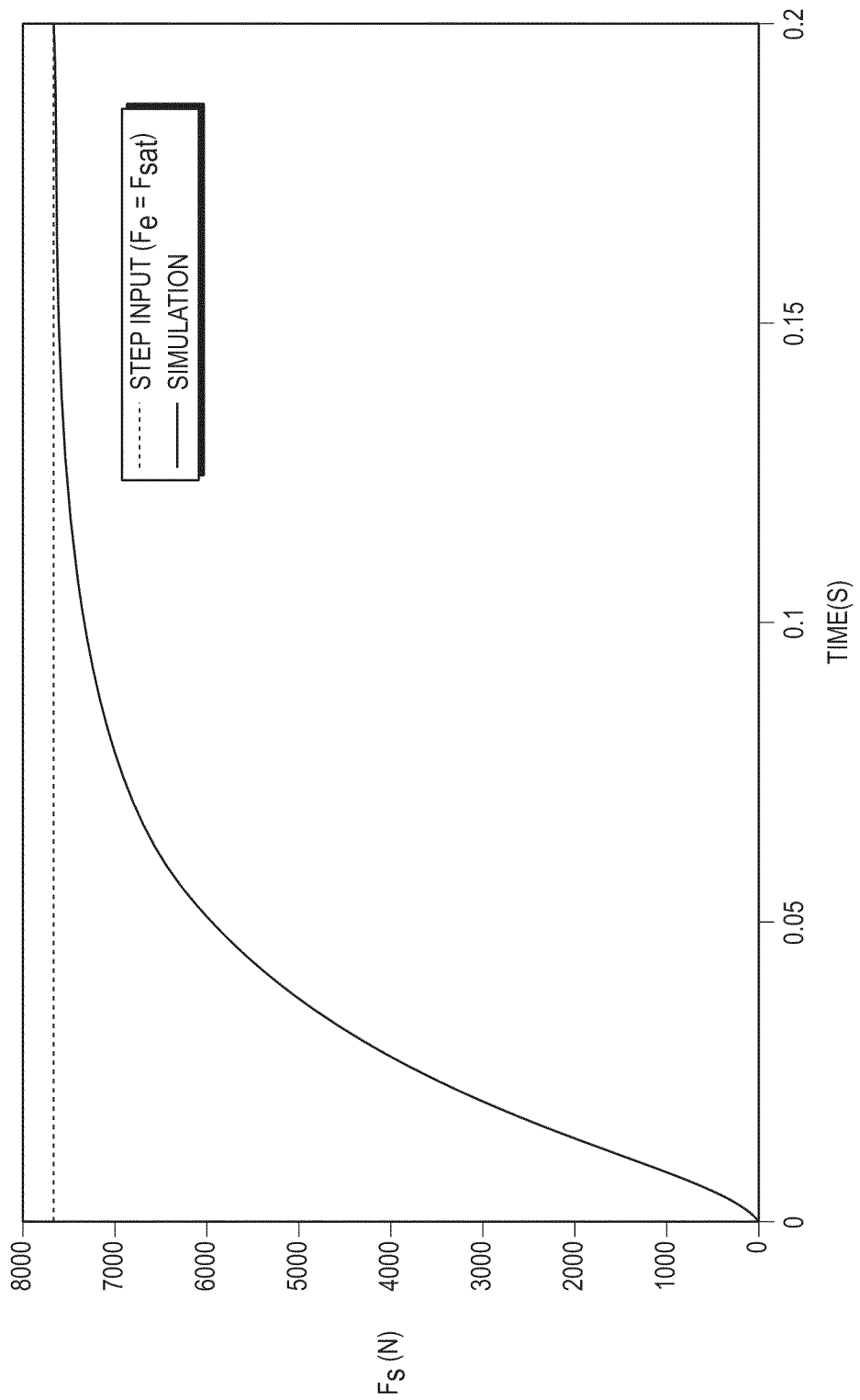
FIG. 16 illustrates a simulation result for the step response

FIG. 16 shows the step response of the prosthesis at Fe=Fsat. Due to the velocity saturation of the motor, the system response is highly over-damped. The settling time of the step response is about 0.2 seconds.

Design Procedure

Below is some suggested procedures/guidelines on the design of the prosthesis.

1 Select a motor and transmission ratio that can fulfill the steady-state requirements in Section 4.4.1.
2 Check the system output acceleration using the suggested motor and transmission ratio using the analysis in Section 4.4.2. Make sure that the suggested motor and transmission can provide sufficient system output acceleration, otherwise re-do step (1).
3 Select the series spring stiffness that have a large force bandwidth larger than the required one in Table 4.1, otherwise re-do step (1) and (2).

Physical Embodiment

FIGS. 17A and 17B, 18A and 18B and 19 show the CAD Model, images, and the schematics of the actual prototype, respectively. The specifications for the current design and the design specifications are compared in Table 4.3. The current design specifications were estimated based on the system components and the simulation results in Section 4.5.1.

TABLE 4.3

A summary of the specifications for the current design

| | Desired Value | Current Design |
|---|---|---|
| Weight (kg) | 2.5 | 2.9 |
| Length (m) | N/A | 0.3 |
| Max. Allowable Dorsiflexion (deg) | 15 | 20 |
| Max. Allowable Plantar flexion (deg) | 25 | 25 |
| Peak Torque (Nm) | 140 | 330 |
| Peak Velocity (rad/s) | 5.2 | 6 |
| Peak Power (W) | 350 | 500 |
| Torque Bandwidth (Hz) | 3.5 | 9 |
| Offset Stiffness (Nm/rad) | 550 | 380 |

Component Selection and Implementation Actuator and Transmission

The firststep in the design is to select an actuator and a transmission to satisfy the torque/power-speed requirements of the human ankle (FIGS. 10A and 10B). In the design, a 150 W d.c. brushed motor from Maxon, Inc (RE-40) was used because its peak power output (500 W) is much larger than the measured peak power in human ankle during walking (350 W). Furthermore, it only weighs 0.45 kg and its stall torque and the maximum angular velocity of the motor are up to 2.5 Nm and 7580 rpm, respectively {A-44}.

Figure 19:
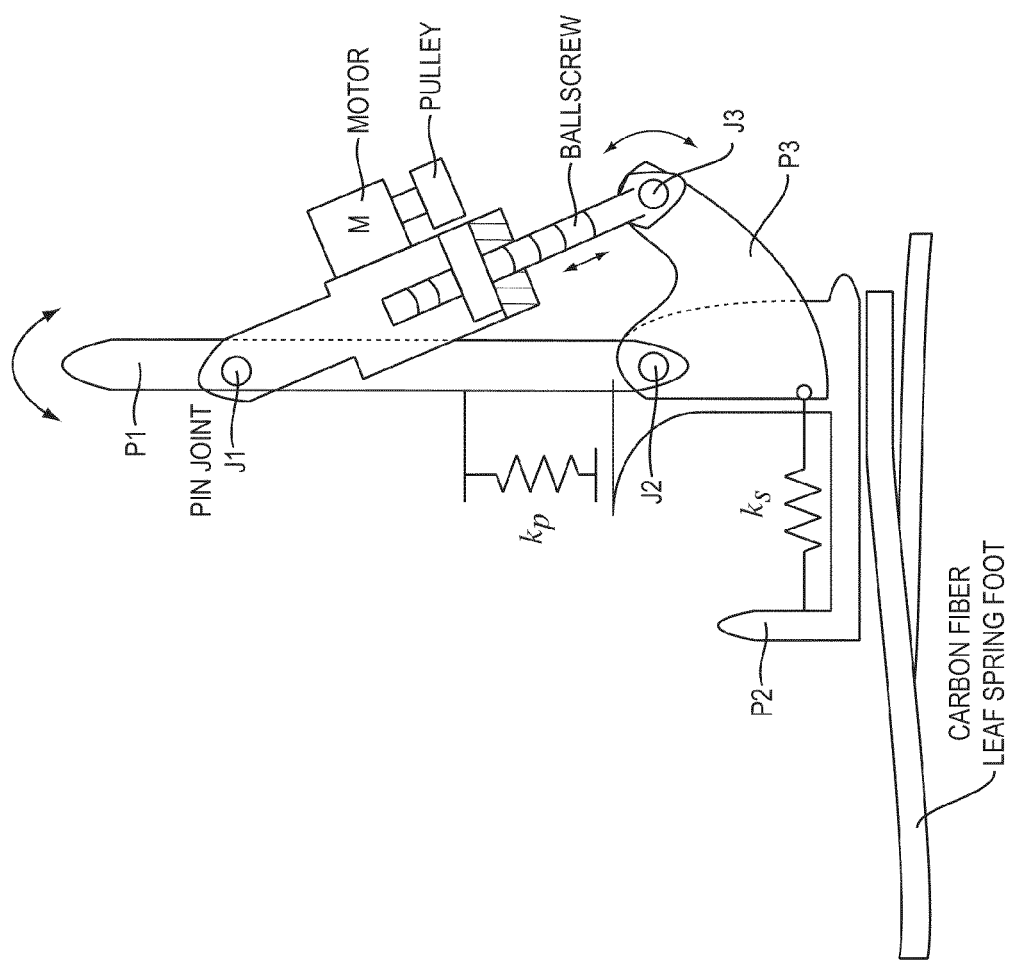
FIG. 19 shows schematics of the actual prototype.

Using the results in FIGS. 10A and 10B, the system required to have a total transmission ratio Rtotal=133 for the given motor and torque-speed constraint. To implement the drive train system, a 3 mm pitch linear ballscrew and a timing-belt drive transmission (ratio=1.7:1) between the motor and the ballscrew were used, i.e. R~3560. The translational movement of the ballscrew causes an angular rotation of the ankle joint FIG. 19 is a schematic of the actual prototype. Torque is transmitted from motor through timing-belt drive, to the ball-nut of the ballscrew. The rotational motion of the ballnut is converted to linear motion of the ballscrew along the line passing through the pins J1 and J3. This linear force is transmitted via rigid link P3 into a compression force on the series springs ks. The other end of the spring pushes on the structure P2 that is attached to joint J2 via a moment arm r=0.0375 m and the series spring (FIG. 17B). The transmission design of a planetary gearhead with a bevel gear {A-26} was not adopted to implement the drive train because the peak torque requirement of an intact ankle often exceeds the torque tolerance of the planetary gearhead. Furthermore, using such a transmission combination often makes the height of the prosthesis taller than the existing one.

Series Spring

According to {A-42}, the selection of the series spring is mainly based on the large force bandwidth criteria. The stiffer the spring is, the higher the SEA bandwidth is at large force. The goal is to choose a series spring such that the large force bandwidth of the SEA is at least two or three times greater than the required force bandwidth.

Based on the results in FIG. 15, a series spring was selected with a spring constant ks equal to 1200 kN/m. With the proposed series and parallel springs, the large force bandwidth of the prosthesis is almost 3 times larger than the required one (FIG. 15). Of course, we can always choose a stiffer series spring to further boost up the system performance, however, it will lower the system's ability in shock absorption and stability of the interaction control {A-42} {A-52}. Furthermore, the stiffer the series spring is used, the more precise measurement of the linear displacement of the series spring is required. This requires for the development of a very high quality analog electronics to sense the linear displacement of the series spring. Regarding the above tradeoffs of using a stiffer spring, we decided to use the proposed spring constant for the series spring.

The series spring was implemented by 4 compression springs which were preloaded and located on the foot (FIGS. 10A and 10B). A detailed descriptions of the ankle mechanism is discussed in {A-26}.

Parallel Spring

A linear parallel spring kp with a moment arm Rp in FIG. 6 provides a rotational joint stiffness $K_{rp}$ (also written as $K_p^r$).

$$K_p^r = (k_p)(R_p)^2 \quad (4.14)$$

The goal is to properly select the moment arm and the spring constant in order to provide the suggested offset stiffness in Table 4.1. In the physical system, due to the size and weight constraints, kp and Rp were chosen to be 770 KN/m and 0.022 m, respectively. Consequently, KPr=385 rad/s. Because this value is smaller than the suggested stiffness (550 rad/s), the SEA supplements the required joint stiffness (see FIG. 7). In FIG. 15, the simulation result suggests that the current design of the parallel spring is necessary to meet the force bandwidth requirement of the prosthesis.

Figure 17A:
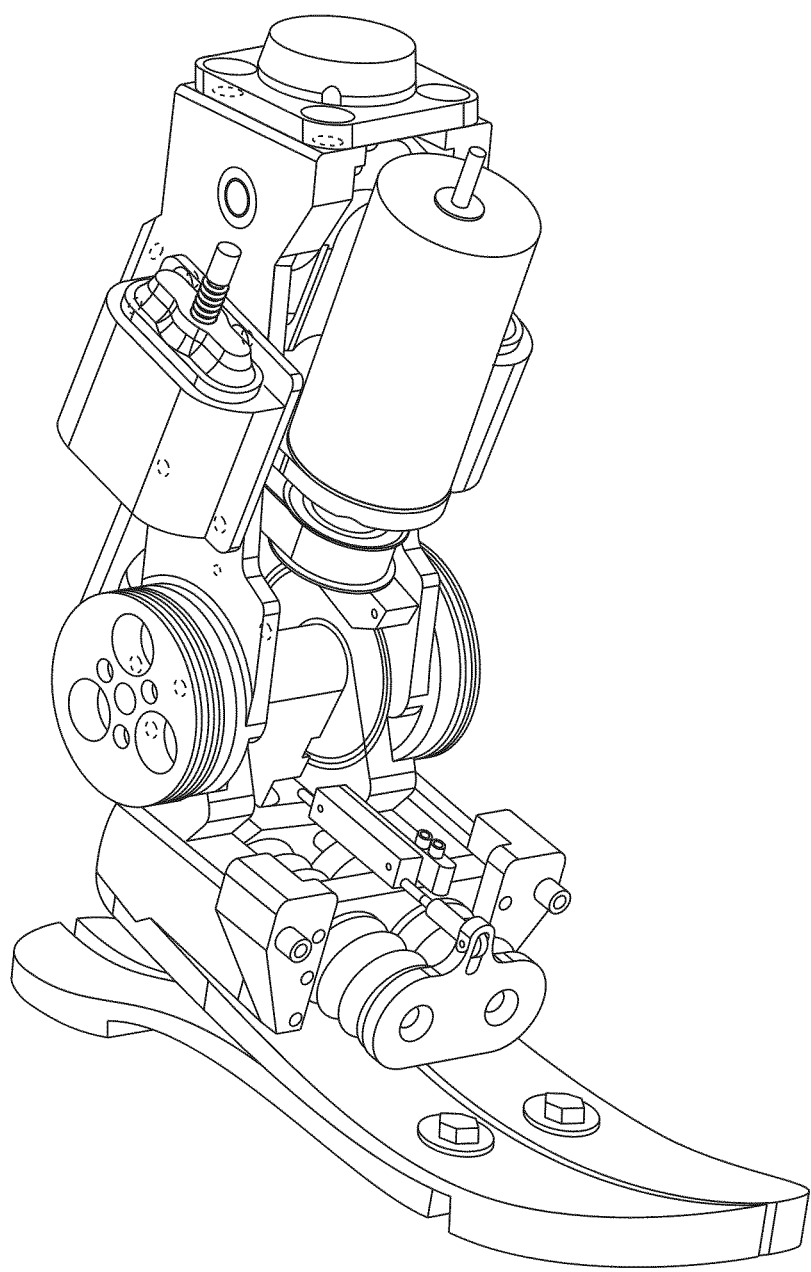
FIGS. 17A and 17B illustrates a mechanical design of the prosthesis.
Figure 17B:
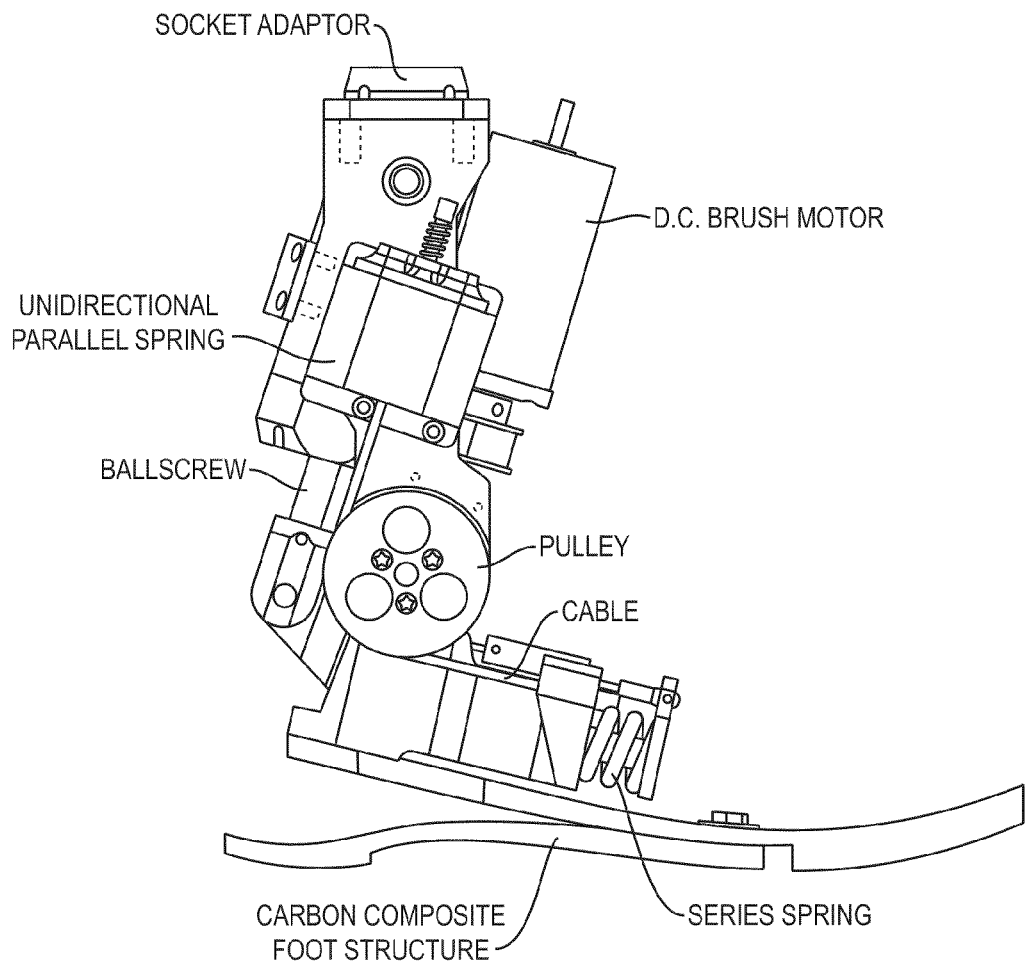
Figure 18A:
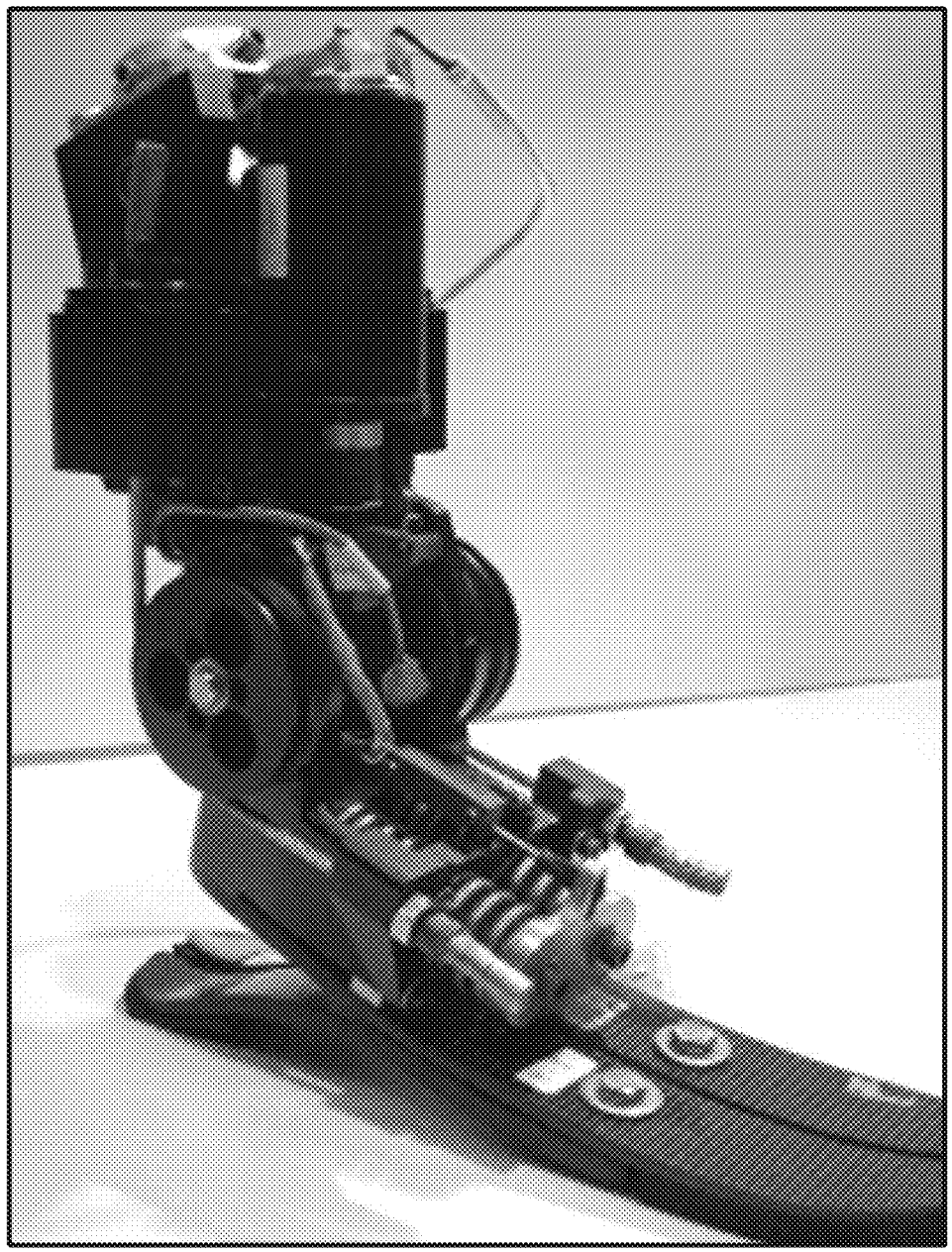
FIGS. 18A and 18B shows pictures of the actual prototype.
Figure 18B:
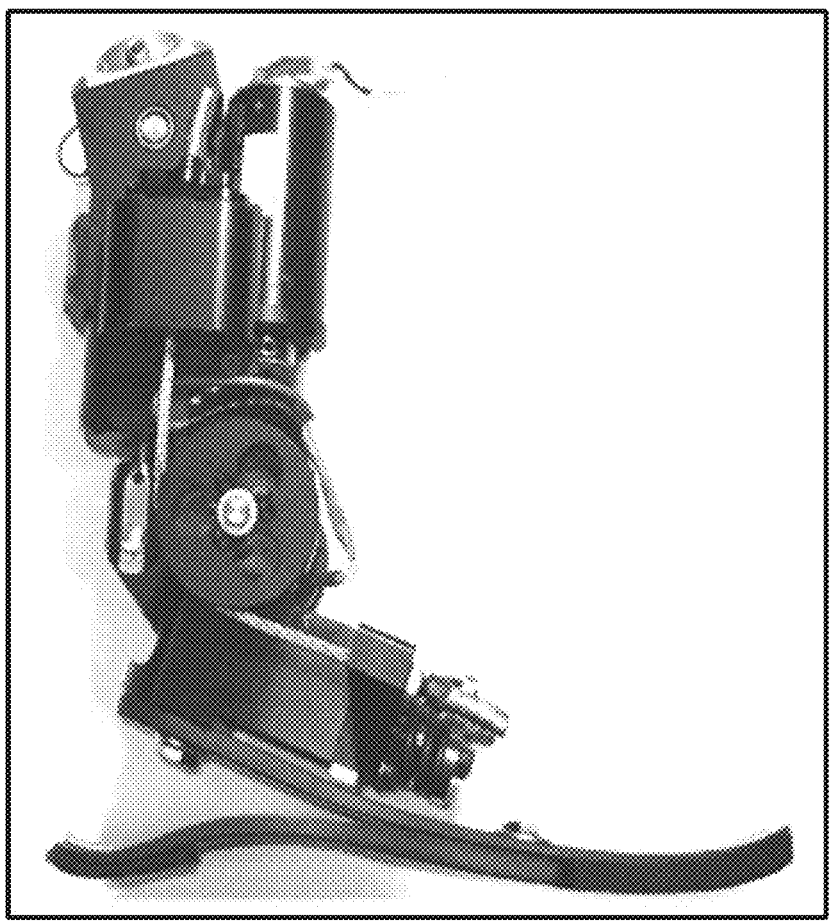

As shown in FIGS. 17A and 17B, the parallel spring was implemented by 4 separate die springs (each with a spring constant equal to 192 Nm/m), two on each side of the structure. There are cables wrapping around a pulley (Rp=0.022 m) on each side to stretch the die springs when the joint angle are larger than zero degree.

System Characterization

Figure 20:
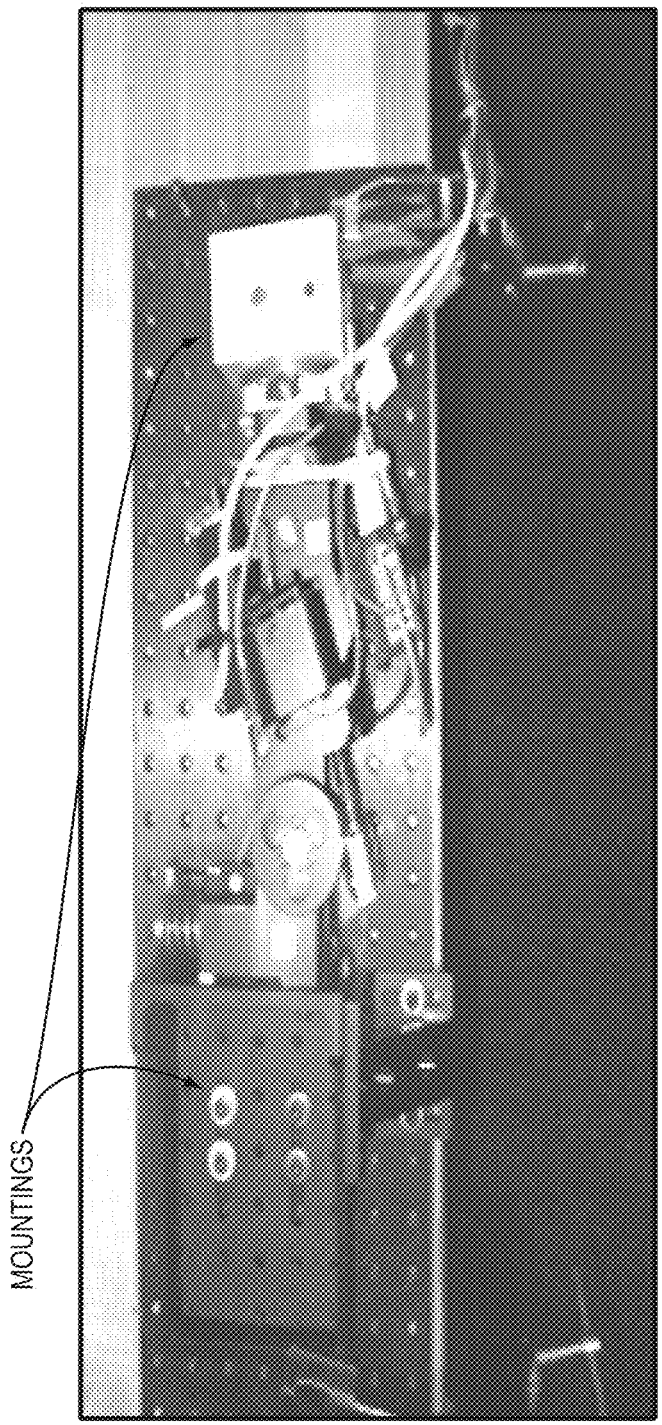
FIG. 20 depicts an experimental setup for the system characterization.

This section presents the experimental results of the study of the open-loop characteristics of the physical prototype. The main goals of the experiment are (1) to see to what extent the proposed linear model can predict the actual system behaviors (see FIG. 14); and (2) to obtain the actual system parameters including Me and Be. During the experiment, both ends of the prosthesis were fixed and the parallel spring was disengaged (see FIG. 20). The prosthesis was controlled by an onboard computer (PC104) with a data acquisition card and the dc motor of the prosthesis was powered by a motor amplifier. A linear potentiometer was installed across the flexion and extension of the series springs to measure their displacement and was used to estimate the output force.

Figure 21:
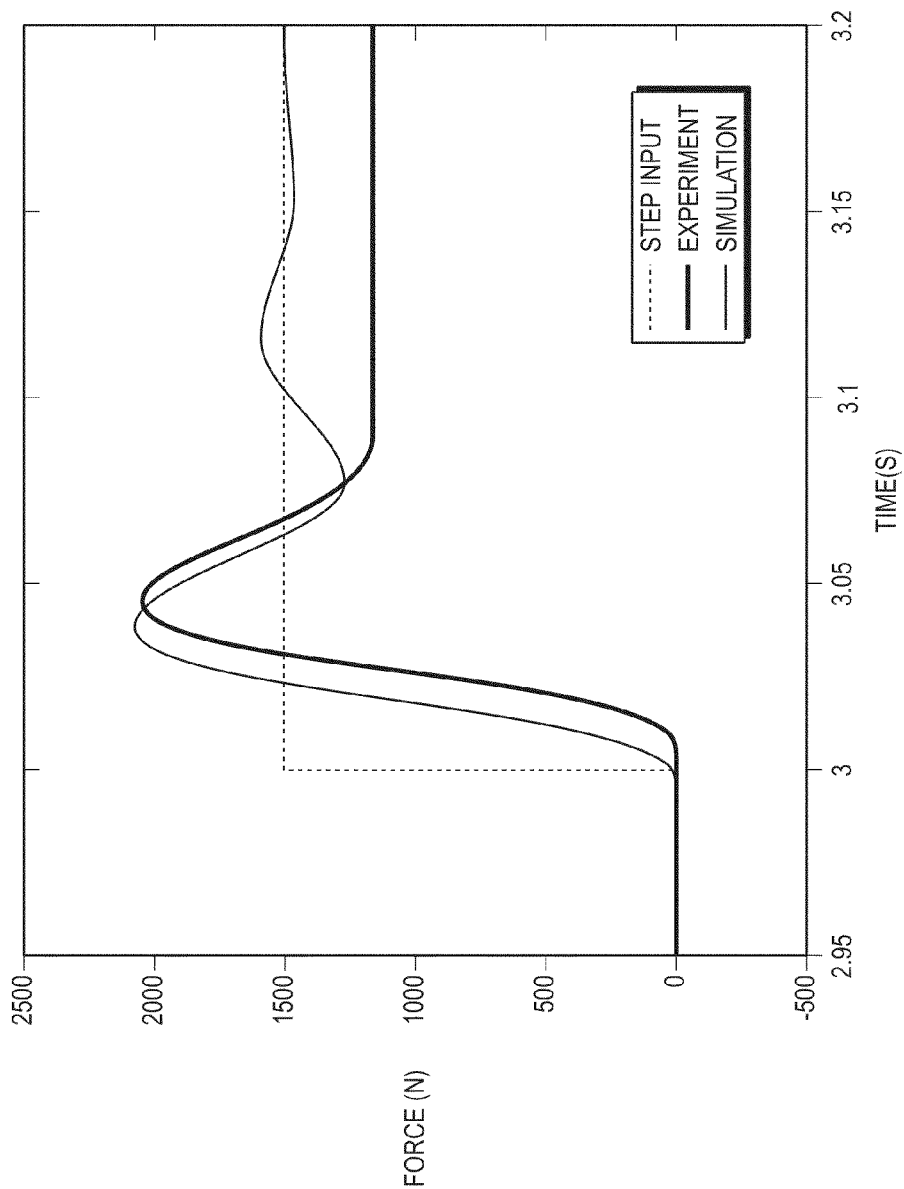
FIG. 21 depicts the experimental open-loop step response.

Both open-loop step response and the frequency response tests were conducted on the actual system. The result of the open-loop step response is shown in FIG. 21. As was illustrated, there was about 8 ms time delay in the system. In addition, the actual step response decayed immediately right after the first overshoot. This discrepancy would seem to stem from the stiction effect of the SEA {A-42}. The settling time of the open-loop step response was 80 ms.

Figure 22A:
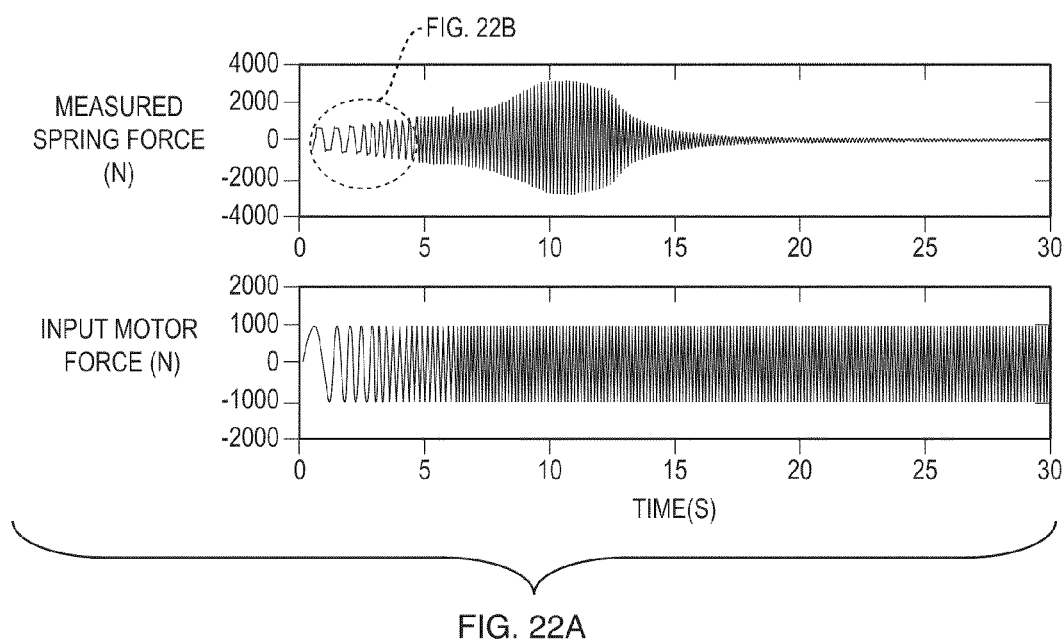
FIG. 22 illustrates a time domain plot for the chirp response.
Figure 22B:
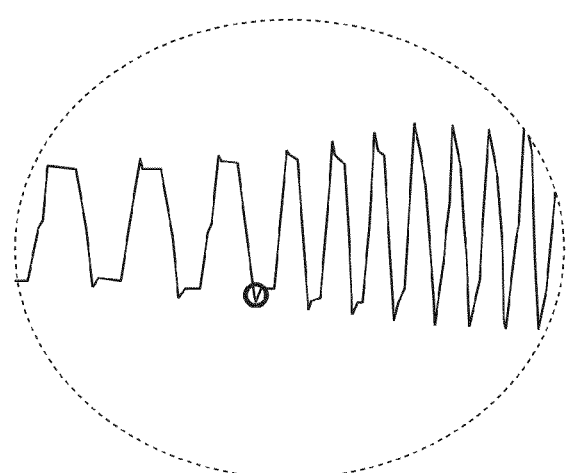

To measure the frequency response of the system, a chirp signal was applied directly to the motor. The chirp had an amplitude of 4.66 A and varied from 0.01 Hz to 30 Hz in 30 seconds. The force associated with the input current was calculated based on the motor specifications and the transmission ratio. The output force was obtained by measuring the deflection of the series spring (see FIG. 22). An open loop Bode plot was plotted for the system based on the input-output from the chirp command (FIG. 23).

Figure 23:
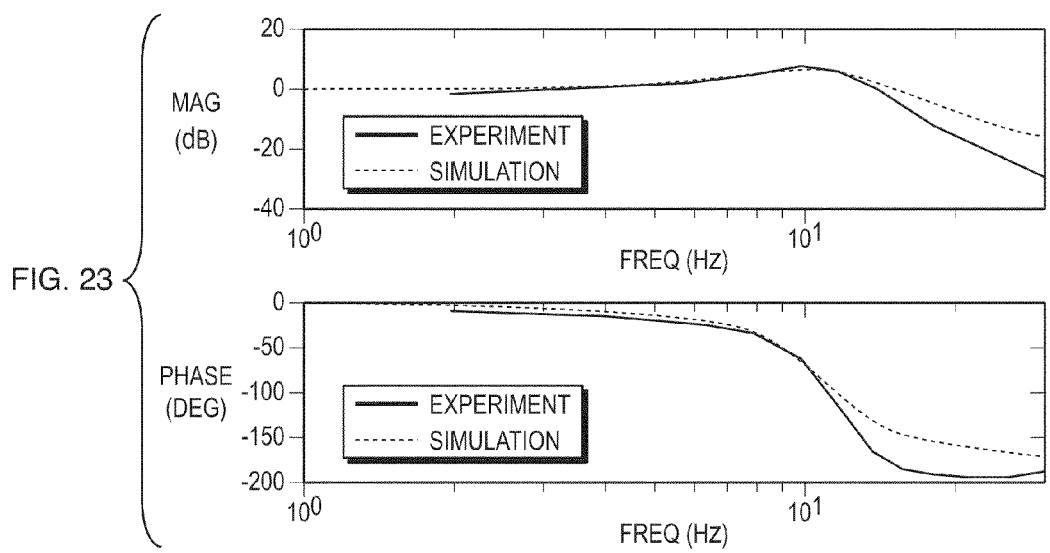
FIG. 23 depicts the experimental open-loop frequency response

In general, the experimental results matched with the simulation of the spring-mass-damper system in FIG. 23. The measured resonance frequency of the system at an input force Fe=1000 N (or input torque T=37.5 Nm) was about 10.4 Hz.

The parameters Me and Be were estimated by fitting a second-order model to the measurement data, i.e. $M\tilde{}e$=250 kg, $B\tilde{}e$=8250 Ns/m.

It is also observed that the low frequency gain of the open-loop frequency response of the actual system did not remain constant, compared to the simulated one. This discrepancy would seem to stem from the stiction effect of the SEA {A-42}. Furthermore, the actual frequency response started to roll off earlier than the simulated response. This suggests that there is an extra pole at high frequency in the actual system, which may be due to the combination of the velocity saturation of the motor and motor amplifier saturation.

Figure 24:
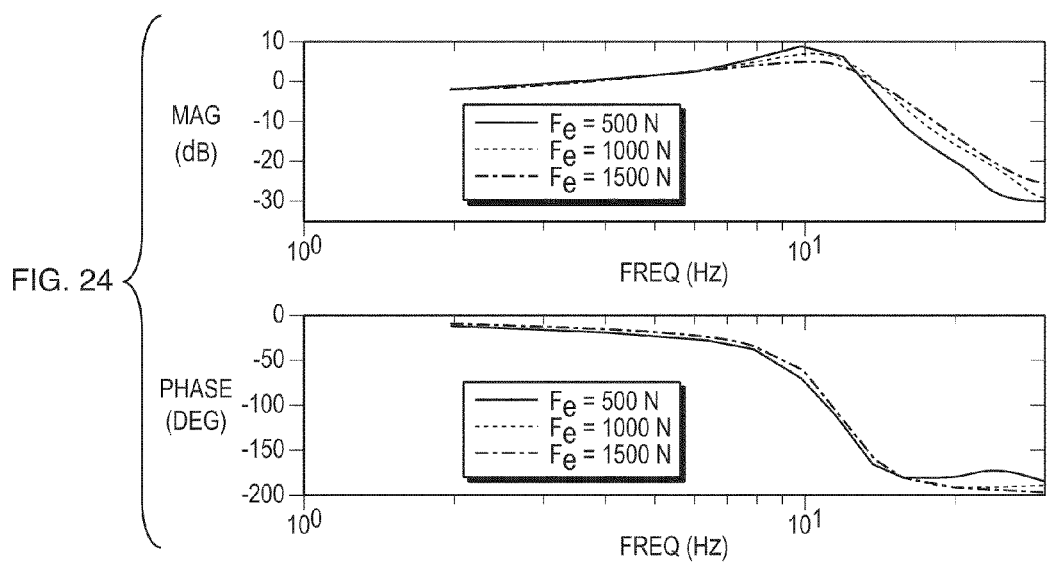
FIG. 24 shows a comparison of experimental open-loop frequency response of the system at different input forces.

FIG. 24 shows a comparison of experimental open-loop frequency response of the system for different input forces Fe. As described in Section 4.4.2, when the output/spring force increased, the system performance decreased due to the motor saturation. The actual open-loop force bandwidth of the prosthesis at Fe=1500 N (56.25 Nm) was 12.6 Hz, which is sufficiently larger than the required force/torque bandwidth (FIG. 15).

Discussion

Feasibility of the Model

In general, it was shown that the proposed second-order model can capture the dominant dynamic behaviors of the actual system. Incorporating an extra pole at high frequency (>11 Hz) may better describe the actual system with motor amplifier saturation. Given the force bandwidth requirement (3.5 Hz) in this application, the second-order model is still sufficient for our application and can be used for control system design.

Furthermore, as expected, for a small output force and low frequency movement, the actual system behaved nonlinearly due to the stiction and slacking in the transmission. In fact, it is challenging to model such kind of nonlinearity precisely {A-45}.

Definitely, to obtain a precise control over the prosthesis, further study on the topics of stiction and high-order model description for the actual system is required. As a main concern is to ensure that the prosthesis can provide a sufficient amount of power to test the hypothesis, the study of the stiction effect is limited for the purpose of improving the peak power output of the system. The next section discusses control system techniques to partially compensate the stiction in the transmission to augment the system performance.

Design Architecture

The prosthetic ankle-foot system requires a high mechanical power output at a large peak torque. To achieve this, a parallel spring with a force-controllable actuator with series elasticity is used. The parallel spring shares the payload with the force-controllable actuator, thus the required peak force from the actuator system is significantly reduced. Consequently, a smaller transmission ratio can be used, and a larger force bandwidth is obtained.

It is always interesting to see if there is any alternative architecture that can satisfy the design requirement. In fact, some researchers {A-46} {A-47} have suggested applying the catapult concept for the development of the powered ankle-foot prosthesis/orthosis, through the usage of a series elastic actuator. They have shown that this method can maintain power optimizations to ⅓ of direct drive needs at a weight 8 times less than that for a direct drive solution {A-47}.

However, this method requires a long soft series spring for energy storage which may make the packaging problem harder. Furthermore, a non-backdrivable transmission is required that lowers down the efficiency of system. In the future, it may be useful to compare and analyze the efficiency of these two approaches and it may lead to a more energy efficient design architecture.

Besides, the basic architecture of parallel and series elasticity may also prove useful for other types of assistive devices that require both high power and torque output, such as a hip-actuated orthosis {A-59}.

Control System Design

This discussion below presents a control system architecture that allows the prosthesis to mimic the target stance phase behavior and begins by describing the overall architecture of the system. Then, the development of three basic low-level servo controllers is presented. A finite state machine that manages the low-level servo controllers to provide the target stance phase behavior during each gait cycle is presented. Finally, the implementation of the controller and the results of basic gait test used to evaluate the performance of the controller are described.

Overall Control System Architecture

Finite-state control approach are usually used in locomotion assistive/prosthetic devices such as A/K prostheses {A-9} {A-54}-{A-57} because gait is repetitive between strides and, within a stride, can be characterized into distinct finite numbers of sub-phases. According to Section 2.1, human ankle also demonstrates such kind of periodic and phasic properties during walking. This motivates the usage of a finite-state controller to control the powered prosthesis.

Referring to Section 3.1, the finite-state controller should be designed to replicate the target stance phase behavior. In order to apply the finite-state control approach to solve this problem, the control system needs to fulfill the following requirements:

The control system must have three types of low-level servo controllers to support the basic ankle behaviors: (i) a torque controller; (ii) an impedance controller; and (iii) a position controller.

The finite-state controller must have sufficient numbers of states to replicate the functional behaviors for each sub-phase of human ankle during walking.

Local sensing is favorable for gait detection and transition among states. The finite-state controller uses these sensing information to manage the state transitions and determine which low-level servo controller should be used to provide proper prosthetic function for a given state condition.

Figure 25:
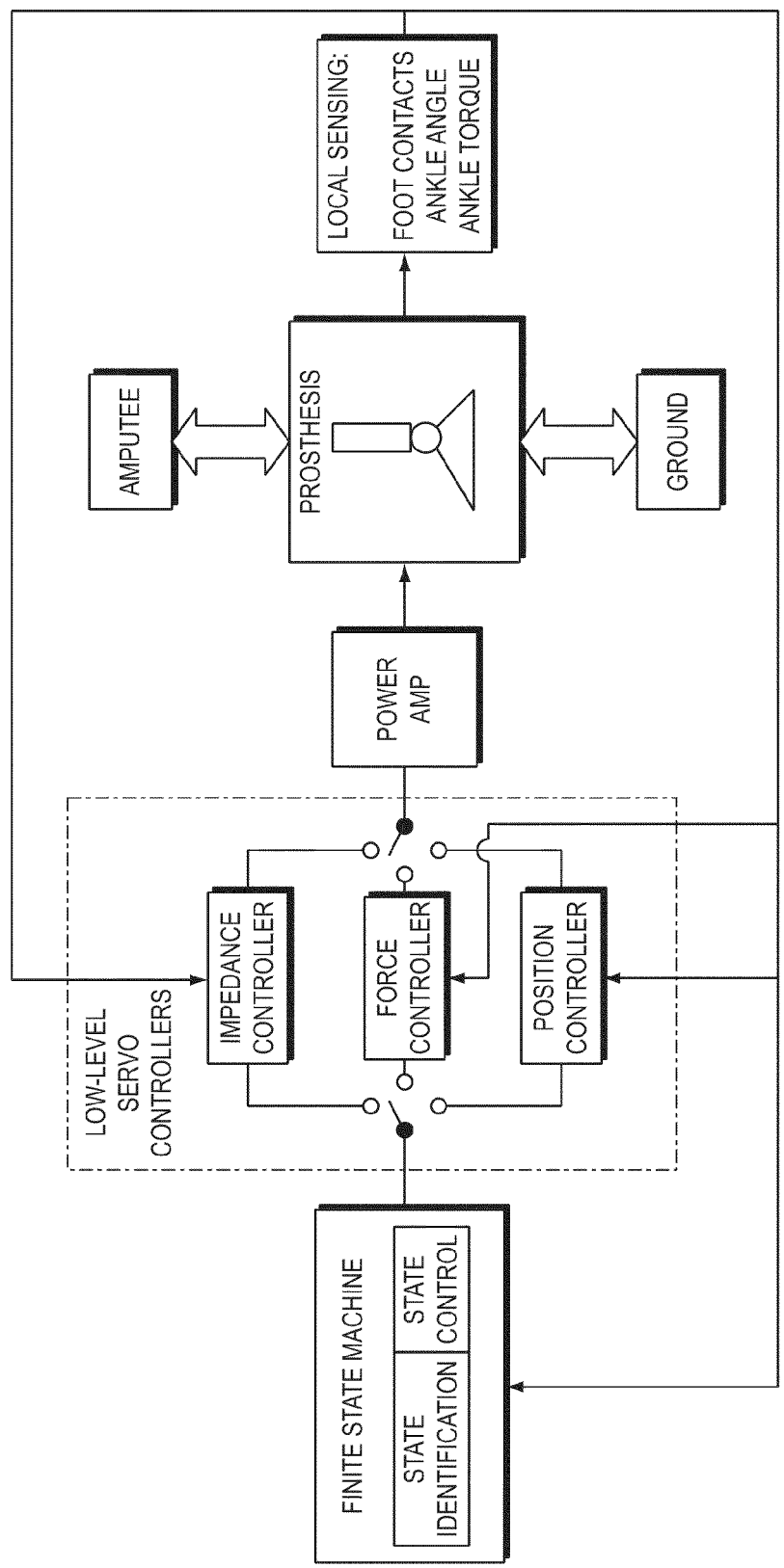
FIG. 25 depicts the overall control architecture of the prosthesis.

In this project, a control system with a finite-state controller and a set of low-level servos controllers was implemented. The overall architecture of the control system is shown in FIG. 25. As can be seen, the control system contained the suggested low-level servo controllers to support the basic human ankle functions. Furthermore, only local sensing variables, including ankle angle, ankle torque, and foot contact were used for state detection and transition. In addition, it also had a finite state machine to manage and determine the transitions among the low-level servo controllers. The finite state machine comprised a state identification and a state control. The former was used to identify the current state of the prosthesis while the latter was used to execute the predefined control procedure for a given state.

The following sections discuss the development of the low-level servo controllers, followed by the design of the finite state machine.

Low-Level Servo Controllers

Standard control techniques were used to design the controllers and hence the design of the each low-level servo controllers is only briefly discussed in the following sections.

Torque Controller

Figure 26C:
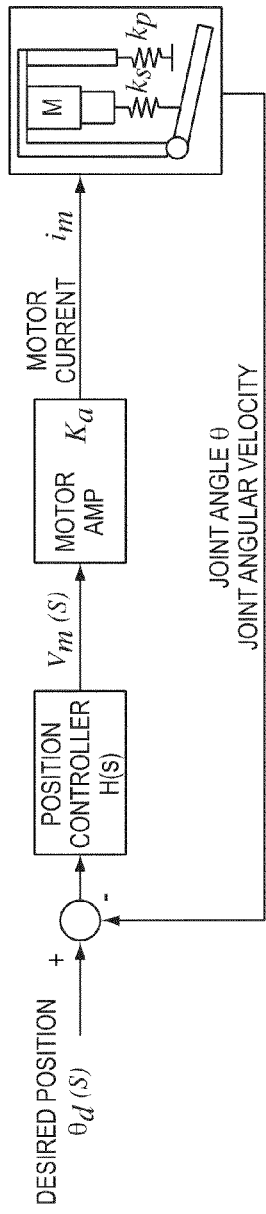

A torque controller was designed to provide the offset torque and facilitate the stiffness modulation. The primary design concern is to satisfy the bandwidth constrain specified in Table 4.3. A torque controller was proposed, that used the force feedback, estimated from the series spring deflection, to control the output joint torque of the SEA {A-42} (FIGS. 26A, 26B and 26C).

The torque/force controller D(s) was essentially implemented based on a PD control law:

$$D(s) = \frac{V_m(s)}{\tau_e(s)} = K_F + sB_F \frac{p}{s+p} \quad (5.1)$$

where te,Vm are the output torque error and input voltage to the motor amplifier, respectively. Furthermore, KF and BF are the proportional gain and damping of the control law, respectively. A simple dominant pole filter s+pp was incorporated into the controller because often, the measured force signal is very noisy and must be filtered before a derivative may be taken. The pole p of the controller was set to 100 Hz (188.5 rad/s), which is sufficiently larger than the dominant frequency of the human ankle during normal walking. In practice, this was also found to be useful to prevent the instability occurred during the transition from a free end condition to a fixed end condition {A-48}. Using the pure P or PD control, if the prosthesis hit a hard boundary such as the end stop of the prosthesis, it bounced back due to the large impact force seen in the sensor (spring) and eventually exhibited limit cycles. The proposed filter was thought to "filter out the components of the signal which were exciting the unstable dynamics" {A-48}.

The desired motor force (or input voltage Vm) was then sent to the motor amplifier to create a force on the motor mass. A current/torque-controlled mode servomotor was adopted using the current/torque-controlled mode, for a given desired force (or input voltage Vm), the motor amplifier outputs a current im into the motor according to an amplifier gain Ka. The input motor force Fe(s) is equal to RKtKaVm(s), where Kt is the torque constant of the motor. If Ktotal=RKtKa that converts voltage into input motor force, i.e. Fe(s)=KtotalVm(s).

Using the controller D(s) and open-loop model with the fixed-load condition in Eqn. 4.12, the close-loop transfer function between the actuator force output Fs and the desired output force Fd can be written as:

$$\frac{F_d}{F_s} = \frac{\left(K_F + B_F s \frac{p}{s+p}\right) K_{total} G_{fixed}(s)}{1 + \left(K_F + B_F s \frac{p}{s+p}\right) K_{total} G_{fixed}(s)}. \quad (5.2)$$

Figure 27:
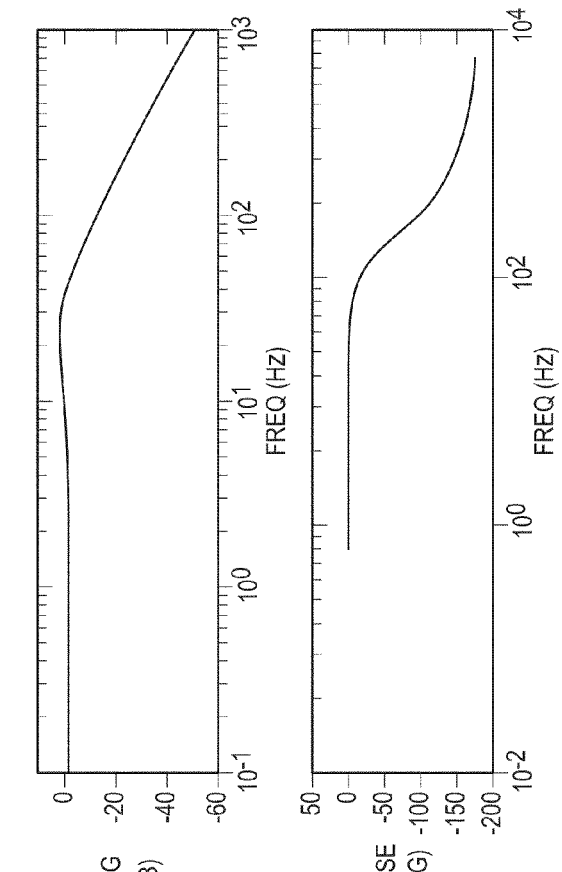
FIG. 27 is a simulation of the closed-loop frequency response.

The controller gains were chosen based on the standard root-locus technique to obtain reasonable force control performance. KF and BF were set to be 4 and 20. A simulation of the frequency response of the closed loop system is shown in FIG. 27. To convert the actual force into voltage, a gain Kfv was multiplied to the controller D(s) in the simulation. All the parameter values for the controller have been listed in Table 5.1.

As indicated in FIG. 27, the bandwidth of the closed-loop system (57.6 Hz) was shown to be much larger than the required bandwidth (3.5 Hz). In practice, due to the velocity saturation of the motor and motor amplifier saturation, the actual closed-loop can be significantly less than the expected one.

TABLE 5.1

Controller Parameters

| | Parameters | | | |
|---|---|---|---|---|
| | $K_F$ | $B_F$ | p | $K_a$ |
| Values | 4 | 20 | 100 Hz | 3.6 A/V |

| | Parameters | | | |
|---|---|---|---|---|
| | $K_t$ | $K_{total}$ | $K_{fv}$ | $f_c$ |
| Values | 0.0603 Nm/A | 773 N/V | 0.0013 V/N | 0.03 |

| | Parameters | | |
|---|---|---|---|
| | $b_c$ | $K_1$ | $K_2$ |
| Values | 0.31 | 1 | 10 |

Impedance Controller

An impedance controller was designed to modulate the output impedance of the SEA, especially the joint stiffness. The impedance controller consisted of three main components: (1) Outer position feedback loop, (2) Inner loop force controller, and (3) feedforward friction compensation (FIG. 26B). The outer loop impedance controller was based on the structure of the "Simple Impedance Control", proposed by Hogan {A-49} {A-50}. The key idea behind the impedance control is to use the motion feedback from the ankle joint to increase the output joint impedance. The controller or desired output impedance of the SEA in S-domain is defined as follows:

$$Z_d = \frac{\tau_d(s)}{s\theta(s)} = \left(B_d + \frac{K_d}{s}\right) \quad (5.3)$$

where td, Kd, Bd are the desired SEA output joint torque, stiffness, and damping, respectively. Taking into the consideration of the parallel elasticity, the total joint impedance is $$Z_{total} = \begin{cases} \left(B_d + \frac{K_d}{s}\right) & \theta \leq 0 \\ \left(B_d + \frac{K_d + K_p^r}{s}\right) & \theta > 0 \end{cases} \quad (5.4)$$

Due to the intrinsic impedance (e.g. friction and inertia), the actual output impedance consists of desired output impedance due to the controller plus that due to the mechanism. For this reason, the aforementioned torque controller was incorporated into the impedance controller to reduce the effect of the intrinsic impedance. Although increasing the gain KF can shadow the intrinsic impedance (e.g. friction or inertia) in the mechanism, it may trigger instability when the system couples to certain environments at high gain {A-48} {A-53}. One way to augment the torque controller without violating the stability criteria is to use a model-based friction compensation term Fr(s). A standard feedforward friction compensation term was applied into the torque controller and defined as:

$$\tau_f = f_c(\tau) sgn(\dot{\theta}) + b_c \dot{\theta}, \quad (5.5)$$

where fc, be are the Coulombic force constant and damping coeficient, respectively {A-45}. All these parameters were identified using experimental data.

Position Controller

A standard PD-controller H(s) was proposed to control the equilibrium position of the foot during swing. Then, the input voltage Vm(s) to the motor amplifier is $V_m(s)=K_1(\theta_1-\theta)+K_2\theta$, where K1 and K2 are the proportional and derivative terms of the controllers.

Finite-State Controller

Figure 28:
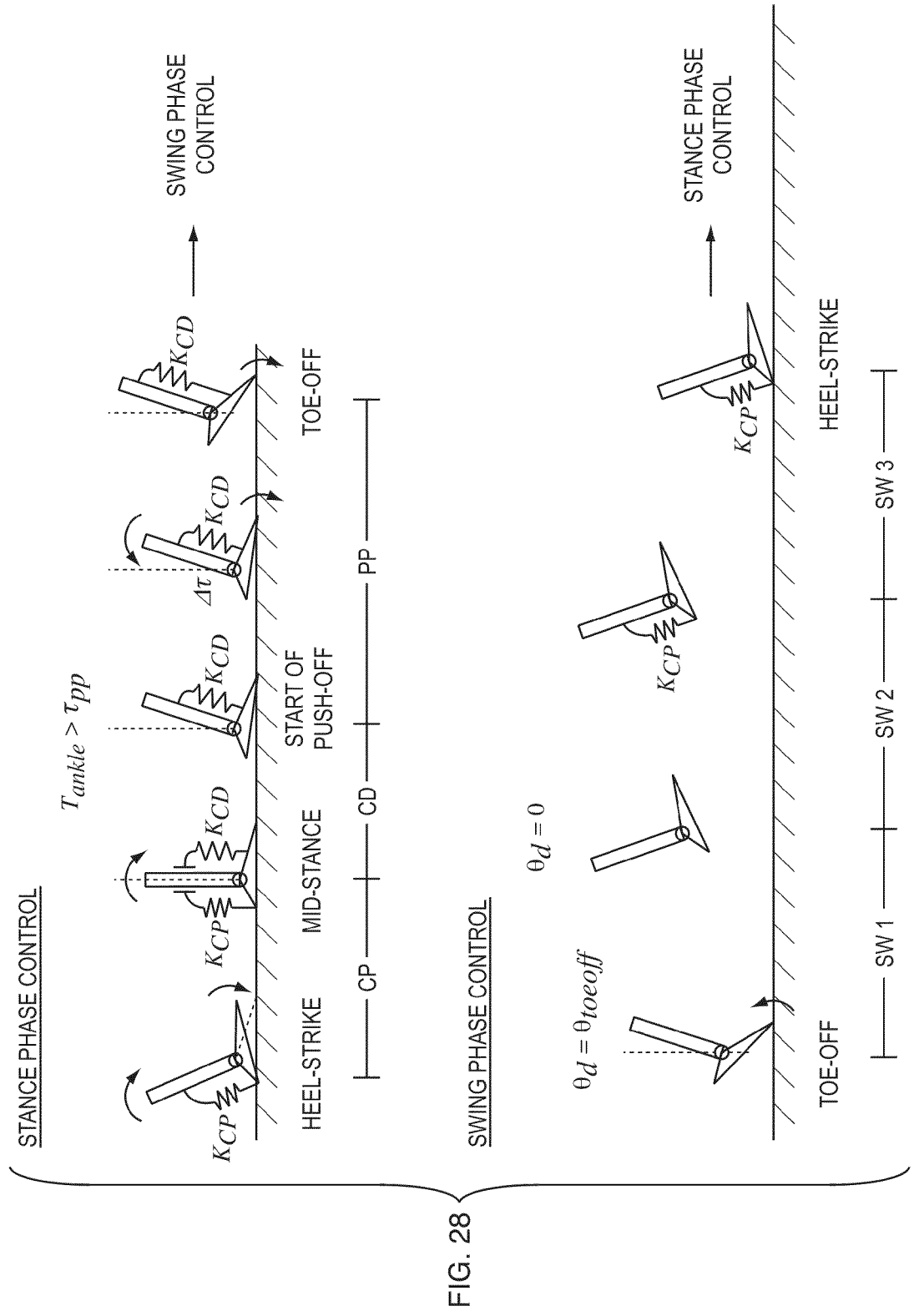
FIG. 28 shows the finite-state control for a typical gait cycle.

A finite-state controller for level-ground walking was implemented to replicate the target ankle behavior (FIG. 28). The controller comprises of two parts: stance phase control and swing phase control. Each part of the controller contains three states and the details are discussed as follows.

Stance Phase Control

Three states (CP, CD, and PP) were designed for stance phase control. The stance phase control for a typical gait cycle is graphically depicted in FIG. 28. Detailed descriptions for each state are shown below.

CP begins at heel-strike and ends at mid-stance. During CP, the prosthesis outputs a joint stiffness1, KCP to prevent foot slapping and provide shock absorption during heel-strike.

CD begins at mid-stance and ends right before PP or toe-off, depending on the measured total ankle torque Tankle. During CD, the prosthesis outputs a joint stiffness, KCD to allow a smooth rotation of the body, where KCD=Kpr+KCD1.

PP begins only if the measured total ankle torque, Tankle is larger than the predefined torque threshold, tpp, i.e. Tankle>tpp. Otherwise, it remains in state CD until the foot is off the ground. During PP, the prosthesis outputs a constant offset torque, Δt superimposing the joint stiffness, KCD as an active push-off.

KCP, KCD, tpp, and Δt are the main parameters affecting the ankle performance during the stance phase control. In particular, the offset torque is directly related to the amount of net work done at the ankle joint. These parameter values were chosen based on the user's walking preference during experiments.

Swing Phase Control

Another three states (SW1, SW2, and SW3) were designed for the swing phase control (see FIG. 28). Descriptions for each state are shown below.

SW1 begins at toe-off and ends in a given time period, tH. During SW1, the prosthesis servos the foot to a predefined foot position, toe-off for foot clearance.

SW2 begins right after SW1 and finishes when the foot reaches zero degree. During SW2, the prosthesis servos the foot back to the default equilibrium position to prepare for the next heel-strike.

SW3 begins right after SW2 and ends at the next heel-strike. During SW3, the controller resets the system to impedance control mode and output a joint stiffness, KCP.

It is important to have state SW3 in the swing phase control to ensure the control system operating in impedance mode before heels-strike. Because the heel-strike event happens very quickly, there is not enough time for the control system to switch from position control mode to impedance control mode during heel-strike. The time period, tH and predefined foot position at toe-off were all tuned experimentally.

Sensing for State Transitions

During state transition and identification, the system mainly relied on four variables:

Heel contact(H). H=1 indicates that the heel is on the ground, and vice versa.

Toe contact(T). T=1 indicates that the toe is on the ground, and vice versa.

Ankle angle

Total ankle torque ($T_{ankle}$)

Figure 29:
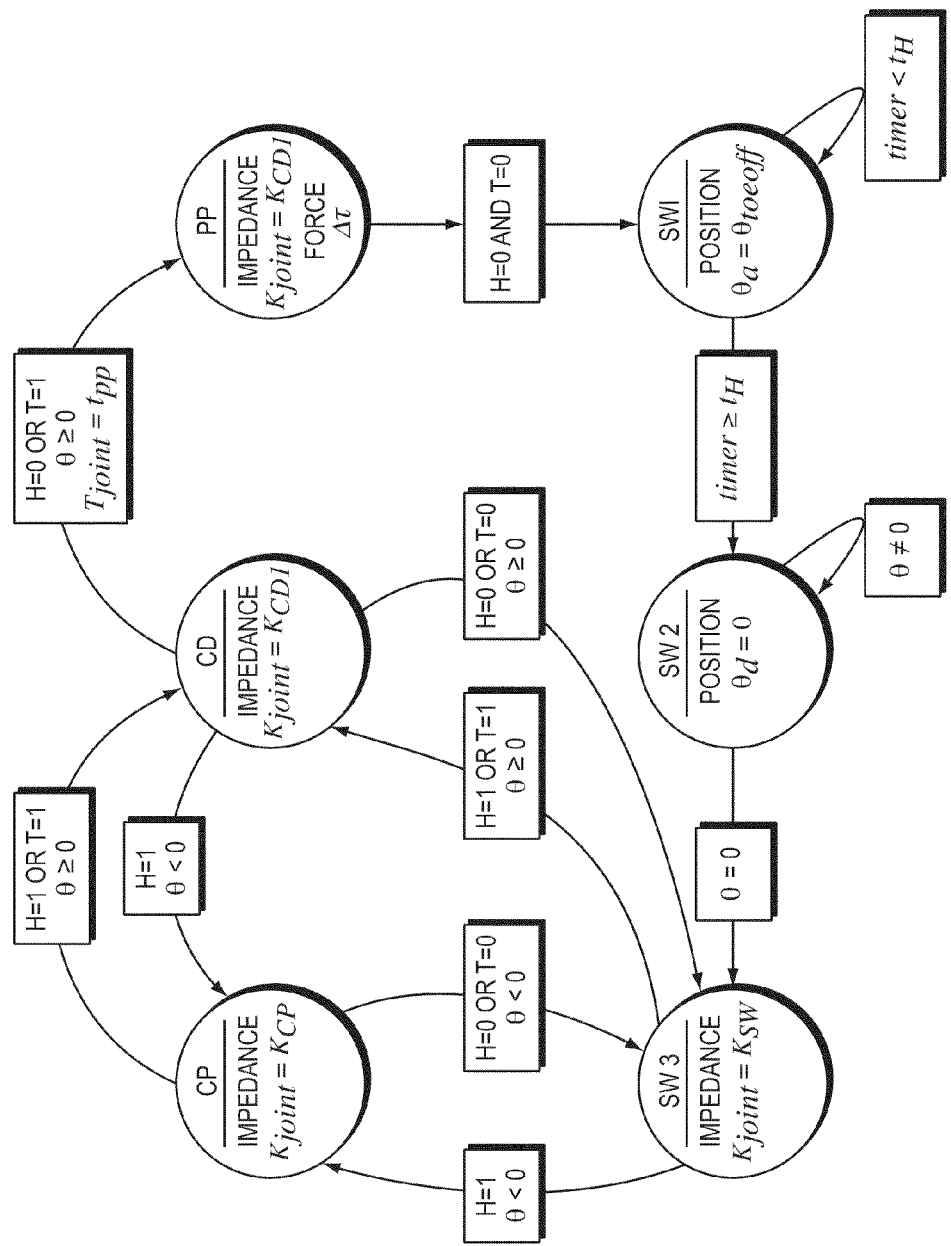
FIG. 29 shows the finite-state controller for level-ground walking.

All these triggering information can be obtained using local sensing; including foot switches to measure heel/toe contact, ankle joint encoder to measure the ankle angle, and the linear spring potentiometer to measure joint torque. The hardware implementation of these local sensing will be discussed in the next section. The finite-state control diagram indicating all triggering conditions is shown in FIG. 29.

Controller Implementation

In this section, the electronics hardware used for implementing the proposed controller onto the MIT powered ankle-foot prosthesis, including sensing and computing platform, is described. This system platform provides a test bed for testing a broad range of human ankle behaviors and control systems experimentally.

Computer System Overview

Figure 30:
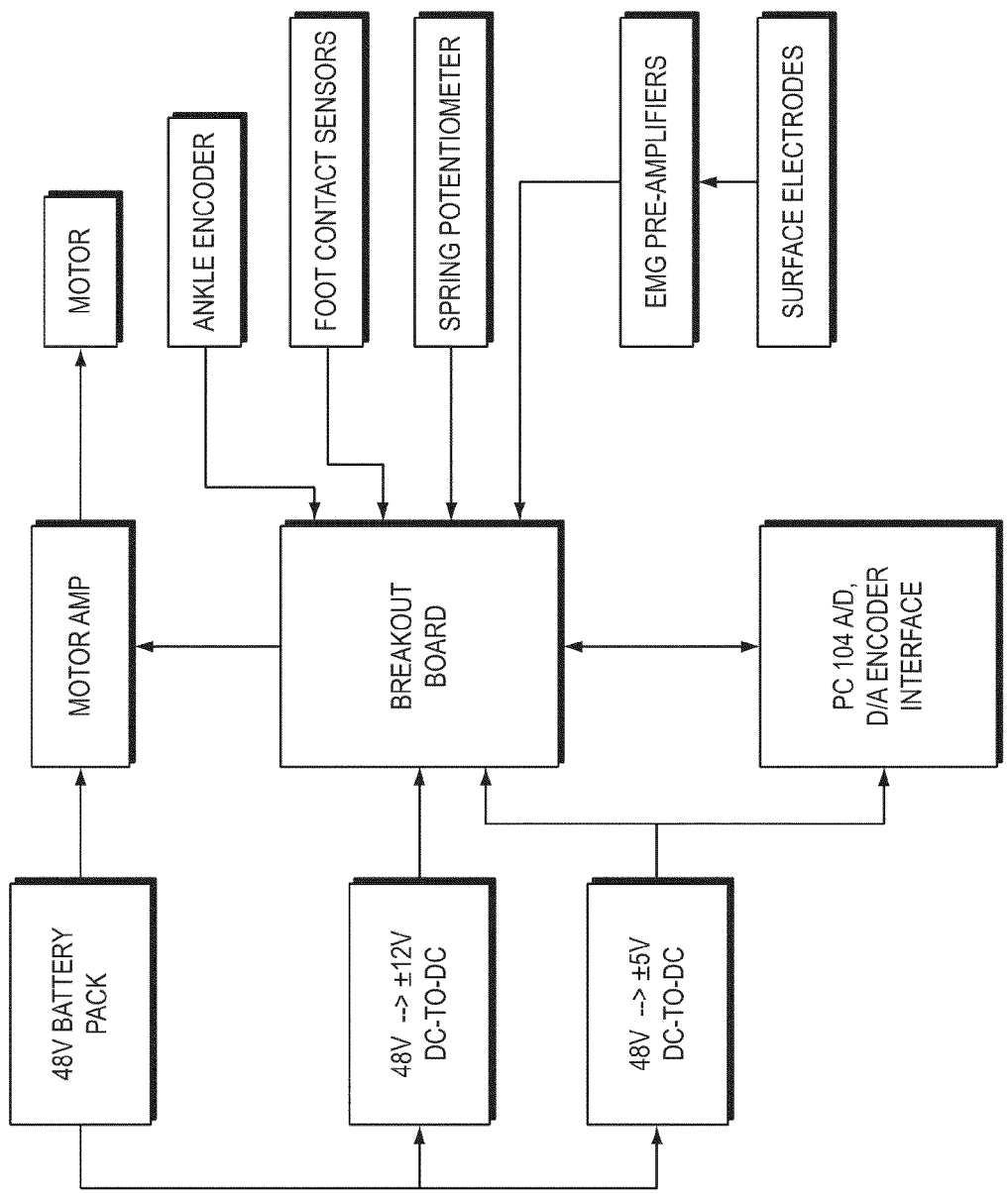
FIG. 30 shows schematics of the overall computer system.

FIG. 30 shows the schematics of the overall computer system. The computer system contained an onboard computer (PC104) with a data acquisition card, power supply, and motor amplifiers. The system was powered by a 48V, 4000 mAh Li-Polymer battery pack. Custom signal conditioning boards amplified sensor (linear pot) reading and provided a differential input to the data acquisition board, in order to minimize common mode noise from pick-up in the system. A custom breakout board interfaced the sensors to the D/A board on the PC104 as well as provided power to the signal conditioning boards.

PC104 and Data Acquisition

The PC used was a MSMP3XEG PC/104 from Advanced Digital Logic, Inc. It was a miniature modular device that incorporated most of the major elements of a PC compatible computer in a small form factor. It was fitted with a PENTIUM III 700 MHz processor.

A PC/104 format multifunctional I/O board (Model 526) from Sensory Co. was connected to the PC/104. It had 8 differential analog inputs, 2 analog outputs, and 4 quadrature encoder counters. Matlab xPC Target was used to run the algorithm for real-time control and data acquisition. The Matlab xPC real-time kernel was installed and run on the PC/104 (remote PC). A model was created using Simulink Matlab xPC Target, which allowed I/O blocks to be added to the model. The model was compiled on the host PC using Matlab Real-Time Workshop and a C++ compiler created executable code. The executable code was downloaded from the host PC to the target PC via TCP/IP and the code was run on the target in real-time. Data were recorded by using the xPC host scopes in the Simulink model. During the program running, the target PC (PC104) could communicate with the host computer via Ethernet. The host computer could send control commands and obtain sensory data from the target PC104. The dc motor of the prosthesis was powered by a motor amplifier (Accelnet Panel ACP-090-36, V=48 volts, Ipk=36A) from Copley Controls Corp.

Sensors

Figure 31:
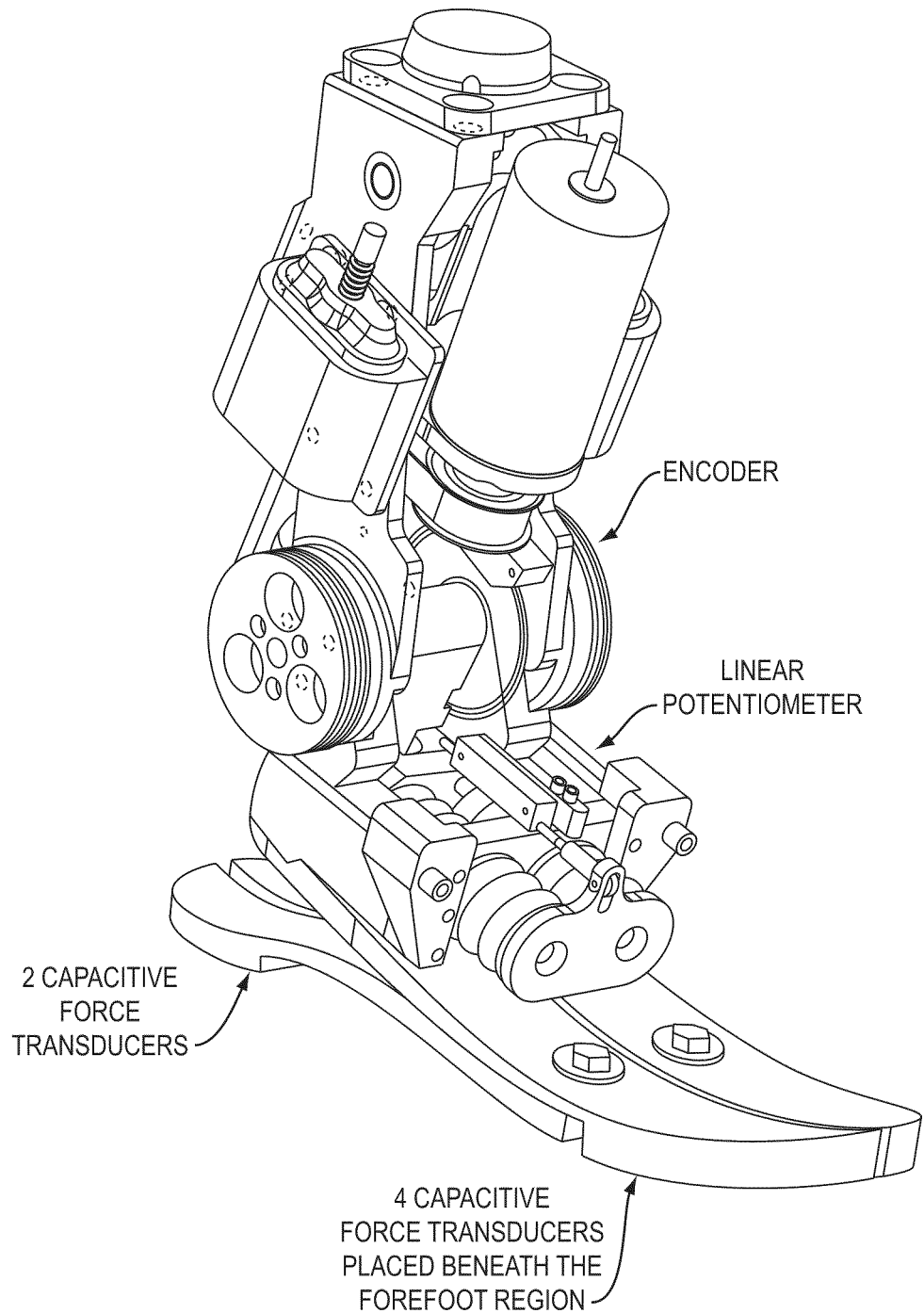
FIG. 31 depicts the sensors on the powered ankle-foot prosthesis.

Three state variables, including heel/toe contact, ankle angle, and joint torque, were measured to implement the proposed finite-state controller. A 5 kohm linear potentiometer is installed across the flexion and extension the series springs to measure their displacement. A 500-line quadrature encoder (US digital, inc.) is positioned between the parent link mounting plate and child link mounting plate to measure the joint angle of the prosthetic ankle. Six capacitive force transducers were placed on the bottom of the foot: two sensors beneath the heel and four beneath the forefoot region. FIG. 31 describes the sensors on the powered prosthesis.

Mobile Computing Platform

Figure 32A:
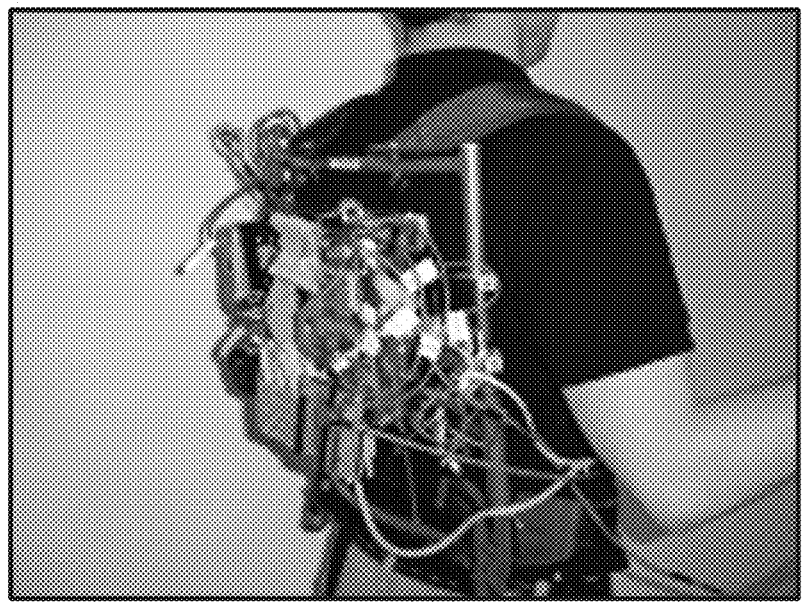
FIGS. 32A and 32B shows a mobile computing platform.
Figure 32B:
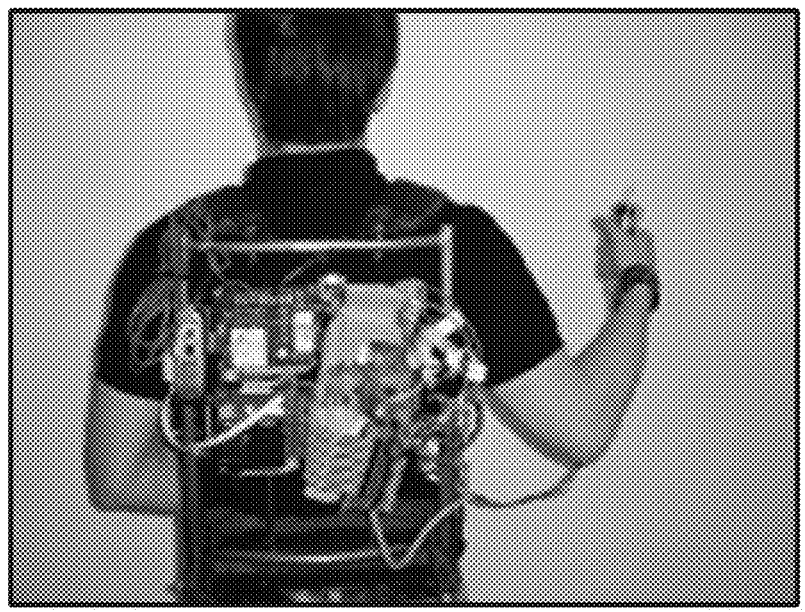

A mobile computing platform that allowed us to conduct untethered walking experiments outside the laboratory is shown in FIGS. 32A and 32B, the mobile platform was mounted on an external frame backpack. Most of the electronic components were mounted on the platform, including a PC104, a power supply, I/O Cards, and a motor amplifier. Using cabling, the prosthesis was connected to the I/O board and motor amplifier on the platform.

Both step response and frequency response tests were conducted on the physical prototype to understand the closed-loop performance (with fixed end condition) of the torque/force controller described in Section 5.2.1. The same bench test setup was used as described in FIG. 20, in which both ends of the prosthesis were fixed on the ground rigidly.

Figure 33B:
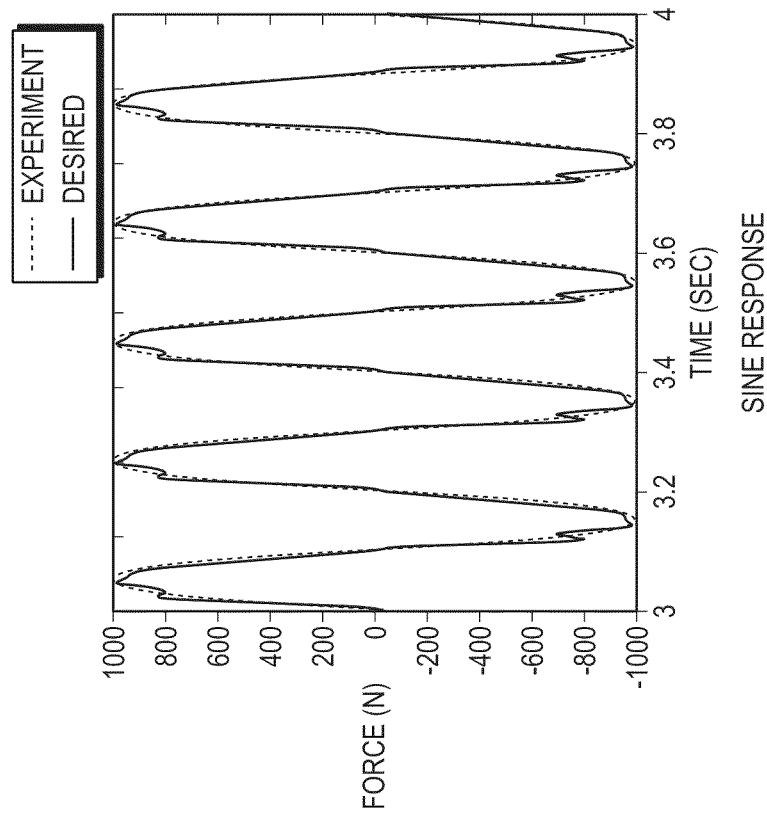
FIG. 33 illustrates tracking performance of the closed-loop force controller.
Figure 33A:
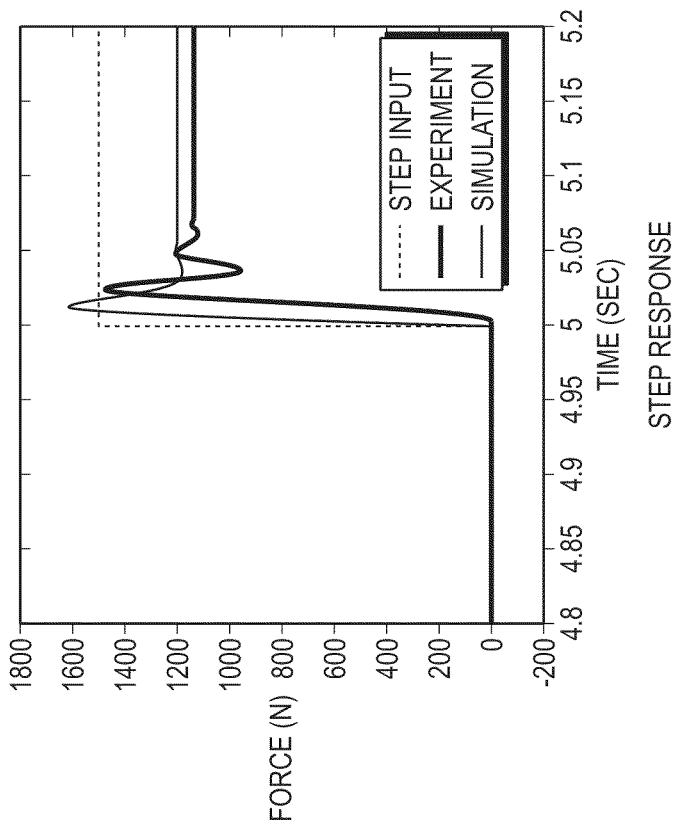

The proportional and derivative gains of the controller were tuned experimentally by examining the step response of the actuator. FIG. 33 shows the controller response to track a step force of 1500 N and a sine wave in force of 1000N at 5 Hz. The corresponding parameters used in the actual were listed in Table 5.1. The simulation can fairly predict the step response of the actual system. To prevent instability occurring during the contact with different environments, the controller gain KF was set to a relative small value, consequently, the steady state error of the closed-loop control (about 25%) is quite large (see FIG. 33(*a*)). One resolution to this problem was to adjust the desired force by a factor of the steady state error. It has been applied in the experiment of tracking the sine wave in force.

Figure 34:
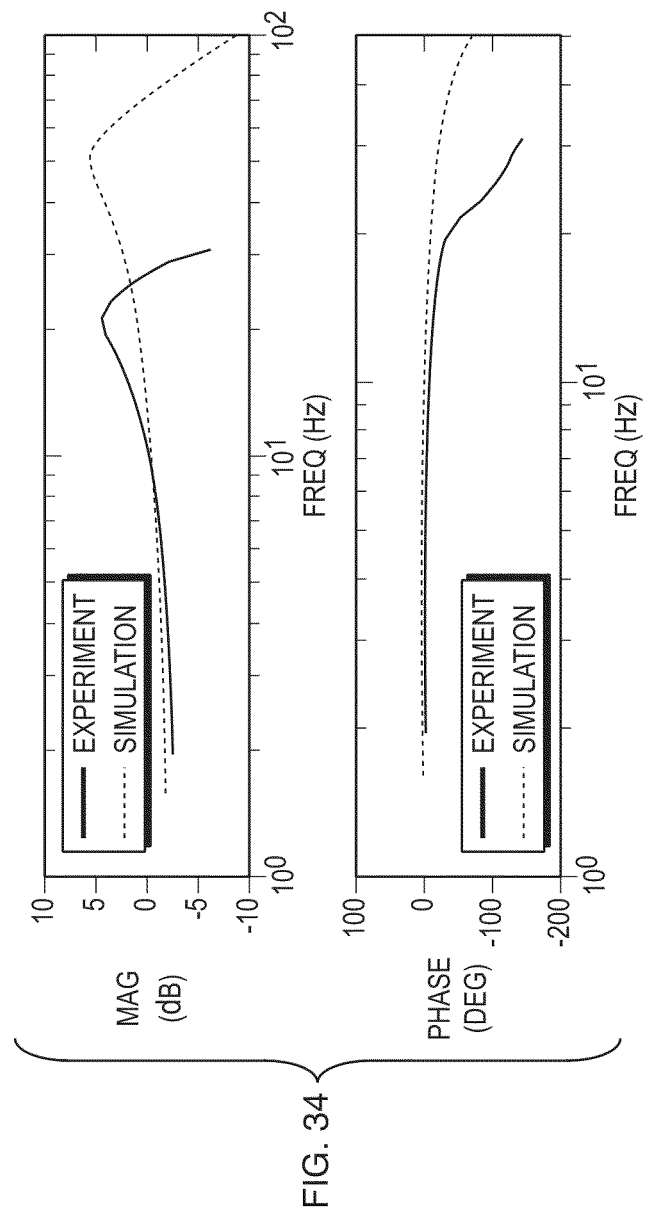
FIG. 34 depicts the experimental closed-loop frequency response.

To determine the closed-loop bandwidth of the control system, a sine wave chirp in force (500 N) was applied from 0.01 Hz to 40 Hz in 40 seconds. FIG. 34 shows both the experimental and theoretical closed loop Bode plots. The measured and theoretical resonance peak were at 21.4 Hz and 51.3 Hz, respectively. Due to the amplifier saturation, the measured frequency response started to roll off much earlier than the simulated one. However, this controller is still sufficient for our application because the required force bandwidth is only 3.5 Hz.

Initial Gait Test

Before testing three unilateral amputee participants, a substantial amount of basic gait tests were conducted with the device on a healthy, bilateral below-knee amputee to evaluate the performance, stability, and robustness of the controller. The amputee wore the powered prosthesis on his right leg and a conventional passive below-knee prosthesis (Ceterus, from Ossur, Inc.) on the left leg. During the experiment, the amputee participant was requested to walk along a 6 foot-long walkway at a self-selected speed. He communicated desired controller parameters such as stiffness values to a separate operator during the walking trials. The results of the basic gait study proved that the proposed finite state machine performed robustly and was capable of mimicking the target stance phase behavior. In the next sections, the results of the gait tests for two kinds of system responses (Virtual Spring Response and Active Mechanical Power) to illustrate the actual performance of the control system.

Virtual Spring Response

Figure 35:
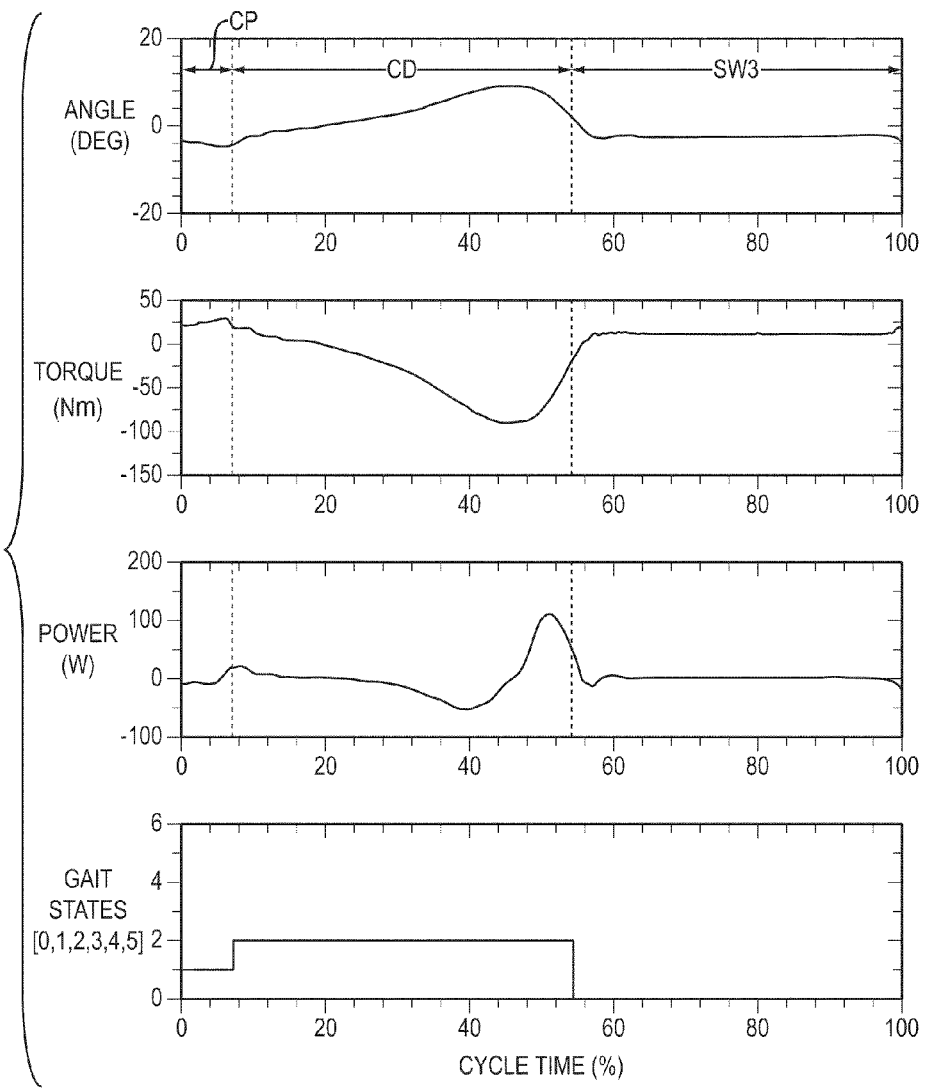
FIG. 35 depicts the measured ankle angle, torque, power, and the gait states of a walking trial.
Figure 36:
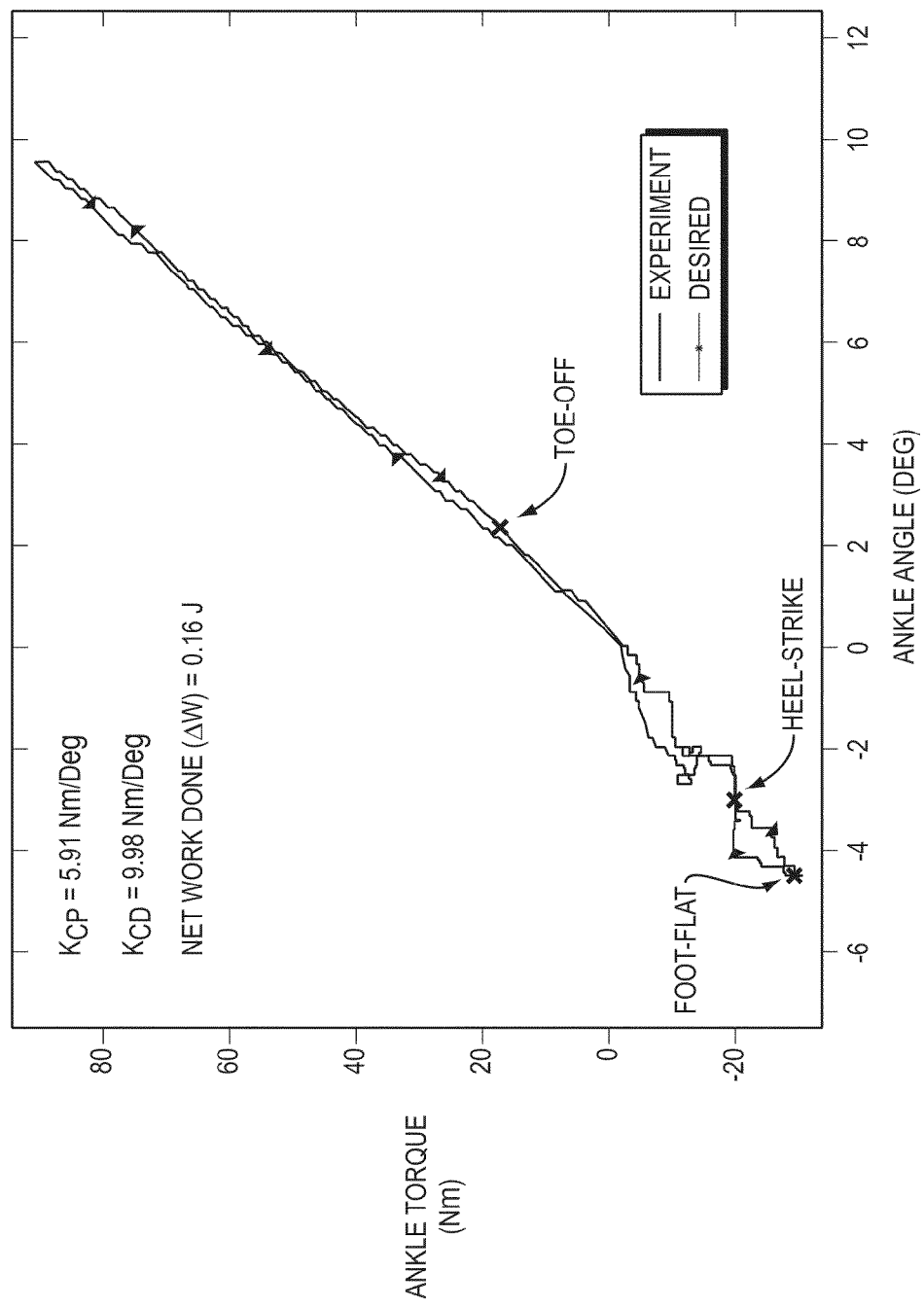
FIG. 36 shows an experimental ankle torque-angle plot for the powered prosthesis.

FIG. 35 shows real time data for one gait cycle of a walking experiment in which the powered prosthesis was controlled to output a virtual spring response. As was proposed in FIG. 29, the system went through the state sequence 1-2-0 for each gait cycle under the virtual spring condition (see FIG. 35*d*). The corresponding ankle torque-angle behavior is shown in FIG. 36. This experimental result demonstrates the system's capacity to track the desired stiffness during CP and CD. As can be seen, the actual stiffness curve is slightly off from the desired curve by approximately 3 Nm because, in the physical system, the engagement position of the unidirectional parallel spring was not exactly equal to zero degree, or the equilibrium position. This error caused the motor system to pre-load the spring at the equilibrium position.

It was expected that the measured stiffness curve would show fluctuations during heel strike because the control system was not designed to satisfy such demanding bandwidth requirements during heel-strike. This justifies the use of a SEA as the force-controllable actuator because with series elasticity, even if the movement of the prosthesis is much faster than the bandwidth of the control system, the prosthesis can still behave as a spring to prevent any impact shock to the transmission {A-42}. Furthermore, there is a heel spring in the compliant foot (Flex-foot) of the proposed prosthesis to reduce additional impact. The subject participant never complained about the performance of the ankle during heel-strike.

Active Mechanical Power

Figure 37:
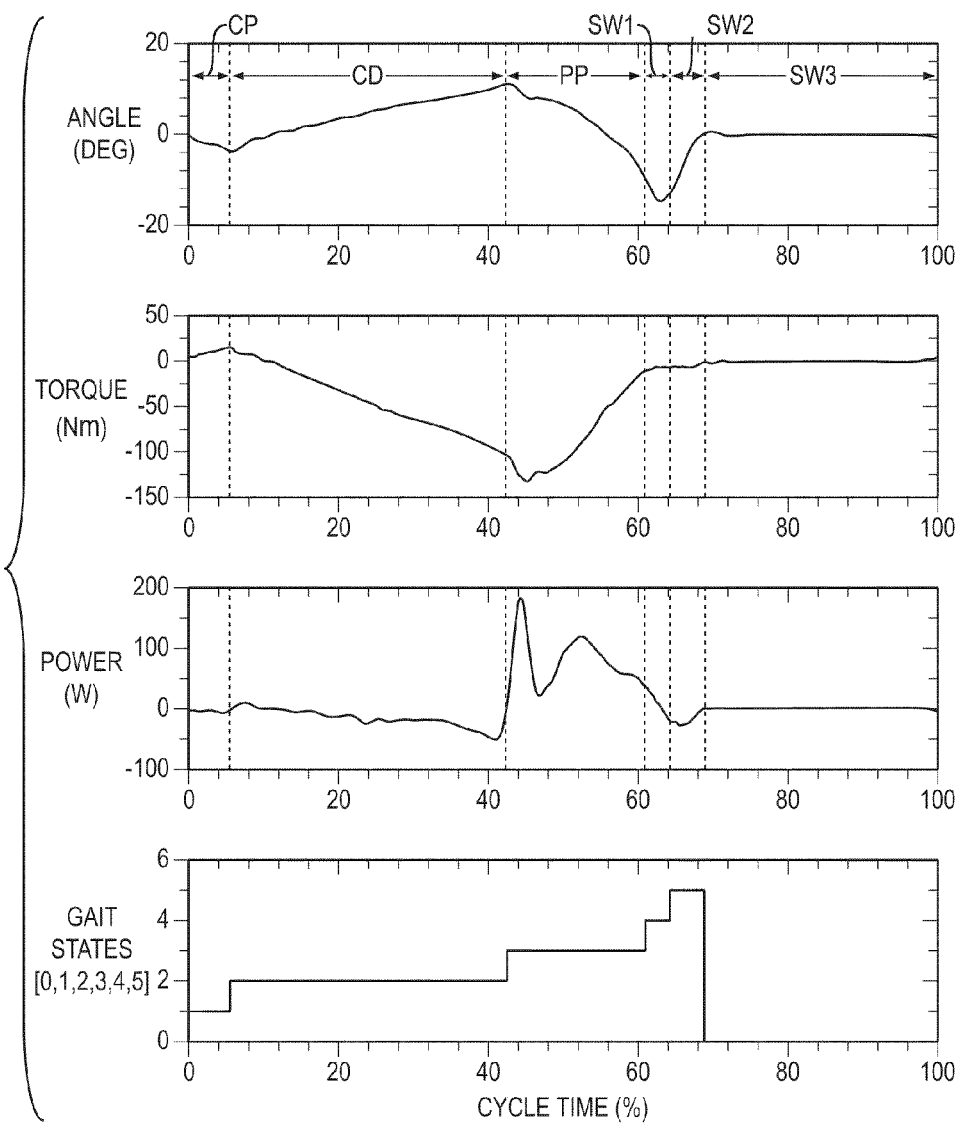
FIG. 37 depicts the measured ankle angle, torque, power, and the gait states of a walking trial.

FIG. 37 shows real time data for one gait cycle of a walking experiment in which the powered prosthesis was controlled to deliver positive net work during stance. The system went through a longer state sequence 1-2-3-4-5-0 than that under the virtual spring condition (FIG. 37d). It is noted that a dramatic change in joint velocity occurred during SW1 (FIG. 37a) due to the controller transition from the impedance controller to position controller during SW1. Furthermore, it is also observed that the power output of the prosthesis during PP behaved differently, as compared to that of normal human ankle {A-12}.

Figure 38:
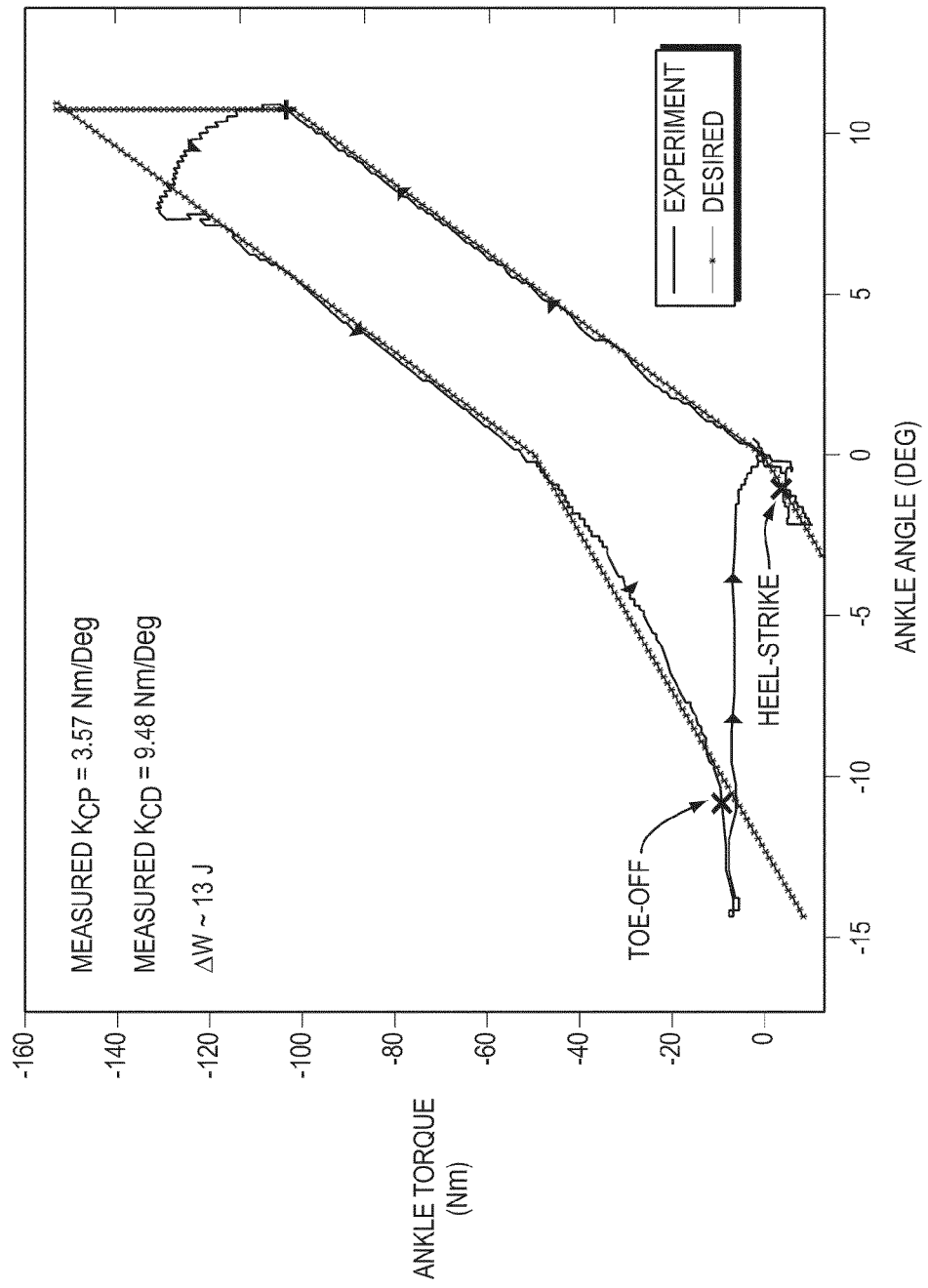
FIG. 38 shows an experimental ankle torque-angle plot for the powered prosthesis.
Figure 39A:
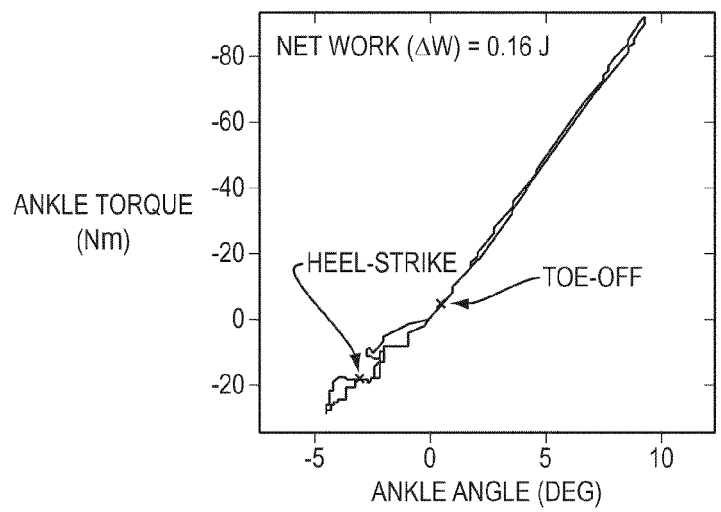
FIGS. 39A to 39E show examples demonstrating the prosthesis's capability of doing different amount of work in a gait cycle.
Figure 39B:
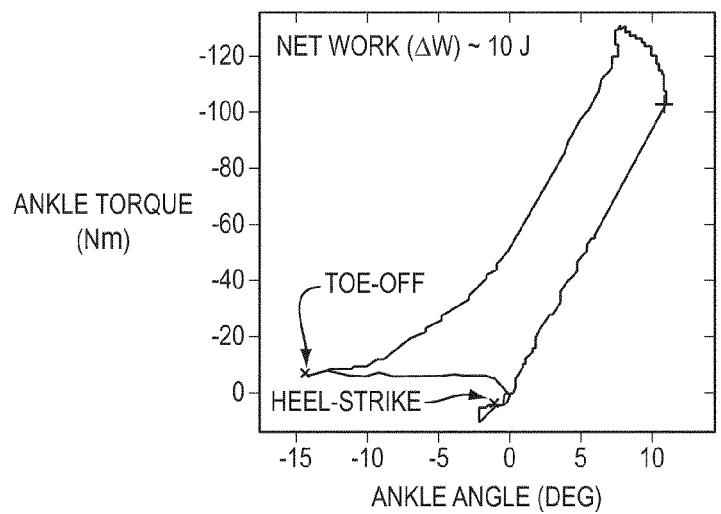
Figure 39C:
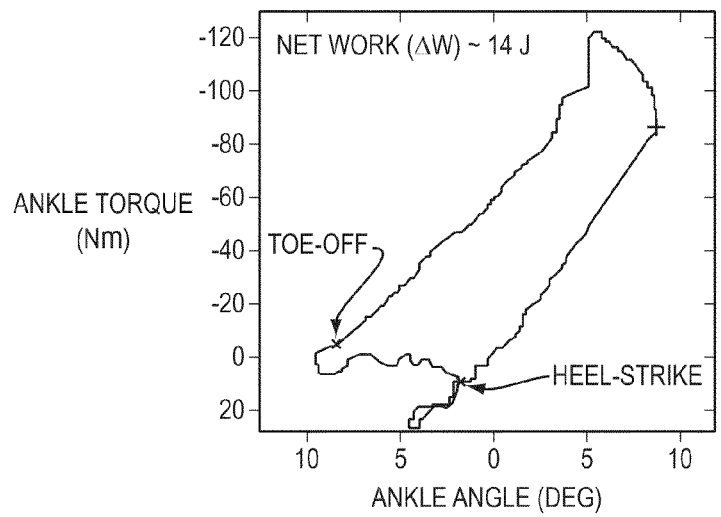
Figure 39D:
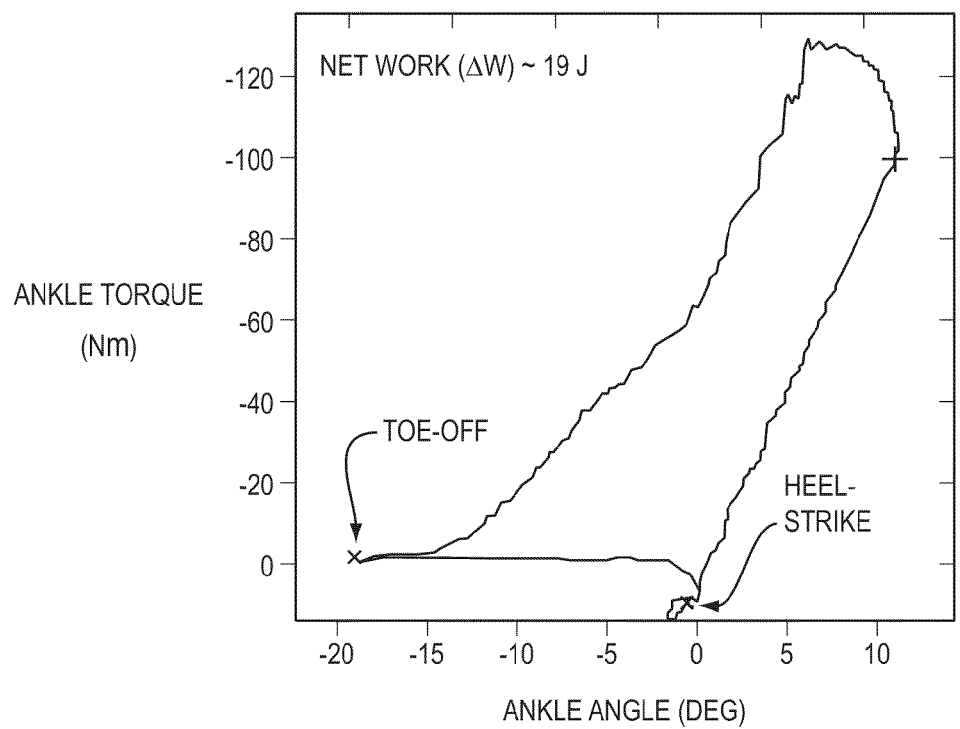
Figure 39E:
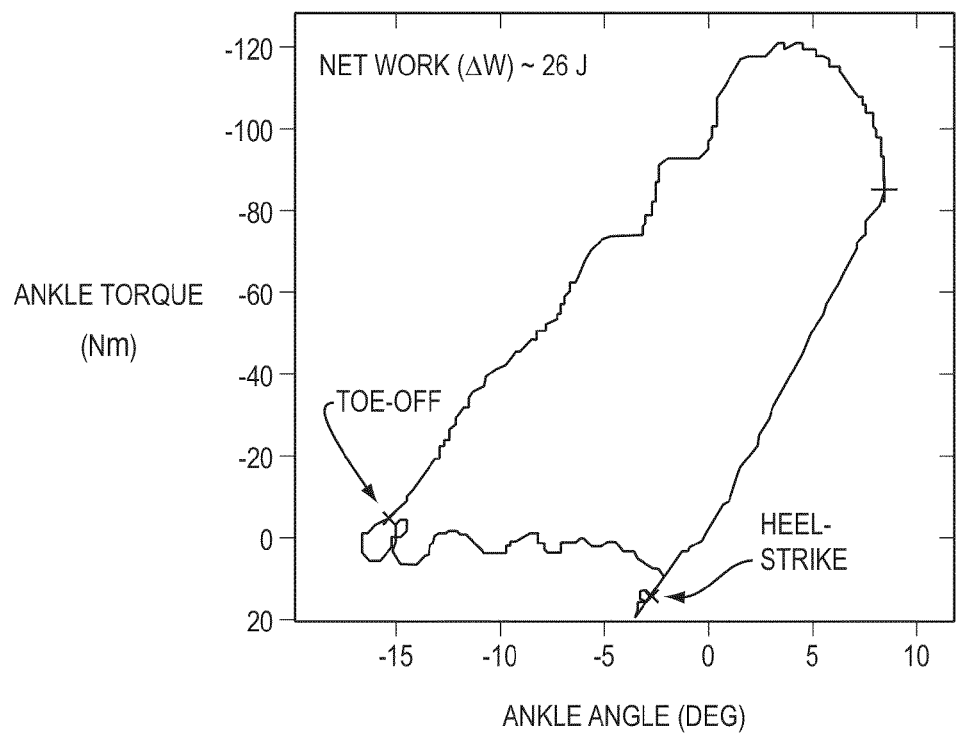
Figure 40:
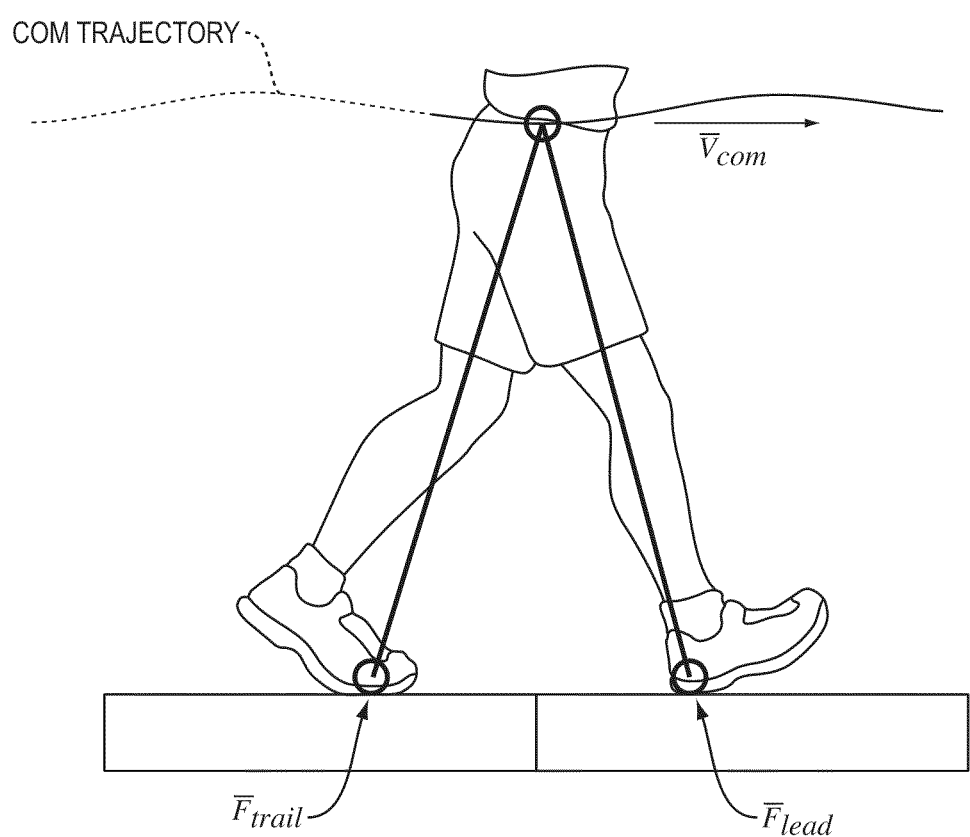
FIG. 40 shows a simple model of bipedal walking.
Figure 41:
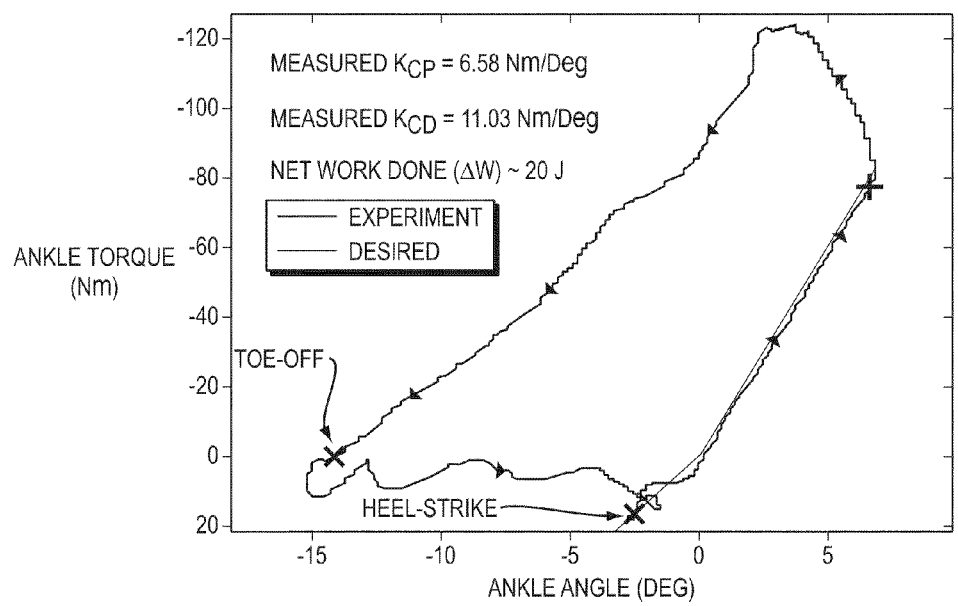
FIGS. 41, 42 and 43 illustrate examples of the powered prosthesis's torque-angle behavior.
Figure 42:
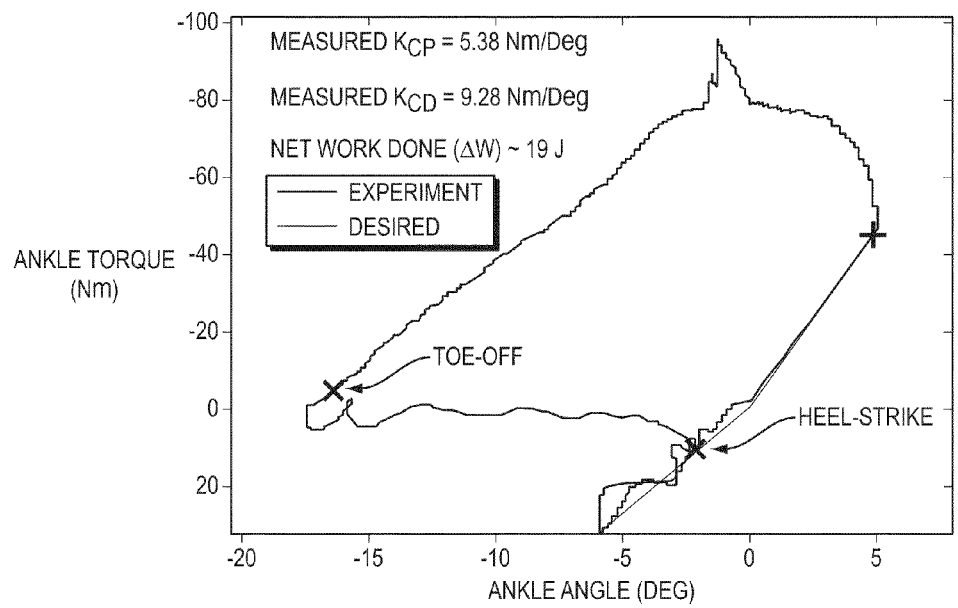
Figure 43:
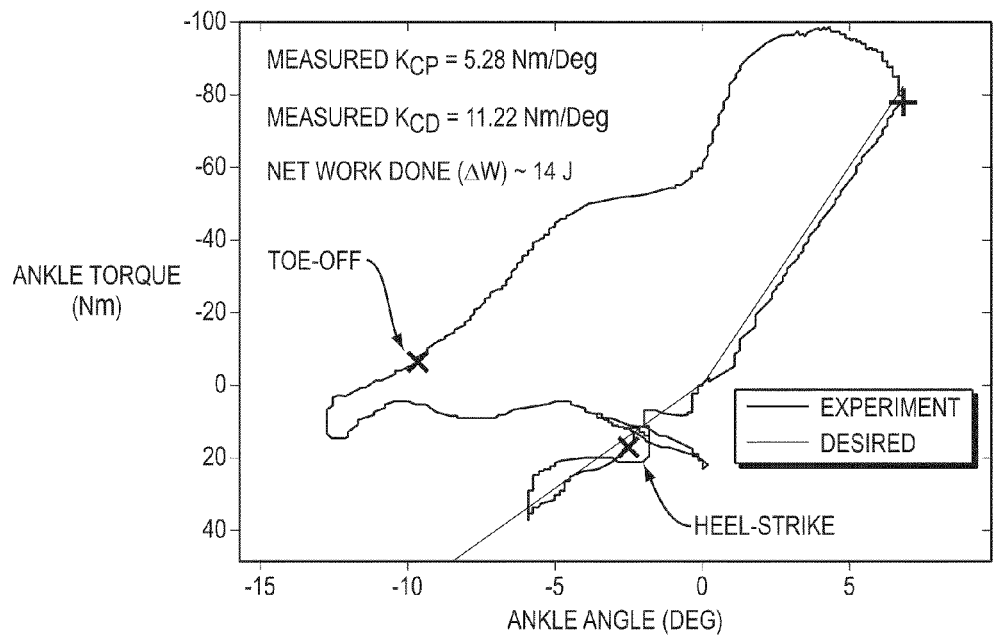

The corresponding ankle torque-angle behavior is shown in FIG. 38. The experimental result demonstrates the system's capacity to track the desired target stance phase behavior. As was designed, a constant offset torque Δt was applied to the amputee participant when the ankle torque was larger than the triggering threshold $t_{pp}$. In this example, Δt and $t_{pp}$ were set at 50 Nm and 105 Nm respectively, based on the amputee participant's preference. It is noted that the measured ankle torque-angle curve flattens around the peak torque region because the actual system required time (about 50 ms) to output the offset torque during the transition from CD to PP.

Also, the toe-off was set to be triggered before the ankle joint reaches the zero torque level (FIG. 38) because it can provide enough time for the control system to switch from impedance control mode to position control mode at the transition from stance to swing. FIGS. 39A to 39E show a summary of gait test results to demonstrate the prosthesis's capability of doing different amount of work at the joint in a gait cycle.

The method of using a constant offset torque was an initial attempt to mimic the active push-off of normal human walking. It was not intent to capture all the nonlinear characteristics of the observed quasi-static stiffness curve, however, it can provide a more intuitive way to relate the user's feedback to the parameter adjustments in the control system during experiments. Because of this fact, it speeds up the process to conduct clinical study for the evaluation of the hypothesis.

The preferred powered ankle-foot prosthesis is proposed comprises an unidirectional spring in parallel with a high performance, force-controllable actuator with series elasticity. By exploiting both parallel and series elasticity, the design is capable of satisfying the restrictive design specifications dictated by normal human ankle walking biomechanics.

Referring to Section I-B, the key question for the control is to define/design a target walking behavior for the prosthesis. For the swing phase, the desired behavior is just to reposition the foot to an predefined equilibrium position. For the stance phase control, it is commonly believed that the best way is to let the prosthesis mimic the normal human ankle impedance during stance, rather than simply tracking ankle kinematics {B-4}-{B-7}. However, the actual mechanical impedance of the human ankle during walking has not been determined experimentally because it is difficult to conduct ankle perturbation experiments on a human subject while walking {B-5}. As a resolution of this difficulty, many researchers have suggested another performance measure, called "quasi static stiffness", that is the slope of the measured ankle torque-angle curve during stance {B-4}-{B-7}. Mimicking the quasi-static stiffness curve of an intact ankle during walking is the main goal for the stance phase controller for the proposed prosthetic ankle-foot system.

FIGS. 10A and 10B show target stance phase behaviors for the powered prosthesis. (A) In this model, the quasi-static stiffness curve of the intact ankle is considered as a representation of the normal human ankle behavior during stance {B-4}-{B-7}. It can be decomposed into a spring component and a torque source. (B) A simplification of the model in (A), in which both the spring component and torque source are linearized.

As can be seen in FIG. 10A, a typical quasi-static stiffness curve can be decomposed into two main components: (1) a spring whose stiffness varies in a similar manner to the normal human ankle does in CP and CD. (2) a torque source that provides positive net work during late stance phase. We then simplified these two components and used them to provide the target stance phase behavior for the prosthesis as depicted in FIG. 5. The detailed descriptions for each component are summarized as follows:

1) A linear torsional spring with a stiffness that varies with the sign of the ankle angle. When the ankle angle is positive, the stiffness value will be set to $K_{CD}$. When the ankle angle is negative, the stiffness value will be set to $K_{CP}$.
2) constant offset torque Δτ that models the torque source during PP. This offset torque will be applied in addition to the linear torsional springs $K_{CD}$ during PP. $\tau_{pp}$ determines the moment at which the offset torque is applied, indicated by the point (4) in FIG. 5.

It is noted here that the conventional passive prostheses only provide the spring behavior but fail to supply the function of the torque source to thrust the body upwards and forwards during PP. Our designed prosthesis eventually will provide both functions during stance.

Using the above biomechanical descriptions and the results from {B-4}-{B-7} {B-19}, the design goals for the prosthesis are summarized as follows:
- the prosthesis should be at a weight and height similar to the intact limb.
- the system must deliver a large instantaneous output power and torque, i.e. about 250 W and 120 Nm for a 75 kg person. Furthermore, the system must produce 10 J of net positive mechanical work at the ankle joint during each stance period.
- the system must be capable of changing its stiffness as dictated by the quasi-static stiffness of an intact ankle.
- the system must be capable of controlling joint position during the swing phase.

The corresponding parameters values of the above design goals are given in Table I.

TABLE I

DESIGN SPECIFICATIONS

| | |
|---|---|
| Weight (kg) | 2.5 kg |
| Length (m) | 0.32 m |
| Max. Allowable Dorsiflexion (Deg) | 25 |
| Max. Allowable Plantarflexion (Deg) | 45 |
| Peak Torque (Nm) | 120 Nm |
| Peak Velocity (rad/s) | 5.2 rad/s at 20 Nm |
| Torque Bandwidth (Hz) | 1.5 Hz |
| Net Work Done (J) | 10 J at 1.3 m/s |
| Required Offset Stiffness (Nm/rad) | 550 Nm/rad |

The basic architecture of our mechanical design is a physical spring, configured in parallel to a high power output force-controllable actuator. The parallel spring and the force-controllable actuator serve as the spring component and the torque source in FIG. 5, respectively. To void hindering the foot motion during swing phase, the parallel spring will be implemented as an unidirectional spring that provides an offset stiffness value only when the ankle angle is larger than zero degree. In addition, we use a Series-Elastic Actuator (SEA) to implement the force-controllable actuator {B-21} {B-22}. FIGS. 6 and 17A and 17B show the Solid Work Model and the basic configuration of the proposed powered prosthesis, respectively.

As can be seen in FIGS. 17A and 17B, there are five main mechanical elements in the system: a high power output d.c. motor, a transmission, a series spring, an unidirectional parallel spring, and a carbon composite leaf spring prosthetic foot. We combine the first three components to form a rotary Series-Elastic Actuator (SEA). A SEA, previously developed for legged robots {B-21} {B-22}, consists of a dc motor in series with a spring (or spring structure) via a mechanical transmission. The SEA provides force control by controlling the extent to which the series spring is compressed. Using a linear potentiometer, we can obtain the force applied to the load by measuring the deflection of the series spring.

In this application, we use the SEA to modulate the joint stiffness as well as provide the constant offset torque $\Delta\tau$ as shown in FIG. 7. It provides a stiffness value $K_{CP}$ during CP and a stiffness value $K_{CD1}$ from CD to PP. From points (4) to (3), it supplies both the stiffness value $K_{CD1}$ and a constant, offset torque $\Delta\tau$. The unidirectional parallel spring provides an offset rotational stiffness value Kpr when the ankle angle is larger than zero degree.

FIGS. 17A and 17B show the Mechanical design, and FIG. 6 is a schematic diagram, of the prosthesis.

As shown in FIGS. 6 and 7, due to the incorporation of the parallel spring, the load borne by the SEA is greatly reduced, thus the SEA will have a substantially large force bandwidth to provide the active push-off during PP. FIG. 7 illustrates exploiting the parallel and series elasticity with an actuator. The parallel spring provides a biased, offset stiffness Kpr when the ankle angle is larger than zero degree. The series spring combined with the actuator, so called an SEA {B-21} {B-22}, is used to modulate the joint stiffness and serve as a torque source to do positive work at the ankle joint.

The elastic leaf spring foot is used to emulate the function of a human foot that provides shock absorption during foot strike, energy storage during the early stance period, and energy return in the late stance period. A standard low profile prosthetic foot, called Flex Foot was used in the prototype {B-13}.

Broadly speaking, there are three main design decisions in this project: (1) choosing the parallel spring stiffness, (2) choosing the actuator and transmission, and (3) choosing the series spring stiffness.

1) Parallel Spring: A linear parallel spring kp with a moment arm Rp in FIG. 6 provides a rotational joint stiffness $K_{pr}$ where $$K_{pr} = (k_p)(R_p)^2 \quad (1)$$

The goal is to properly select the moment arm and the spring constant in order to provide the suggested offset stiffness in Table I. In the physical system, due to the size and weight constraints, $k_p$ and $R_p$ were chosen to be 770 KN/m and 0.022 m, respectively. Consequently, $K_{pr}$=385 rad/s. Because this value is smaller than the suggested offset stiffness (550 rad/s), the SEA supplements the required joint stiffness (see FIG. 7).

Actuator and Transmission: The goal is to select an actuator and a transmission to bracket the maximum torque and speed characteristics of the prosthesis, so as to match the intact ankle torque/power-speed requirements (FIGS. 10A and 10B compare the joint torque/power-speed characteristic of the prosthesis to that of the normal human ankle during walking. FIG. 10A shows the Joint Torque vs. Joint Velocity and FIG. 10B shows the Absolute Joint Power vs. Absolute Joint Velocity.

In our design, a 150 W d.c. brushed motor from Maxon, Inc. (RE-40) was used because its peak power output (500 W) is much larger than that of the human ankle in walking (250 W). For the drive train system, the motor drives a 3 mm pitch linear ballscrew via a timing-belt drive transmission with a 1.7:1 ratio. The translational movement of the ballscrew causes an angular rotation of the ankle joint via a moment arm r=0.0375 m and the series spring.

Assuming the series spring will be chosen to be very stiff, the total transmission ratio $R_{total}$~133 was selected, where $R_{total}$ is defined as the ratio of the input motor velocity to the output ankle joint velocity. The peak torque/speed characteristics of the prosthesis has shown that the prosthesis is capable to generating normal human ankle-foot walking behavior. Furthermore, the power output characteristics of the prosthesis were designed to match that of the intact ankle during walking.

Series Spring: According to {B-22}, the selection criteria for the series spring is mainly based on the large force bandwidth because the series elasticity substantially reduces the system bandwidth at large force due to the motor saturation. The stiffer the spring is, the higher the SEA bandwidth is at large force. Therefore, by choosing a stiffer spring, our design goal was to have the large force bandwidth of the SEA much greater than the required force bandwidth in the specifications (Table I).

Figure 53:
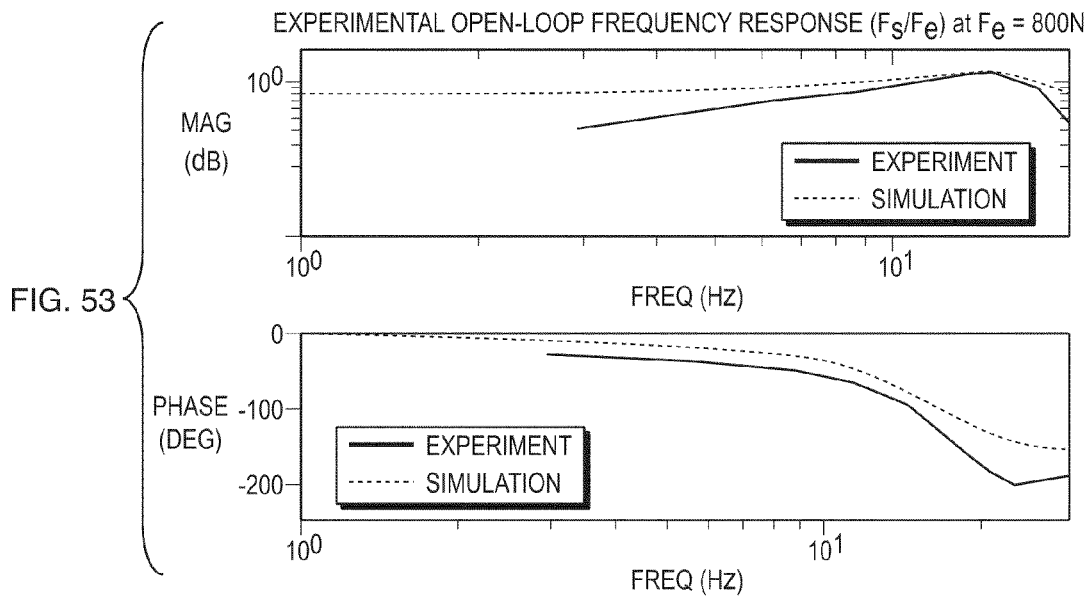
FIG. 53 illustrates an experimental open-loop frequency response.

FIG. 53 shows a simple linear model of the prosthesis for the bandwidth analysis. All degrees of freedom are transferred to the translation domain of the ballscrew. $M_e$, $B_e$, and $F_e$ represent the effective mass, damping, and linear motor force acting on effective mass, respectively, while x and $k_s$ are the displacement and the spring constant of the series spring. The parallel spring was not considered in this analysis because we assumed that the parallel spring does not inhibit controllers' ability to specify desired dynamics, at least within the operating range of torque level and bandwidth.

Figure 52:
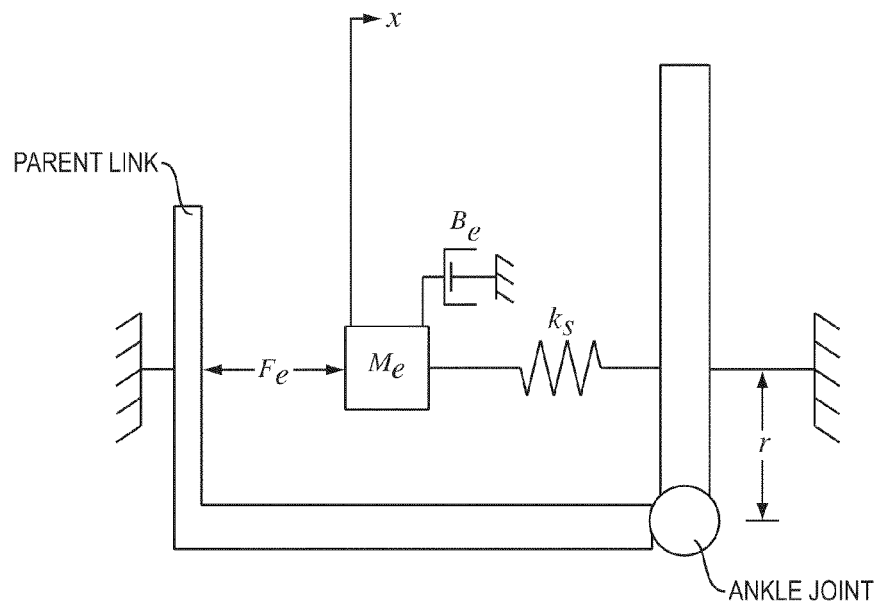
FIG. 52 shows a simple linear model of the prosthesis for the bandwidth analysis.

To analyze the large force bandwidth, we proposed a simple linear model (FIG. 52) for the prosthesis based on {B-22}. All system parameters and variables were converted to the linear motion of the ball screw in the prosthesis. We define a transmission ratio R that converts rotary motion of the motor into linear compression on the series spring (See FIG. 4-1). The effective motor mass $M_e$, damping $B_e$, and linear motor force $F_e$ can be obtained using the following equations:

$$M_e = I_m R^2$$

$$F_e = T_m R$$

$$B_e = b_m R$$

where $I_m$, $T_m$, $b_m$ are the rotary motor inertia, motor torque, the damping term of the motor, respectively. Both ends of the prosthesis are fixed for the bandwidth analysis, consequently, the equation of motion for this model becomes a standard second-order differential equation for a spring-mass-damper system. The spring force Fs was considered as the system output. According to {B-22}, the large force bandwidth is defined as the frequency range over which the actuator can oscillate at a force amplitude $F_{smax}$ due to the maximum input motor force, $F_{sat}$. The transfer function that describes the large force bandwidth is:

$$F_{smax}/F_{sat} = k_s/(M_e s^2 + (B_e + F_{sat}/V\text{sat})s + k_s) \quad (2)$$

where $F_{smax}$ and $V_{sat}$ are the maximum output force and maximum linear velocity of the motor respectively. They are defined as $F_{sat} = RT_{maxmotor}$ and $V_{sat} = \omega^{max}/R$. As can be seen in equation (2) above, the large force bandwidth is independent of the control system, but rather depends on the intrinsic system behaviors which are determined by the choices of the motor, transmission ratio, and the spring constant.

TABLE II

MODEL PARAMETERS

| Parameters | $F_{sat}$ | $V_{sat}$ | $M_e$ | $B_e$ |
|---|---|---|---|---|
| Values | 7654N | 0.23 m/s | 170 kg | 8250 Ns/m |

In our design, the total spring constant for the series springs is set to 1200 KN/m. Using the motor parameters (Maxon RE40) in {B-23} and transmission ratio (R=3560), the model parameters were obtained and shown in Table II.

The simulation result for the large force bandwidth has shown in FIG. 15. As shown in FIG. 15, the estimated large force bandwidth of the system with and without the parallel spring was at 9.4 Hz (at 50 Nm) and 3.8 Hz (at 120 Nm), respectively. As the parallel spring shared some of the payloads of the SEA, the required peak force for the system was significantly reduced. With the parallel spring, the estimated force bandwidth were much larger than the designed criteria in Table I. In practice, it is favorable to design a system whose large force bandwidth is several times larger than the required bandwidth as there are many factors that can substantially reduce the large force bandwidth, such as unmodeled friction {B-22}.

We also conducted open-loop bandwidth tests for the system by applying a chirp signal as the desired input command for the controller. The result for the bandwidth test is shown in FIG. 53. In general, the experimental result matched with the simulation of the spring-mass-damper system. The force bandwidth of the system using an input force Fe=800N (or input torque T=30 Nm) was about 14 Hz. As can be seen, the experimental frequency response curve dropped off rapidly at high frequency, mainly due to the motor and amplifier saturation. It also appeared that there was an unmodeled zero at low frequency.

Again, the above bandwidth analysis was used for the design purpose that provided a guideline for the selection of the series spring. For a better prediction of the actual system behavior, an advanced system model needs to be proposed. In {B-18}, we had shown that the proposed biomimetic mechanical design allowed the control system to mimic normal human ankle walking behavior. The pilot clinical studies supports the hypothesis that a powered ankle-foot prosthesis that mimics normal human ankle stance phase behavior can improve an amputee's gait.

A finite-state controller that allows the prosthesis to mimic human ankle behavior during walking.

As previously discussed, for level ground walking, human ankle provides three main functions: (i) it behaves as a spring with variable stiffness from CP to CD; (ii) it provides additional energy for push-off during PP; and (iii) it behaves as a position source to control the foot orientation during SW.

A key question for the design and control is to define a target walking behavior for the prosthesis. For the swing phase, the desired behavior is just to re-position the foot to an predefined equilibrium position. For the stance phase control, instead of simply tracking ankle kinematics, it is commonly believed that the best way is to let the prosthesis mimic the "quasi-static stiffness", that is the slope of the measured ankle torque-angle curve during stance {C-1} {C-2}. Mimicking the quasi-static stiffness curve of an intact ankle during walking (FIG. 2) is the main goal for the stance phase control.

A typical quasi-static stiffness curve (FIG. 2) can be decomposed into two main components: (1) a spring whose stiffness varies in a similar manner to the normal human ankle does in CP and CD. (2) a torque source that provides positive net work during late stance phase. For the ease of implementation, we modified these two components to obtain the target stance phase behavior as depicted in FIG. 5. Each component is described as follows:

1) A linear torsional spring with a stiffness that varies with the sign of the ankle angle. When the ankle angle is positive, the stiffness value will be set to $K_{CD}$. When the ankle angle is negative, the stiffness value will be set to $K_{CP}$.

2) A constant offset torque $\Delta t$ is used to model the torque source during PP. This offset torque is applied in addition to the torsional spring KCD during PP. $\tau_{pp}$ determines the moment at which the offset torque is applied, indicated by the point (4) in FIG. 5.

It is noted that the conventional passive prostheses only provide the spring behavior but fail to supply the function of the torque source to propel the body during PP {C-3}. Our designed prosthesis eventually will provide both functions during stance.

Using the above biomechanical descriptions and the results from {C-1} {C-2} {C-14}, the design goals for the prosthesis are summarized as follows:

the prosthesis should be at a weight and height similar to the intact limb.

the system must deliver a large instantaneous output power and torque during push-off.

the system must be capable of changing its stiffness as dictated by the quasi-static stiffness of an intact ankle.

the system must be capable of controlling joint position during the swing phase.

the prosthesis must provide sufficient shock tolerance to prevent any damage in the mechanism during the heel-strike.

The corresponding parameters values of the above design goals are given in Table I. These parameters values are estimated based on the human data from {C-1} {C-2} {C-14} {C-15}.

TABLE I

DESIGN SPECIFICATIONS

| | |
|---|---|
| Weight (kg) | 2.5 |
| Max. Allowable Dorsiflexion (Deg) | 15 |
| Max. Allowable Plantarflexion (Deg) | 25 |
| Peak Torque (Nm) | 140 |
| Peak Velocity (rad/s) | 5.2 |
| Peak Power (W) | 350 |
| Torque Bandwidth (Hz) | 3.5 |
| Net Work Done (J) | 10 J at 1.3 m/s |
| Required Offset Stiffness (Nm/rad) | 550 |

Finite-state controllers are usually used in locomotion assistive/prosthetic devices such as A/K prostheses {C-17} {C-12} because gait is repetitive between strides and, within a stride, can be characterized into distinct finite number of sub-phases. According to Section II-A, human ankle also demonstrates such kind of periodic and phasic properties during walking. This motivates the usage of a finite-state controller to control the powered prosthesis.

The finite-state controller should be designed to replicate the target stance phase behavior. To this end, a finite-state controller for level-ground walking was implemented (FIG. 28). The details of the proposed finite-state controller for level-ground walking are discussed as follows.

Three states (CP, CD, and PP) were designed for stance phase control. Descriptions for each state are shown below.

CP begins at heel-strike and ends at mid-stance. During CP, the prosthesis outputs a joint stiffness, $K_{CP}$.

CD begins at mid-stance and ends at PP or toe-off, depending on the measured total ankle torque $T_{ankle}$. During CD, the prosthesis outputs a joint stiffness, $K_{CD}$, where $K_{CD}=K_{rp}+K_{CD1}$.

PP begins only if the measured total ankle torque, $T_{ankle}$ is larger than the predefined torque threshold, $\tau pp$. Otherwise, it remains in state CD until the foot is off the ground. During PP, the prosthesis outputs a constant offset torque, $\Delta\tau$ superimposing the joint stiffness, $K_{CD}$ as an active push-off.

$K_{CP}$, $K_{CD}$, $\tau_{pp}$, and $\Delta\tau$ are the main parameters affecting the ankle performance during the stance phase control. In particular, the offset torque is directly related to the amount of net work done at the ankle joint. These parameter values were chosen based on the user's walking preference during experiments. The stance phase control for a typical gait cycle is graphically depicted in FIG. 28.

Swing Phase Control

Another three states (SW1, SW2, and SW3) were designed for the swing phase control. Descriptions for each state are shown below.

SW1 begins at toe-off and ends in a given time period, $\tau_H$. During SW1, the prosthesis servos the foot to a predefined foot position, $\theta_{toeoff}$ for foot clearance.

SW2 begins right after SW1 and finishes when the foot reaches zero degree. During SW2, the prosthesis servos the foot back to the default equilibrium position $\theta_d=0$.

SW3 begins right after SW2 and ends at the next heel strike. During SW3, the controller will reset the system to impedance mode and output a joint stiffness, $K_{CP}$.

The time period, $t_H$ and predefined foot position, $\theta_{toeoff}$ are all tuned experimentally.

During state transition and identification, the system mainly relied on four variables:

Heel contact(H). H=1 indicates that the heel is on the ground, and vice versa.

Toe contact(T). T=1 indicates that the toe is on the ground, and vice versa.

Ankle angle($\theta$)

Total ankle torque($T_{ankle}$)

All these triggering information can be obtained using local sensing; including foot switches to measure heel/toe contact, ankle joint encoder to measure the ankle angle, and the linear spring potentiometer to measure joint torque.

Low-Level Servo Controllers

To support the proposed stance phase and swing phase controls, three types of low-level servo controllers were developed: (i) a high performance torque controller to provide an offset torque during push-off as well as facilitate the stiffness modulation; (ii) an impedance controller to modulate the joint stiffness during the entire stance phase; (iii) a position controller to control the foot position during the swing phase. The details of the controller designs can be found in {C-15}.

The human ankle varies impedance and delivers net positive work during the stance period of walking. In contrast, commercially available ankle-foot prostheses are passive during stance, causing problems of locomotory economy, balance and shock absorption for transtibial amputees. In this investigation we advance an adaptive control approach for a force-controllable ankle-foot prosthesis. The system employs both sensory inputs measured local to the prosthesis, and electromyographic (EMG) inputs measured from residual limb muscles. Using local prosthetic sensing, we advance finite state machine controllers designed to produce human-like movement patterns for level-ground and stair-descent gaits. To transition from level-ground to stairs, the amputee flexes his gastrocnemius muscle, triggering the prosthetic ankle to plantar flex at terminal swing, and initiating the stair-descent state machine algorithm. To transition back to level-ground walking, the amputee flexes his tibialus anterior, keeping the ankle dorsiflexed at terminal swing, and initiating the level-ground state machine algorithm. As a preliminary evaluation of clinical efficacy, a transtibial amputee walks using both the adaptive controller and a conventional passive-elastic control. We find that the amputee can robustly transition between local state controllers through direct muscle activation, allowing rapid transitioning from level-ground to stair walking patterns. Additionally, we find that the adaptive control results in a more human-like ankle response, producing net propulsive work during level-ground walking and greater shock absorption during stair descent. The results of this study highlight the importance of prosthetic leg controllers that exploit neural signals to trigger terrain-appropriate local prosthetic leg behaviors.

Several engineering challenges hinder the development of a powered ankle-foot prosthesis {D-8} {D-16} {D-17}. With current actuator technology, it is challenging to build an ankle-foot prosthesis that matches the size and weight of the human ankle, but still provides a sufficiently large instantaneous power and torque output to propel an amputee's locomotion. Ankle-foot mechanisms for humanoid robots are often too heavy or not sufficiently powerful to meet the human-like specifications required for a prosthesis {D-18} {D-19}. Furthermore, a powered prosthesis must be position and impedance controllable. Often robotic ankle controllers follow pre-planned kinematic trajectories during walking {D-18} {D-19}, whereas the human ankle is believed to operate in impedance control mode during stance and position control mode during swing {D-2} {D-3}. Finally, when developing a powered ankle-foot prosthesis, a key challenge to overcome is how to measure and respond to the amputee's movement intent. For some time, researchers have attempted to use electromyographic (EMG) signals measured from the residual limb as control commands for an external prosthesis or exoskeleton {D-20}-{D-26}. However, due to the nonlinear and non-stationary characteristics of the EMG signal {D-21}, researchers have only been able to provide discrete or binary levels of position or velocity control, whereas a prosthetic ankle-foot system requires a continuous joint control where both position and impedance are actively modulated.

A long-term objective in the field of prosthetic leg design is to advance prosthetic joints that mimic the dynamics of the missing limb, not only for level-ground gait patterns, but also for irregular terrain ambulation. In this investigation we seek a prosthetic intervention that captures human-like gait patterns for two terrain surfaces, namely level-ground and stairs. We investigate these particular gait patterns as an initial pilot investigation, with the long-term objective of prostheses with multi-terrain capability. To this end, we advance a powered prosthesis comprising a unidirectional spring, configured in parallel with a force-controllable actuator with series elasticity. The prosthesis employs both sensory inputs measured local to the prosthesis, and electromyographic (EMG) inputs measured from residual limb muscles. Using local prosthetic sensing of joint state and ground reaction force, we develop finite state machine controllers designed to produce human-like gait patterns for level-ground walking and stair descent. To transition between these gaits, EMG signals measured from the tibialis anterior, soleus and gastrocnemius are used as control commands. We conduct a pilot clinical evaluation to test whether the adaptive control results in a more human-like ankle response. Specifically, we measure prosthetic ankle state, torque, and power during level-ground and stair descent using both the adaptive controller and a conventional passive-elastic control. Finally, for the adaptive control, we test whether the amputee participant can robustly and accurately transition between the local state controllers through direct muscle activation.

One of the key challenges in this research is to obtain user intent on the choice of the finite-state controllers such as level ground walking and stair descent. Our approach is to use electromyographic (EMG) signals measured from the residual limb of an amputee to infer his/her intent on the choice of the controllers. We present methods used for acquiring the MEA and the paradigm we have chosen to infer motor commands based on these signals. Finally, we describe the experimental protocol for the evaluation of controller performance as well as the control system implementation and hardware development.

In earlier sections, the biomechanics of normal human ankle for level ground walking and stair climbing were reviewed. We use these biomechanical descriptions to motivate the mechanical and control system design.

Stair Descent

Normal human ankle biomechanics for stair descent is significantly different from that of level-ground walking. A stair descent gait cycle is typically defined as beginning with the toe strike of one foot and ending at the next toe strike of the same foot {D-3} {D-29} {D-30}. The stance phase of stair descent is divided into three sub-phases: Controlled Dorsiflexion 1 (CD1), Controlled Dorsiflexion 2 (CD2), and Powered Plantarflexion (PP). These phases of gait are described in FIG. 54. The detailed descriptions for each sub-phase are provided below.

Controlled Dorsiflexion 1 (CD1)

Figure 54:
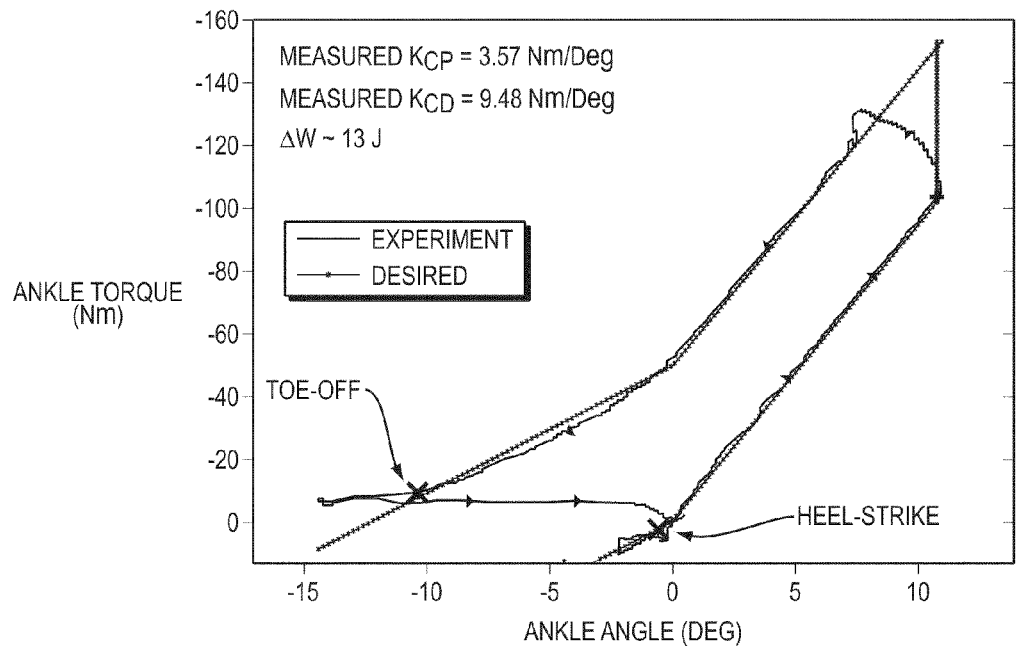
FIG. 54 shows an experimental ankle torque-angle plot for the powered prosthesis across a single gait cycle with positive net work.

CD1 begins at foot strike and ends at foot-flat. In this phase, the foot strikes the step in a more plantarflexed position where the center of pressure is on the forefoot rather than the heel (FIG. 54). As the body moves from a higher position, a significant amount of potential energy is absorbed. Over a gait cycle, the power absorbed by the human ankle in this phase is much greater than the power released in PP {D-3} {D-29} {D-30} (FIG. 54). Therefore, during CD1, the human ankle can be modeled as a damper.

Controlled Dorsiflexion 2 (CD2)

CD2 starts at foot flat and continues until the ankle reaches a maximum dorsiflexion posture. Here, the ankle acts as a linear spring in parallel with a variable-damper designed to effectively control the amount of energy absorbed {D-3}.

Powered Plantar Flexion (PP)

PP begins at the maximum position of the ankle and ended at foot off (FO). In this phase, the ankle releases the energy stored during CD2, propelling the body upwards and forwards. The ankle can be modeled as a linear spring in parallel with a linear damper {D-3}.

Swing Phase (SP)

SP begins at foot off and ends at toe-strike. For stair descent, the foot will plantarflex down during SP before the next toe strike. During SP, the ankle can be modeled as a position source.

Summary of the Biomechanics Study Human ankle provides three main functions: (i) it modulates the joint impedance (joint stiffness/damping) during the stance phase of walking. (ii) it provides active mechanical power or does net positive work during PP for level ground walking; and (iii) it behaves as a position source to control the foot orientation during SW. The above human ankle properties define the basic functional requirements of a powered ankle-foot prosthesis. Furthermore, the biomechanics descriptions also outline the target prosthesis behavior for the control system.

Motivated by the human ankle-foot walking biomechanics, we developed a powered ankle-foot prosthesis, called MIT Powered Ankle-Foot Prosthesis, to study amputee-machine interaction (FIG. 6) {D-31}-{D-33}. The prosthesis is capable of varying impedance and delivers net positive work during the stance period of walking, in a similar manner to normal human ankle. In particular, it can provide a sufficiently large instantaneous power output and torque to propel an amputee during PP, while still matches the size and weight of the intact ankle. This has been claimed as the main challenge and hurdle in the development of a powered ankle-foot prosthesis {D-8} {D-16}.

The basic architecture of the mechanical design is a physical spring, configured in parallel to a high-power, force-controllable actuator with series elasticity (see FIG. 6C). As can be seen, there are five main mechanical components in the system: a high power output d.c. motor, a transmission, a series spring, a unidirectional parallel spring, and a carbon composite leaf spring prosthetic foot. We combine the first the d.c motor, transmission, and the series spring to form a rotary Series-Elastic Actuator (SEA). A SEA, previously developed for legged robots {D-33} {D-34}, consists of a dc motor in series with a spring (or spring structure) via a mechanical transmission. The SEA provides force control by controlling the extent to which the series spring is compressed. Using a linear potentiometer, we can obtain the force applied to the load by measuring the deflection of the series spring. The SEA is used to modulate the joint stiffness/damping as well as provide the motive power output for active push-off {D-34}. Because of the requirements of high output torque and power for an ankle-foot prosthesis {D-32} {D-33}, we incorporate a physical spring, configured in parallel to SEA, so that the load borne by the SEA is greatly reduced. Because of this fact, the SEA will have a substantially large force bandwidth to provide the active push-off during PP. To avoid hindering the foot motion during swing phase, the parallel spring is implemented as a unidirectional spring that provides an offset stiffness value only when the ankle angle is larger than zero degree. As the main focus in this paper is on the control schemes design and evaluation, the details about the mechanical design and component selections will not be discussed in this paper. Those information can be obtained from {D-32} {D-33}.

Hybrid Control System

Finite-state controllers are usually used in locomotion assistive/prosthetic devices such as A/K prostheses {D-16} {D-35}-{D-37} because gait is repetitive between strides and, within a stride, can be characterized into distinct finite numbers of sub-phases. Human ankle also demonstrates such kind of periodic and phasic properties during walking. This motivates the usage of a finite-state controller to control the powered prosthesis.

Five basic requirements for the design of the control system are listed below:

- A finite-state controller should contain sufficient numbers of states to replicate the functional behaviors for each sub-phase of human ankle during walking.
- The control system must have three types of low-level servo controllers to support the basic ankle behaviors: (i) a torque controller; (ii) an impedance controller; and (iii) a position controller.
- Local sensing is favorable for gait detection and transition among states. The finite-state controller will use the sensing information to manage the state transitions and determine which low-level servo controller should be used to provide proper prosthetic function for a given state condition.
- Due to the intrinsic behavioral difference between the level-ground walking and stair descent, two separate finite-state controllers need to be designed.
- A high-level control input is required to manage the transition between the finite-state controls for level-ground walking and stair descent.

A control system with two finite-state controllers was implemented to allow the prosthesis to mimic the human ankle behavior for both level-ground walking and stair descent. The overall architecture of the control system is shown in FIG. 7. First, as can be seen, the control system contains the suggested, three low-level servo controllers to support the basic human ankle functions. Second, only local variables are adopted for state detection and transition, which are ankle angle, ankle torque, and foot contact. Third, one finite-state controller is designed for level-ground walking while the other is designed for stair descent. Fifth, we use electromyographic (EMG) signals measured from the residual limb of an amputee as control commands to manage the switching between the finite-state controllers for level-ground walking and stair descent (FIG. 25). An EMG Processing Unit is designed to detect amputee's intent on the controller transition, based on the muscular activities (EMG signals) of the residual limb. To transit from level-ground walking to stair descent, the amputee flexes his gastrocnemius and soleus muscles during the swing phase of walking. Once the EMG Processing Unit detects the corresponding muscle activity pattern, it then triggers the prosthetic ankle to plantar flex during terminal swing, and initiating the stair-descent state machine algorithm. To transition back to level-ground walking, the amputee flexes his tibialis anterior, changing the foot landing condition and initiating the level-ground state machine algorithm.

In the next sections, we first talk about the design of the finite-state controllers for level-ground walking and stair descent. We then describe how we use electromyographic (EMG) signals to determine the switching between the proposed finite-state controllers. Finally, we discuss the details of the control system implementation and hardware development. As the main focus in this paper is on the design and implementation of the high level finite-state controllers, the details descriptions of the low-level servo controllers are not covered in this paper. Further information on this topics can be obtained in {D-31}.

Finite-State Control for Level-Ground Walking

Stance Phase Control: A finite-state controller for level-ground walking was implemented based on the biomechanical descriptions in Section 2.2.1 (4-ure 5). Three states were designed for stance phase control, which are named CP, CD, and PP respectively. For the ease of implementation, we made a couple of modifications in state definitions and desired state behaviors, as compared those described in Section 2.2.1. Descriptions for each state of the stance phase control are shown below.

CP begins at heel-strike and ends at mid-stance. During CP, the prosthesis outputs a joint stiffness, $K^r_{CP}{}^1$ to prevent foot slapping and provide shock absorption during heel-strike.

CD begins at mid-stance and ends at PP or toe-off, depending on the measured total ankle torque $T_{ankle}$. During CD, the prosthesis outputs a total joint stiffness $K^r_{CD}$ to allow a smooth rotation of the body. The total joint stiffness is $$K_{CD} = K_P + K_{CD1}$$

where $K_P$, $K_{CD1}$ are the rotary stiffness components contributed by the parallel spring and SEA, respectively. The conversion of the joint stiffness between translational and rotary domains is $K^r = r^2 K$, where K and r are the joint stiffness in translational domain and moment arm, respectively. For example, $K_{CP} = r^2 K_{CP}$.

PP begins only if the measured total ankle torque, $T_{ankle}$ is larger than the predefined torque threshold, $\tau_{pp}(T_{ankle} > \tau_{pp})$. Otherwise, it remains in state CD until the foot is off the ground. During PP, the prosthesis outputs a constant offset torque, $\Delta\tau$ superimposing the linear joint stiffness, $K_{CD}$ as an active push-off.

$K_{CP}$, $K_{CD}$, $\tau_{pp}$, $\Delta\tau$ are the main parameters affecting the ankle performance during the stance phase control. In particular, the offset torque, $\Delta\tau$ is directly related to the amount of net work done at the ankle joint. These parameter values are chosen based on the user's walking preference during experiments. The stance phase control for a typical gait cycle is graphically depicted in FIG. 28A.

Swing Phase Control

To implement the ankle behavior during swing and allow user to voluntarily control the equilibrium position of the foot, three states are designed for the swing phase control, which are named SW1, SW2, and SW3. Descriptions for each state of the swing phase control are shown below.

SW1 begins at toe-off and ends in a given time period, $t_H$. During SW1, the prosthesis servos the foot to a predefined foot position, $\theta_{toeoff}$ for foot clearance.

SW2 begins right after SW1 and finishes in a time period, $t_2$. During SW2, the operator is allowed to voluntarily control the equilibrium position of the foot for a time period, $t_2$ as a mean of selecting appropriate finite-state controllers. The operator's motor intent is determined from available EMG signals. In this application, the motor intent is only inferred to a binary output command or foot position, $\theta_{EMG}$: (i) $\theta_{EMG} = 0$ which implies the participant's intent for level-ground walking (ii)

$\theta_{EMG}$=−20 degrees which implies the participant's intent for stair descent. The output foot position, $\theta_{EMG}$ is then sent to the position controller as the equilibrium position, $\theta_d$ and the controller servos the foot to the desired position within the time period, $t_2$. Once the time period $t_2$ is over, the control system will determine whether the system should stay in the level-ground walking mode or stair descent mode, depending on the current $\theta_d$. If $\theta_d \geq 0$, the state control will enter state SW3. Otherwise, the system will switch to the stair descent mode and enter state CD1.

SW3 begins right after SW2 and ends at the next heel-strike. During SW3, the state controller resets the system to impedance mode and outputs a joint stiffness, $K_{CP}{}^r$.

The time periods $t_H$, $t_2$, and predefined foot position $\theta_{toeoff}$ are all tuned experimentally. The swing phase control for a typical gait cycle is graphically depicted in FIG. 28A.

Sensing for State Transitions

Besides EMG signals, during state transition and identification, the system mainly relied on four variables:

1. Heel contact (H). H=1 indicates that the heel is on the ground, and vice versa.
   Toe contact (T). T=1 indicates that the toe is on the ground, and vice versa.
   Ankle angle ($\theta$)
2. Total ankle torque ($T_{ankle}$)

All these triggering information can be obtained using local sensing; including foot switches to measure heel/toe contact, ankle joint encoder to measure the ankle angle, and the linear spring potentiometer to measure joint torque. The hardware implementation for the local sensing will be discussed below. A state machine diagram with all triggering conditions is shown in FIG. 29.

Finite-State Control for Stair Descent

Stance Phase Control

Figure 55:
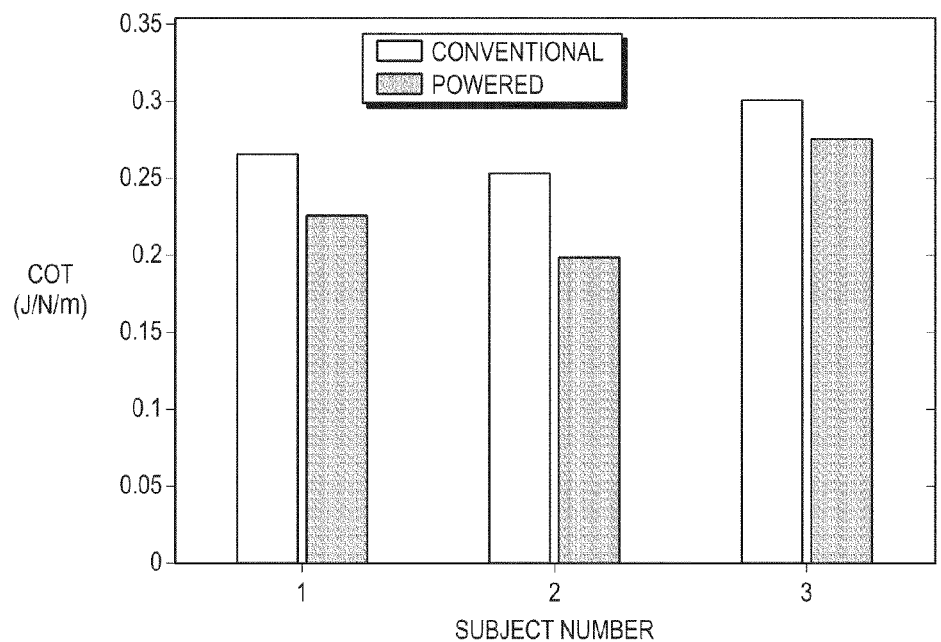
FIG. 55 is a bar graph illustrating the metabolic cost of transport for three participants.

Another finite state machine was implemented to allow the prosthesis to mimic human ankle behavior during stair descent (see FIG. 55). As can be seen, only two states (CD1, CD2) were designed for stance phase control. We did not explicitly implement/indicate state PP in our controller because according to Section 2.12, the ankle behavior during CD2 is basically the same as that during PP. The modified state definitions and desired state behaviors for the stance phase control are shown below.

CD1 begins just before toe-strike and ends at foot-flat. During CD1, the prosthesis outputs a joint damping, $K_{D01}{}^r$ to reduce the impact generated due to the toe-strike on the ground.

CD2 begins at foot-flat and ends at toe-off. During CD2, the prosthesis outputs a joint stiffness, $K_{CD}{}^r$ (it has already included the stiffness of the parallel spring) if the ankle is larger than zero degree. Otherwise, it outputs another joint stiffness. Also, it resets the equilibrium position of the impedance controller back to zero degree $\theta_d$=0.

In this controller, we do not use the SEA to provide the damping component in state CD2 because according to human ankle data {D-3}, the damping component in state CD2 is relatively less significant than the spring component. Nevertheless, the intrinsic damping in the transmission of the mechanical system can provide part of the required damping.

Swing Phase Control

Two states (SW1, SW2) were designed for the swing phase control for stair descent. Although state CD1 begins at the late swing phase and finishes until foot-flat, we only consider it as a state in the stance phase control. Descriptions for each state of the swing phase control are shown below.

SW1 begins at toe-off and ends in a given time period, $t_1$. During SW1, the prosthesis servos the foot to the default equilibrium position $\theta_d$=0. This state serves as a buffer for foot clearance before the use of operator's motor commands to control the foot orientation.

SW2 begins right after SW1 and finishes in a time period, $t_2$. During SW2, the operator is allowed to voluntarily control the equilibrium position of the foot for a time period, $t_2$ as a mean of selecting appropriate finite-state controllers. As mentioned above, if $\theta_{EMG}$=−20 degrees (i.e. $\theta_d \geq 0$), the system remains in the stair descent mode and enters state CD1. Otherwise it will switch to the level-ground walking mode and enter state SW3 of the level-ground walking finite-state controller.

The time periods $t_1$, $t_2$ are all tuned experimentally. The swing phase control for a typical gait cycle is graphically depicted in FIG. 55A. The corresponding state machine diagram with all triggering conditions is shown in FIG. 55B.

EMG Processing Unit

An EMG processing unit was designed to detect amputee's intent on the choice of finite-state controllers, based on the residual limb muscular activities (EMG signals). The inputs of the unit were raw EMG signals recorded from Gastrocnemius, Soleus, and Tibialis Anterior muscles of the residual limb. While the output was a discrete command (foot orientation), $\theta_{EMG}$ which is either 0 or −20. According to Section 2.3, if $\theta_{EMG}$=0, it implies the participant intends to use the level-ground walking finite-state controller, otherwise, the stair descent finite-state controller should be used for the next gait cycle. The output foot orientation $\theta_{EMG}$ was then sent to the position controller as the equilibrium position, $\theta_d$ to trigger the controller transition.

The EMG processing unit comprised of two parts: EMG Pre-processing and Neural Network Motor-Intent Estimator. The details for each part will be discussed in the next sections.

EMG Pre-Processing

Since the goal of this investigation was to use EMG signals to infer user's intent on the desired ankle-behavior, it was desirable to measure EMG signals from those residual limb muscles that previously actuated the biological ankle before amputation. Thus, using surface electrodes, we recorded from the Gastrocnemius and Soleus muscles for prosthetic ankle plantar flexion control, and from the Tibialis Anterior for prosthetic ankle dorsiflexion control. Signals were amplified and sampled at 2 kHz. The raw, digitized EMG data was band-pass filtered between 20 and 300 Hz to further eliminate noise.

A 100 ms sliding window was then used to compute a running standard deviation of the EMG signal. Many models {D-38} {D-39} of EMG assume that it is a white noise process whose standard deviation is proportional to the strength of the motor command. Though our control paradigm does not rely on these specific assumptions, in practice, computing the standard deviation of EMG was a robust indicator of the muscle's excitation level.

Neural Network Motor-Intent Estimator

As for our study, we were concerned with making transitions between different motor states. Rather than deducing what could be a continuously varying character of the ankle {D-40}, we infer the subject's discrete motor intent via the variances of the measured EMG signals. In this study, the motor intent is parsimoniously defined by three discrete ankle states: plantarflexed, relaxed, and dorsiflexed.

In order to learn a relationship between EMG measurements of the residual muscles and the ankle states, a feed-forward neural network with a single hidden layer was used. The network has a single output for the ankle state, three units in the hidden layer, and one input unit for each EMG-derived standard deviation estimate (in most cases, three). Each unit has a nonlinear sigmoidal activation function, ensuring the ability to learn a potentially nonlinear mapping between inputs and ankle state.

Figure 56:
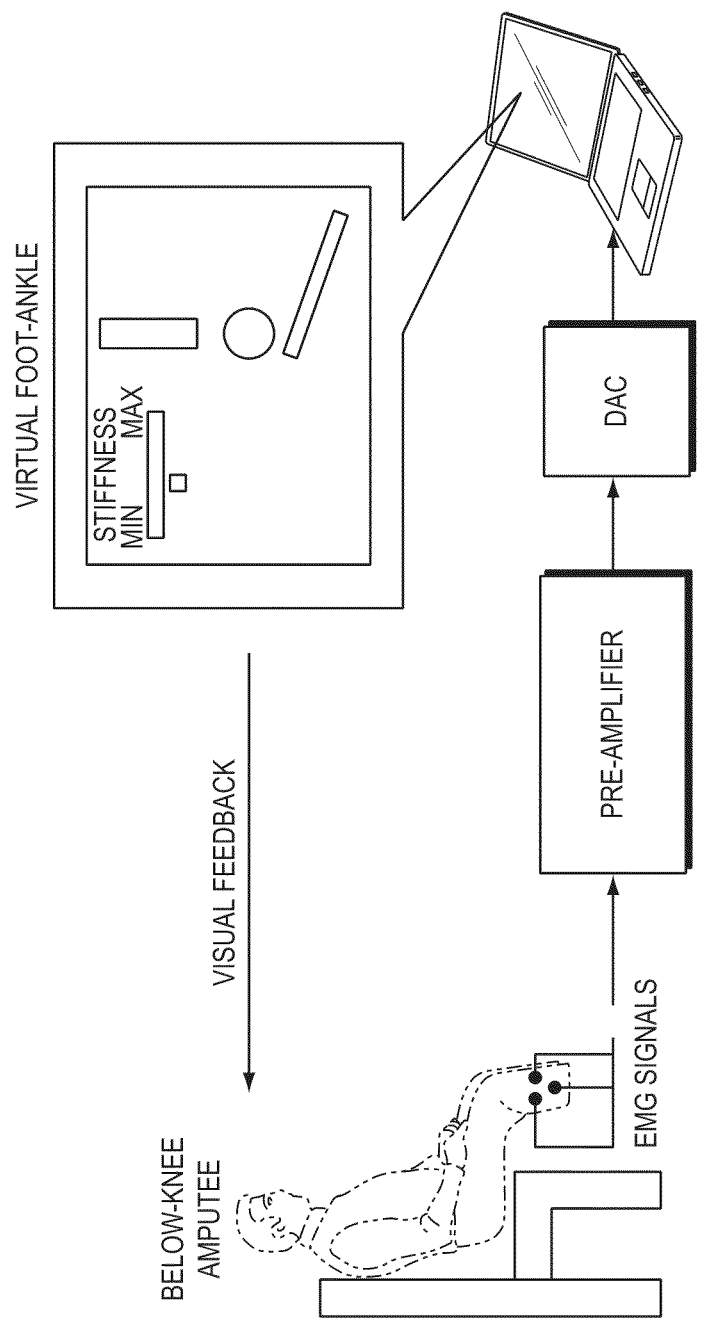
FIG. 56 is a schematic of a training setup.

To obtain training data for the network, we need both EMG signals from residual limb muscles as well as the intended ankle state. A training protocol was developed to capture these input-output pairs of data. After subjects had surface electrodes suitably located on their limb (in order to maximize the signal to noise ratio of the EMG), they performed a brief training procedure. The subject was shown an iconic representation of an ankle on a computer monitor and asked to mimic a series of displayed orientations (See FIG. 56). Once this procedure was complete, the recorded EMG measurements, as well as the presented ankle orientations could be used to train the network. The network was trained using a standard back propagation and gradient descent algorithm.

Figure 57:
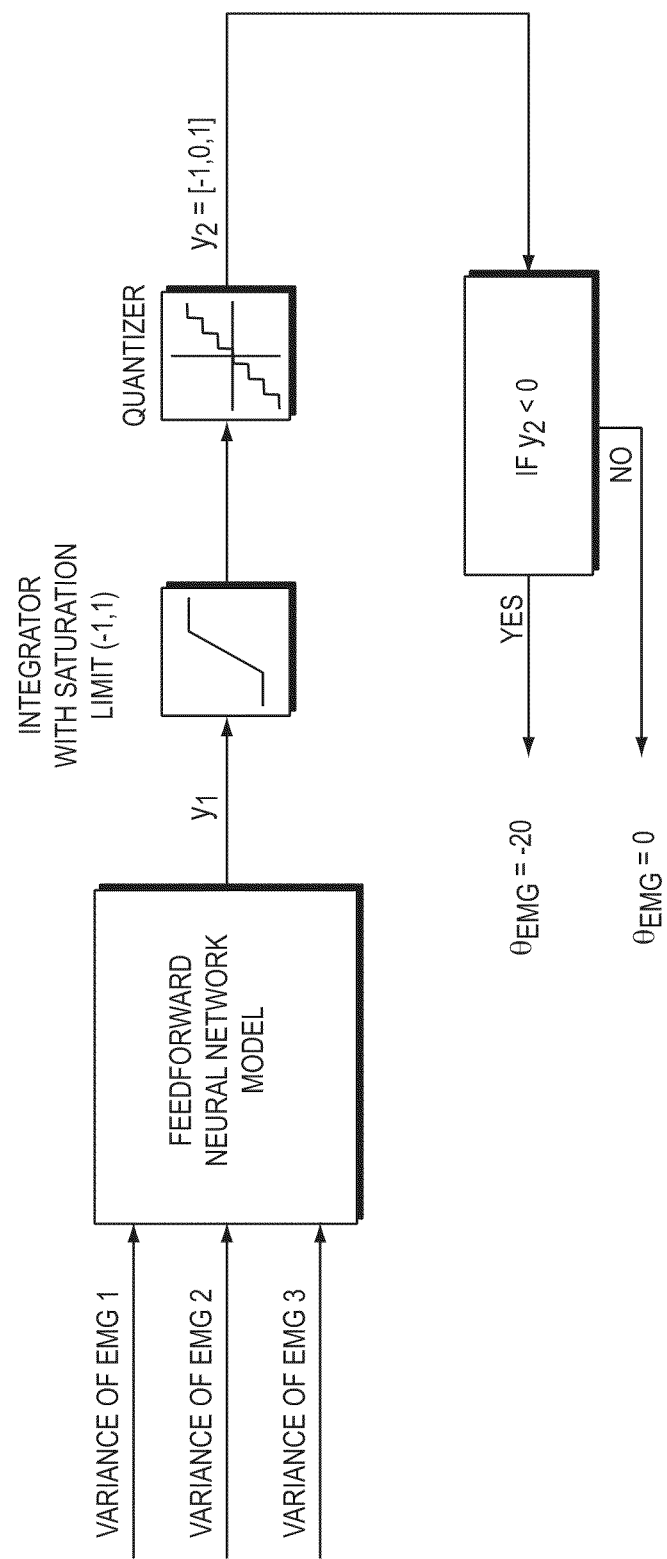
FIG. 57 shows the neural network motor-intent estimator.

The motor intent obtained by the NN model, $y_1$ is a continuous number in the range $(-1, 1)$, where $-1$ is plantar flexion and 1 is dorsiflexion. As we were only concerned with making transitions among different motor states, we numerically integrated $y_1$ and then thresholded between $-1$ and $1$ (FIG. 57). This allows the subject to toggle between different motor states as they would with a common remote control, i.e. flexing their limb muscles for a brief period of time would signify a transition to a new motor state. The new motor state would persist until the subject flexed the appropriate muscles to switch to another state. We then quantized the new motor state to obtain a discrete motor output command, $y_2$, whose value can be either $-1$, 0, and 1.

In our investigation, we were only concerned with motor intents for level-ground walking ($y_2=0$, relaxed) and stair descent ($y_2=-1$, plantar flexed) and used these motor intents to determine the desired output foot orientation, $\theta_{EMG}$. As can be seen in FIG. 57, if $y_2<0$, the Neural Network Motor-Intent Estimator would set $\theta_{EMG}=-20$ degrees, otherwise, $\theta_{EMG}=0$. The desired output foot orientation, $\theta_{EMG}$ was sent to the position controller to adjust equilibrium position, $\theta_d$ during state SW1 (stair descent mode) or SW 2 (level-ground mode). We set $\theta_{EMG}=-20$ for stair descent because human ankle normally plantar flexes to about 20 degrees to prepare for the toe-strike during stair descent {D-3}.

Hardware Implementation

This section describes the electronics hardware used for implementing the proposed controllers onto the MIT powered ankle-foot prosthesis, including sensors and computing platform. This system platform provides a test bed for testing a broad range of human ankle behaviors and control systems experimentally.

Sensors

Three local state variables, including heel/toe contact, ankle angle, and joint torque, were measured to implement the proposed finite-state controllers. We installed a 5 kOhm linear potentiometer across the flexion and extension the series springs to measure their displacement. We also mounted a 500-line quadrature encoder (US digital, inc.) in between the parent link mounting plate and child link mounting plate to measure the joint angle of the prosthetic ankle. Six capacitive force transducers were placed on the bottom of the foot: two sensors beneath the heel and four beneath the forefoot region.

For the EMG signal acquisition, we used EMG electrodes (disposable 22×33 mm Ag/AgCl EMG medical sensors Grass F-E10ND) to record the EMG signals from the residual limb muscles. To preprocess EMG signals measured from each electrode, we developed an onboard analog amplification/ filtering circuit interface, powered from a dedicated split supply derived from a pair of 9V batteries. The front-end of the EMG amplifier consisted of an Ohmic subject safety isolation (100K), a differential (3.3 KHz) and common mode filtering (16 KHz), and amplification gain of 25. Later stages applied gain of 504, a pair of 1st order high pass filters (16 Hz), a $2^{nd}$ order lowpass (300 Hz), and final output lowpass filter of 800 Hz. Total system gain was 12,600. The subject's reference potential was established by connecting "ground" electrodes though a safety resistance (100K) to the EMG amplifier's local "ground". Finally, the outputs of the EMG amplifiers were digitized by the PC 104 data acquisition system at 2000 Hz.

Computing System

Figure 58:
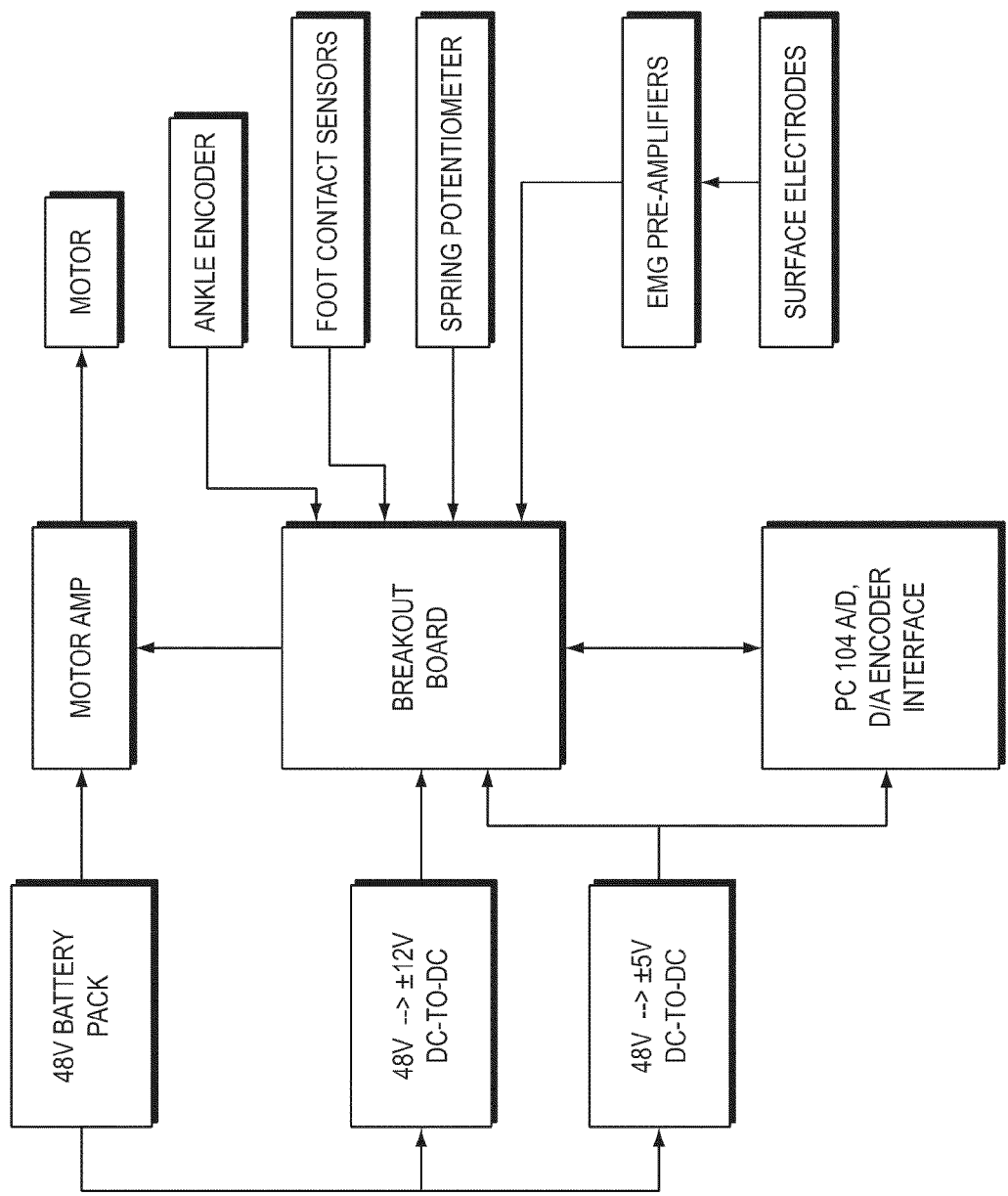
FIG. 58 contains schematics of the computer system.

FIG. 58 shows the schematics of the computer system. The computer system contained an onboard computer (PC104) with a data acquisition card, power supply, and motor amplifiers. The system was powered by a 48V, 4000 mAh Li-Polymer battery pack. The PC104 used was a MSMP3XEG PC/104 from Advanced Digital Logic, Inc. It was fitted with a PENTIUM III 700 MHz processor. Custom signal conditioning boards amplified sensor (linear pot) reading and provided a differential input to the data acquisition board, in order to minimize common mode noise from pick-up in the system. A PC/104 format multifunctional I/O board, Model 526 (from Sensory, Inc) was connected to the PC/104 to provide I/O to interface with sensors and motor controller (8× diff. AI, 2× AO, and 4× quadrature encoder counters). The system ran the Matlab Kernel for xPC target application. The target PC (PC104) could communicate with a host computer via Ethernet. The host computer sends control commands and obtains sensory data from the target PC104. A custom breakout board interfaced the sensors to the D/A board on the PC104 as well as provided power the signal conditioning boards. The dc motor of the prosthesis was powered by a motor amplifier (Accelnet Panel ACP090-36, V=48 volts, Ipk=36A) from Copley Controls Corp.

A mobile computing platform was developed that allowed us to conduct untethered walking experiments outside the laboratory. The mobile platform was mounted on an external frame backpack. Most of the electronic components were mounted on the platform, including a PC104, a power supply, I/O Cards, and a motor amplifier. Using cabling, the prosthesis was connected to the I/O board and motor amplifier on the platform.

Metabolic Walking Economy

The human ankle provides a significant amount of net positive work during the stance period of walking, especially at moderate to fast walking speeds. On the contrary, conventional ankle-foot prostheses are completely passive during stance, and consequently, cannot provide net positive work. Clinical studies indicate that transtibial amputees using conventional prostheses exhibit higher gait metabolic rates than is normal. Researchers believe the main cause for the observed increase in metabolism is due to the inability of conventional prostheses to provide net positive work at terminal stance in walking.

A powered ankle-foot prosthesis, capable of providing human-like power at terminal stance, can increase amputee metabolic walking economy compared to a conventional passive-elastic prosthesis. To test the hypothesis, a powered prosthesis is built that comprises a unidirectional spring, configured in parallel with a force-controllable actuator with series elasticity. The prosthesis is controlled to deliver the high mechanical power and net positive work observed in normal human walking. The rate of oxygen consumption is measured as a determinant of metabolic rate on three unilateral transtibial amputees walking at self-selected speeds. We find that the powered prosthesis improves amputee metabolic economy from 7% to 20% compared to the conventional passive-elastic prostheses evaluated (Flex-Foot Ceterus and Freedom Innovations Sierra), even though the powered system is twofold heavier than the conventional devices. These results highlight the clinical importance of prosthetic interventions that closely mimic the mass distribution, kinetics, and kinematics of the missing limb.

Today's commercially available below-knee prostheses are completely passive during stance, and consequently, their mechanical properties remain fixed with walking speed and terrain. These prostheses typically comprise elastic bumper springs or carbon composite leaf springs that store and release energy during the stance period, e.g. the Flex-Foot or the Seattle-Lite {E-1} {E-2}.

Lower extremity amputees using these conventional passive prostheses experience many problems during locomotion. For example, transtibial amputees expend 20-30% more metabolic power to walk at the same speed as able-bodied individuals, and therefore, they prefer a slower walking speed to travel the same distance. Thus, their average self-selected walking speed is normally 30-40% lower than the mean speed of intact individuals {E-3} {E-4}. Also, many clinical studies report that amputees exhibit an asymmetrical gait pattern {E-5} {E-6} {E-7}. For example, unilateral below-knee amputees generally have higher than normal hip extension, knee flexion, and ankle dorsiflexion on the unaffected side. On the affected side, such individuals have less than normal hip and knee flexion during stance. Additionally, there is a significant ankle power difference between the affected and unaffected sides during ankle powered plantar flexion in walking.

There are many differences between the mechanical behavior of conventional ankle-foot prostheses during the walking cycle and that of the human ankle-foot complex. Most notably, the human ankle performs more positive mechanical work than negative, especially at moderate to fast walking speeds {E-8} {E-9} {E-10} {E-11}. Researchers hypothesize {E-12} {E-13} {E-14} that the inability of conventional passive prostheses to provide net positive work over the stance period is the main cause for the above clinical difficulties.

Although the idea of a powered ankle-foot prosthesis has been discussed since the late 1990s, only two attempts {E-15} {E-16} have been made to develop such a prosthesis to improve the locomotion of amputees. However, although mechanisms were built, no further publications have demonstrated their capacity to improve amputee gait compared to conventional passive-elastic prostheses. Additional research has focused on the advancement of a quasi-passive ankle-foot prosthesis. Researchers in {E-17} and {E-18} developed prostheses that used active damping or clutch mechanisms to allow ankle angle adjustment to occur under the force of gravity or the amputee's weight.

In the commercial sector, the most advanced ankle-foot prosthesis, the Ossur ProprioFoot™ {E-1}, has an electric motor to adjust foot position during the swing phase to achieve foot clearance during level-ground walking. Although active during the swing phase, the Proprio ankle joint is locked during stance, and therefore becomes equivalent to a passive spring foot. Consequently, since it is essentially a passive prosthesis during the stance period of walking, the mechanism cannot provide net positive power to the amputee.

According to {E-5} {E-19} {E-20}, two main engineering challenges hinder the development of a powered ankle-foot prosthesis.

Mechanical design: With current actuator technology, it is challenging to build an ankle-foot prosthesis that matches the size and weight of the human ankle, but still provides a sufficiently large instantaneous power and torque output to propel an amputee's locomotion. For example, a 75 kg person has an ankle-foot weight approximately equal to 2.5 kg, and a peak power and torque output at the ankle during walking at 1.7 m/s equal to 350 W and 150 Nm, respectively {E-19} {E-20}. Current ankle-foot mechanisms for humanoid robots are not appropriate for this application, as they are either too heavy or not powerful enough to meet the human-like specifications required for a prosthesis {E-21} {E-22}.

Control system design: The control system of a highly functional ankle-foot prosthesis will be very different from the ankle-foot controllers of the humanoid robots described in {E-21} {E-22}. Such ankle controllers follow pre-planned kinematic trajectories during walking, whereas an intact ankle is believed to operate in impedance control mode or torque control mode in walking {E-8} {E-9}.

A key objective of this research is to address both the mechanical and control system design challenges. We design and build a novel motorized prosthesis that exploits both series and parallel elasticity to fulfill the demanding human-like ankle specifications {E-19} {E-20}. To solve the control system problem, we design and evaluate an impedance and force controller that allows the prosthesis to mimic human ankle behavior during the stance period of walking. Using the powered system, we conduct a preliminary investigation to test the hypothesis that a powered ankle-foot prosthesis can increase amputee walking economy compared to a conventional passive-elastic prosthesis. Using measures of oxygen consumption during level-ground walking at self-selected speeds, we estimate walking metabolic rates on three transtibial amputee participants using the proposed prosthesis and a conventional passive-elastic prosthesis.

As previously discussed, for level ground walking, human ankle provides three main functions: (i) it behaves as a spring with variable stiffness from CP to CD; (ii) it provides additional energy for push-off during PP; and (iii) it behaves as a position source to control the foot orientation during SW.

A key question for the control is to define a target walking behavior for the prosthesis. For the swing phase, the desired ankle behavior is just to re-position the foot to a predefined equilibrium position. For the stance phase control, it is commonly believed that the best control approach is to mimic normal human ankle impedance during stance, rather than simply tracking ankle kinematics {E-8}-{E-11}. However, the actual mechanical impedance of the human ankle during walking has not been determined experimentally simply because it is difficult to conduct ankle perturbation experiments on a human subject while walking {E-9}. As a resolution of this difficulty, many researchers have suggested another performance measure, called "quasi-static stiffness", that is the slope of the measured ankle torque-angle curve during stance {E-8}-{E-11}. Mimicking the quasi-static stiffness curve of a human ankle during walking is the main goal for the stance phase controller.

TABLE I

| DESIGN SPECIFICATIONS | |
| --- | --- |
| Weight (kg) | 2.5 kg |
| Length (m) | 0.32 m |

TABLE I-continued

DESIGN SPECIFICATIONS

| | |
|---|---|
| Max. Allowable Dorsiflexion (deg) | 25 |
| Max. Allowable Plantarflexion (deg) | 45 |
| Peak Torque (Nm) | 140 Nm |
| Peak Velocity (rad/s) | 5.2 rad/s at 20 Nm |
| Torque Bandwidth (Hz) | 1.5 Hz |
| Net Work Done (J) | 10 J at 1.3 m/s |
| | 20 J at 1.7 m/s |
| Required Offset Stiffness (Nm/rad) | 550 Nm/rad |

Figures 5A, 5B:
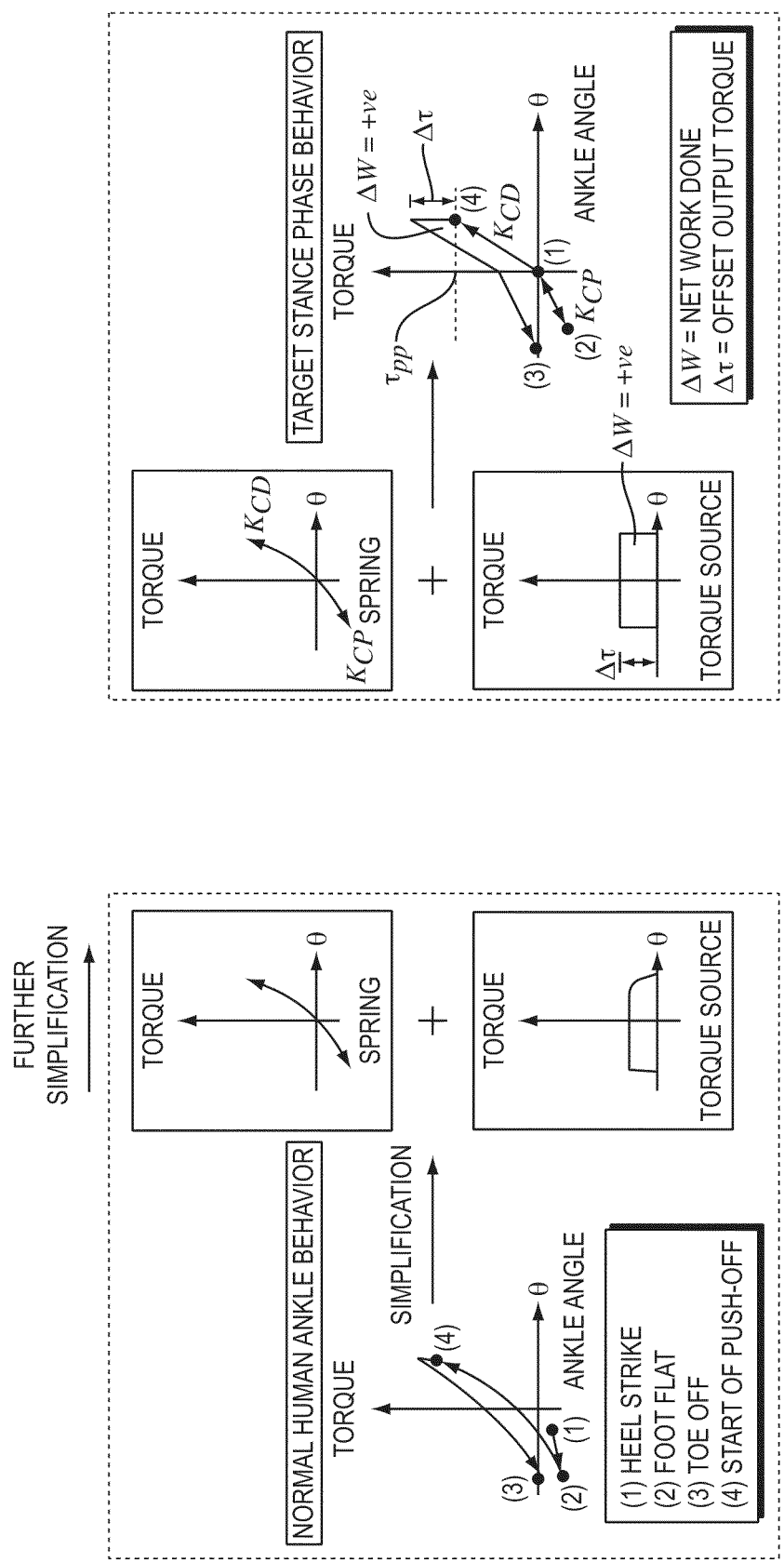
FIG. 5 depicts target stance phase behavior.

As can be seen in FIG. 5(A), a typical quasi-static stiffness curve can be decomposed into two main components: (1) a spring whose stiffness varies in a similar manner to the normal human ankle does in CP and CD. (2) a torque source that provides positive network during fate stance phase.

We then simplified these two components and used them to provide the target stance phase behavior for the prosthesis as depicted in FIG. 5B. Detailed descriptions for each component are summarized as follows:

1) A linear torsional spring with a stiffness that varies with the sign of the ankle angle. When the ankle angle is positive, the stiffness value will be set to KCD. When the ankle angle is negative, the stiffness value will be set to KCP.
2) A constant offset torque $\Delta\tau$ that models the torque source during PP. This offset torque will be applied in addition to the linear torsional springs KCD during PP. $\tau$pp determines the moment at which the offset torque is applied, indicated by the point (4) in FIG. 3B. The actual work done at the ankle joint due to the torque source is $$\Delta W = \Delta\tau\left(\frac{t_{pp}}{K_{CD}} + \frac{\Delta\tau}{K_{CP}}\right) \quad (1)$$

It is noted here that the conventional passive prostheses only provide the spring behavior but fail to supply the function of the torque source to thrust the body upwards and forwards during PP. Our designed prosthesis eventually will provide both functions during stance.

Design Specifications

Using the above biomechanical descriptions and the results from {E-8}-{E-11} {E-23}, the design goals for the prosthesis are summarized as follows:

the prosthesis should be at a weight and height similar to the missing human limb.

the system must deliver a large instantaneous output power and torque, i.e. about 350 W and 140 Nm for a 75 kg person. Furthermore, the system must produce 10 J of net positive mechanical work at the ankle joint during each stance period.

the system must be capable of changing its stiffness as dictated by the quasi-static stiffness of an intact ankle.

the system must be capable of controlling joint position during the swing phase.

The basic architecture of our mechanical design is a physical spring, configured in parallel to a high-power, force-controllable actuator. The parallel spring and the force-controllable actuator serve as the spring component and the torque source in FIG. 5B, respectively. To avoid hindering the foot motion during swing phase, the parallel spring is implemented as a unidirectional spring that provides an offset stiffness value only when the ankle angle is larger than zero degree. In addition, we use a Series-Elastic Actuator (SEA) to implement the force-controllable actuator {E-24} {E-25}.

FIGS. 17A and 17B and 6 show the SolidWork Model and the basic configuration of the proposed powered prosthesis, respectively.

As can be seen in FIG. 6, there are five main mechanical elements in the system: a high power output d.c. motor, a transmission, a series spring, a unidirectional parallel spring, and a carbon composite leaf spring prosthetic foot. We combine the first three components to form a rotary Series-Elastic Actuator (SEA). A SEA, previously developed for legged robots {E-24} {E-25}, consists of a dc motor in series with a spring (or spring structure) via a mechanical transmission. The SEA provides force control by controlling the extent to which the series spring is compressed. Using a linear potentiometer, we can obtain the force applied to the load by measuring the deflection of the series spring.

In this application, we use the SEA to modulate the joint stiffness as well as provide the constant offset torque $\Delta\tau$ as shown in FIG. 7. It provides a stiffness value KCP during CP and a stiffness value KCD1 from CD to PP. From points (4) to (3), it supplies both the stiffness value KCD1 and a constant, offset torque $\Delta\tau$. The unidirectional parallel spring provides an offset rotational stiffness value K$^r$ when the ankle angle is larger than zero degree.

As shown in FIG. 7, due to the incorporation of the parallel spring, the load borne by the SEA is greatly reduced. Because of this fact, the SEA will have a substantially large force bandwidth to provide the active push-off during PP.

The elastic leaf spring foot is used to emulate the function of a human foot that provides shock absorption during foot strike, energy storage during the early stance period, and energy return in the late stance period. A standard low profile prosthetic foot, called the FlexFootLPVari-Flex was used in the prototype {E-1}.

System Model

A simple linear model is proposed in FIGS. 9A and 9B that is sufficient to describe the essential linear behavior of the prosthesis. The basic concept of this model is similar to the standard SEA model in {E-25}, except that we applied his model to a rotational joint system and also included an unidirectional parallel spring into the model. Referring to the FIGS. 9A and 9B, the motor is modeled as a torque source Tm with a rotary internal inertia Im, applying a force to the series spring ks through a transmission R. The damping term bm represents the brush and bearing friction acting on the motor. x and θ are the linear displacement of the series spring and the angular displacement of the ankle joint, respectively. Again, the transmission has a ratio R that converts rotary motion of the motor into linear compression on the series spring.

In this model, we assume the foot as a rigid body with negligible inertia because it is relatively very small compared to the effective motor inertia, i.e., Text=rFs where Text and r are the moment arm of the spring about the ankle joint and the torque exerted by the environment to the prosthesis. This model ignores the amplifier dynamics, nonlinear friction, internal resonances, and other complexities.

For simplicity, we then convert the model into translational domain (see FIG. 10(b)). Me, Be, and Fe represent the effective mass, damping, and linear force acting on effective mass, respectively. These components are defined as follows: $M_e = I_m R^2$, $F_e = T_m R$, $B_e = B_m R$. The equation of motion becomes:

$$M_e \ddot{x} + B_e \dot{x} + k_s x = F_e - F_s \quad (2)$$

$$F_s = k_s(r\theta - x) \quad (3)$$

while the total external torque or total joint torque $$T_{ext} = \begin{cases} rF_s & \theta < 0 \\ rF_s + R_p k_p \theta & \theta \geq 0 \end{cases} \quad (4)$$

Equations (2) and (3) are the standard dynamic equations for a SEA {E-25}. Equation (4) reveals that with the parallel spring, less spring force Fs is required for a given total joint torque.

Large Force Bandwidth

According to {E-25}, before designing any controllers, we need to guarantee that the physical system would not run into any saturation within the operating range of torque level and bandwidth. One of the suggested index is the large force bandwidth. The large force bandwidth is defined as the frequency range over which the actuator can oscillate at a force amplitude $F_s^{max}$ due to the maximum input motor force, Fsat {E-25}. Because the series elasticity substantially reduces the system bandwidth at large force due to the motor saturation. The stiffer the spring is, the higher SEA bandwidth is at large force. Our goal is to have the large force bandwidth of the SEA much greater than the required force bandwidth in the specifications (Table I) by choosing proper system components such as ks.

TABLE II

MODEL PARAMETERS

| Parameters | Fsat | Vsat | Me | Be |
|---|---|---|---|---|
| Values | 7654N | 0.23 m/s | 170 kg | 8250 Ns/m |

To study the large force bandwidth, we fix both ends of the model in FIG. 9A, consequently, the equation of motion for this model (2) becomes a standard second-order differential equation for a spring-mass-damper system. The spring force Fs was considered as the system output. Then, the transfer function that describes the large force bandwidth is:

$$\frac{F_s^{max}}{F_{sat}} = \frac{k_s}{M_e s^2 + \left(B_e + \frac{F_{sat}}{V_{sat}}\right)s + k_s} \quad (5)$$

where $F_s^{max}$, Vsat are the maximum output force and maximum linear velocity of the motor respectively. They are defined as $$F_{sat} = RT_{motor}^{max} \text{ and } V_{sat} = \frac{\omega^{max}}{R}.$$

As can be seen in FIG. 15, the large force bandwidth is independent of the control system, but rather depends on the intrinsic system behaviors which are determined by the choices of the motor, transmission ratio, and the spring constant. In our design, the total spring constant for the series springs is set to 1200 KN/m. Using the motor parameters (Maxon RE-40) in {E-27} and transmission ratio (R=3560), the model parameters were obtained and shown in Table II. The simulation result for the large force bandwidth has shown in FIG. 15.

As shown in FIG. 15, the estimated large force bandwidth of the system with and without the parallel spring was at 9.4 Hz (at 50 Nm) and 3.8 Hz (at 120 Nm), respectively. As in (4), the parallel spring shared some of the payloads of the SEA, the required peak force for the system was significantly reduced. With the parallel spring, the estimated force bandwidth were much larger than the designed criteria in Table I. In practice, it is favorable to design a system whose large force bandwidth is several times larger than the required bandwidth as there are many factors that can substantially reduce the large force bandwidth, such as unmodeled friction {E-25}.

The goal of the control system is to allow the prosthesis to track the target stance phase behavior. To this end, the prosthesis must have three types of low-level servo controllers: (i) a high performance torque controller to provide an offset torque during push-off as well as facilitate the stiffness modulation, (ii) an impedance controller to modulate the joint stiffness during the entire stance phase, (iii) a position controller to control the foot position during the swing phase.

Furthermore, it is necessary to have a high-level control system to manage and determine the transitions among the low-level servo controllers so as to provide proper prosthetic functions for a given condition. For examples, if the prosthesis is detected to be off ground, then the high-level control system will use the position controller to modulate foot position for foot clearance. The overall architecture of the control system is shown in FIG. 25. As can be seen, the control system contains a set of low-level servo controllers and a finite state machine, widely used in the high-level control of A/K prostheses {E-28} {E-29}. The finite state machine comprises two parts: a state identification and a state control. The former is used to identify the current state of the prosthesis while the latter is used to execute the predefined control procedure for a given state. In the following sections, we first discuss the development of the low-level servo controllers, followed by the design of the finite state machine.

Low-Level Servo Controllers

Throughout this section, we assume that the parallel spring does not inhibit controllers' ability to specify desired dynamics, at least within the operating range of torque level and bandwidth.

Figure 59:
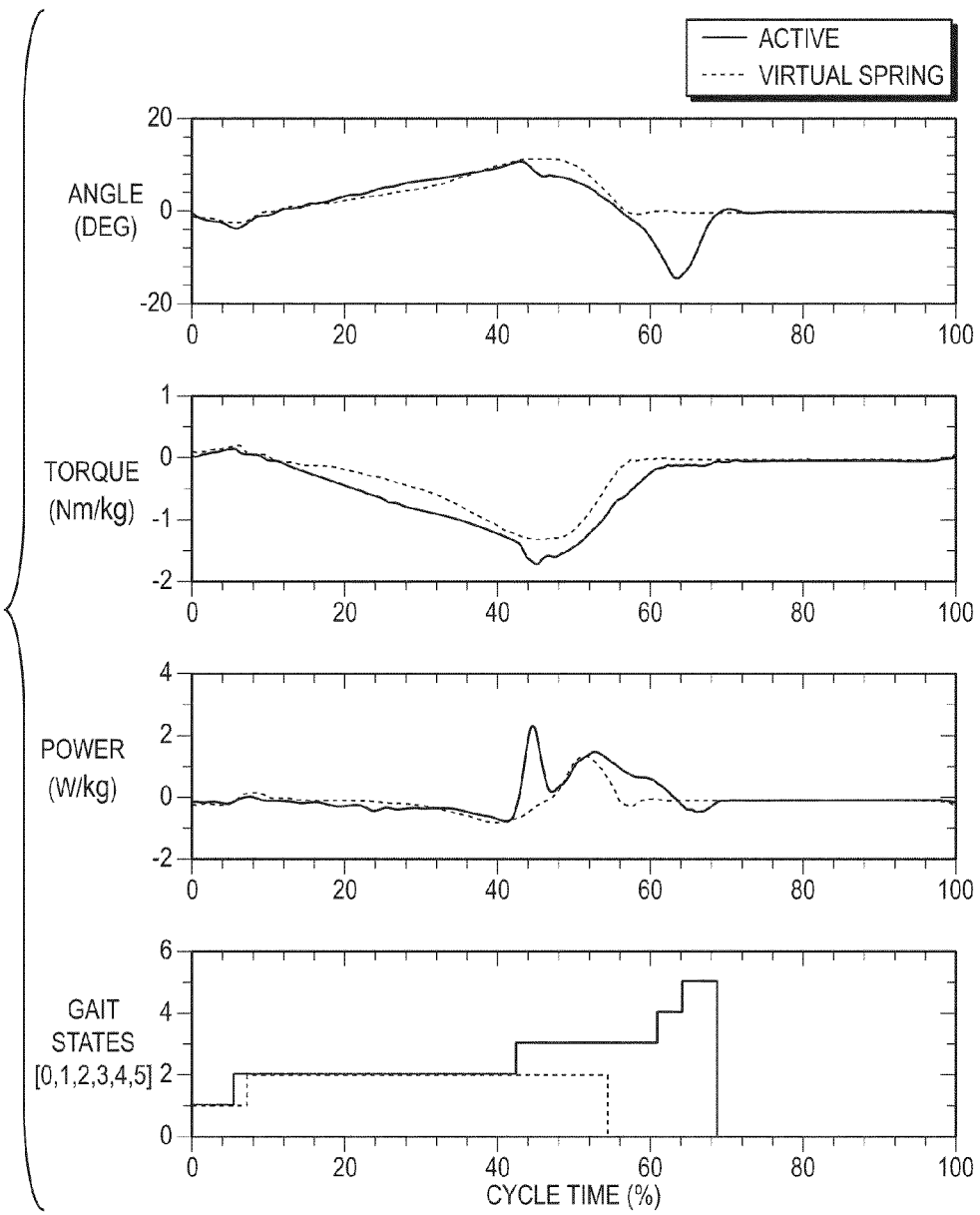
FIG. 59 illustrates prosthetic ankle performance for level ground walking

1) Torque Controller: A high performance torque controller was designed to provide the offset torque and facilitate the stiffness modulation. The design consists of (i) an inner force/torque control loop and (ii) a feed forward friction compensation term (see FIG. 59). The basic concept of the inner force/torque control loop is to use the force feedback, estimated from the series spring deflection, to control the output joint torque of the SEA {E-25}. We proposed a controller D(s) that has a P-term plus a lead-compensator to control the inner force loop {E-20} as below.

$$D(s) = \frac{V_m(s)}{\tau_e(s)} = K_F + B_F \frac{s}{s+p} \quad (6)$$

where τe, Vm are the output torque error and input voltage to the motor amplifier, respectively. Furthermore, $K_F$, $B_F$, p are the proportional gain, damping, and pole of the force controller, respectively. The main function of the lead compensator in (6) is as a differentiator that only differentiates the low frequency components of the signal measured by the potentiometer. The pole p of the controller was set to 30 Hz, which is sufficiently larger than the dominant frequency of the human ankle during normal walking (3 Hz).

By increasing the gain KF, we can shadow the effect of the intrinsic impedance (e.g. friction or inertia) in the mechanism, and consequently, the torque tracking performance will be improved. However, one cannot fully compensate for the intrinsic impedance by increasing KF simply because instability results when the system couples to certain environments at high gain. This is so because the system becomes non passive {E-33}. Therefore, we introduce a model-based friction compensation term Fr(s) to augment the torque controller. Adding the friction compensation term reduces the effect of the intrinsic friction in the system while maintaining the coupled stability {E-33}. A standard friction compensation term was used and defined as $$\tau_f = f_c(\tau)sgn(\dot{\theta}) + b_c\dot{\theta},$$

where fc, bc are the Coulombic force constant and damping coefficient, respectively {E-34}. All these parameters were identified using experimental data.

Impedance Controller: An impedance controller was designed to modulate the output impedance of the SEA, especially the joint stiffness. As shown in FIG. 59(b), we introduced an outer position feedback loop/outer impedance control loop onto the proposed force controller to modulate the output impedance. The outer impedance control loop is based on the structure of the "Simple Impedance Control", proposed by Hogan {E-30}. The key idea is to use the motion feedback from the ankle joint (θ) to increase the output joint impedance. The outer impedance controller in S-domain is defined as $$Z_d(s) = \frac{\tau_d(s)}{s\theta(s)} = \left(B_d + \frac{K_d}{s}\right) \quad (8)$$

where $\tau_d$, $K_d$, $B_d$ are the desired SEA output joint torque, stiffness, and damping, respectively. An offset torque Δτ will be applied in addition to the total joint impedance $Z_{total}$ during PP. The desired output torque of the SEA during PP becomes $$\tau_d(s) = \left(B_d + \frac{K_d}{s}\right)s\theta + \Delta\tau \quad (9)$$

Taking into the consideration of the parallel elasticity, the total joint impedance Ztotal(s) is $$Z_{total} = \begin{cases} \left(B_d + \frac{K_d}{s}\right) & \theta \leq 0 \\ \left(B_d + \frac{K_d + K_p^\tau}{s}\right) & \theta > 0 \end{cases} \quad (10)$$

Position Controller:

A standard PD-controller H(s) was proposed to control the equilibrium position θ1 of the foot during swing. Then, the input voltage Vm(s) to the motor amplifier is Vm(s)=K1 (θ$_1$−θ)+K$_2$θ, where K$_1$ and K$_2$ are the proportional and derivative terms of the controllers. Finite State Machine Control A finite state machine was implemented to allow the prosthesis to mimic the target stance phase behavior (see FIG. 60). As indicated, six states were designed: CP, CD, PP, SW1, SW2, and SW3, respectively. The definition, objective, and corresponding action taken for each state are summarized in Table III. During state transitions, the system mainly relied on four variables:

1) Heel contact (H). H=1 indicates that the heel is on the ground, and vice versa
2) Toe contact(T). T=1 indicates that the toe is on the ground, and vice versa
3) Ankle angle (θ)
4) Total ankle torque(Tjoint)

All the triggering information was obtained from the sensors mentioned below, including foot switches to measure heel/toe contact, ankle joint encoder to measure the ankle angle, and the linear spring potentiometer to measure joint torque.

Upon entering one of the system states, the prosthesis employed one of the low-level controllers to provide certain pre-defined ankle functions. For example, when the system entered state CP, the prosthesis used the impedance controller to provide the stiffness KCP to prevent foot slapping (Table III).

For a typical gait cycle, state CP began when the heel switch was compressed (H=1) and the ankle angle was less then zero (θ<0). In state CP, the system used the impedance controller to output a joint stiffness $K_{joint}=K_{CP}$. The transition from states CP to CD occurred when either the toe or heel switches was compressed (H=1 or T=1) as well as the ankle angle was larger than zero (θ≧0). In state CD, the system outputted another joint stiffness $K_{joint}=K_{CD1}$. The system would only enter state PP if the total joint torque was larger than the predefined torque threshold for push-off ($T_{joint} \geq t_{pp}$). Otherwise, it remained in state CD until the foot was off the ground (H=0 and T=0).

Figure 61A:
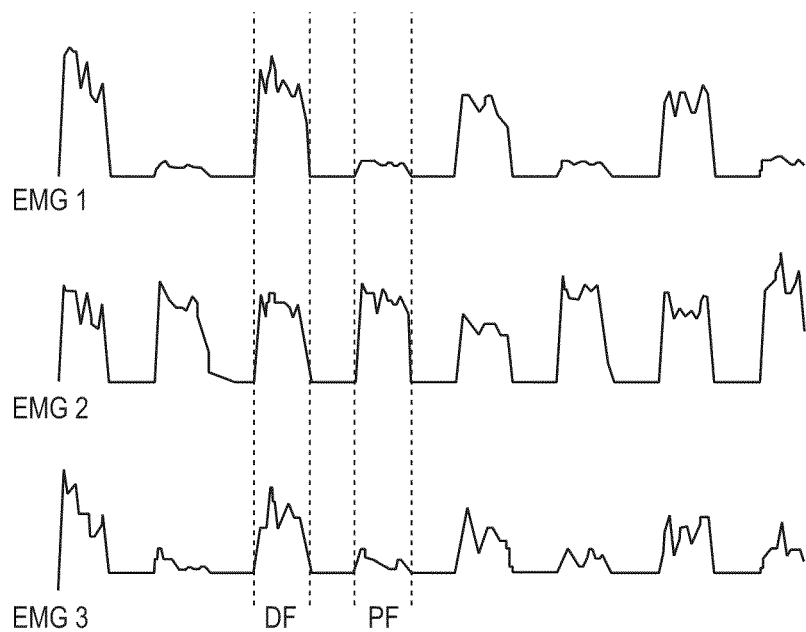
FIG. 61A shows an example EMG recordings obtained during subject's training procedure.
Figure 61B:
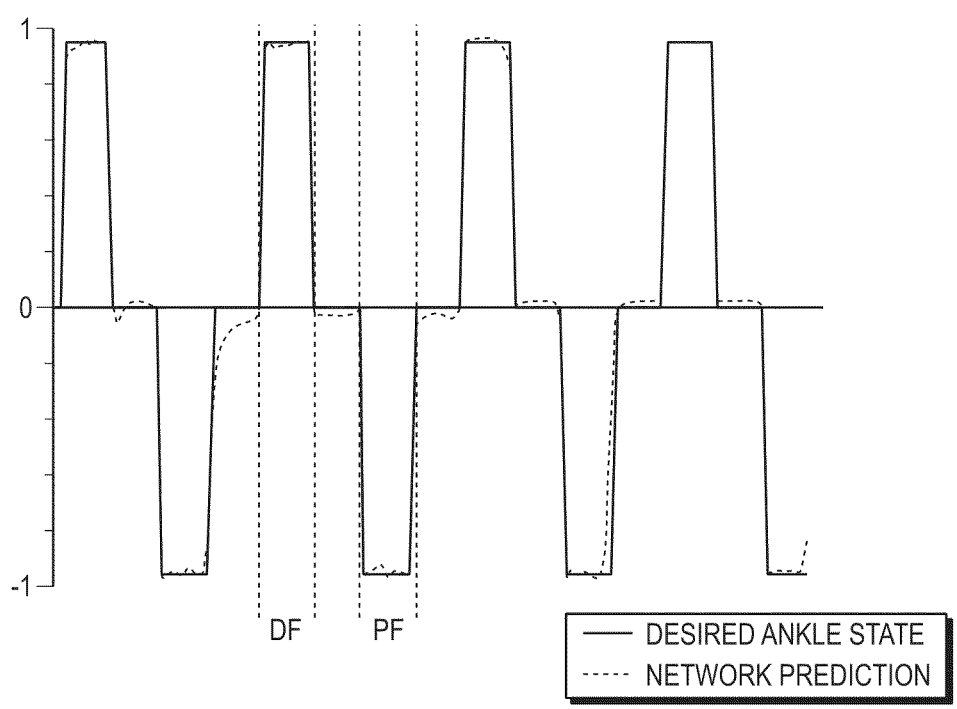
FIG. 61B shows the resulting predictions of motor intent, obtained after the neural network has been trained
Figure 62:
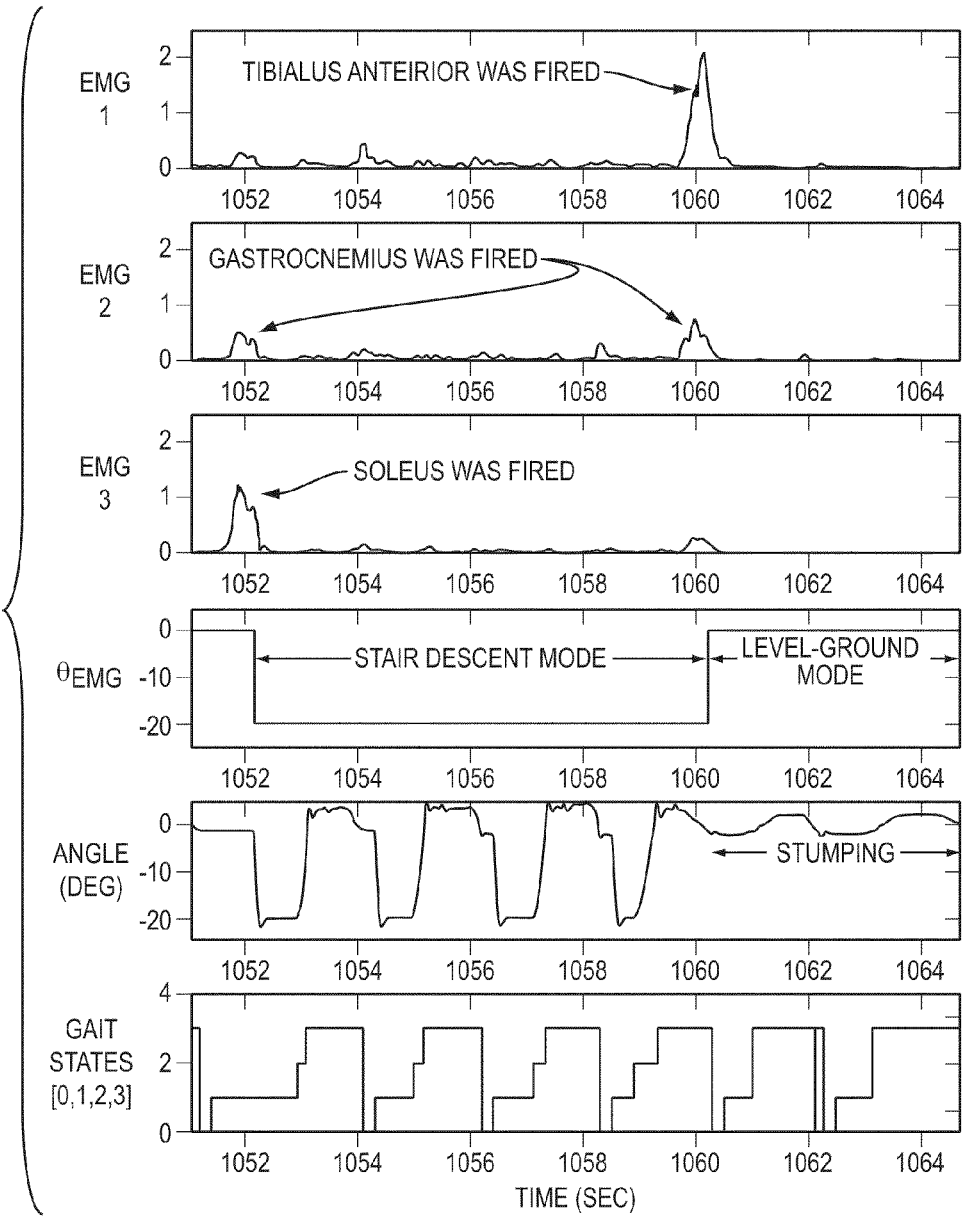
FIG. 62 shows EMG and triggering waveforms.
Figure 63:
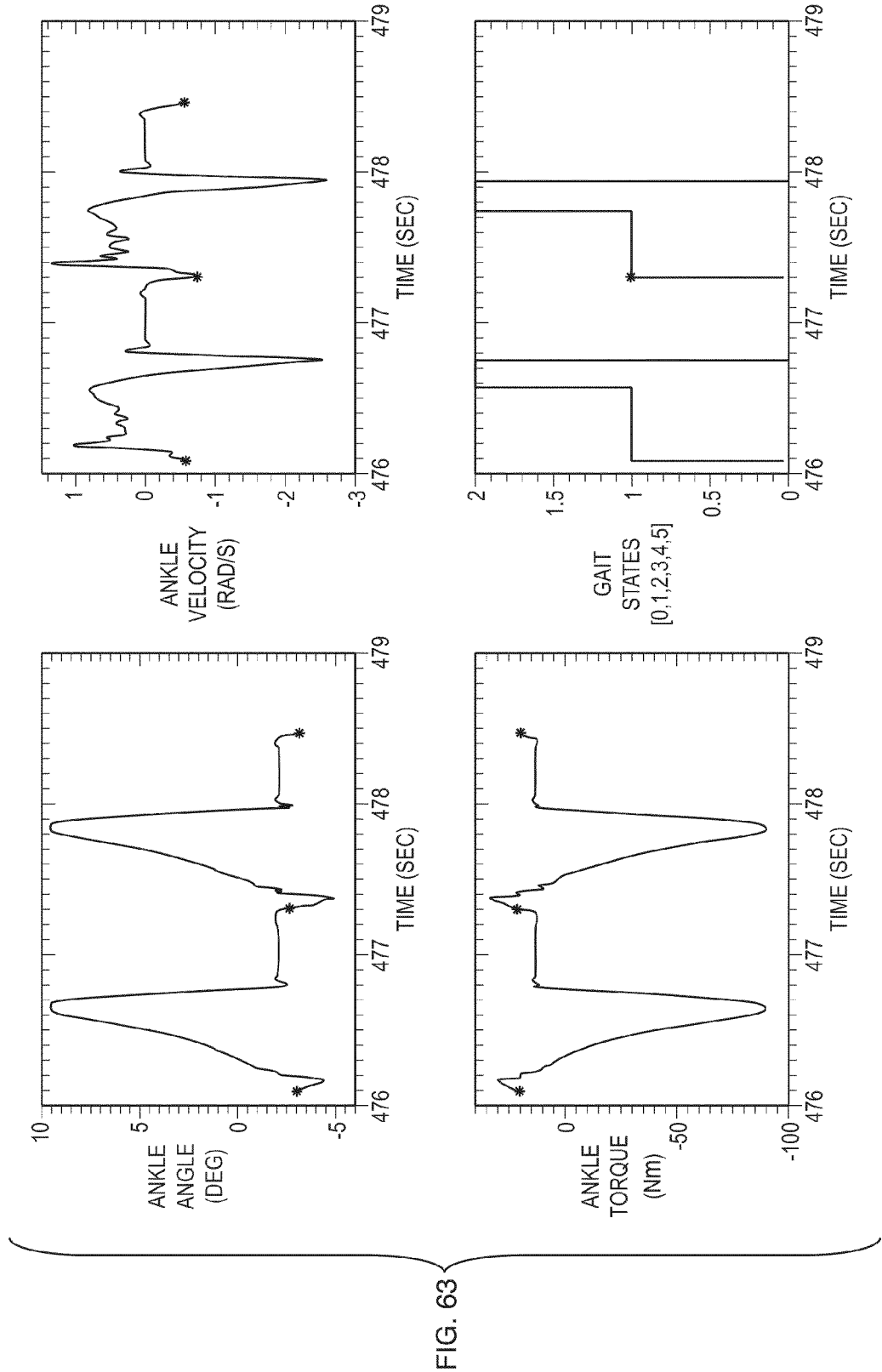
FIG. 63 shows waveforms of measured ankle angle, velocity, torque, and the gait states of a walking trial

In state PP, the SEA outputted an offset torque Δτ in addition to the joint stiffness $K_{joint}=K_{CD1}$ that contributed to the net positive work done at the ankle joint. Once entering the state PP, the system could only move to state SW1 provided that the foot was off the ground (H=0 and T=0). In state SW1, the foot was positioned to a predefined ankle angle $\theta_d=\theta_{toeoff}$ and remained at that position for a given time period tH for foot clearance. The controller then entered state SW2 automatically when the time period tH was over. The foot then started to move to the nominal position equal to zero degree. Once the ankle reached zero degrees, the system entered the state SW3, given that the foot was still off the ground (H=0 and T=0). A new gait cycle was triggered when the heel-strike occurred once gain. The state control for a typical gait cycle is graphically depicted in FIG. 61.

Sensors and Computing Platform

We installed a 5 kOhm linear potentiometer across the flexion and extension the series springs to measure their displacement. We also mounted a 500-line quadrature encoder (US digital, inc.) in between the parent link mounting plate and child link mounting plate to measure the joint angle of the prosthetic ankle. Six capacitive force transducers were placed on the bottom of the foot: two sensors beneath the heel and four beneath the forefoot region. Using cabling, the prosthesis was connected to a multifunctional I/O board from Sensory Co., Inc (Model 526) that was interfaced with a PC104 Pentium III CPU (MSMP3XEG, from Advanced Digital Logic, Inc). The system runs the Matlab Kernel for xPC target application {E-35}. The target PC (PC104) can communicate with a host computer via Ethernet. The host computer sends control commands and obtains sensory data from the target PC104. We powered the dc motor with a motor amplifier (AccelnetPanelACP-090-36,V=48 volts, Ipk=36A) from Copley Controls Corp.

Finally, a mobile computing platform was developed that allowed us to conduct untethered walking experiments outside the laboratory. As shown in FIGS. 32A and 32B, the mobile platform was mounted on an external frame backpack. Most of the electronic components were mounted on the platform, including a PC104, a power supply, I/O Cards, and a motor amplifier.

Intent Recognition for Ankle Prosthetic

General Purpose

Traditional passive prosthetic and orthotic devices rely fully on control by the human user; the human learns to use the device, adapting his or her gait and balance control strategies to accommodate the device. As prosthetic devices become enabled with actuation capabilities, the question of how these capabilities should be controlled arises. For example, an ankle prosthesis or orthosis with an electric actuator might allow for changing the pitch angle of the foot with respect to the shank, and might allow for exertion of torques about the artificial ankle joint that could be transmitted to the ground. Control of such an actuator requires knowledge of the goals and intentions of the user. For example, the actuator should do different things depending on whether the user is about to walk up stairs, walk down stairs, or walk on level ground.

This section presents a method for predicting whether the user of an active ankle prosthesis or orthosis is about to step up, step down, or step on level ground. Our method makes a highly accurate prediction in real time, shortly after the step begins. Thus, the prediction is made with enough time to allow for control of the actuator in a desirable way, based on the prediction.

Figure 64:
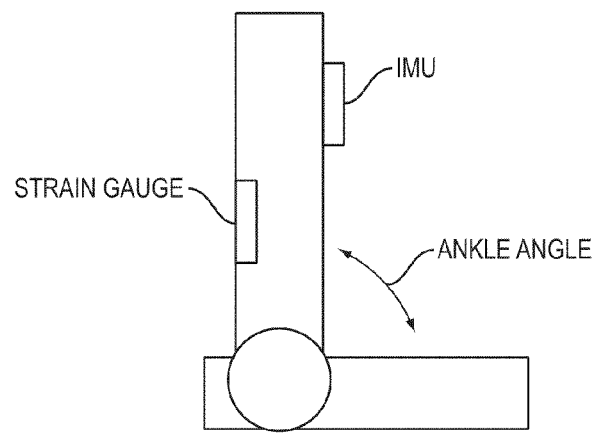
FIG. 64 shows an Active ankle device in which an imu attached at the shank measures absolute inclination and linear acceleration and a strain gauge on the shank measures contact forces.

A key requirement for such a device is that its sensors not require onerous activity by the user. Hence, it should not require the user to communicate intent through a joy stick or hand controlled device, and it should not require the user to wear or attach extensive sensor devices separate from the device itself. For this reason, we restrict our sensors to an Inertial Measurement Unit (IMU) attached at the shank of the prosthesis/orthosis, and simple force sensors that indicate when the toe or heel of the artificial foot are in contact with the ground, as shown in FIG. 64. Thus, our algorithm makes its prediction based on the minimal amount of sensory information, and possibly noisy Another key requirement for such a device is that it be easily usable by people of different sizes, and that it should adapt to changing conditions in the sensors, the environment, and the user. Our algorithm uses a machine learning approach that allows it to adapt to different users and varying conditions.

Technical Description

We assume that the prosthesis/orthosis has at least one actuator at the ankle, which is used to adjust the dorsi/plantar flexion angle of the ankle with respect to the shank, as shown in FIG. 64. This capability to adjust the ankle angle improves the user's ability to perform a variety of walking tasks, including walking up and down stairs, in a more natural, safe, and efficient manner. For example, when walking down stairs, the ankle angle is more plantar flexed than during level ground walking. This results in the toes touching before the heel as the foot descends to the next step, allowing for better absorption of impact forces. This is in contrast to level ground walking, where the heel strikes before the toe.

In order for the ankle angle control to be safe, the system must recognize user intent in a timely manner. For example, the system should recognize a transition from level ground walking to walking down stairs soon enough so that the ankle angle can be adjusted before the first descending step. Furthermore, the system must have a very high degree of certainty in intent recognition; an error could result in an incorrect control action, possibly causing the user to trip. Recognition of intent is based on sensory information. The prosthetic/orthotic device has an Inertial Measurement Unit (IMU), as well as a strain gauge, mounted on the shank.

The IMU provides very accurate information about the three-dimensional orientation of the shank. It also provides translational acceleration, but this has some error. When this acceleration is integrated to obtain translational velocity and position estimates, the acceleration error can cause drifting of these estimates over time. The strain gauge is used to determine if the foot is on the ground or not.

Intent Recognition Through Hybrid Estimation

Figure 65:
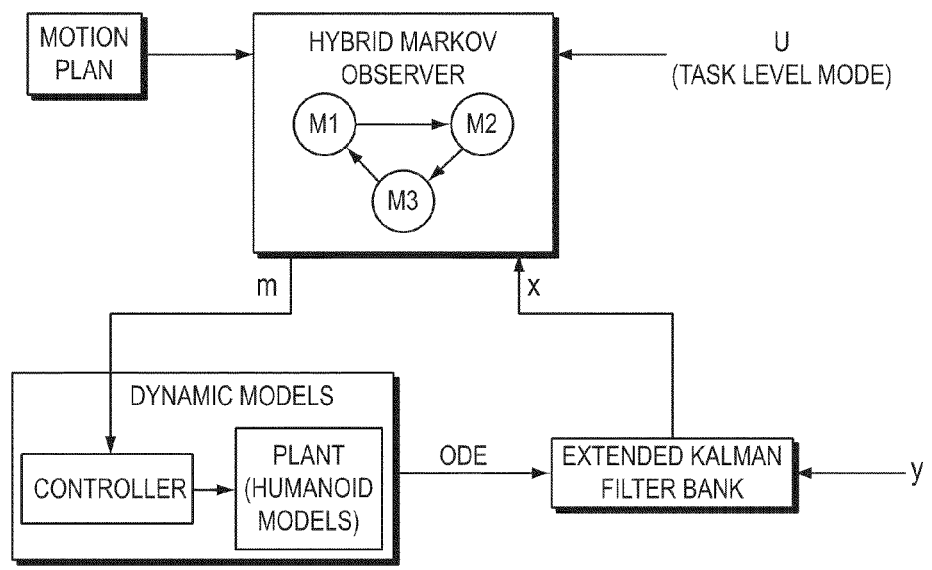
FIG. 65 is a diagram of a hybrid Markov observer

We represent the state of the combined user/device system using a discrete/continuous hybrid state vector. The type of task being performed (taking a step on level ground, taking a step to walk down stairs, slopes, etc.) is represented using a discrete mode variable, and position and velocity state is represented by continuous variables. We estimate and predict this hybrid state using a hybrid mode estimation architecture [Williams 2001, Hofbaur 2002] that combines the predictive capabilities of physical models of human motion, with observations from the sensors on the device. Prediction of the discrete mode corresponds to prediction, or recognition, of intent. We frame this tracking and prediction process as belief state update for a hybrid HMM. In a hybrid HMM, each discrete mode has an associated continuous dynamics for the continuous state variables. The continuous state variables and system observations are given by stochastic difference equations. Mode transition is a probabilistic function of the current mode and continuous state estimates. We use a Hybrid Markov Observer (FIG. 65) to interpret the hybrid HMM. The observer computes a sequence of hybrid state estimates, each of which is a tuple $$\hat{x}_k = \langle \hat{x}_{d,k}, p_{c,k} \rangle, \text{ where } \hat{x}_{d,k}$$

is the estimate of the discrete mode, and $p_{c,k}$ is the continuous state estimate expressed as a multi-variate probability distribution function with mean $\hat{x}_{c,k}$ and covariance matrix $P_k$.

Parameter Learning Using Expectation Maximization

The Hybrid Markov Observer requires numerous parameters to be set appropriately in order for it to work properly. One important set of parameters is associated with the observation function. This function gives the conditional probability of particular discrete modes given the current observations.

Our algorithm implements this function using a set of multi-dimensional Gaussians. Thus, for each discrete mode, we use a multi-dimensional Gaussian to represent the probability of that mode. The dimensions of the Gaussian correspond to continuous observations such as pitch angle and pitch angular velocity. These observations are obtained from the IMU.

A key challenge is to learn the parameters of these Gaussians; they should not have to be entered manually. Hence, we use an expectation maximization (EM) {F-4} to learn these parameters. This algorithm iteratively performs state estimation (E step) and parameter estimation (M step), converging to optimal estimates and parameters after a period of time. The algorithm can be used in supervised, or unsupervised learning modes. In supervised mode, a labeled training data set is used, so the E step is skipped. In unsupervised mode, the data is supplied to the algorithm in real time, incrementally, and there is no labeled training data set. We use a combination of supervised and unsupervised approaches. We begin with a supervised approach, using training data corresponding to different body types. We then use this as a starting point, for an unsupervised mode, where the user begins using the device, and the device performance improves over time as the EM algorithm adjusts parameters for this particular user.

Advantages and Improvements Over Existing Methods

We know of no current method that performs this type of prediction.

Our method is provably optimal, given a particular sensor configuration.

Our method adapts to new conditions over time.

Our method requires only a minimal sensor configuration.

Commercial Applications

Ankle-foot prostheses, orthoses, exoskeleton,

May be extended to other prosthetics, and also orthotic devices

Prothesis Construction

The sections that follow describes the construction of five ankle-foot prosthesis designs as shown in FIGS. 66-83.

Figure 66:
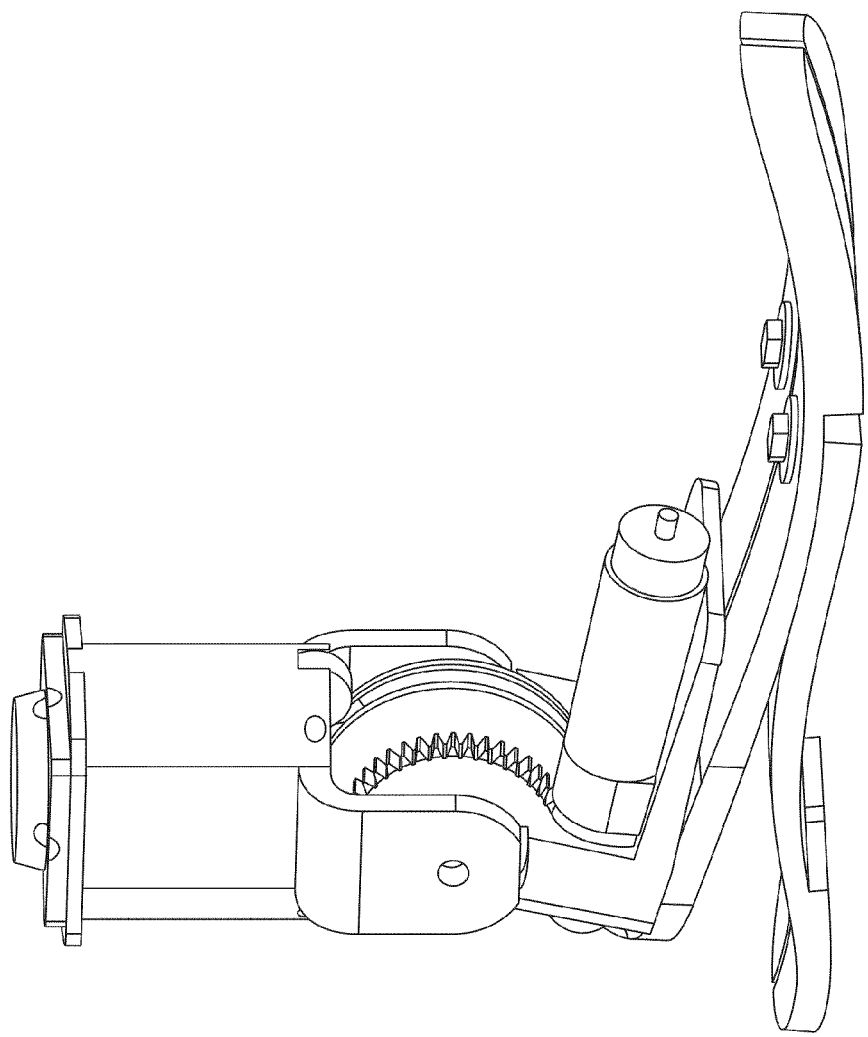
FIGS. 66, 67 and 68 are right, cutaway and overhead views respectively of an ankle foot prosthesis.
Figure 67:
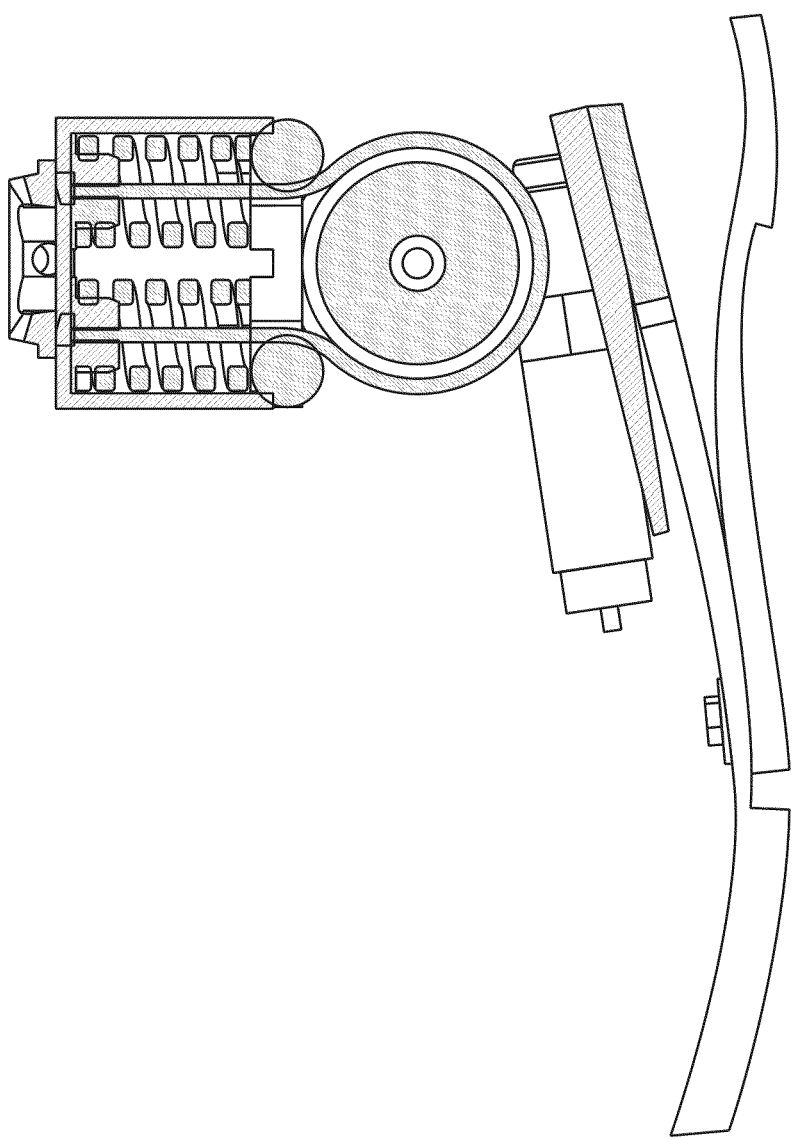
Figure 68:
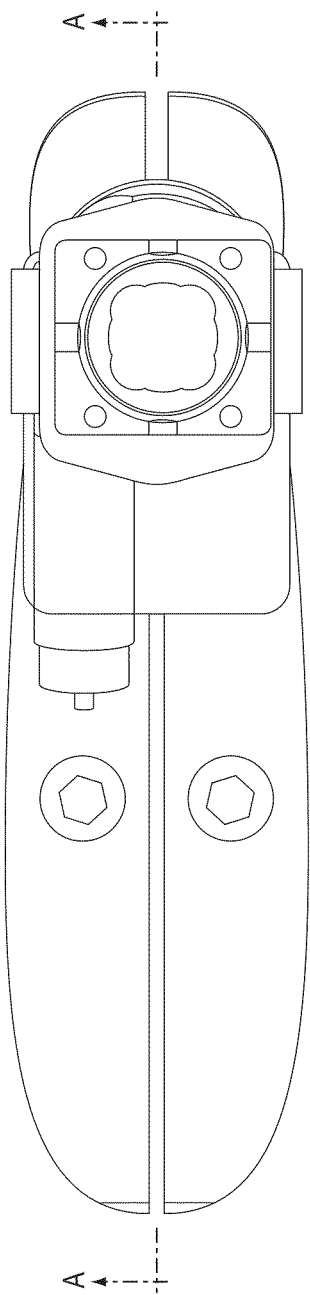
Figure 69:
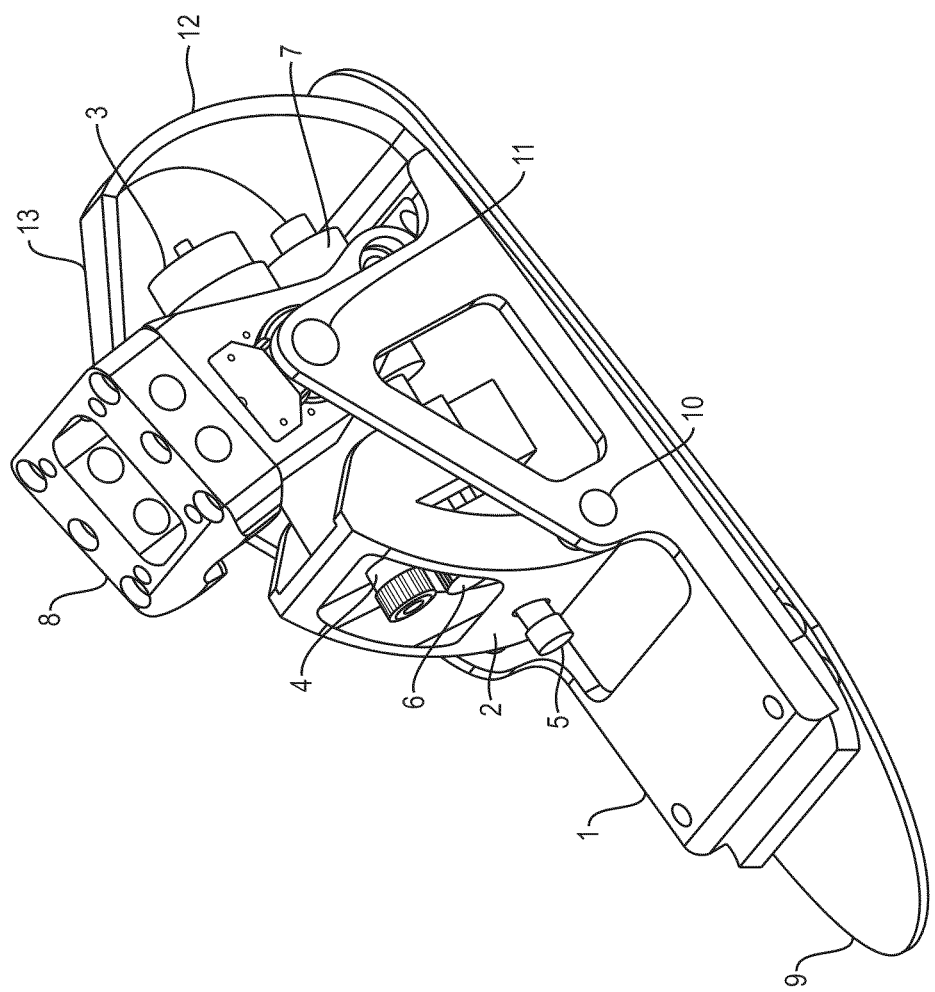
FIGS. 69, 70 and 71 are perspective, cross-sectional, overhead views respectively of an ankle foot prosthesis.
Figure 70:
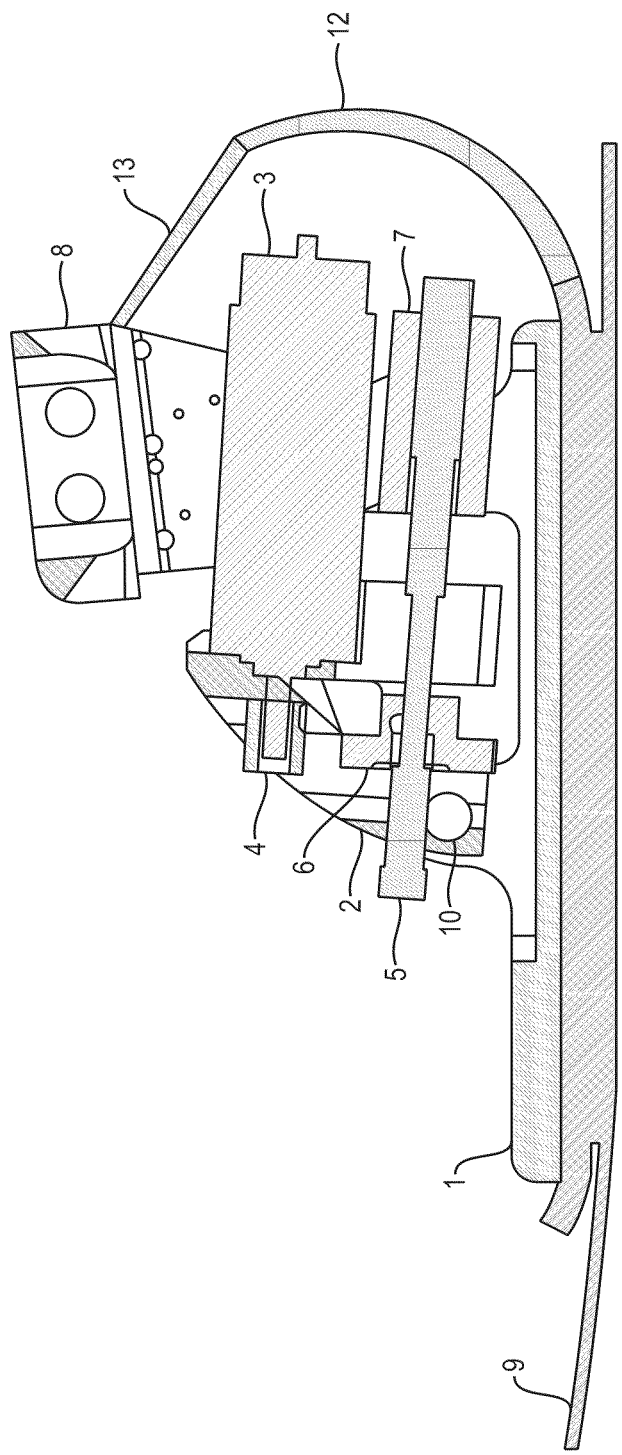

The first embodiment is an ankle-foot design for the efficient control of spring-equilibrium position shown in FIGS. 66, 67 and 68. The components of the prosthesis are listed below:

FIG. 66 Right View
1 DC Motor
2 motor position encoder
3 composite foot
4 worm gear
5 ankle rotation axis
6 spring housing
7 pyramid mount
8 positioning worm gear
9 spring cable hub
10 spring compression cable FIG. 67 Cut Away
1 motor position encoder
2 DC motor
3 worm gear
4 spring compression cable
5 spring cable hub
6 die spring
7 spring housing
8 pyramid mount
9 cable termination and spring compression cap
10 spring cable roller guides
11 ankle rotation axis
12 composite foot Referring to FIG. 66, the motor 1 shaft drives the worm gear 4 and the motor 1 is mounted to the composite foot 3. A shaft integral encoder 2 is mounted on the motor 1 and is used to position the ankle accurately via closed loop feedback control. The worm gear 4 drives the positioning worm gear 8 on the ankle rotation axis 5. A spring cable hub 9 is concentrically attached to the positioning worm gear 8. A spring compression cable 10 is wound around the spring cable hub 9. Two coil springs are passed on each end of the cable and are supported on roller guides that rotate the spring housing 6 on the spring cable hub around the ankle rotation axis 5. The spring cable hub 9 transfers the torque from the motor 1 and applies force on the spring compression cable. The leg is bolted to the pyramid mount 7 fastened to the spring housing 6.

FIG. 67 shows the sagittal plane cross sectional view. This cross sectional layout shows the details inside the spring housing 7 and the drive mechanism. In this figure the spring compression cable 4 is crimped in the cable termination cap 9 at the top of the spring housing 7. The DC motor 2 is shown with position encoder 1 and drives a worm gear 3 that is geared to rotate the spring cable hub 5 on the ankle joint axis which is perpendicular to the motor shaft axis. The spring compression cable 4 is wound around the hub 5 and is crimped to cable termination cap 9. Two die springs 6 are passed around each end of the cable 4 and are supported between the cable termination cap 9 and plate supporting roller guides 10. The pyramid mount 8 connects the ankle mechanism to the leg prosthesis.

This novel ankle-foot mechanism provides for dorsiflexion and plantar flexion of the ankle during the swing phase of walking. When the motor drives the worm gear counter clockwise, the cable pulls the rear spring in compression and extends the front spring. This rolls the spring housing backwards on the rollers resulting in ankle plantar flexion. When the motor drives the worm gear clockwise, the cable is pulled and the rear spring releases and the front spring gets compressed resulting in the spring housing rotating forward on the ankle joint axis.

The dominant advantage of this design over the prior art is its inherent ability to provide ankle spring equilibrium control while requiring only a minimal amount of electrical power from a power supply. In embodiment 1 shown in FIGS. 66-67, the worm gear and cable transmission is non backdriveable. Thus, no energy is required by the motor to maintain an ankle spring equilibrium position and impedance. During the swing phase of walking, a microprocessor located on the artificial ankle-foot mechanism would adjust the position of the ankle joint such that the ankle position (joint spring equilibrium position) is ideal given environmental conditions such as walking speed and surface terrain. Once the ankle position has been adjusted during the swing phase, the motor can turn off to conserve power-supply energy during the subsequent stance period.

The control of ankle position and spring equilibrium position during the swing phase can be achieved using sensory information measured on the mechanism. The sensors of the ankle include a motor encoder 2 shown in FIG. 1. An ankle angle encoder senses the position of the foot with respect to the shank. Additionally an inertial measurement unit (IMU) is located on the ankle-foot mechanism. The IMU is composed of a three axis accelerometer and one to three ceramic gyroscopes. The IMU is thus capable of measuring three dimensional angles of the shank with respect to gravity, angular velocities, and accelerations. The acceleration can also be double integrated, after subtracting the acceleration component of gravity, to give a change in linear position. The IMU is useful in detecting stair ascent and descent, and ramp ascent and descent where adjustments in spring equilibrium position are necessary for proper ankle function.

The second embodiment is rotary ankle-foot design for the control of joint impedance and power output shown in FIGS. 69-73. The components of the prosthesis are listed below:

1 Foot Frame
2 Drive Frame
3 Maxon PowerMax 30 motor plus encoder
4 Driver Gear
5 10 mm Ball Screw
6 Driven Gear
7 Ball Nut with side pins
8 Drive Arm Assembly
9 Composite Foot Plate
10 Drive Frame Pin 1
11 Ankle Joint Pin 1
12 Parallel Composite Spring
13 Parallel Spring Strap The powered artificial ankle-foot system shown in FIGS. 69-73 is a bolt-on external prosthesis for lower extremity amputees. The ankle attempts to simulate the natural joint mechanics of a normal human ankle during walking, stair ascent/descent, and ramp ascent/descent via a combination of springs, a motor with drivetrain, and a linkage. Several sensors provide feedback necessary to control the motor, determine the current state in the gait cycle, and to determine whether the user is on stairs, a ramp, or level ground.

The entire ankle mechanism is supported on the Foot Frame 1. The Drive Frame 2 is cradled in the Foot Frame 1 by pin joints located at 10 and 11. The Drive Frame 2 carries the motor 3 which can be the Maxon PowerMax 30 motor or the Maxon RE 40 brushed DC motor, or a motor of similar size and power output. The Drive Frame 2 also carries the Driver Gear 4, the Driven Gear 6, the Ball Screw 5 and the Ball Nut 7. The Driver Gear 4 is attached to the motor 3 output shaft and is connected to the Driven Gear 6 via a timing belt (timing belt not shown for clarity). The Driven Gear 6 is mounted on the Ball Screw 5 and rotates the Ball Screw 5, transmitting torque from motor 3 to Ball Screw 5. The rotational motion of Ball Screw 5 is converted into screw motion of the Ball Nut 7 moving on the Ball Screw 5. The Ball Nut 7 is connected to the Drive Arm 8 by the side pins. The Drive Arm 8 acts as a rocker on the ankle joint pin 11 in the Foot Frame 1.

Figure 71:
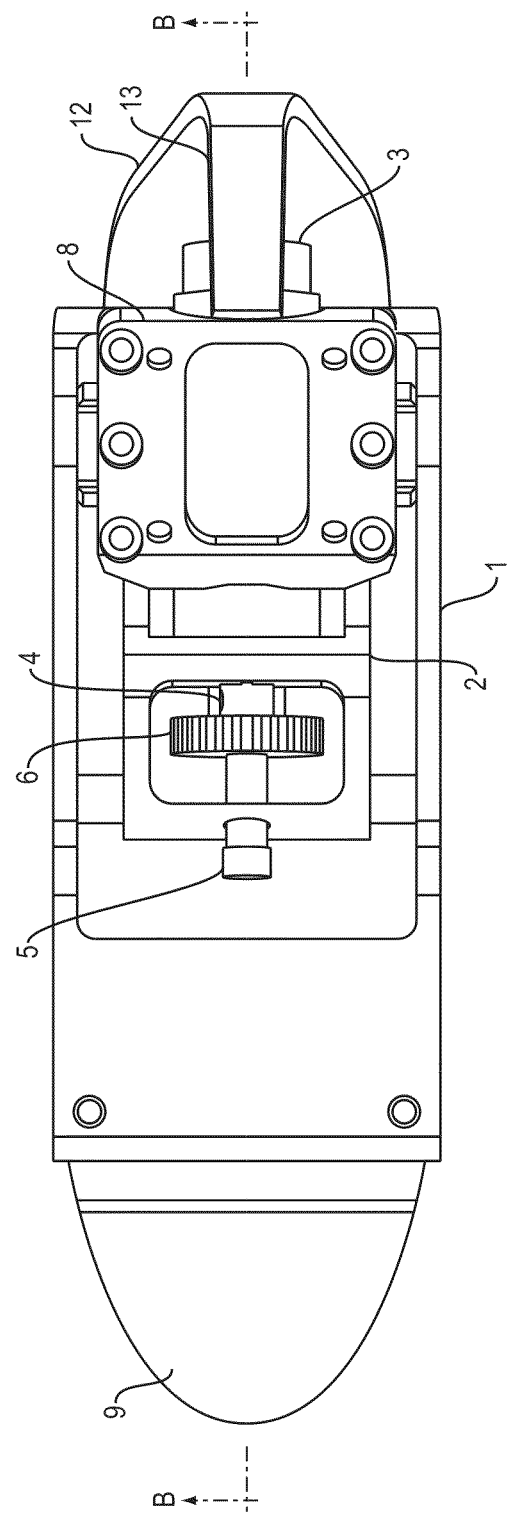
Figure 72:
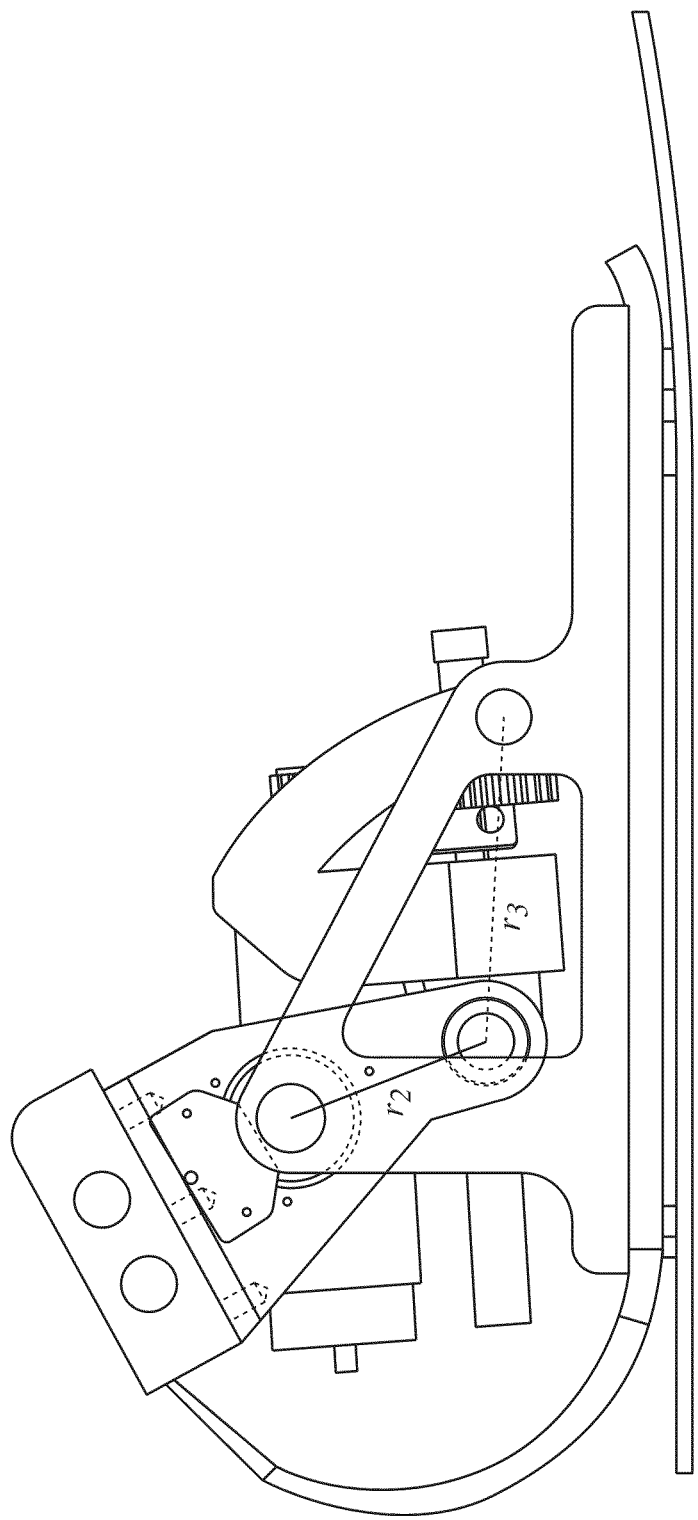
FIGS. 72 and 73 are elevational views of a prosthesis in plantar flexed and dorsiflexed positions, respectively.
Figure 73:
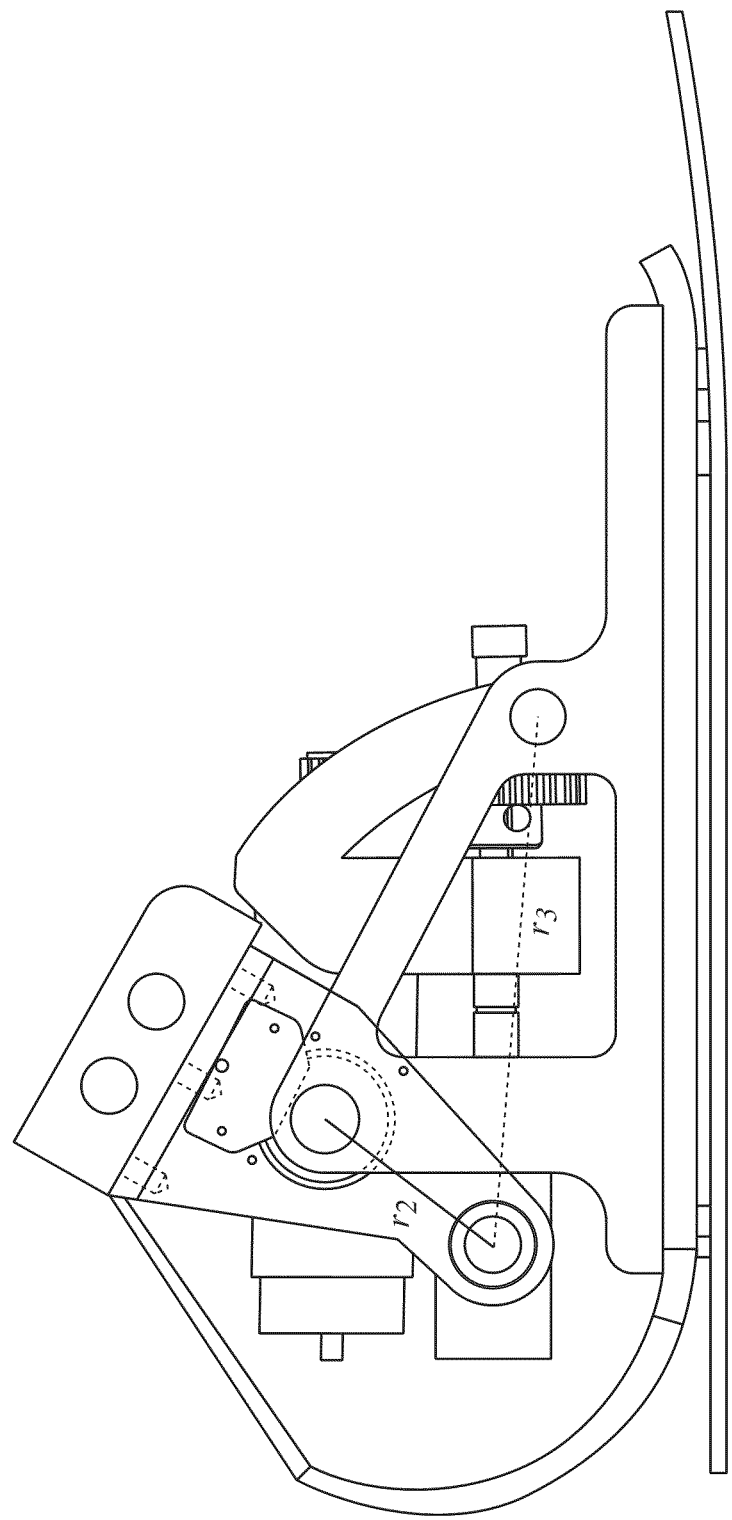

The position of the ankle joint can be actively controlled during walking and other movement tasks. FIG. 71 shows the plantar flexion mode of the ankle. This position is achieved when motor 3 turns Driver Gear 4 which in turns drives the Ball Screw 5 via the Driven Gear 6 and moves the Ball Nut 7. The Ball Nut 7 climbs towards the Drive Frame 2 consequently reducing the vector $r_3$ in length and rotating the vector $r_2$ CCW to achieve a plantar flexion position. FIG. 72 shows the dorsiflexion mode in which the vector $r_3$ is increased in length by turning the motor 3 and engaging the drive train (Driver Gear 4, Ball Screw 5, Driven Gear 6 and Ball Nut 7) in the opposite direction. The vector $r_2$ is now rotated CW swinging the Drive Arm assembly 8 forward.

To offset motor torque required and thus reduce electric power required by the electric motor 1, a spring is placed in parallel with the ankle joint. A composite spring 12 acts in parallel to the actuator system and is connected between the composite foot plate 9 and Drive Arm 8 by a Parallel Spring Strap 13. The flexible parallel spring strap 13 enables the spring 12 to deflect when the ankle angle decreases in dorsiflexion below a critical engagement angle. However, the strap 13 goes slack for any plantar flexion angles greater than that strap engagement angle, thus not deflecting the composite parallel spring 12. The strap engagement angle of the parallel spring 12 is set precisely with adjustment screws located in the base of the Drive Arm Assembly 8. The engagement angle is set such that, when the ankle-foot mechanism is placed in a shoe, the longitudinal axis running through Drive Arm Assembly 8 becomes vertically aligned. The function of Parallel Spring 12 is to store energy during dorsiflexion as shown in FIG. 72, lowering force requirements of the actuator system thereby increasing force bandwidth.

The sensors of the ankle-foot mechanism include a motor encoder 3. An ankle angle encoder senses the position of the foot with respect to the shank. Using the motor encoder 3 and the motor 1, a simple impedance control can be provided to the ankle joint. A load cell, constructed by placing strain gauges on the inside surfaces of the Drive Arm Assembly 8, is used to get an accurate measurement of ankle torque. Additionally an inertial measurement unit (IMU) is located on an electronic board attached to the ankle-foot assembly. The IMU is composed of a three axis accelerometer and one to three ceramic gyroscopes. The IMU is thus capable of measuring three dimensional angles of the shank with respect to gravity, angular velocities, and accelerations. The acceleration can also be double integrated, after subtracting the acceleration component of gravity, to give a change in linear position. The IMU is useful in detecting stair ascent and descent, and ramp ascent and descent.

The entire apparatus is mounted to a composite foot plate 9, that provides a normal foot profile and provides compliance at the heel and toe. The size of the composite foot plate 9 is set to be appropriate for the user by the prosthetist. Stiffness of the toe and heel can be adjusted by selecting different composite foot plates 9 with different integral stiffnessses.

Figure 74:
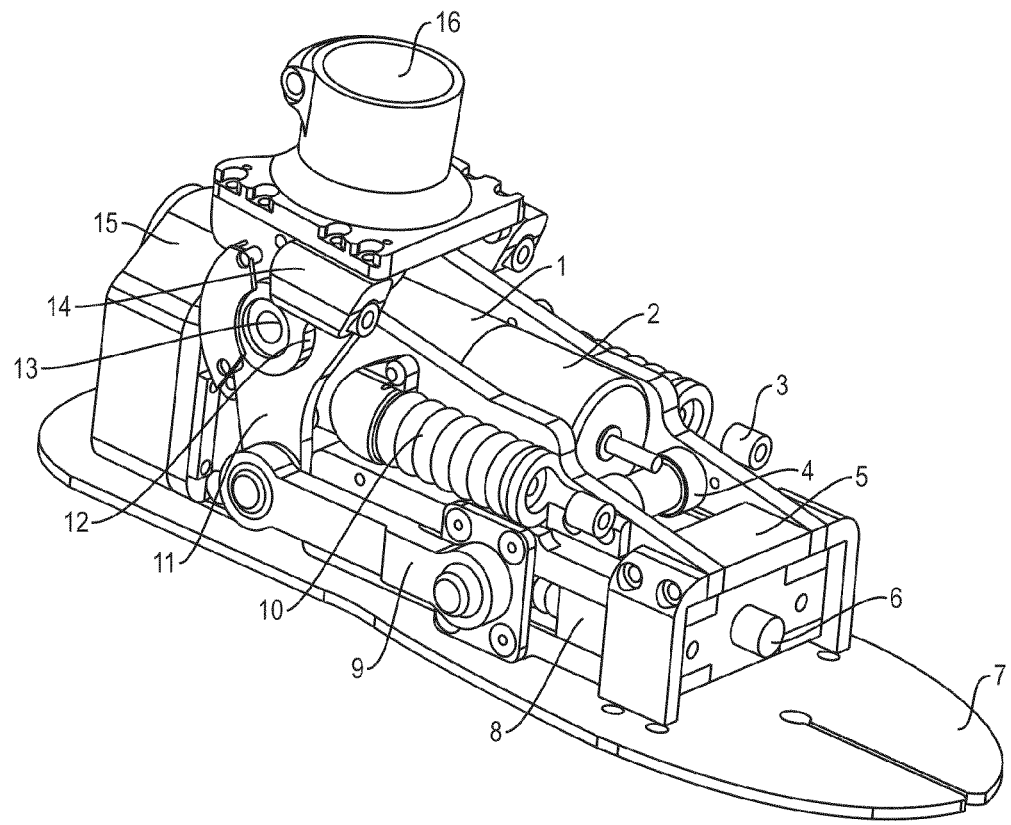
FIGS. 74 and 75 are perspective and end views of an ankle foot prosthesis.
Figure 75:
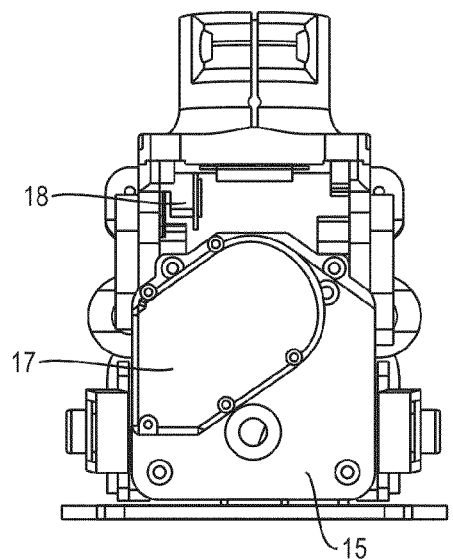
Figure 76:
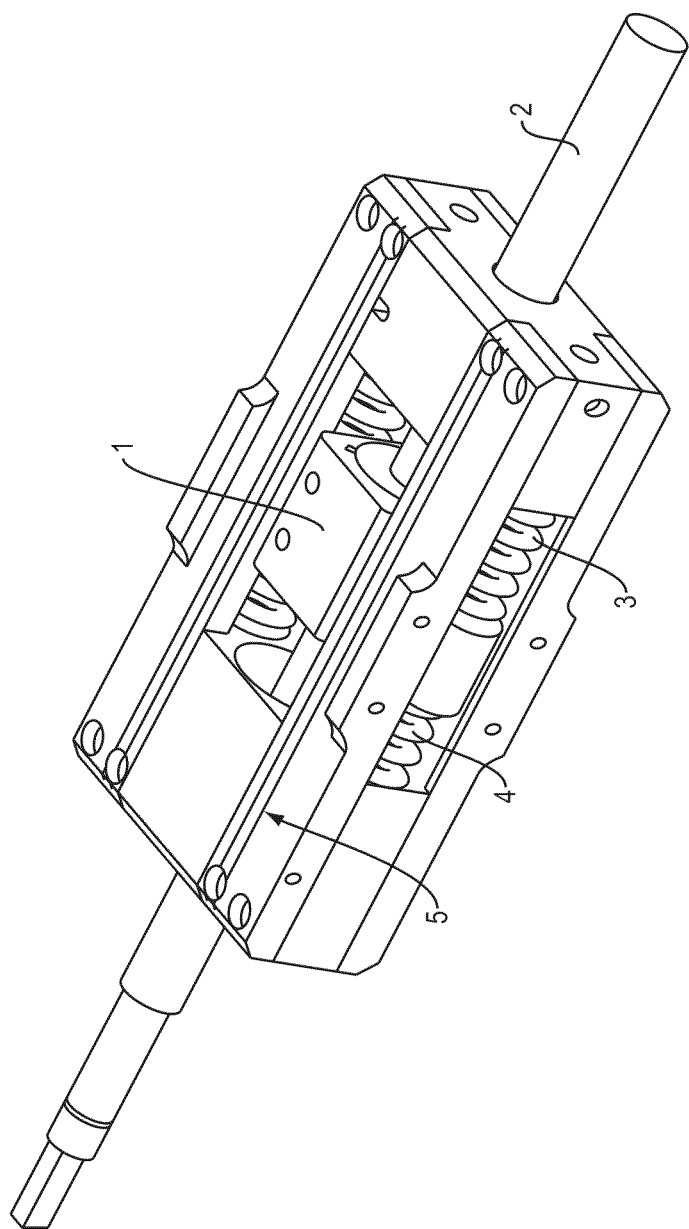
FIGS. 76, 77 and 78 are perspective, overhead and cutaway views of a spring cage used in the arrangement seen in FIGS. 74-75.
Figure 77:
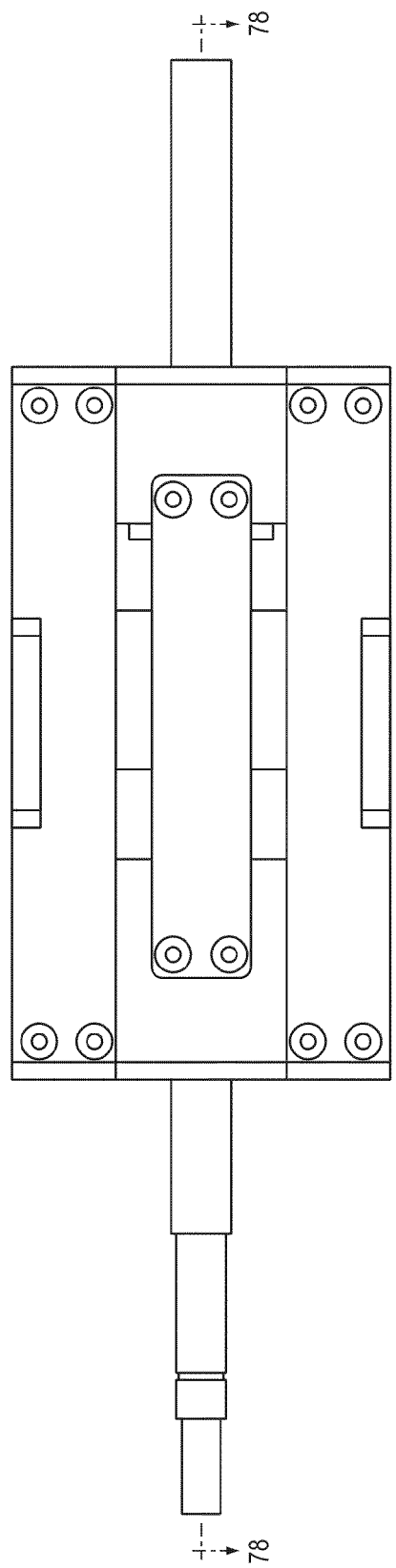
Figure 78:
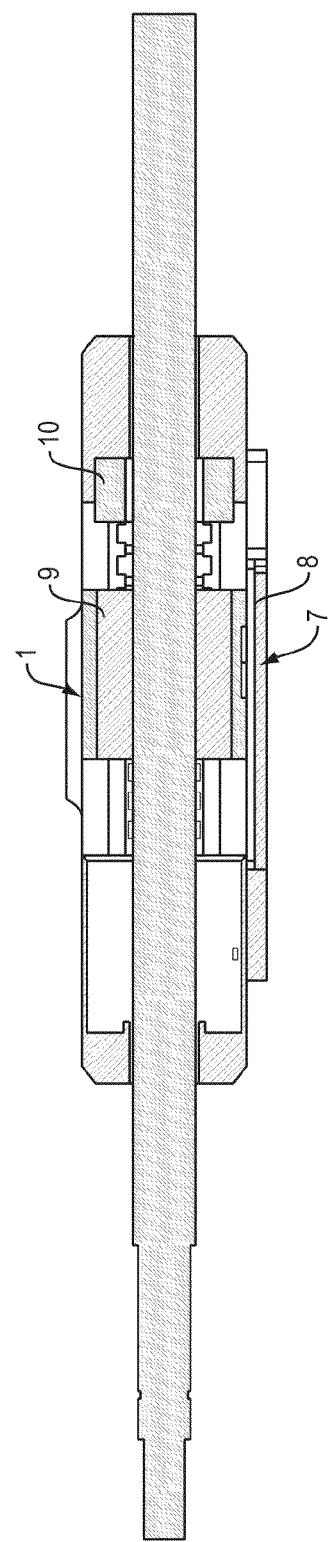

The third embodiment illustrates the Motor, Spring, and Clutch Design in FIGS. 74-78 having the following components:

FIGS. 74 and 75
 1 electric motor
 2 motor clutch
 3 cable stop
 4 spring cage roller
 5 toe box
 6 power screw
 7 composite foot plate
 8 spring cage
 9 connecting link
 10 parallel compression spring
 11 crank arm
 12 cable guide
 13 ankle axis pin
 14 parallel spring adjustment
 15 gearbox
 16 prosthetic tube clamp
 17 motor encoder cover
 18 ankle angle encoder
FIGS. 76, 77 and 78
 1a nut housing
 2a power screw
 3a dorsiflexion series compression spring
 4a plantarflexion series compression spring
 5a bearing roller track
 6a linear potentiometer housing
 7a linear potentiometer brush
 8a linear potentiometer element
 9a nut 10a dorsiflexion bumper The powered prosthetic ankle-foot system is a bolt-on external prosthesis for lower extremity amputees. The prosthetic ankle-foot mechanism is connected to the existing socket via the prosthetic tube clamp 16. The ankle attempts to simulate the natural joint mechanics of a normal human ankle during walking, stair ascent and descent, and ramp ascent and descent via a combination of springs, a motor with drivetrain, and a linkage. Several sensors provide feedback necessary to control the motor, determine the current state in the gait cycle, and to determine whether the user is on stairs, a ramp, or level ground.

In FIGS. 74 and 75, an electric motor 1 provides active power input to the prosthetic ankle. The electric motor 1 is either a Maxon powermax 30 brushless DC motor with a 200 W continuous rating (pictured), or a Maxon RE 40 brushed DC motor with a 150 W continuous rating, or any other motor of similar power capability. The electric motor 1 is connected to a gearbox 15, which provides a reduction in speed to drive the parallel power screw 6. The gearbox 15 is a two stage spur gear train with a total reduction of 4:1. The power screw 6 is a Nook industries 10 mm diameter 3 mm lead ball screw. The power screw 6 drives a nut 9a, which is within the spring cage 8.

Ankle torque is transmitted to the spring cage 8 via a slider crank mechanism. The prosthetic tube clamp 16 bolts to the crank arm 11, which rotates about the ankle axis pin 13. The connecting link 9 connects the crank arm 11 to the spring cage 8 with pin joints at each connection. The spring cage 8 slides on a linear bearing comprised of plastic bearing surfaces below and a spring cage roller 4 and a series of bearing rollers that ride in the bearing roller track 5a from above. The spring cage 8 has a moment arm of 1.5" to the ankle axis. The relation between input motor angular velocity and output ankle angular velocity is the transmission ratio. The transmission ratio is a nonlinear function of ankle angle due to the kinematics of the slider crank mechanism. The transmission ratio reaches a maximum of 319.2:1 at 9° ankle dorsiflexion, with 0° referring to a vertical shank while the foot is flat on the ground. The transmission ratio reduces to 318.6:1 at 13° ankle dorsiflexion and 206.6:1 at 32° ankle plantar flexion. The reduction in transmission ratio during plantar flexion helps to increase angular velocity of the ankle at extreme plantar flexion angles to servo the ankle quickly at reduced power screw speed and thus reduce related power screw noise. A higher transmission ratio is necessary during dorsiflexion when ankle torques are higher, thus reducing the torque required by the motor.

Within the spring cage, the nut 9a is encapsulated by the nut housing 1a, which provides rotational stability for the nut by using two parallel linear guide rods. Two linear ball bearings are press fit into the nut housing 1a, and the two cylindrical guide rods are fixed to the spring cage 8. This allows the nut 9a and nut housing 1a to slide axially within the spring cage 8, except as is prevented by series springs mounted between the nut housing 1a and the spring cage 8. Each linear guide has two series springs concentric to it, for a total of 4 series springs. The series springs create an effective stiffness at the ankle joint. The plantar flexion series compression spring 4a compresses during controlled plantar flexion. The spring constant of the plantar flexion spring is in the range of that of a spring constant fit to a normal human ankle during walking, determined with a linear fit to the ankle angle vs. torque diagram starting from heel strike and ending at foot flat. The spring constant however is tunable by the prosthetist to the user's preference. This value could range from 40% to 300% from a median value of 0.6 normalized rotational stiffness about the ankle joint, normalized by body weight and foot length (e.g. a 70 kg person with foot length 26 cm gives a median stiffness of 107 N–m/rad). In dorsiflexion, the dorsiflexion series spring 3a comprises only a portion of the ankle stiffness. The remainder of the stiffness is carried by the parallel spring as discussed in the next section. The stiffness is set so that the force produced by compressing the dorsiflexion series spring will not exceed the motor clutch 2 torque for the range of possible ankle dorsiflexion angles. This dorsiflexion spring is necessary to center the nut housing 1a within the spring cage 8 and has a rotational stiffness about the ankle axis of 100 N–m/rad. The dorsiflexion series compression spring 3a compresses during dorsiflexion. At the end of dorsiflexion when the dorsiflexion series compression spring 3a has reached its maximum value the nut housing 9a contacts the dorsiflexion bumper 10a, which provides high drivetrain stiffness during powered plantar flexion. The dorsiflexion bumper 10a is a steel coil spring concentric to the power screw 6 with a stiffness of 2080 lb/in. The dorsiflexion bumper may also be a polyurethane spring or a rigid material.

To offset motor torque required and thus reduce electric power required by the electric motor 1, a spring is placed in parallel with the ankle joint. The parallel spring 10 compresses and produces ankle torque when the ankle angle decreases in dorsiflexion below a critical engagement angle. The parallel compression spring 10 is compressed by a cable, which is connected to the crank arm 11. A cable stop 3 enables the spring to compress when the ankle angle decreases in dorsiflexion below a critical engagement angle but allows the cable to slide freely for any plantar flexion angles greater than that engagement angle. The cable wraps around the cable guide 12, which keeps a constant moment arm of 0.5" for the parallel spring about the ankle axis. The engagement angle of the parallel spring is set precisely with the parallel spring adjustment 14, via a set screw acting on a cable stop. The engagement angle is set such that, when the ankle-foot mechanism is placed in a shoe, the longitudinal axis running through prosthetic tube clamp 16 becomes vertically aligned.

The sum of the parallel spring stiffness and the dorsiflexion series spring stiffness comprises the desired total stiffness felt by the user during dorsiflexion. This value is initially with a normalized stiffness of a spring constant fit to a normal human ankle during walking, determined with a linear fit to the ankle angle vs. torque diagram starting from 0° and ending at peak torque/dorsiflexion angle. The normalized value of stiffness is 3.4, normalized by body weight and foot length (e.g. a 70 kg person with foot length 26 cm gives a median stiffness of 600 N–m/rad). The stiffness may be tuned by the prosthetist within the range of 40% to 200% of the median value.

The motor is outfitted with a parallel motor clutch 2, which fixes the motor shaft from spinning. The motor clutch has a default state to lock the motor shaft when power is cut to the system. This allows the ankle to continue to be used safely and efficiently without power. Additionally, the clutch is used during walking, since the spring constants are tuned for a locked motor shaft. The clutch is locked during heel strike until the dorsiflexion bumper 10a is contacted by the nut housing 1a at approximately 11° ankle dorsiflexion. At that time simultaneously the clutch is unlocked and the motor is driven actively with a constant current until either a predetermined ankle plantar flexion angle is reached, or the ankle moment falls below a predetermined threshold. The predetermined values are set by the prosthetist during tuning of the ankle. At that time, the motor servos the ankle to 0° and then the clutch is locked to prepare for the next heel strike. If the ankle angle of 11° dorsiflexion is not reached, the clutch will not unlock for that gait cycle. Using the clutch in this method saves energy because the clutch uses no power when locked, compared to the energy that would be required to drive the motor to maintain a locked shaft.

The sensors of the ankle include a motor encoder located underneath the motor encoder cover 17. An ankle angle encoder 18 senses the position of the foot with respect to the shank. A linear potentiometer senses the position of the nut housing within the spring cage. This measures the both the dorsiflexion and plantar flexion series spring compression. Using this compression measurement and the known stiffness of the series springs, force can be calculated. The force can be converted to ankle torque to get an accurate measurement of the ankle mechanics. The linear potentiometer consists of linear potentiometer brush 7a mounted to the nut housing 1a, a linear potentiometer element 8a, mounted to the spring cage 8, and a protective linear potentiometer housing 6a, also mounted to the spring cage 8.

The entire apparatus is mounted to a composite foot plate 7, which provides a normal foot profile and provides compliance at the heel and toe.

Figure 79:
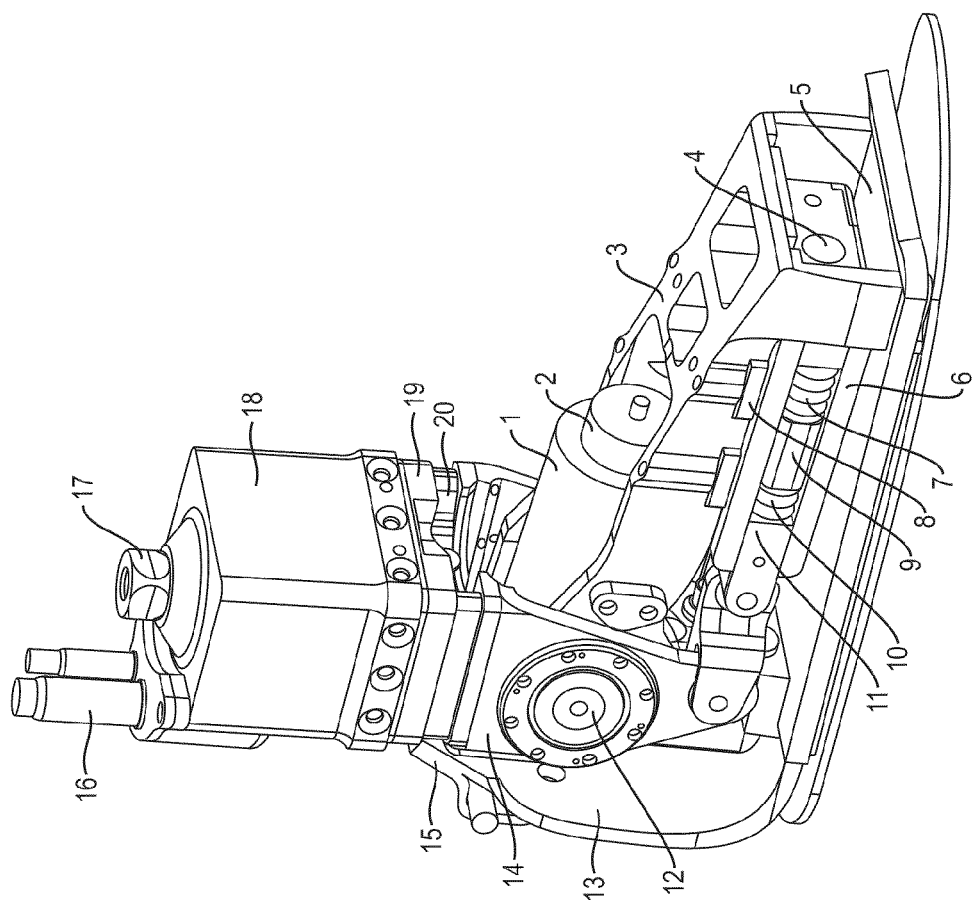
FIG. 79 is a perspective view of a prosthesis using a catapult design.
Figure 80:
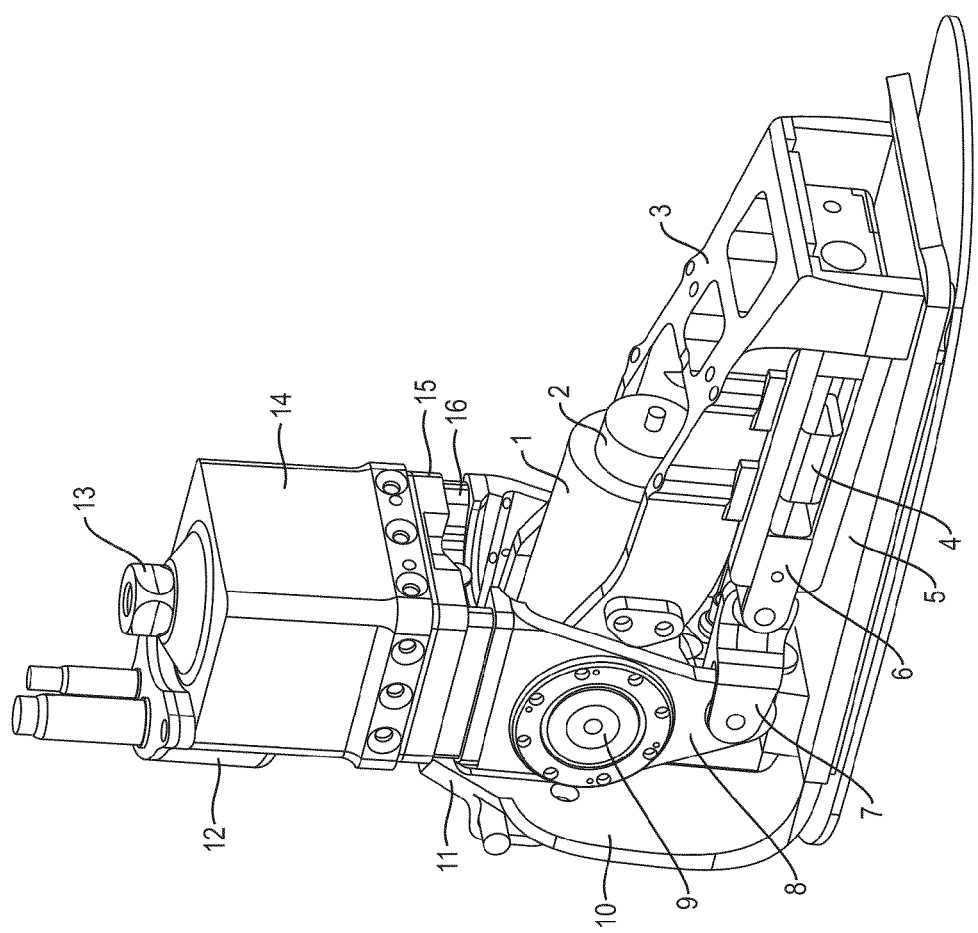
FIG. 80 is a perspective view of an ankle foot system.
Figures 81, 82:
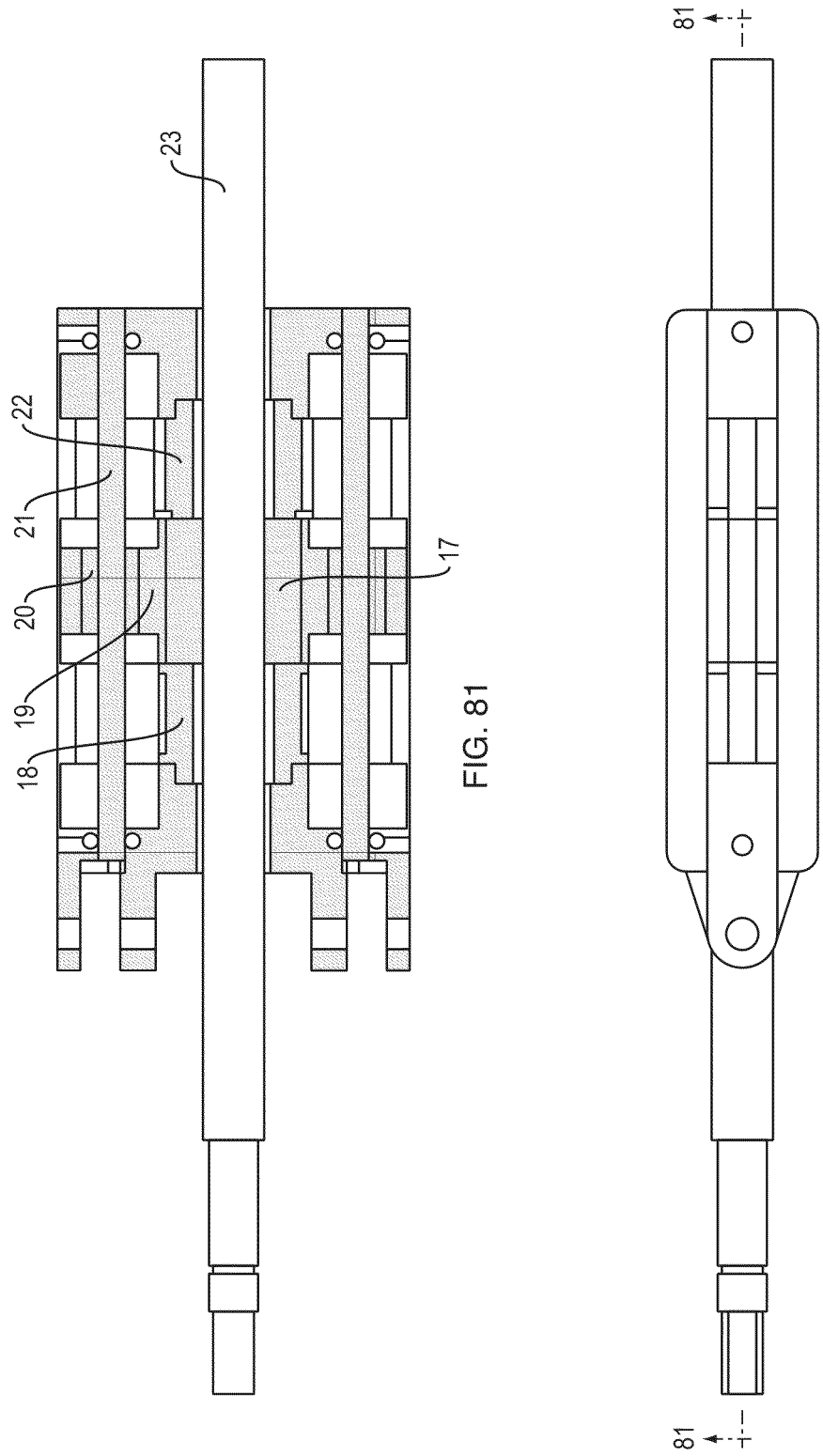
FIGS. 81, 82 and 83 are views of the spring cage used in the system of FIG. 80.
Figure 83:
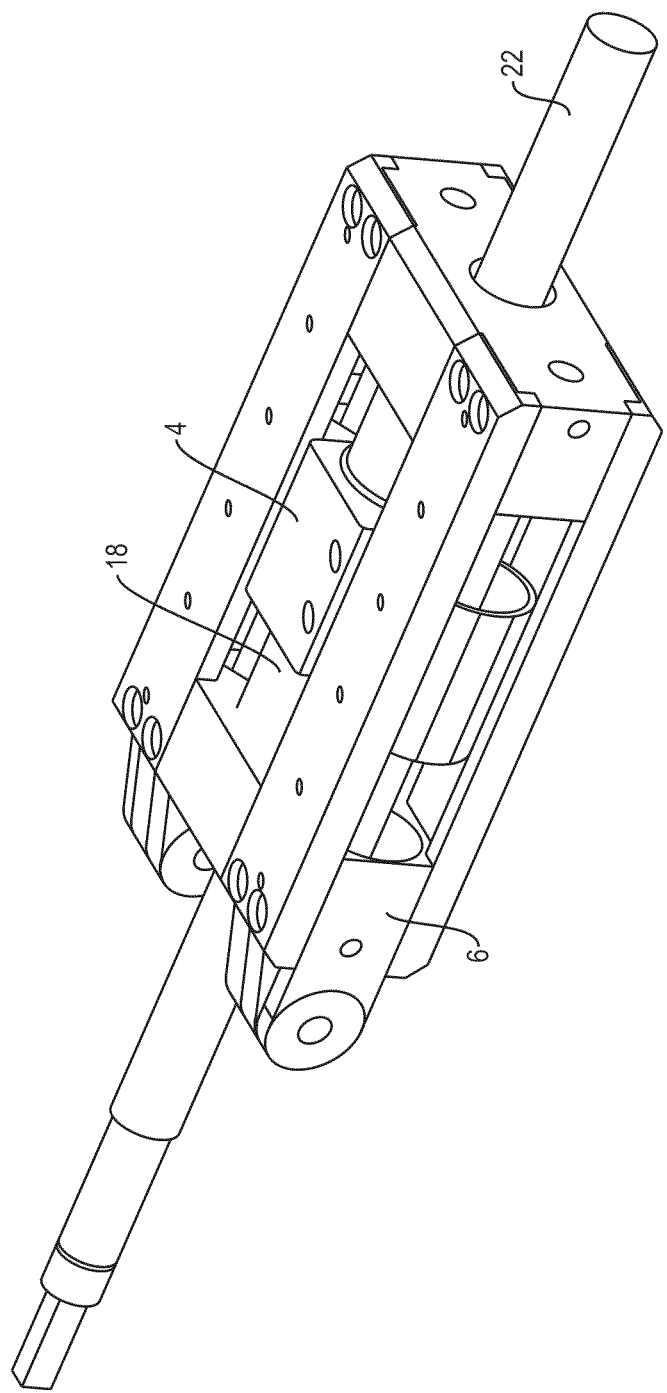

The fourth embodiment illustrates a catapult design for the control of joint impedance and power output as shown in FIG. 79. The components of design as seen in FIG. 79 are:
1. electric motor
2. motor angle encoder
3. toe box
4. power screw 5. composite foot
6. spring cage
7. dorsiflexion compression spring
8. linear guide carriage
9. nut housing
10. plantarflexion compression spring
11. spring cage
12. ankle axis pin
13. composite parallel spring
14. crank arm
15. parallel spring strap
16. power and data connection
17. pyramid mount
18. load cell and electronic hardware housing
19. inversion/eversion assembly
20. inversion/eversion springs The powered artificial ankle-foot system shown in FIG. 79 is a bolt-on external prosthesis for lower extremity amputees. The prosthetic ankle-foot system is connected to the existing socket via the pyramid mount 17. The ankle attempts to simulate the natural joint mechanics of a normal human ankle during walking, stair ascent and descent, and ramp ascent and descent via a combination of springs, a motor with drivetrain, and a linkage. Several sensors provide feedback necessary to control the motor, determine the current state in the gait cycle, and to determine whether the user is on stairs, a ramp, or level ground.

An electric motor 1 provides active power input to the prosthetic ankle. The electric motor 1 is either a Maxon powermax 30 brushless DC motor with a 200 W continuous rating or a Maxon RE 40 brushed DC motor (pictured) with a 150 W continuous rating, or any other motor of similar power capability. The electric motor 1 is connected to a timing belt drive, that provides a reduction in speed to drive the parallel power screw 4. The belt drive is a single stage timing belt reduction. The timing belt drive tends to be quieter than other similar transmission technologies since the neoprene or polyurethane belt tends to absorb noise. The power screw 4 is either a Nook industries or NSK 10 mm diameter 3 mm lead ball screw or a 8 mm diameter 3 mm lead roller screw. The power screw 4 drives a nut and rigidly attached nut housing 9, which is within the spring cage 6.

Ankle torque is transmitted to the spring cage 6 via a slider crank mechanism. Torque load is applied from the shank of the user to the two crank arms 14, which rotate about the ankle axis pin 12. There is one crank arm 14 on each side of the ankle to balance loads. Large 0.875" diameter torque tube type bearings are used at the ankle axis pin in order to maintain rigidity for inversion/eversion and internal/external rotation loads. The connecting links connect the crank arms 14 to the spring cage 6 with pin joints at each connection. The spring cage 6 slides on a linear bearing comprised of two parallel linear guides, each with two carriages, from above. The linear guides are mounted on the spring cage 6 and the carriages are mounted to the toe box 3. The spring cage 6 has a moment arm of 1.5" to the ankle axis. The relation between input motor angular velocity and output ankle angular velocity is the transmission ratio. The transmission ratio is a nonlinear function of ankle angle due to the kinematics of the slider crank mechanism. The transmission ratio reaches a maximum at 9° ankle dorsiflexion, with 0° referring to a vertical shank while the foot is flat on the ground. The transmission ratio reduces slightly at 25° ankle dorsiflexion and significantly at 35° ankle plantar flexion. The reduction in transmission ratio during plantar flexion helps to increase angular velocity of the ankle at extreme plantar flexion angles to servo the ankle quickly at reduced power screw speed and thus reduce related power screw noise. A higher transmission ratio is necessary during dorsiflexion when ankle torques are higher, thus reducing the torque required by the motor.

Within the spring cage 6, the nut is encapsulated by the nut housing 9, which provides rotational stability for the nut by using two parallel linear guide rods. Two linear ball bearings are press fit into the nut housing 19, and the two cylindrical guide rods are fixed to the spring cage 6. This allows the nut and nut housing 19 to slide axially within the spring cage 6, except as is prevented by series springs mounted between the nut housing 19 and the spring cage 6. The two series springs are mounted between the spring cage 6 and the nut housing 9, concentric to the power screw 4.

The series springs are of low stiffness and only compress significantly during use. During operation the motor can compress the springs from one end while the ankle compresses them from the other end. By driving the motor to compress the spring while the spring is being loaded externally, a virtual spring stiffness which is higher than the series spring is created. The control algorithm is likely to be constructed so that the motor compresses the spring when load applied to it is increasing, then holds the spring end constant when the spring is being unloaded. This creates a high virtual stiffness during compression and a low stiffness during unloading. The high stiffness followed by a low stiffness creates a triangular shaped ankle angle vs. torque profile, which encloses area and thus provides net energy to the user. This control algorithm would be useful for both controlled plantar flexion and for dorsiflexion.

The plantar flexion series spring 10 compresses during controlled plantar flexion. The dorsiflexion series spring 7 compresses during dorsiflexion.

The actual stiffness felt by the user is set by a virtual spring algorithm for the motor. The motor will output a torque based on the angle and angular velocity at the ankle axis, or possibly by measured ankle torque, or by applying an impedance control on the motor encoder. This allows for a controlled virtual stiffness and damping of the angle joint. The virtual stiffness is tunable by the prosthetist to the user's preference. For the plantar flexion series spring 10, this value could range from 40% to 300% from a median value of 0.3 normalized rotational stiffness about the ankle joint, normalized by body weight and foot length (e.g. a 70 kg person with foot length 26 cm gives a median stiffness of 50 N–m/rad). The damping is set to a low value, high enough to reduce oscillations of the system, but low enough so that significant energy loss is not felt at the ankle. In dorsiflexion, the spring constant value could range from 40% to 300% from a median value of 1.2 normalized rotational stiffness about the ankle joint, normalized by body weight and foot length (e.g. a 70 kg person with foot length 26 cm gives a median stiffness of 200 N–m/rad). The dorsiflexion virtual stiffness will increase this value by 0% to 300%. The dorsiflexion virtual stiffness carries only a portion of the ankle stiffness. The remainder of the stiffness is carried by the parallel spring as discussed in the next section.

To offset motor torque required and thus reduce electric power required by the electric motor 1, a spring is placed in parallel with the ankle joint. The composite parallel spring 10 is deflected by means of a parallel spring strap 15, which connects the top of the composite parallel spring 13 to the base of the load cell and electronic hardware housing 18. The flexible parallel spring strap 15 enables the spring to deflect when the ankle angle decreases in dorsiflexion below a critical engagement angle. However, the strap goes slack for any plantar flexion angles greater than that strap engagement angle, thus not deflecting the composite parallel spring 13. The strap engagement angle of the parallel spring is set precisely with adjustment screws located in the base of the load cell and electronic hardware housing 18. The engagement angle is set such that, when the ankle-foot mechanism is placed in a shoe, the longitudinal axis running through pyramid mount 17 is vertically aligned.

The parallel stiffness plus the controlled virtual stiffness of the motor comprise the desired total stiffness felt by the user during dorsiflexion. This value is initially set with a normalized stiffness of a spring constant fit to a normal human ankle during walking, determined with a linear fit to the ankle angle vs. torque diagram starting from 0° and ending at peak torque/dorsiflexion angle. The normalized value of stiffness is 3.4, normalized by body weight and foot length (e.g. a 70 kg person with foot length 26 cm gives a median stiffness of 600 N–m/rad). The stiffness for the composite parallel spring will be on average about ⅓ of the desired total stiffness, with the controlled virtual stiffness maxing up the other ⅔rds. The stiffness may be tuned by the prosthetist within the range of 40% to 200% of the median value. The stiffness is tuned by means of swapping composite parallel spring plates. The virtual stiffness, set by the motor control algorithm provides fine control over the total stiffness and also allows the stiffness to be adjusted in real time for terrain variations.

In order to provide additional comfort and natural feeling to the user, the ankle has an additional degree of freedom which provides subtalar joint inversion/eversion. This is accomplished by inversion/eversion assembly 19. The inversion/eversion assembly 19 consists of three main parts, a bottom plate that mounts to the two crank arms 14, a top plate that mounts to the load cell and electronic hardware housing 18, and a center pin which provides the rotational degree of freedom. The center pin is parallel to the motor 1 and the power screw 4. The plates rotate about the center pin to provide inversion/eversion movements. Two inversion/eversion springs 20 provide rotational inversion/eversion stiffness. This stiffness is tuned by the prosthetist to the user's preference, and to achieve a natural gait pattern. This stiffness is typically in the range of 20%-500% about a median normalized stiffness of 0.3, normalized by foot width and body weight (e.g. a 70 kg person with a foot width of 9 cm has a median stiffness of 20 N–m/rad). The two inversion/eversion springs 16 can each be set to distinct stiffnesses to enable separate tuning of inversion and eversion. Typically eversion is set to a slightly stiffer value than inversion. The inversion/eversion springs 16 are currently polyurethane springs, but could be any suitable spring material.

The sensors of the ankle include a motor encoder 2. An ankle angle encoder senses the position of the foot with respect to the shank. The load cell, constructed by placing strain gauges on the inside surfaces of the load cell and electronic hardware housing 18, is used to get an accurate measurement of the ankle mechanics. Additionally an inertial measurement unit (IMU) is located inside the load cell and electronic hardware housing 18. The IMU is composed of a three axis accelerometer and one to three ceramic gyroscopes. The IMU is thus capable of measuring three dimensional angles of the shank with respect to gravity, angular velocities, and accelerations. The acceleration can also be double integrated, after subtracting the acceleration component of gravity, to give a change in position. The IMU is useful in detecting stair ascent and descent, and ramp ascent and descent.

The entire apparatus is mounted to a composite foot plate 5, which provides a normal foot profile and provides compliance at the heel and toe. The size of the composite foot plate 5 is set to be appropriate for the user by the prosthetist. Stiffness of the toe and heel can be adjusted by selecting different composite foot plates 5 with different integral stiffnessses.

The fifth embodiment illustrates a force-controllable actuator design for the control of joint impedance and power as shown in FIGS. 80-83. The components of design as seen in FIGS. 80-83 are:

1 electric motor
2 motor angle encoder
3 toe box
4 nut housing
5 composite foot
6 spring cage
7 connecting link
8 crank arm
9 ankle axis pin
10 composite parallel spring
11 parallel spring strap
12 power and data connection
13 pyramid mount
14 load cell and electronic hardware housing
15 inversion/eversion assembly
16 inversion/eversion springs
17 nut
18 plantar flexion compression spring
19 nut housing
20 linear ball bearing
21 linear guide rod
22 dorsiflexion compression spring
23 power screw The powered artificial ankle-foot system shown in FIGS. 80-83 is a bolt-on external prosthesis for lower extremity amputees. The prosthetic ankle-foot system is connected to the existing socket via the pyramid mount 13. The ankle attempts to simulate the natural joint mechanics of a normal human ankle during walking, stair ascent and descent, and ramp ascent and descent via a combination of springs, a motor with drivetrain, and a linkage. Several sensors provide feedback necessary to control the motor, determine the current state in the gait cycle, and to determine whether the user is on stairs, a ramp, or level ground.

An electric motor 1 provides active power input to the prosthetic ankle. The electric motor 1 is either a Maxon powermax 30 brushless DC motor with a 200 W continuous rating or a Maxon RE 40 brushed DC motor (pictured) with a 150 W continuous rating, or any other motor of similar power capability. The electric motor 1 is connected to a timing belt drive, that provides a reduction in speed to drive the parallel power screw 23. The belt drive is a single stage timing belt reduction with a pulley ratio of 21:10. The timing belt drive tends to be quieter than other similar transmission technologies since the neoprene or polyurethane belt tends to absorb noise. The power screw 23 is either a Nook industries or NSK 10 mm diameter 3 mm lead ball screw or a 8 mm diameter 3 mm lead roller screw. The power screw 23 drives a nut 17, that is within the spring cage 6.

Ankle torque is transmitted to the spring cage 6 via a slider crank mechanism. Torque load is applied from the shank of the user to the two crank arms 8, which rotate about the ankle axis pin 9. There is one crank arm 8 on each side of the ankle to balance loads. Large 0.875" diameter torque tube type bearings are used at the ankle axis pin in order to maintain rigidity for inversion/eversion and internal/external rotation loads. The connecting links 7 connect the crank arms 8 to the spring cage 6 with pin joints at each connection. The spring cage 6 slides on a linear bearing comprised of two parallel linear guides, each with two carriages, from above. The linear guides are mounted on the spring cage 6 and the carriages are mounted to the toe box 3. The spring cage 8 has a moment arm of 1.5" to the ankle axis. The relation between input motor angular velocity and output ankle angular velocity is the transmission ratio. The transmission ratio is a nonlinear function of ankle angle due to the kinematics of the slider crank mechanism. The transmission ratio reaches a maximum of 167:1 at 9° ankle dorsiflexion, with 0° referring to a vertical shank while the foot is flat on the ground. The transmission ratio reduces to 165:1 at 25° ankle dorsiflexion and 55:1 at 35° ankle plantar flexion. The reduction in transmission ratio during plantar flexion helps to increase angular velocity of the ankle at extreme plantar flexion angles to servo the ankle quickly at reduced power screw speed and thus reduce related power screw noise. A higher transmission ratio is necessary during dorsiflexion when ankle torques are higher, thus reducing the torque required by the motor.

Within the spring cage 6, the nut 17 is encapsulated by the nut housing 19, which provides rotational stability for the nut by using two parallel linear guide rods 21. Two linear ball bearings 20 are press fit into the nut housing 19, and the two cylindrical guide rods are fixed to the spring cage 6. This allows the nut 17 and nut housing 19 to slide axially within the spring cage 6, except as is prevented by series springs 18, 22 mounted between the nut housing 19 and the spring cage 6. The two series springs 18, 22 are mounted between the spring cage 6 and the nut housing 19, concentric to the power screw 23. The series springs 18, 22 are of high stiffness and only compress minimally during use (~1 to 2 mm maximum compression in walking). The main feature provided by the springs is that they provide shock tolerance to the drivetrain, they increase the stability of the control algorithm, and they provide noise absorption. The plantar flexion series spring 18 compresses during controlled plantar flexion. The dorsiflexion series spring 22 compresses during dorsiflexion.

The actual stiffness felt by the user is set by a controlled back-driving algorithm for the motor. The motor will output a torque based on the angle and angular velocity that it is being back-driven with. This allows for a controlled virtual stiffness and damping of the ankle joint. The virtual stiffness is tunable by the prosthetist to the user's preference. This value could range from 40% to 300% from a median value of 0.6 normalized rotational stiffness about the ankle joint, normalized by body weight and foot length (e.g. a 70 kg person with foot length 26 cm gives a median stiffness of 107 N-m/rad). The damping is set to a low value, high enough to reduce oscillations of the system, but low enough so that significant energy loss is not felt at the ankle. In dorsiflexion, the dorsiflexion virtual stiffness carries only a portion of the ankle stiffness. The remainder of the stiffness is carried by the parallel spring as discussed in the next section.

To offset motor torque required and thus reduce electric power required by the electric motor 1, a spring is placed in parallel with the ankle joint. The composite parallel spring 10 is deflected by means of a parallel spring strap 11, which connects the top of the composite parallel spring 10 to the base of the load cell and electronic hardware housing 14. The flexible parallel spring strap 11 enables the spring to deflect when the ankle angle decreases in dorsiflexion below a critical engagement angle. However, the strap goes slack for any plantar flexion angles greater than that strap engagement angle, thus not deflecting the composite parallel spring 10. The strap engagement angle of the parallel spring is set precisely with adjustment screws located in the base of the load cell and electronic hardware housing 14. The engagement angle is set such that, when the ankle-foot mechanism is placed in a shoe, the longitudinal axis running through pyramid mount 13 is vertically aligned.

The parallel stiffness plus the controlled virtual stiffness of the motor comprise the desired total stiffness felt by the user during dorsiflexion. This value is initially set with a normalized stiffness of a spring constant fit to a normal human ankle during walking, determined with a linear fit to the ankle angle vs. torque diagram starting from 0° and ending at peak torque/dorsiflexion angle. The normalized value of stiffness is 3.4, normalized by body weight and foot length (e.g. a 70 kg person with foot length 26 cm gives a median stiffness of 600 N-m/rad). The stiffness may be tuned by the prosthetist within the range of 40% to 200% of the median value. The stiffness is tuned by means of swapping composite parallel spring plates. The virtual stiffness, set by the motor control algorithm provides fine control over the total stiffness and also allows the stiffness to be adjusted in real time for terrain variations.

In order to provide additional comfort and natural feeling to the user, the ankle has an additional degree of freedom which provides subtalar joint inversion/eversion. This is accomplished by inversion/eversion assembly 15. The inversion/eversion assembly 15 consists of three main parts, a bottom plate which mounts to the two crank arms 8, a top plate which mounts to the load cell and electronic hardware housing 14, and a center pin which provides the rotational degree of freedom. The center pin is parallel to the motor 1 and the power screw 23. The plates rotate about the center pin to provide inversion/eversion. Two inversion/eversion springs 16 provide rotational inversion/eversion stiffness. This stiffness is tuned by the prosthetist to the user's preference, and to achieve a natural gait pattern. This stiffness is typically in the range of 20%-500% about a median normalized stiffness of 0.3, normalized by foot width and body weight (e.g. a 70 kg person with a foot width of 9 cm has a median stiffness of 20 N-m/rad). The two inversion/eversion springs 16 can each be set to distinct stiffnesses to enable separate tuning of inversion and eversion. Typically eversion is set to a slightly stiffer value than inversion. The inversion/eversion springs 16 are currently polyurethane springs, but could be any suitable spring material.

The sensors of the ankle include a motor encoder 2. An ankle angle encoder senses the position of the foot with respect to the shank. The load cell, constructed by placing strain gauges on the inside surfaces of the load cell and electronic hardware housing 14, is used to get an accurate measurement of the ankle mechanics. Additionally an inertial measurement unit (IMU) is located inside the load cell and electronic hardware housing 14. The IMU is composed of a three axis accelerometer and one to three ceramic gyroscopes. The IMU is thus capable of measuring three dimensional angles of the shank with respect to gravity, angular velocities, and accelerations. The acceleration can also be double integrated, after subtracting the acceleration component of gravity, to give a change in position. The IMU is useful in detecting stair ascent and descent, and ramp ascent and descent.

The entire apparatus is mounted to a composite foot plate 5, which provides a normal foot profile and provides compliance at the heel and toe. The size of the composite foot plate 5 is set to be appropriate for the user by the prosthetist. Stiffness of the toe and heel can be adjusted by selecting different composite foot plates 5 with different integral stiffnessses.

Bibliography

In the foregoing description, reference has frequently been made to items listed below. Note that some references are listed more than once since they were cited in different sections of the description (as noted by the letter prefix in the citation).

{A-1} www.ossur.com.

{A-2} S. Ron, Prosthetics and Orthotics: Lower limb and Spinal. Lippincott Williams & Wilkins, 2002.

{A-3} N. H. Molen, "Energy/speed relation of below-knee amputees walking on motor-driven treadmill," Int. Z. Angew. Physio, Vol. 31, pp. 173, 1973.

{A-4} G. R. Colborne, S. Naumann, P. E. Longmuir, and D. Berbrayer, "Analysis of mechanical and metabolic factors in the gait of congenital below knee amputees," Am. J. Phys. Med. Rehabil., Vol. 92, pp. 272-278, 1992.

{A-5} R. L. Waters, J. Perry, D. Antonelli, H. Hislop. "Energy cost of walking amputees: the influence of level of amputation," J Bone Joint Surg. Am., Vol. 58, No. 1, pp. 4246, 1976.

{A-6} D. A. Winter and S. E. Sienko, "Biomechanics of below-knee amputee gait," Journal of Biomechanics, Vol. 21, No. 5, pp. 361-7, 1988.

{A-7} H. B. Skinner and D. J. Effeney, "Gait analysis in amputees," Am J Phys Med, Vol. 64, pp. 82-89, 1985.

{A-8} H. Bateni and S. Olney, "Kinematic and kinetic variations of below-knee amputee gait," Journal of Prosthetics & Orthotics, Vol. 14, No. 1, pp. 2-13, 2002.

{A-9} K. Koganezawa, and I. Kato, "Control aspects of artificial leg," IFAC Control Aspects of Biomedical Engineering, pp. 71-85, 1987.

{A-10} D. A. Winter, "Biomechanical motor pattern in normal walking," Journal of Motor Behavior, Vol. 15, No. 4, pp. 302-330, 1983.

{A-11} M. Palmer, "Sagittal plane characterization of normal human ankle function across a range of walking gait speeds," Master's Thesis, Massachusetts Institute of Technology, 2002.

{A-12} D. H. Gates, "Characterizing ankle function during stair ascent, descent, and level walking for ankle prosthesis and orthosis design," Master's thesis, Boston University, 2004.

{A-13} R. B. Davis and P. A. Deluca, "Gait characterization via dynamic joint stiffness," Gait & Posture, Vol. 4, pp. 224-23, 1996.

{A-14} A. Hansen, D. S. Childress, S. C. Miff, S. A. Gard, K. P. Mesplay, "The human ankle during walking: implication for the design of biomimetric ankle prosthesis," Journal of Biomechanics, Vol. 37, Issue 10, pp. 1467-1474, 2004.

{A-15} A. L. H of, B. A. Geelen, J. Van den Berg, "Calf muscle moment, work and efficiency in level walking; role of series elasticity," Journal of Biomechanics, Vol. 16, No. 7, pp. 523-537, 1983.

{A-16} A. D. Kuo, "A simple model of bipedal walking predicts the preferred speed-step length relationship," Journal of Biomechanical Engineering, Vol. 123, pp. 264-269, 2001.

{A-17} A. D. Kuo, "Energetics of actively powered locomotion using the simplest walking model," Journal of Biomechanical Engineering, Vol. 124, pp. 113-120, 2002.

{A-18} A. D. Kuo, J. M. Donelan, and A. Ruina, "Energetic consequences of walking like an inverted pendulum: Step-to-step transitions," Exercise and Sport Sciences Reviews, Vol. 33, pp. 88-97, 2005.

{A-19} A. Ruina, J. E. Bertram, and M. Srinivasan, "A collisional model of the energetic cost of support work qualitatively explains leg sequencing in walking and galloping, pseudo-elastic leg behavior in running and the walk-to-run transition," Journal of Theoretical Biology, Vol. 237, Issue 2, pp. 170-192, 2005.

{A-20} G. K. Klute, J. Czerniecki, and B. Hannaford, "Development of powered prosthetic lower limb," Proc. 1st National Mtg, Veterans Affairs Rehab. R&D Service, Washington, D.C., October 1998.

{A-21} S. H. Collins and A. D. Kuo, "Controlled energy storage and return prosthesis reduces metabolic cost of walking," Proc. on ISB XXth Congress and the American Society of Biomechanics Annual Meeting, Cleveland, Ohio, pp. 804, August 2003.

{A-22} C. Li, T. Miwa, J. Furusho, S. Morimoto, K. Koyanagi, A. Nakagawa, Yasushi-Akazawa, and Y. Hashimoto, "Research and development of the intelligently-controlled prosthetic ankle joint," Proc. of IEEE Int. Conf. on Mechatronics and Automation, Luoyang, China, pp. 1114-1119, 2006.

{A-23} U.S. Pat. No. 6,443,993, Sep. 3, 2002.

{A-24} V. T. Inman, H. J. Ralston, and F. Todd, Human walking. Baltimore: Williams and Wilkins; 1981.

{A-25} J. Perry, Gait Analysis: Normal and Pathological Function. New Jersey: SLACK Inc.; 1992.

{A-26} S. K. Au, J. Weber, and H. Herr, "An ankle-foot emulator system for the study of human walking biomechanics," Proc. IEEE Int. Conf. on Robotics and Automation, Orlando, Fla., pp. 2939-2945, May 2006.

{A-27} K. Hirai, M. Hirose, Y. Haikawa, and T. Takenaka, "The development of Honda humanoid robot," Proceedings on IEEE/RSJ International Conference on Intelligent Robots and Systems, Leuven, Belgium, pp. 1321-1326, May 1998.

{A-28} K. Kaneko, et. al., "Humanoid robot HRP-2," Proc. IEEE Int. Conf. on Robotics and Automation, New Orleans, La., pp. 1083-1090, April 2004.

{A-29} S. Mochon and T. A. McMahon, "Ballistic walking," Journal of Biomechanics, Vol. 13, pp. 49-57, 1980.

{A-30} F. C. Anderson and M. G. Pandy, "Dynamic optimization of human walking," Journal of Biomechanical Engineering, Vol. 123, pp. 381-390, 2001

{A-31} R. McN. Alexander, "Simple models of human motion," Appl. Mech. Rev., Vol. 48, pp. 461-469, 1995.

{A-32} D. A. Winter, "Energy generation and absorption at the ankle and knee during fast, natural, and slow cadences," Clinical Orthopedics and Related Research, Vol. 175, pp. 147-154, 1983.

{A-33} D. A. Winter, The Biomechanics and Motor Control of Human Gait. Waterloo, Ontario: University of Waterlo; 1987.

{A-34} D. H. Nielsen, D. G. Shun, J. C. Golden, and K. Meier, "Comparison of energy cost and gait efficiency during ambulation in below-knee amputees using different prosthetic feet—a preliminary report," Journal of Prosthetics & Orthotics, Vol. 1, No. 1, pp. 24-29, 1989.

{A-35} P. A. Macfarlane, D. H. Nielsen, D. G. Shun, and K. Meier, "Gait comparisons for below-knee amputees using a flex-foot versue a conventional prosthetic foot," Journal of Prosthetics & Orthotics, Vol. 3, No. 4, pp. 150-159, 1991.

{A-36} D. G. Barth, L. Schumacher, and S. Sienko, "Gait analysis and energy cost of below-knee amputees wearing six different prosthetic feet," Journal of Prosthetics & Orthotics, Vol. 4, No. 2, pp. 63-72, 1992.

{A-37} J. Perry and S. Shanfield, "Efficiency of dynamic elastic response prosthetic feet," Journal of Rehabilitation Research and Development, Vol. 30, No. 1, pp. 137-143, 1993.

{A-38} J. F. Lehmann, R. Price, S. Boswell-Bessette, A. Dralle, and K. Questad, "Comprehensive analysis of dynamic elastic response feet: Seattle Ankle/Lite Foot versus standard SACH Foot," Arch Phys Med Rehabil, Vol. 74, pp. 853861, 1993.

{A-39} J. M. Casillas, V. Dulieu, M. Cohen, I. Marcer, and J. P. Didier, "Bioenergetic comparison of a new energy-storing foot and SACH foot in traumatic below-knee vascular amputations," Arch Phys Med Rehabil, Vol. 76, No. 1, pp. 3944, 1995.

{A-40} G. K. Klute, C. F. Kallfelz, J. M. Czerniecki, "Mechanical properties of prosthetic limbs adapting to the patient," Journal of Rehabilitation Research and Development, Vol. 38, No. 3, pp. 299-307, 2001.

{A-41} G. A. Pratt and M. M. Williamson, "Series elastic actuators," Proceedings on IEEE/RSJ International Conference on Intelligent Robots and Systems, Pittsburgh, pp. 399-406, 1995.

{A-42} D. Robinson, "Design and an analysis of series elasticity in closed-loop actuator force control," Ph.D. Thesis, Massachusetts Institute of Technology, 2000.

{A-43} S. K. Au, J. Weber, and H. Herr, "Biomechanical design of a powered ankle-foot prosthesis," Accepted by ICORR 2007.

{A-44} www.maxon.com

{A-45} C. T. Johnson and R. D. Lorenz, "Experimental identification of friction and its compensation in precise, position controlled mechanisms," IEEE Trans. on Industry Applications, Vol. 28, No. 6, pp. 1392-1398.

{A-46} D. Paluska and H. Herr, "The effect of series elasticity on actuator power and work output: implications for robotic and prosthetic joint design," Robotics and Autonomous Systems, Vol. 54, pp. 667-673, 2006.

{A-47} K. W. Hollander, T. G. Sugar, and D. E. Herring, "Adjustable robotic tendon using a 'Jack Spring'™," Proceedings on IEEE International Conference on Rehabilitation Robotics, Chicago, pp. 113-118, 2005.

{A-48} S. D. Eppinger and W. P. Seering, "Three dynamic problems in robot force control," IEEE Transactions on Robotics and Automation, Vol. 8, No. 6, pp. 751-758, 1992.

{A-49} N. Hogan, "Impedance control: an approach to manipulation: Part I-III," AMSE J. Dynamic Syst. Meas. Control, Vol. 107, pp. 1-24, 1985.

{A-50} N. Hogan and S. P. Buerger, "Impedance and Interaction Control," Robotics and Automation Handbook, CRC Press, pp. 19.1-19.24, 2005.

{A-51} K. A. Pasch and W. P. Seering, "On the drive systems for high performance machines," AMSE J. Mechanisms, Transmissions, and Automation in Design Vol. 106, pp. 102-108, 1984.

{A-52} N. Hogan and S. P. Buerger, "Impedance and Interaction Control," Chapter 19 in: Robotics and Automation Handbook, T. R. Kurfess, (ed.) CRC Press; 2004.

{A-53} J. E. Colgate, "The control of dynamically interaction systems," Massachusetts Institute of Technology, Ph.D. Thesis, 1998.

{A-54} D. L. Grimes, "An active multi-mode above-knee prosthesis controller," Ph.D. Thesis, Massachusetts Institute of Technology, 1976.

{A-55} D. Zlatnik, B. Steiner, and G. Schweitzer, "Finite-state control of a trans-femoral prosthesis," IEEE Trans. on Control System Technology, Vol. 10, No. 3, pp. 408-420.

{A-56} A. J. Wilkenfeld, "Biologically inspired auto adaptive control of a knee prosthesis," Ph.D. Thesis, Massachusetts Institute of Technology, 2000.

{A-57} J. A. Blaya and H. Herr, "Adaptive control of a variable-impedance ankle-foot orthosis to assist drop-foot gait," IEEE Transactions on Neural Systems and Rehabilitation Engineering, Vol. 12, No. 1, pp. 24-31, 2004

{A-58} www.mathworks.com

{A-59} C. J. Walsh, "Biomimetic Design of an Under-Actuated Leg Exoskeleton For Load-Carrying Augmentation," Master's Thesis, Massachusetts Institute of Technology, 2006.

{A-60} H. Geyer, A. Seyfarth, and R. Blickhan, "Positive force feedback in bouncing gaits," Proceeding of Royal Society of London in Biological Sciences, Vol. 270, No. 1529, pp. 2173-2183, 2003.

{A-61} C. Hausswirth, A. X. Bigard, and J. M. Lechevelier, "The Cosmed K4 telemetry system as an accurate device for oxygen uptake measurement during exercise," Int. J. of Sports Medicine, Vol. 18, pp. 449-453, 1997.

{A-62} J. M. Brockway, "Derivation of formulae used to calculate energy expenditure in man," Human Nutrition Clinical Nutrition, Vol. 41, pp. 463-471, 1987.

{A-63} J. M. Donelan, R. Kram, and A. D. Kuo, "Mechanical work for step-to-step transitions is a major determinant of the metabolic cost of human walking," J. Exp. Biol., 205, pp. 3717-3727, 2002.

{A-64} J. M. Donelan, R. Kram, and A. D. Kuo, "Simultaneous positive and negative external work in human walking," Journal of Biomechanics, 35, pp. 117-124, 2002.

{A-65} J. L. Johansson et al., "A clinical comparison of variable damping and mechanically passive prosthetic knee devices," American Journal of Physical Medicine & Rehabilitation, Vol. 84, no. 8, pp. 563-575, 2005.

{A-66} M. Srinivasan, "Energetics of legged locomotion: Why is total metabolic cost proportional to the cost of stance work," Proc. on ISB XXth Congress and the American Society of Biomechanics Annual Meeting, Cleveland, Ohio, pp. 829, August 2003.

{A-67} J. Doke, J. M. Donelan, and A. D. Kuo, "Mechanics and energetics of swinging the human leg," The Journal of Experimental Biology, No. 208, pp. 439-445, 2005.

{A-68} R. Riener, M. Rabuffetti, and C. Frigo, "Stair ascent and descent at different inclinations," Gait Posture, Vol. 15, pp. 32-44, 2002.

{A-69} B. J. McFadyen and D. A. Winter, "An integrated biomechanical analysis of normal stair ascent and descent," Journal of Biomech, Vol. 21, No. 9, pp. 73344, 1988.

{B-1} D. A. Winter and S. E. Sienko, "Biomechanics of below-knee amputee gait," Journal of Biomechanics, Vol. 21, No. 5, pp. 361-7, 1988.

{B-2} N. H. Molen, "Energy/speed relation of below-knee amputees walking on motor-driven treadmill," Int. Z. Angew. Physio, Vol. 31, pp. 173, 1973.

{B-3} G. R. Colborne, S. Naumann, P. E. Longmuir, and D. Berbrayer, "Analysis of mechanical and metabolic factors in the gait of congenital below knee amputees," Am. J. Phys. Med. Rehabil., Vol. 92, pp. 272-278, 1992.

{B-4} M. Palmer, "Sagittal plane characterization of normal human ankle function across a range of walking gait speeds," Master's Thesis, Massachusetts Institute of Technology, 2002.

{B-5} D. H. Gates, "Characterizing ankle function during stair ascent, descent, and level walking for ankle prosthesis and orthosis design," Master's thesis, Boston University, 2004.

{B-6} A. Hansen, et al., "The human ankle during walking: implication for the design of biomimetric ankle prosthesis," Journal of Biomechanics, Vol. 37, Issue 10, pp. 1467-1474, 2004.

{B-7} A. L. H of, et al., "Calf muscle moment, work and efficiency in level walking; role of series elasticity," Journal of Biomechanics, Vol. 16, No. 7, pp. 523-537, 1983.

{B-8} A. D. Kuo, "Energetics of actively powered locomotion using the simplest walking model," Journal of Biomechanical Engineering, Vol. 124, pp. 113-120, 2002.

{B-9} A. D. Kuo, J. M. Donelan, and A. Ruina, "Energetic consequences of walking like an inverted pendulum: Step-to-step transitions," Exercise and Sport Sciences Reviews, Vol. 33, pp. 88-97, 2005.

{B-10} A. Ruina, J. E. Bertram, and M. Srinivasan, "A collisional model of the energetic cost of support work qualitatively explains leg sequencing in walking and galloping, pseudo-elastic leg behavior in running and the walk-to-run transition," Journal of Theoretical Biology, Vol. 237, Issue 2, pp. 170-192, 2005.

{B-11} G. K. Klute, J. Czerniecki, and B. Hannaford, "Development of powered prosthetic lower limb,' Proc. 1st National Mtg, Veterans Affairs Rehab. R&D Service, Washington, D.C., October 1998.

{B-12} S. H. Collins and A. D. Kuo, "Controlled energy storage and return prosthesis reduces metabolic cost of walking," Proc. on ISB XXth Congress and the American Society of Biomechanics Annual Meeting, Cleveland, Ohio, pp. 804, August 2003.

{B-13} www.ossur.com.

{B-14} K. Koganezawa, and I. Kato, "Control aspects of artificial leg," IFAC Control Aspects of Biomedical Engineering, pp. 71-85, 1987.

{B-15} S. K. Au, P. Dilworth, and H. Herr, "An ankle-foot emulator system for the study of human walking biomechanics," Proc. IEEE Int. Conf. on Robotics and Automation, Orlando, Fla., pp. 2939-2945, May 2006.

{B-16} K. Hirai, et al., "The development of Honda humanoid robot," Proceedings on IEEE/RSJ International Conference on Intelligent Robots and Systems, Leuven, Belgium, pp. 1321-1326, May 1998.

{B-17} K. Kaneko, et al., "Humanoid robot HRP-2," Proc. IEEE Int. Conf. on Robotics and Automation, New Orleans, La., pp. 1083-1090, April 2004.

{B-18} S. Au, and H. Herr, "A biomimetic powered ankle-foot prosthesis that improves an amputee's gait," IEEE Trans. on Robotics, Pending.

{B-19} V. T. Inman, H. J. Ralston, and F. Todd, Human walking. Baltimore: Williams and Wilkins; 1981.

{B-20} S. Ron, Prosthetics and Orthotics: Lower limb and Spinal. Lippincott Williams & Wilkins, 2002.

{B-21} G. A. Pratt and M. M. Williamson, "Series elastic actuators," Proceedings on IEEE/RSJ International Conference on Intelligent Robots and Systems, Pittsburgh, pp. 399-406, 1995.

{B-22} D. Robinson, "Design and an analysis of series elasticity in closed-loop actuator force control," Ph.D. Thesis, Massachusetts Institute of Technology, 2000.

{B-23} www.maxon.com

{C-1} M. Palmer, "Sagittal plane characterization of normal human ankle function across a range of walking gait speeds," Master's Thesis, Massachusetts Institute of Technology, 2002.

{C-2} D. H. Gates, "Characterizing ankle function during stair ascent, descent, and level walking for ankle prosthesis and orthosis design," Master's thesis, Boston University, 2004.

{C-3} S. Ron, Prosthetics and Orthotics: Lower limb and Spinal. Lippincott Williams&Wilkins, 2002.

{C-4} D. A. Winter and S. E. Sienko, "Biomechanics of below-knee amputee gait," Journal of Biomechanics, Vol. 21, No. 5, pp. 361-7, 1988.

{C-5} N. H. Molen, "Energy/speed relation of below-knee amputees walking on motor-driven treadmill," Int. Z. Angew. Physio, Vol. 31, pp. 173, 1973.

{C-6} G. R. Colborne, S. Naumann, P. E. Longmuir, and D. Berbrayer, "Analysis of mechanical and metabolic factors in the gait of congenital below knee amputees," Am. J. Phys. Med. Rehabil., Vol. 92, pp. 272-278, 1992.

{C-7} G. K. Klute, J. Czerniecki, and B. Hannaford, "Development of powered prosthetic lower limb,' Proc. 1st National Mtg, Veterans Affairs Rehab. R&D Service, Washington, D.C., October 1998.

{C-8} S. H. Collins and A. D. Kuo, "Controlled energy storage and return prosthesis reduces metabolic cost of walking," Proc. on ISB XXth Congress and the American Society of Biomechanics Annual Meeting, Cleveland, Ohio, pp. 804, August 2003.

{C-9} C. Li, et al., "Research and development of the intelligently-controlled prosthetic ankle joint," Proc. of IEEE Int. Conf. on Mechatronics and Automation, Luoyang, China, pp. 1114-1119, 2006.

{C-10} U.S. Pat. No. 6,443,993, Sep. 3, 2002.

{C-11} www.ossur.com.

{C-12} K. Koganezawa, and I. Kato, "Control aspects of artificial leg," IFAC Control Aspects of Biomedical Engineering, pp. 71-85, 1987.

{C-13} S. K. Au, P. Dilworth, and H. Herr, "An ankle-foot emulator system for the study of human walking biomechanics," Proc. IEEE Int. Conf. on Robotics and Automation, Orlando, Fla., pp. 2939-2945, May 2006.

{C-14} V. T. Inman, H. J. Ralston, and F. Todd, Human walking. Baltimore: Williams and Wilkins; 1981.

{C-15} S. K. Au, "Powered Ankle-Foot Prosthesis for the Improvement of Amputee Walking Economy," Ph.D. Thesis, Massachusetts Institute of Technology, 2007.

{C-16} D. Robinson, "Design and an analysis of series elasticity in closed-loop actuator force control," Ph.D. Thesis, Massachusetts Institute of Technology, 2000.

{C-17} D. L. Grimes, "An active multi-mode above-knee prosthesis controller," Ph.D. Thesis, Massachusetts Institute of Technology, 1976.

{D-1} S. Ron. (2002) Prosthetics and Orthotics: Lower limb and Spinal. Lippincott Williams & Wilkins.

{D-2} M. Palmer. (2002) Sagittal plane characterization of normal human ankle function across a range of walking gait speeds. Masters Thesis, Massachusetts Institute of Technology, Cambridge.

{D-3} D. Gates. (2004) Characterizing ankle function during stair ascent, descent, and level walking for ankle prosthesis and orthosis design. Masters Thesis, Boston University, Boston.

{D-4} A. Hansen, D. Childress, S. Miff, S. Gard, and K. Mesplay. (2004) The human ankle during walking: Implication for the design of biomimetic ankle prosthesis. Journal of Biomechanics. Vol. 37, Issue 10, pp. 1467-1474.

{D-5} A. L. H of, B. A. Geelen, and Jw. Van den Berg. (1983) Calf muscle moment, work and efficiency in level walking; role of series elasticity. Journal of Biomechanics. Vol. 16, No. 7, pp. 523-537.

{D-6} N. H. Molen. (1973) Energy/speed relation of below-knee amputees walking on motor-driven treadmill. Int. Z. Angew. Physio. Vol. 31, pp. 173.

{D-7} G. R. Colborne, S. Naumann, P. E. Longmuir, and D. Berbrayer. (1992) Analysis of mechanical and metabolic factors in the gait of congenital below knee amputees. Am. J. Phys. Med. Rehabilitation. Vol. 92, pp. 272-278.

{D-8} D. A. Winter and S. E. Sienko. (1988) Biomechanics of below-knee amputee gait. Journal of Biomechanics. Vol. 21, No. 5, pp. 361-7.

{D-9} H. B. Skinner, et al. (1985) Gait analysis in amputees. Am J Phys Med, Vol. 64, pp. 82-89.

{D-10} H. Bateni and S. Olney. (2002) Kinematic and kinetic variations of below-knee amputee gait. Journal of Prosthetics & Orthotics. Vol. 14, No. 1, pp. 2-13.

{D-11} G. K. Klute, J. Czerniecki, and B. Hannaford. (1998) Development of powered prosthetic lower limb. Proc. 1st National Mtg, Veterans Affairs Rehab. R&D Service, Washington, D.C.

{D-12} S. H. Collins and A. D. Kuo. (2003) Controlled energy storage and return prosthesis reduces metabolic cost of walking. Proc. on ISB XXth Congress and the American Society of Biomechanics Annual Meeting. Cleveland, Ohio, pp. 804.

{D-13} C. Li, et al. (2006) Research and development of the intelligently-controlled prosthetic ankle joint. Proc. of IEEE Int. Conf. on Mechatronics and Automation. Luoyang, China, pp. 1114-1119.

{D-14} U.S. Pat. No. 6,443,993, Sep. 3, 2002.

{D-15} www.ossur.com.

{D-16} K. Koganezawa, and I. Kato. (1987) Control aspects of artificial leg. IFAC Control Aspects of Biomedical Engineering. pp. 71-85.

{D-17} S. K. Au, P. Dilworth, H. Herr. (2006) An ankle-foot emulation system for the study of human walking biomechanics. Proc. IEEE Int. Conf. on Robotics and Automation. Orlando, Fla., pp. 2939-2945.

{D-18} K. Hirai, et al. (1998) The development of Honda humanoid robot. Proc. on IEEE/RSJ Int. Conf. on Intelligent Robots and Systems. Leuven, Belgium, pp. 1321-1326.

{D-19} K. Kaneko, et al. (2004) Humanoid robot HRP-2. Proc. IEEE Int. Conf. on Robotics and Automation. New Orleans, La., pp. 1083-1090.

{D-20} D. Graupe et al. (1978) A microprocessor system for multifunctional control of upper-limb prostheses via myoelectric signal identification. IEEE Transaction on Automatic Control. Vol. AC-23, No. 4, pp. 538-544.

{D-21} K. A. Farry et al. (1996) Myoelectric teleoperation of a complex robotic hand. IEEE Transactions on Robotics and Automation. Vol. 12, No. 5, pp. 775-788.

{D-22} H. P. Huang and C. Y. Chen. (1999) Development of a myoelectric discrimination system for a multi-degree prosthetic hand. Proceeding of the IEEE International Conference on Robotics and Automation. Detroit, Mich., pp. 2392-2397.

{D-23} O. Fukuda et al. (2003) A human-assisting manipulator teleoperated by EMG signals and arm motions. IEEE Transactions on Robotics and Automation. Vol. 19, No. 2, pp. 210-222.

{D-24} C. J. Abul-haj and N. Hogan. (1990) Functional assessment of control systems for cybernetic elbow prostheses. Part I, Part II. IEEE Transactions on Biomedical Engineering. Vol. 37, No. 11, pp. 1025-1047.

{D-25} K. Akazawa, R. Okuno, and M. Yoshida. (1996) Biomimetic EMG prosthesis-hand. Proceedings of the 18th Annual International Conference of the IEEE Engineering in Medicine and Biology Society. Vol. 2, pp. 535-536.

{D-26} J. Rosen et al. (2001) A myosignal-based powered exoskeleton system. IEEE Transactions on Systems, Man, and Cybernetics-Part A: Systems and Humans. Vol. 31, No. 3, pp. 210-222.

{D-27} V. T. Inman, H. J. Ralston, and F. Todd. *Human walking*. Baltimore: Williams and Wilkins; 1981.

{D-28} D. A. Winter. (1983) Biomechanical motor pattern in normal walking. Journal of Motor Behavior. Vol. 15, No. 4, pp. 302-330.

{D-29} B. J. McFadyen and D. A. Winter. (1988) An integrated biomechanical analysis of normal stair ascent and descent. Journal of Biomechanics. Vol. 21, No. 9, pp. 733-744.

{D-30} Riener, R., Rabuffetti, M., and Frigo, Carlo. (2002) Stair ascent and descent at different inclinations. Gait Posture. Vol. 15, pp. 32-44.

{D-31} S. K. Au. (2007) Powered ankle-foot prosthesis for the improvement of amputee walking economy. Ph.D. Thesis, Massachusetts Institute of Technology.

{D-32} S. K. Au, J. Weber, and H. Herr. (2007) Biomechanical design of a powered ankle-foot prosthesis. Accepted by ICORR 2007.

{D-33} G. A. Pratt and M. M. Williamson. (1995) Series elastic actuators. Proceedings on IEEE/RSJ International Conference on Intelligent Robots and Systems. Pittsburgh, Vol. 1, pp. 399-406.

{D-34} D. Robinson. (2000) Design and an analysis of series elasticity in closed-loop actuator force control. Ph.D. Thesis, Massachusetts Institute of Technology.

{D-35} D. L. Grimes. (1976) An active multi-mode above-knee prosthesis controller. Ph.D. Thesis, Massachusetts Institute of Technology.

{D-36} D. Zlatnik, B. Steiner, and G. Schweitzer. (2002) Finite-state control of a trans-femoral prosthesis. IEEE Trans. on Control System Technology. Vol. 10. No. 3. pp. 408-420.

{D-37} H. Herr and A. Wilkenfeld. (2003) User-Adaptive Control of a Magnetorheological Prosthetic Knee. Industrial Robot: An International Journal. Vol. 30, pp. 42-55.

{D-38} N. Hogan (1976) A review of the methods of processing EMG for use as a proportional control signal. Biomedical Engineering. pp. 81-86.

{D-39} P. C. Doerschuk, D. E. Gustafson, and A. Willsky. (1983) Upper extremity limb function discrimination using EMG signal analysis. IEEE Transactions on Biomedical Engineering. Vol. 30. No. 1. pp. 18-28.

{D-40} S. K. Au, P. Bonato, and H. Herr. (2005) An EMG-position controlled system for an active ankle-foot prosthesis: an initial experimental study. Proc. IEEE International Conference on Rehabilitation Robotics. Chicago, USA.

{E-1} www.ossur.com.

{E-2} S. Ron, *Prosthetics and Orthotics: Lower limb and Spinal*. Lippincott Williams & Wilkins, 2002.

{E-3} N. H. Molen, "Energy/speed relation of below-knee amputees walking on motor-driven treadmill," *Int. Z. Angew. Physio*, Vol. 31, pp. 173, 1973.

{E-4} G. R. Colborne, S. Naumann, P. E. Longmuir, and D. Berbrayer, "Analysis of mechanical and metabolic factors in the gait of congenital below knee amputees," *Am. J. Phys. Med. Rehabil.*, Vol. 92, pp. 272-278, 1992.

{E-5} D. A. Winter and S. E. Sienko, "Biomechanics of below-knee amputee gait," *Journal of Biomechanics*, Vol. 21, No. 5, pp. 361-7, 1988.

{E-6} H. B. Skinner, et al. "Gait analysis in amputees," *Am J Phys Med*, Vol. 64, pp. 82-89, 1985.

{E-7} H. Bateni and S. Olney, "Kinematic and kinetic variations of below-knee amputee gait," *Journal of Prosthetics & Orthotics*, Vol. 14, No. 1, pp. 213, 2002.

{E-8} M. Palmer, "Sagittal plane characterization of normal human ankle function across a range of walking gait speeds," *Master's Thesis*, Massachusetts Institute of Technology, 2002.

{E-9} D. H. Gates, "Characterizing ankle function during stair ascent, descent, and level walking for ankle prosthesis and orthosis design," *Master's Thesis*, Boston University, 2004.

{E-10} A. Hansen, et al., "The human ankle during walking: implication for the design of biomimetric ankle prosthesis," *Journal of Biomechanics*, Vol. 37, Issue 10, pp. 1467-1474, 2004.

{E-11} A. L. H of, et al., "Calf muscle moment, work and efficiency in level walking; role of series elasticity," *Journal of Biomechanics*, Vol. 16, No. 7, pp. 523-537, 1983.

{E-12} A. D. Kuo, "Energetics of actively powered locomotion using the simplest walking model," *Journal of Biomechanical Engineering*, Vol. 124, pp. 113-120, 2002.

{E-13} A. D. Kuo, J. M. Donelan, and A. Ruina, "Energetic consequences of walking like an inverted pendulum: Step-to-step transitions," *Exercise and Sport Sciences Reviews*, Vol. 33, pp. 88-97, 2005.

{E-14} A. Ruina, J. E. Bertram, and M. Srinivasan, "A collisional model of the energetic cost of support work qualitatively explains leg sequencing in walking and galloping, pseudo-elastic leg behavior in running and the walk-to-run transition," *Journal of Theoretical Biology*, Vol. 237, Issue 2, pp. 170-192, 2005.

{E-15} G. K. Klute, J. Czerniecki, and B. Hannaford, "Development of powered prosthetic lower limb,' *Proc. 1st National Mtg*, Veterans Affairs Rehab. R&D Service, Washington, D.C., October 1998.

{E-16} S. H. Collins and A. D. Kuo, "Controlled energy storage and return prosthesis reduces metabolic cost of walking," *Proc. on ISB XXth Congress and the American Society of Biomechanics Annual Meeting*, Cleveland, Ohio, pp. 804, August 2003.

{E-17} C. Li, et al., "Research and development of the intelligently-controlled prosthetic ankle joint," *Proc. of IEEE In Conf. on Mechatronics and Automation*, Luoyang, China, pp. 1114-1119, 2006.

{E-18} U.S. Pat. No. 6,443,993, Sep. 3, 2002.

{E-19} K. Koganezawa, and I. Kato, "Control aspects of artificial leg," *IFAC Control Aspects of Biomedical Engineering*, pp. 71-85, 1987.

{E-20} S. K. Au, et al. "An ankle-foot emulator system for the study of human walking biomechanics," *Proc. IEEE Int. Conf. on Robotics and Automation*, Orlando, Fla., pp. 2939-2945, May 2006.

{E-21} K. Hirai, et al., "The development of Honda humanoid robot," *Proc. on IEEE/RSJ Int. Conf. on Intelligent Robots and Systems*, Leuven, Belgium, pp. 1321-1326, May 1998.

{E-22} K. Kaneko, et al., "Humanoid robot HRP-2," Proc. *IEEE Int. Conf. on Robotics and Automation*, New Orleans, La., pp. 1083-1090, April 2004.

{E-23} V. T. Inman, H. J. Ralston, and F. Todd, *Human walking*. Baltimore: Williams and Wilkins; 1981.

{E-24} G. A. Pratt and M. M. Williamson, "Series elastic actuators," *Proc. on IEEE/RSJ Int. Conf. on Intelligent Robots and Systems*, Pittsburgh, pp. 399-406, 1995.

{E-25} D. Robinson, "Design and an analysis of series elasticity in closed-loop actuator force control," *Ph.D. Thesis*, Massachusetts Institute of Technology, 2000.

{E-26} S. K. Au, J. Weber, and H. Herr, "Biomechanical design of a powered ankle-foot prosthesis," Submitted to ICORR 2007.

{E-27} www.maxon.com

{E-28} D. L. Grimes, "An active multi-mode above-knee prosthesis controller," *Ph.D. Thesis*, Massachusetts Institute of Technology, 1976.

{E-29} D. Zlatnik, B. Steiner, and G. Schweitzer, "Finite-state control of a trans-femoral prosthesis," *IEEE Trans. on Control System Technology*, Vol. 10, No. 3, pp. 408-420.

{E-30} N. Hogan, "Impedance control: an approach to manipulation:Part I-III," *AMSEJ. Dynamic Syst. Meas. Control*, Vol. 107, pp. 1-24, 1985.

{E-31} N. Hogan and S. P. Buerger, "Impedance and Interaction Control," Chapter 19 in: *Robotics and Automation Handbook*, T. R. Kurfess, (ed.) CRC Press; 2004.

{E-32} K. A. Pasch and W. P. Seering, "On the drive systems for high performance machines," *AMSEJ. Mechanisms, Transmissions, and Automation in Design*, Vol. 106, pp. 102-108, 1984.

{E-33} J. E. Colgate, "The control of dynamically interaction systems," *Ph.D. Thesis*, Massachusetts Institute of Technology, 1998.

{E-34} C. T. Johnson and R. D. Lorenz, "Experimental identification of friction and its compensation in precise, position controlled mechanisms," *IEEE Trans. on Industry Applications*, Vol. 28, No. 6, pp. 1392-1398.

{E-35} www.mathworks.com

{E-36} C. Hausswirth, A. X. Bigard, and J. M. Lechevelier, "The Cosmed K4 telemetry system as an accurate device for oxygen uptake measurement during exercise," *Int. J. of Sports Medicine*, Vol. 18, pp. 449-453, 1997.

{E-37} J. M. Brockway, "Derivation of formulae used to calculate energy expenditure in man," *Human Nutrition Clinical Nutrition*, Vol. 41, pp. 463-471, 1987.

{E-38} S. K. Au, "A Powered ankle-foot prosthesis that improves transtibital amputee ambulation," *Ph.D. Thesis*, Massachusetts Institute of Technology, Pending.

{E-39} C. J. Walsh, "Biomimetic Design of an Under-Actuated Leg Exoskeleton For Load-Carrying Augmentation," *Master's Thesis*, Massachusetts Institute of Technology, 2006.

{F-1} Hofbaur, M., Williams, B., "Mode Estimation of Probabilistic Hybrid Systems", HSSC 2002, LNCS 2289, pp. 253-266, Tomlin and Greenstreet (Eds.), Springer-Verlag {F-2} Hofbaur, M., Williams, B., "Hybrid Diagnosis with Unknown Behavioral Modes", Proceedings of the 13th International Workshop on Principles of Diagnosis (DX02), 2002

{F-3} Williams, B., Chung, S., Gupta, V., 2001. "Mode Estimation of Model-based Programs: Monitoring Systems with Complex Behavior." *Proceedings of the International Joint Conference on Artificial Intelligence, Seattle, Wa.*

{F-4} Radford Neal, Geoffrey Hinton. "A view of the EM algorithm that justifies incremental, sparse, and other variants". In Michael I. Jordan (editor), *Learning in Graphical Models* pp 355-368. Cambridge, Mass.: MIT Press, 1999.

Conclusion

It is to be understood that the methods and apparatus described above are merely illustrative applications of the principles of the invention. Numerous modifications may be made to the methods and structures described without departing from the spirit and scope of the invention.

What is claimed is:

1. A device comprising:
   a) a mechanical ankle joint that is a rotational joint bearing axis which joint defines an angle between two structures that are joined by the joint, which angle can vary over a first range of angles during normal operation of the device;
   b) a controllable actuator comprising a motor connected to a series spring for imparting a first torque about the joint; and c) a parallel spring connected in parallel with the actuator, for imparting a second torque about the joint only when the angle is within a second range of angles, the second range being a subset of, and not identical to, the first range.

2. The device of claim 1, wherein the first range of angles includes a maximum dorsiflexion angle of about 15 degrees and a maximum plantar flexion angle of about 25 degrees.

3. The device of claim 1, wherein the motor modulates compression of the series spring.

4. The device of claim 1, wherein the actuator modulates joint stiffness.

5. The device of claim 4, wherein the actuator has a first stiffness during controlled plantar flexion and a second stiffness during controlled dorsiflexion.

6. The device of claim 1, wherein the actuator provides stiffness and torque from the start of powered plantar flexion to toe off.

7. The device of claim 1, wherein the actuator provides active push-off during powered plantar flexion.

8. The device of claim 1, wherein the actuator imparts a peak torque of about 140 Nm.

9. The device of claim 1, wherein the actuator provides a large force bandwidth that is about 3.5 Hz.

10. The device of claim 1, wherein the parallel spring has a parallel spring stiffness, the device provides an offset stiffness during controlled dorsiflexion, and the offset stiffness is greater than or equal to the parallel spring stiffness.

11. The device of claim 1, wherein the parallel spring reduces a load borne by the actuator.

12. The device of claim 1, wherein the two structures comprise a foot structure and a shin structure, respectively, and each angle in the second range of angles is not more than 90 degrees.

13. The device of claim 1 further comprising a linear potentiometer adapted to measure deflection of the series spring.

14. The device of claim 1 further comprising a prosthetic foot coupled to the joint.

15. The device of claim 1, wherein the device provides shock absorption during foot strike, energy storage during mid-stance period, and energy return in a late stance period.

16. The device of claim 1, wherein the device modifies its net work according to walking speed.

17. The device of claim 1, wherein the device adjusts joint spring equilibrium position in a swing phase according to at least one of walking speed and surface terrain.

18. The device of claim 1, wherein the device adjusts stiffness of the joint in real time for terrain variations.

19. The device of claim 1, wherein the actuator provides a torque bandwidth of about 9 Hz.

20. The device of claim 1, further including an artificial sensory system comprising at least one sensor selected from the group consisting of an ankle angle sensor, an ankle torque sensor, a heel contact sensor, a toe contact sensor, a foot contact sensor, a potentiometer measuring joint torque, an inertial measurement unit, and an electromyographic sensor.

21. The device of claim 20, wherein the inertial measurement unit includes a three-axis accelerometer and from one to three ceramic gyroscopes.

22. The device of claim 20, further including an operative connection to the motor and the at least one sensor, wherein the motor stores elastic energy in the series spring during ankle-controlled dorsiflexion, and wherein the series and parallel springs release elastic energy during ankle-powered flexion.

23. A device, comprising:
a) a mechanical ankle joint, which joint defines an angle between two structures that are joined by the joint, which angle can vary over a first range of angles during normal operation of the device;
b) a controllable actuator including a motor connected to a series spring for imparting a first torque about the joint;
c) a parallel spring connected in parallel with the actuator, for imparting a second torque about the joint only when the angle is within a second range of angles, the second range being a subset of, and not identical to, the first range;
d) an artificial sensory system including at least one sensor selected from the group consisting of a position sensor, a velocity sensor, and a force sensor; and
e) an operative connection to the motor and the at least one sensor, wherein the motor is adapted to store elastic energy in the series spring during ankle-controlled dorsiflexion, wherein the series and parallel springs release elastic energy during ankle-powered plantar flexion.

* * * * *

UNITED STATES PATENT AND TRADEMARK OFFICE
CERTIFICATE OF CORRECTION

PATENT NO. : 8,512,415 B2
APPLICATION NO. : 12/157727
DATED : August 20, 2013
INVENTOR(S) : Hugh M. Herr et al.

It is certified that error appears in the above-identified patent and that said Letters Patent is hereby corrected as shown below:

On the Title Page, Item (54) and in the Specification, Column 1, Title delete:

"Powered Ankle-Foot Prothesis"

and insert:

--Powered Ankle-Foot Prosthesis--

Signed and Sealed this
First Day of October, 2013

Teresa Stanek Rea
*Deputy Director of the United States Patent and Trademark Office*